(12) United States Patent
Kreutzer et al.

(10) Patent No.: US 9,587,240 B2
(45) Date of Patent: *Mar. 7, 2017

(54) COMPOSITIONS AND METHODS FOR INHIBITING EXPRESSION OF A TARGET GENE

(71) Applicant: Alnylam Pharmaceuticals, Inc., Cambridge, MA (US)

(72) Inventors: Roland Kreutzer, Weidenberg (DE); Stefan Limmer, Kulmbach (DE); Sylvia Limmer, Kulmbach (DE); Philipp Hadwiger, Altenkunstadt (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/737,304

(22) Filed: Jun. 11, 2015

(65) Prior Publication Data

US 2015/0353937 A1    Dec. 10, 2015

Related U.S. Application Data

(63) Continuation of application No. 14/012,994, filed on Aug. 28, 2013, now Pat. No. 9,074,213, which is a continuation of application No. 12/894,018, filed on Sep. 29, 2010, now Pat. No. 8,546,143, which is a continuation of application No. 10/384,339, filed on Mar. 7, 2003, now Pat. No. 7,829,693, which is a continuation-in-part of application No. PCT/EP02/00152, filed on Jan. 9, 2002.

(30) Foreign Application Priority Data

| | | |
|---|---|---|
| Jan. 9, 2001 | (DE) | 10100586 |
| Oct. 26, 2001 | (DE) | 10155280 |
| Nov. 29, 2001 | (DE) | 10158411 |
| Dec. 7, 2001 | (DE) | 10160151 |

(51) Int. Cl.

| | |
|---|---|
| *A61K 31/713* | (2006.01) |
| *A61K 31/7115* | (2006.01) |
| *C12N 15/113* | (2010.01) |
| *C12N 15/63* | (2006.01) |
| *C12N 15/11* | (2006.01) |
| *A61K 38/00* | (2006.01) |

(52) U.S. Cl.
CPC ........ *C12N 15/1138* (2013.01); *C12N 15/111* (2013.01); *C12N 15/1131* (2013.01); *A61K 38/00* (2013.01); *C12N 2310/14* (2013.01); *C12N 2310/53* (2013.01); *C12N 2320/50* (2013.01)

(58) Field of Classification Search
USPC ....... 435/6.11, 6.14, 91.1, 91.31, 320.1, 325, 435/366, 455, 375; 514/44; 536/23.1, 536/24.3, 24.33, 24.5
See application file for complete search history.

(56) References Cited

U.S. PATENT DOCUMENTS

| | | |
|---|---|---|
| 4,309,492 A | 1/1982 | Bernard |
| 5,112,734 A | 5/1992 | Kramer et al. |
| 5,225,347 A | 7/1993 | Goldberg et al. |
| 5,246,921 A | 9/1993 | Reddy et al. |
| 5,340,318 A | 8/1994 | Kunihiro |
| 5,472,802 A | 12/1995 | Holland et al. |
| 5,496,698 A | 3/1996 | Draper et al. |
| 5,525,468 A | 6/1996 | McSwiggen |
| 5,574,142 A | 11/1996 | Meyer, Jr. et al. |
| 5,616,459 A | 4/1997 | Kramer et al. |
| 5,635,385 A | 6/1997 | Leopold et al. |
| 5,639,655 A | 6/1997 | Thompson et al. |
| 5,712,257 A | 1/1998 | Carter |
| 5,811,275 A | 9/1998 | Wong-Staal et al. |

(Continued)

FOREIGN PATENT DOCUMENTS

| | | |
|---|---|---|
| CA | 2334951 A1 | 12/1999 |
| DE | 19618797 | 11/1997 |

(Continued)

OTHER PUBLICATIONS

"Introduction of DNA into Mammalian Cells," Current Protocols in Molecular Biology, Supplement 48, Edited by Frederick M. Ausubel et al., John Wiley & Sons, Inc., pp. 9.4.7-9.4.8 (1999).
Agrawal et al., "Self-Stabilized Oligonucleotides as Novel Antisense Agents," Delivery Strategies for Antisense Oligonucleotide Therapeutics, Edited by Saghir Akhtar, CRC Press, pp. 105-121 (1995).
Agrawal, S. et al., Molecular Med. Today, vol. 6, pp. 72-81 (2002).
Agrawal, S., et al., "Antisense oligonucleotides: towards clinical trials." Trends in Biotechnology. Oct. 1996, vol. 14, pp. 376-387.
Alfonzo et al., "The mechanism of U insertion/deletion RNA editing in kinetoplastid mitochondria" Nucleic Acids Res. 25:3751-3759 (1997).
Ambros, V., (2001), "Dicing Up RNAs", Science, 293:811-813.
Anderson et al., "Human gene therapy" Nature 392:25-30 (1998).

(Continued)

*Primary Examiner* — Jane Zara
(74) *Attorney, Agent, or Firm* — Fenwick & West LLP

(57) ABSTRACT

The present invention relates to a double-stranded ribonucleic acid (dsRNA) having a nucleotide sequence which is substantially identical to at least a part of a target gene and which is no more than 49, preferably less than 25, nucleotides in length, and which comprises a complementary (antisense) RNA strand having a 1 to 4 nucleotide overhang at the 3'-end and a blunt 5'-end. The invention further relates to a pharmaceutical composition comprising the dsRNA and a pharmaceutically acceptable carrier. The pharmaceutical compositions are useful for inhibiting the expression of a target gene, as well as for treating diseases caused by expression of the target gene, at low dosages (i.e., less than 5 milligrams, preferably less than 25 micrograms, per kg body weight per day). The invention also relates to methods for inhibiting the expression of a target gene, as well as methods for treating diseases caused by the expression of the gene.

20 Claims, 20 Drawing Sheets

(56) References Cited

U.S. PATENT DOCUMENTS

| | | | |
|---|---|---|---|
| 5,811,300 A | 9/1998 | Sullivan et al. |
| 5,814,500 A | 9/1998 | Dietz |
| 5,824,519 A | 10/1998 | Norris et al. |
| 5,837,510 A | 11/1998 | Goldsmith et al. |
| 5,854,067 A | 12/1998 | Newgard et al. |
| 5,864,028 A | 1/1999 | Sioud |
| 5,866,701 A | 2/1999 | Hampel et al. |
| 5,891,717 A | 4/1999 | Newgard et al. |
| 5,898,031 A | 4/1999 | Crooke |
| 5,908,779 A | 6/1999 | Carmichael et al. |
| 5,939,262 A | 8/1999 | Pasloske et al. |
| 5,968,737 A | 10/1999 | Ali-Osman et al. |
| 5,985,620 A | 11/1999 | Sioud |
| 6,057,156 A | 5/2000 | Akhtar et al. |
| 6,071,890 A | 6/2000 | Scheule et al. |
| 6,077,705 A | 6/2000 | Duan et al. |
| 6,080,851 A | 6/2000 | Pachuk et al. |
| 6,087,164 A | 7/2000 | Hochberg et al. |
| 6,087,172 A | 7/2000 | Veerapaneni et al. |
| 6,099,823 A | 8/2000 | Falb |
| 6,100,087 A | 8/2000 | Rossi et al. |
| 6,100,444 A | 8/2000 | Frelinger et al. |
| 6,107,094 A | 8/2000 | Crooke |
| 6,183,959 B1 | 2/2001 | Thompson |
| 6,187,585 B1 | 2/2001 | Bennett et al. |
| 6,224,868 B1 | 5/2001 | Wong et al. |
| 6,225,291 B1 | 5/2001 | Lewin et al. |
| 6,245,560 B1 | 6/2001 | Lisziewicz |
| 6,245,748 B1 | 6/2001 | Wellstein et al. |
| 6,255,071 B1 | 7/2001 | Beach et al. |
| 6,346,398 B1 | 2/2002 | Pavco et al. |
| 6,355,415 B1 | 3/2002 | Wagner et al. |
| 6,410,176 B1 | 6/2002 | Genc et al. |
| 6,423,489 B1 | 7/2002 | Anderson et al. |
| 6,482,803 B1 | 11/2002 | Roth et al. |
| 6,486,299 B1 | 11/2002 | Shimkets |
| 6,506,559 B1 | 1/2003 | Fire et al. |
| 7,105,656 B2 | 9/2006 | Colgan |
| 7,427,605 B2 | 9/2008 | Davis et al. |
| 7,718,629 B2 | 5/2010 | Bumcrot et al. |
| 7,829,693 B2 * | 11/2010 | Kreutzer ............... C12N 15/111 435/455 |
| 8,546,143 B2 * | 10/2013 | Kreutzer ............... C12N 15/111 435/455 |
| 9,074,213 B2 * | 7/2015 | Kreutzer ............... C12N 15/111 |
| 2002/0086356 A1 | 7/2002 | Tuschl et al. |
| 2002/0114784 A1 | 8/2002 | Li et al. |
| 2002/0123034 A1 | 9/2002 | Canaani et al. |
| 2002/0132346 A1 | 9/2002 | Cibelli |
| 2002/0162126 A1 | 10/2002 | Beach et al. |
| 2002/0173478 A1 | 11/2002 | Gewirtz |
| 2003/0027783 A1 | 2/2003 | Zernicka-Goetz et al. |
| 2003/0108923 A1 | 6/2003 | Tuschl et al. |
| 2003/0125281 A1 | 7/2003 | Lewis et al. |
| 2003/0143732 A1 | 7/2003 | Fosnaugh et al. |
| 2003/0148341 A1 | 8/2003 | Sin et al. |
| 2003/0157030 A1 | 8/2003 | Davis et al. |
| 2003/0170891 A1 | 9/2003 | McSwiggen |
| 2003/0176671 A1 | 9/2003 | Reed et al. |
| 2003/0180756 A1 | 9/2003 | Shi et al. |
| 2003/0190635 A1 | 10/2003 | McSwiggen |
| 2003/0198627 A1 | 10/2003 | Arts et al. |
| 2004/0102408 A1 | 5/2004 | Kreutzer et al. |
| 2004/0259247 A1 | 12/2004 | Tuschl et al. |
| 2006/0263435 A1 | 11/2006 | Davis et al. |
| 2007/0004664 A1 | 1/2007 | McSwiggen et al. |
| 2007/0031844 A1 | 2/2007 | Khvorova et al. |
| 2007/0281899 A1 | 12/2007 | Bumcrot et al. |
| 2009/0149403 A1 | 6/2009 | MacLachlan et al. |
| 2011/0015250 A1 | 1/2011 | Bumcrot et al. |
| 2012/0244207 A1 | 9/2012 | Fitzgerald et al. |

FOREIGN PATENT DOCUMENTS

| | | |
|---|---|---|
| DE | 19631919 | 7/1998 |
| DE | 19956568 A1 | 8/2000 |
| DE | 10155280 | 10/2001 |
| DE | 10158411 | 11/2001 |
| DE | 10100586 | 1/2002 |
| DE | 10100586 C1 | 4/2002 |
| DE | 10100588 A1 | 7/2002 |
| DE | 10100587 C1 | 11/2002 |
| DE | 10163098 | 4/2003 |
| DE | 10160151 A1 | 6/2003 |
| DE | 20023125 A1 | 6/2003 |
| DE | 10230997 A1 | 7/2003 |
| DE | 10230966 A1 | 1/2004 |
| EP | 0126325 | 11/1991 |
| EP | 1001666 A2 | 5/2000 |
| EP | 1107340 A2 | 6/2001 |
| EP | 1214945 A2 | 6/2002 |
| WO | WO 92/19732 | 11/1992 |
| WO | WO 94/01550 | 1/1994 |
| WO | WO 98/05770 | 2/1998 |
| WO | WO 98/53083 | 11/1998 |
| WO | WO 99/15682 | 4/1999 |
| WO | WO 99/32619 A1 | 7/1999 |
| WO | WO 99/49029 | 9/1999 |
| WO | WO 99/53050 A1 | 10/1999 |
| WO | WO 99/61631 A1 | 12/1999 |
| WO | WO 00/01846 A1 | 1/2000 |
| WO | WO 00/44895 A1 | 8/2000 |
| WO | WO 00/44914 A1 | 8/2000 |
| WO | WO 00/63364 A1 | 10/2000 |
| WO | WO 00/68374 A2 | 11/2000 |
| WO | WO 01/18197 A1 | 3/2001 |
| WO | WO 01/29058 A1 | 4/2001 |
| WO | WO 01/36646 A1 | 5/2001 |
| WO | WO 01/42443 A1 | 6/2001 |
| WO | WO 01/48183 A2 | 7/2001 |
| WO | WO 01/68836 A2 | 9/2001 |
| WO | WO 01/70949 A1 | 9/2001 |
| WO | WO 01/75164 A2 | 10/2001 |
| WO | WO 01/92513 A1 | 12/2001 |
| WO | WO 02/16620 A1 | 2/2002 |
| WO | WO 02/26780 A2 | 4/2002 |
| WO | WO 02/44321 A2 | 6/2002 |
| WO | WO 02/055692 A2 | 7/2002 |
| WO | WO 02/055693 A2 | 7/2002 |
| WO | WO 02/061034 A1 | 8/2002 |
| WO | WO 02/068635 A2 | 9/2002 |
| WO | WO 02/068637 A2 | 9/2002 |
| WO | WO 03/006477 A1 | 1/2003 |
| WO | WO 03/012052 A2 | 2/2003 |
| WO | WO 03/012082 A1 | 2/2003 |
| WO | WO 03/016572 A1 | 2/2003 |
| WO | WO 03/033700 A1 | 4/2003 |
| WO | WO 03/035082 A1 | 5/2003 |
| WO | WO 03/035083 A1 | 5/2003 |
| WO | WO 03/035868 A1 | 5/2003 |
| WO | WO 03/035869 A1 | 5/2003 |
| WO | WO 03/035870 A1 | 5/2003 |
| WO | WO 03/035876 A1 | 5/2003 |
| WO | WO 03/070283 A2 | 8/2003 |
| WO | WO 03/070750 A2 | 8/2003 |
| WO | WO 03/070969 A2 | 8/2003 |
| WO | WO 03/070972 A2 | 8/2003 |
| WO | WO 03/074654 A2 | 9/2003 |
| WO | WO 03/080794 A2 | 10/2003 |
| WO | WO 03/080807 A2 | 10/2003 |
| WO | WO 2004/080406 A2 | 9/2004 |
| WO | WO 2004/090108 A2 | 10/2004 |
| WO | WO 2010/147992 A1 | 12/2010 |

OTHER PUBLICATIONS

Annex to Decision on Reject of the Opposition, Opposition Application No. 02710786.1 for European Patent No. EP1352061, Aug. 25, 2009, 20 Pages (English translation of claims included within document).

(56) References Cited

OTHER PUBLICATIONS

Asanuma et al., "Photoregulation of the Formation and Dissociation of a DNA Duplex by Using the cis-trans Isomerization of Azobenzene" Angew. Chem. Int. Ed. 38:2393-2395 (1999).
Azhayeva et al., "Inhibitory properties of double helix forming circular oligonucleotides" Nucleic Acids Res. 25:4954-4961 (1997).
Bahramian et al., "Transcriptional and Posttranscriptional Silencing of Rodent .alpha.1(I) Collagen by a Homologous Transcriptionally Self-Silenced Transgene" Mol. Cell. Biol. 19:274-283 (1999).
Barawkar et al., "Synthesis, biophysical properties, and nuclease resistance properties of mixed backbone oligodeoxynucleotides containing cationic internucleoside guanidinium linkages: Deoxynucleic guanidine/DNA chimeras" Proc. Natl. Acad. Sci. USA 95:11047-11052 (1998).
Bass, B., "The short answer," Nature, May 24, 2001, pp. 428-429, vol. 411.
Bass, B.L., (2000), "Double-Stranded RNA as a Template for Gene Silencing", Cell, 101:235-238.
Bhan et al., "2',5'-Linked oligo-3'-deoxyribonucleoside phosphorothioate chimeras: thermal stability and antisense inhibition of gene expression" Nucleic Acids Res. 25:3310-3317 (1997).
Billy et al., "Specific interference with gene expression induced by long, double-stranded RNA in mouse embryonal teratocarcinoma cell lines" Proc. Natl. Acad. Sci. USA 98:14428-14433 (2001).
Borecky et al., "Therapeutic use of double-stranded RNAs in man" Tex. Rep. Biol. Med. 41:575-581 (1981-1982) (Abstract only).
Boutla et al., "Short 5'-Phosphorylated double-stranded RNAs induce RNA interference in *Drosophila*" Current Biol. 11:1776-80, 2001.
Braich et al., "Regiospecific Solid-Phase Synthesis of Branched Oligonucleotides. Effect of Vicinal 2',5'- (or 2',3'-) and 3',5'-Phosphodiester Linkages on the Formation of Hairpin DNA" Bioconjug. Chem. 8:370-377 (1997).
Branch, A.D., Trends in Biochem. Sci., vol. 23, pp. 45-50 (1998).
Bumcrot et al., "RNAi Therapeutics: a potential new class of pharmaceutical drugs" Nature Chem. Biol. 2:711-719, 2006.
Caplen, N.J. et al., (2001), "Specific inhibition of gene expression by small double-stranded RNAs in invertebrate and vertebrate systems", Proc. Natl. Acad. Sci. USA, 98(17):9742-9747.
Caplen, N.J., (2002), "A new approach to the inhibition of gene expression", Trends in Biotechnology, 20(2):49-51.
Castelli et al., "The 2-5A system in viral infection and apoptosis" Biomed. Pharmacother. 52:386-390 (1998).
Chirila, T.V. et al., Biomaterials, vol. 23, pp. 321-342 (2002).
Cobaleda, C. et al., (2000), "In vivo inhibition by a site-specific catalytic RNA subunit of Rnase P designed against the BCR-ABL oncogenic products: a novel approach for cancer treatment", Blood, 95(3):731-737.
Communication from the European Patent Office including Response to Patentee's Submission of May 21, 2010, filed by SIRNA Therapeutics on Sep. 7, 2010, in opposition to European Patent No. 1352061, 15 Pages.
Crooke, S.J., Antisense Research & Application, Chapter 1, pp. 1-50, Ed. By S. Crooke, Publ. By Springer-Verlag (1998).
Czauderna et al., "Structural variations and stabilizing modifications of synthetic siRNAs in mammalian cells," Nucleic Acids Res., 31(1):1-12 (2003).
Decision on Rejection of the Opposition, Opposition Application No. 02710786.1 for European Patent No. EP1352061, Aug. 25, 2009, 40 Pages.
Doench, J.G. et al., (2003), "siRNAs can function as miRNAs", Genes & Development, 17:438-442.
Dolinnaya et al., "Oligonucleotide circularization by template-directed chemical ligation" Nucleic Acids Res., 21:5403-5407 (1993).
Donze, O. et al., (2002), "RNA interference in mammalian cells using siRNAs synthesized with T7 RNA Polymerase", Nucleic Acids Research, 30(10):e46(4pages).

Downward, J. et al., (1990), "Identification of a nucleotide exchange-promoting activity for p21.sup.ras", Proc. Natl. Acad. Sci. USA, 87:5998-6002.
Elbashir, S., et al., "Analysis of gene function in somatic mammalian cells using small interfering RNAs," Methods, 2002, pp. 199-213, vol. 26.
Elbashir, S., et al., "Duplexes of 21-nucleotide RNAs mediate RNA interference in mammalian cell culture," Nature, May 24, 2001, p. 494-498, vol. 411.
Elbashir, S., et al., "Functional Anatomy of siRNAs for Mediating Efficient RNAi in *Drosophila melanogaster* Embryo Lysate", The EMBO Journal, 2001, pp. 6877-6888, vol. 20, No. 23.
Elbashir, S., et al., "RNA Interference is Mediated by 21-and 22 Nucleotide RNAs," Genes & Development, 2001, pp. 188-200, vol. 15.
Expert-Bezancon et al., "Precise localization of several covalent RNA-RNA cross-link in *Escherichia coli* 16S RNA" Eur. J. Biochem. 136:267-274 (1983).
Fire et al., "Production of antisense RNA leads to effective and specific inhibition of gene expression in C. elegans muscle" Development 113:503-514 (1991).
Fire, A., "RNA-triggered Gene Silencing," Trends in Genetics, Sep. 1999, pp. 358-363, vol. 15, No. 9.
Fire, A., et al., "Potent and Specific Genetic Interference by Double Stranded RNA in Caenorhabditis elegans," Nature, Feb. 19, 1998, pp. 806-811, vol. 391.
Gao et al., "Circularization of oligonucleotides by disulfide bridge formation" Nucleic Acids Res., 23:2025-2029 (1995).
Gautschi, O. et al., (2001), "Activity of a Novel bcl-2/bcl-xL-Bispecific Antisense Oligonucleotide Against Tumors of Diverse Histologic Origins", Journal of the National Cancer Institute, 93(6):463-471.
Gewirtz et al., "Nucleic Acid Therapeutics: State of the Art and future prospects" Blood 92:712-736, 1998.
Gibbs, J.B. et al., (1988), "Purification of ras GTPase activating protein from bovine brain", Proc. Natl. Acad. Sci. USA, 85:5026-5030.
Grasby et al., "Purine Functional Groups in Essential Residues of the Hairpin Ribozyme Required for Catalytic Cleavage of RNA" Biochemistry 34:4068-4076 (1995).
Griffey et al., "2'-O-Aminopropyl Ribonucleotides: A Zwitterionic Modification That Enhances the Exonuclease Resistance and Biological Activity of Antisense Oligonucleotides" J. Med. Chem. 39:5100-5109 (1996).
Grounds for Appeal in opposition to European Patent No. EP1352061, filed by SiRNA Therapeutics, filed on Jan. 4, 2010, 39 Pages.
Gryaznov et al., "Template controlled coupling and recombination of oligonucleotide blocks containing thiophosphoryl groups" Nucleic Acids Res. 21:1403-1408 (1993).
Ha et al., "A bulged lin-4/lin-14 RNA duplex is sufficient for Caenorhabditis elegans lin-14 temporal gradient formation" Genes & Development 10:3041-3050 (1996).
Hamilton et al., "A Species of Small Antisense RNA in Post-transcriptional Gene Silencing in Plants" Science 286:950-952 (1999).
Hammond, S.M. et al., (2000), "An RNA-directed nuclease mediates post-transcriptional gene silencing in *Drosophila* cells", Nature, 404:293-296.
Hanazawa et al., "Use of cDNA subtraction and Rna interference screens in combination reveals genes required for germ-line development in Caenorhabditis elegans" Proc. Natl. Acad. Sci. 97:8686-91, 2001.
Harborth, J. et al., (2001), "Identification of essential genes in cultured mammalian cells using small interfering RNAs", Journal of Cell Science, 114(24):4557-4565.
Harfe et al., "Analysis of a Caenorhabditis elegans Twist homolog identifies conserved and divergent aspects of mesodermal patterning" Genes Dev. 12:2623-2635 (1998).
Hoke et al., "Effects of phosphorothioate capping on antisense oligonucleotide stability, hybridization and antiviral efficacy versus herpes simplex virus infection" Nucleic Acids Res. 19:5743-5748 (1991).

(56) References Cited

OTHER PUBLICATIONS

Holen, T. et al., (2002), "Positional effects of short interfering RNAs targeting the human coagulation trigger Tissue Factor", Nucleic Acids Research, 30(8):1757-1766.
Horn et al., "Chemical synthesis and characterization of branched oligodeoxyribonucleotides (bDNA) for use as signal amplifiers in nucleic acid quantification assays" Nucleic Acids Res. 25:4842-4849 (1997).
Hornung, V., et al., "Sequence-specific potent induction of IFN-αby short interfering RNA in plasmacytoid dendritic cells throughTLR7," Nature Medicine, Mar. 2005, pp. 263-270, vol. 11, No. 3.
Huang et al., "Epidermal growth factor receptor inhibition in cancer therapy: biology, rationale and preliminary clinical results" Investig. New Drugs 17:259-69, 1999.
Hunter, "Genetics: A touch of elegance with RNAi" Curr. Biol. 9:R440-R442 (1999).
International Search Report for International Application No. PCT/EP2002/00151, Jun. 12, 2003, 7 Pages.
International Search Report for International Application No. PCT/EP2002/00152, Jul. 17, 2003, 10 Pages.
Iwase et al., "Gene regulation by decoy approach (I): synthesis and properties of photo-crosslinked oligonucleotides" Nucleic Acids Symp. Ser. 37:203-204 (1997).
Jacobs et al., "When Two Strands Are Better Than One: The Mediators and Modulators of the Cellular Responses to Double-Stranded RNA" Virology 219:339-349 (1996).
James, H.A, et al., "The therapeutic potential of ribozymes," Blood (1998) 91 :371-82.
Jansen, B., et al., "Chemosensitisation of malignant melanoma by BCL2 antisense therapy," The Lancet (2000) 356:1728-1733.
Jaschke et al., "Synthesis and Analytical Characterization of RNA-Polyethylene Glycol Conjugates" Nucleosides & Nucleotides 15:1519-1529 (1996).
Jiang and Milner, "Selective silencing of viral gene expression in HPV-positive human cervical carcinoma cells treated with siRNA, a primer of RNA interference" Oncogene 21:6041-6048 (2002).
Judge et al., "Sequence-dependent stimulation of the mammalian innate immune response by synthetic siRNA" Nature Biotech 23:457-62, 2005.
Kaufman, "Double-stranded RNA-activated protein kinase mediates virus-induced apoptosis: A new role for an old actor" Proc. Natl. Acad. Sci. USA 96:11693-11695 (1999).
Kennerdell et al., "Use of dsRNA-Mediated Genetic Interference to Demonstrate that frizzled and frizzled 2 Act in the Wingless Pathway" Cell 95:1017-1026 (1998).
Kreutzer et al., "Specific inhibition of viral gene expression by double-stranded RNA in vitro" Annual Fall Meeting of the GBH, Abstract for Poster Paper No. 328, p. S169 (1999).
Kumar et al., "Antisense RNA: function and fate of duplex RNA in cells of higher eukaryotes" Microbiol. Mol. Biol. Rev. 62:1415-1434 (1998).
Lee et al., "The C. elegans Heterochronic Gene lin-4 Encodes Small RNAs with Antisense Complementarity to lin-14" Cell 75:843-854 (1993).
Lewis, D.L. et al., (2002), "Efficient delivery of siRNA for inhibition of gene expression in postnatal mice", Nature Genetics, 32:107-108.
Li et al., "Double-stranded RNA injection produces null phenotypes in zebrafish" Dev. Biol. 210:238, Abstract No. 346 (1999).
Lima, W., et al., "Cleavage of Single Strand RNA Adjacent to RNA-DNA Duplex Regions by *Escherichia coli* RNase H1," The Journal of Biological Chemistry, Oct. 31, 1997, pp. 27513-27516, vol. 272, No. 44.
Lin et al., "Policing rogue genes" Nature 402:128-129 (1999).
Lipardi, C. et al., (2001), "RNAi as Random Degradative PCR: siRNA Primers Convert mRNA into dsRNAs that are Degraded to Generate New siRNAs", Cell, 107:297-307.
Lipinski et al., "Experimental and computational approaches to estimate solubility and permeability in drug discovery and development settings" Adv. Drug Deliv. Rev. 23:3-25 (1997).
Lipson et al., "Psoralen Cross-Linking of Ribosomal RNA" Methods Enzymol. 164:330-341 (1988).
Liu et al., "Detection of a Novel ATP-Dependent Cross-Linking Protein at the 5' Splice-Site U1 Small Nuclear RNA Duplex by Methylene Blue-Mediated Photo-Cross-Linking" Mol. Cell. Biol. 18:6910-6920 (1998).
Lowy, D.R. et al., (1993), "Function and Regulation of RAS", Annu. Rev. Biochem., 62:851-891.
Ma et al., "Design and Synthesis of RNA Miniduplexes via a Synthetic Linker Approach", Biochemistry 32:1751-1758 (1993).
Majumdar et al., "Targeted gene knockout mediated by triple helix forming oligonucleotides" Nat. Genet. 20:212-214 (1998).
Manche, L et al., (1992), "Interactions between Double-Stranded DNA Regulators and the Protein Kinase DAI", Molecular and Cellular Biology, 12(11):5238-5248.
Marques et al., "Activation of the mammalian immune system by siRNAs" Nature Biotech 11:139-1405, 2005.
Martinez et al., "Synthetic small inhibiting RNAs: Efficient tools to inactivate oncogenic mutations and restore p53 pathways" Proc. Nat. Acad. Sc. 99:14849-14854 (2002).
McCaffrey, A.P. et al., (2002), "RNA interference in adult mice", Nature, 418:38-39.
Micura et al., "Cyclic Oligoribonucleotides (RNA) by Solid-Phase Synthesis" Chem. Eur. J. 5:2077-2082 (1999).
Milhaud et al., "Free and Liposome-Encapsulated Double-Stranded RNAs as Inducers of Interferon, Interleukin-6, and Cellular Toxicity" J. Interferon Res., 11:261-265 (1991).
Minks et al., "Structural Requirements of Double-stranded RNA for the Activation of 2',5'Olgo(A) Polymerase and Protein Kinase of Interferon-treated HeLa Cells" J. Biol. Chem. 254(20):10180-10183 (1979).
Minutes of the oral proceedings of the Opposition Division, Opposition Application No. 02710786.1 for European Patent No. EP1352061, Aug. 25, 2009, 11 Pages.
Misquitta et al., "Targeted disruption of gene function in *Drosophila* by RNA interference (RNA-i): A role for nautilus in embryonic somatic muscle formation" Proc. Natl. Acad. Sci. USA 96:1451-1456 (1999).
Montgomery et al., "RNA as a target of double-stranded RNA-mediated genetic interference in Caenorhabditis elegans" Proc. Natl. Acad. Sci. USA 95:15502-15507 (1998).
Montgomery, M.K. et al., (1998), "Double-stranded RNA as a mediator in sequence-specific genetic silencing and co-suppression", TIG, 14(7):255-258.
Moss et al., "The Cold Shock Domain Protein LIN-28 Controls Developmental Timing in C. elegans and is Regulated by the lin-4 RNA" Cell 88:637-646 (1997).
Ngo, H. et al., (1998), "Double-stranded RNA induces mRNA degradation in Trypanosoma brucei", Proc. Natl. Acad. Sci., 95:14687-14692.
Nielsen et al., "A novel class of conformationally restricted oligonucleotide analogues: synthesis of 2',3'-bridged monomers and RNA-selective hybridization" Chem. Commun. pp. 825-826 (1997).
Nikiforov et al., "Oligodeoxynucleotides containing 4-thiothymidine and 6-thiodeoxyguanosine as affinity labels for the Eco RV restriction endonuclease and modification methylase" Nucleic Acids Res. 20:1209-1214 (1992).
Nolen, T. et al., (2002), "Positional effects of short interfering RNAs targeting the human coagulation trigger Tissue Factor", Nucleic Acids Research, 30(8):1757-1766.
Notice of Appeal in opposition to European Patent No. EP1352061, filed by SiRNA Therapeutics, filed on Oct. 23, 2009, 39 Pages.
Notice of Opposition by SiRNA Therapeutics, Inc. against EP application No. 02710786.1 (Feb. 28, 2007).
Nykanen, "ATP Requirements and small interfering RNA structure in the RNA interference pathway" Cell 107:309-21, 2001.
Opalinska, J.B. et al., Nature Reviews, vol. 1, pp. 503-514 (2002).

(56) References Cited

OTHER PUBLICATIONS

Paddison, P.J. et al., (2002), "Short hairpin RNAs (shRNAs) induce sequence-specific silencing in mammalian cells", Genes & Development, 16:948-958.
Park et al., "Specific inhibition of HIV-1 gene expression by double-stranded RNA" Nucleic Acids Res. Suppl. No. 1:219-20, 2001.
Parrish S. et al. Nov. 2000, Functional Anatomy of a dsRNA Trigger: Differential Requirement for the Two Trigger Strands in RNA Interference, Molecular Cell, vol. 6, 1077-87.
Patentees Observations filed in opposition proceedings for EP application No. 02710786.1 (Oct. 15, 2007).
Pegram et al., "Phase II Study of Receptor-Enhanced Chemosensitivity Using Recombinant Humanized Anti-p185.sup. HER2/neu Monoclonal Antibody Plus Cisplatin in Patients With HER2/neu-Overexpressing Metastatic Breast Cancer Refractory to Chemotherapy Treatment" J. Clin. Oncol. 16:2659-2671 (1998).
Peracchi, A., Rev. Med. Virol., vol. 14, pp. 47-64 (2003).
Petition by Sirna Therapeutics in opposition proceedings for European Patent No. 1352061 (May 14, 2009).
Randall, G. et al., (2003), "Clearance of replicating hepatitis C virus replicon RNAs in cell culture by small interfering RNAs", PNAS, 100(1):235-240.
Response to Grounds of Appeal Filed by Opponent in opposition to European Patent No. EP1352061, filed by Alnylam Europe AG on May 21, 2010, 15 Pages.
Reynolds, et al. (2004) "Rational siRNA design for RNA interference," Nature Biotechnology, vol. 22, No. 3, pp. 326-330.
Robbins, M., et al., "Stable expression of shRNAs in human CD34* progenitor cells can avoid induction of interferon responses to siRNAs in vitro," Nature Biotechnology, May 2006, pp. 566-571, vol. 24, No. 5.
Rose, S., et al., "Functional polarity is introduced by Dicer processing of short substrate RNAs," Nucleic Acids Research, 2005, pp. 4140-4156, vol. 33, No. 13.
Schilingensiepen et al., Blackwell Science Ltd., vol. 6, 1997, "Antisense—From Technology to Therapy".
Seydoux et al., "Repression of gene expression in the embryonic germ lineage of C. elegans" Nature 382:713-716 (1996).
Sharp et al., "RNA Interference" Science 287:2432-33, 2000.
Sharp et al., "RNAi and double-strand RNA" Genes Dev. 13:139-141 (1999).
Sharp, P.A., (2001), "RNA interference—2001", Genes & Development, 15:485-490.
Shi et al., "A CBP/p300 homolog specifies multiple differentiation pathways in Caenorhabditis elegans" Genes Dev. 12:943-955 (1998).
Sijen, T. et al., (2001), "On the Role of RNA Amplification in dsRNA-Triggered Gene Silencing", Cell, 107:465-476.
Skorski, T. et al., Suppression of Philadelphia.sub.1 leukemia cell growth in mice by BCR-ABL antisense oligodeoxynucleotides, Proc. Natl. Acad. Sci. USA (1994) 91:4504-4508.
Skripkin et al., "Psoralen crosslinking between human immunodeficiency virus type 1 RNA and primer tRNA.sub.3.sup.Lys" Nucleic Acids Res. 24:509-514 (1996).
Sledz et al., "Activation of interferon system by short-interfering RNAs" Nature Cell Biol. 5:834-839, 2003.
Spankuch-Schmitt et al., "Effect of RNA Silencing of Polo-Like Kinase-1 (PLK1) on Apoptosis and Spindle Formation in Human Cancer Cells" J. Nat. Cancer Inst. 94:1863-1877 (2002).
Strauss, "Candidate 'Gene Silencers' Found" Science 286:886 (1999).
Submission and Auxiliary Request by Sirna Therapeutics in opposition proceedings for European Patent No. 1352061 (May 13, 2009).
Summons to Attend oral proceedings in the opposition proceedings for EP application No. 02710786.1 (Mar. 17, 2009).
Thompson, "Shortcuts from gene sequence to function" Nature 17:1158-1159 (1999).
Tijsterman, M. et al., (2002), "The Genetics of RNA Silencing", Annu. Rev. Genet., 36:489-519.
Timmons et al., "Specific interference by ingested dsRNA" Nature 395:854 (1998).
Tuschl T., "RNA Interference and Small Interfering RNAs" Chembiochem, 2001, pp. 239-245, vol. 2.
Tuschl, T., "Expanding small RNA interference," Nature Biotechnology, May 2002, pp. 446-448, vol. 20.
Tuschl, T., "Functional genomics: RNA sets the standard," Nature, Jan. 16, 2003, vol. 421, No. 6920, pp. 220-221.
Tuschl, T., "Mammalian RNA Interference," RNAi, A Guide to Gene Silencing, Chapter 13, G.J. Hannon (ed,), 2003, pp. 265-295.
Tuschl, T., et al., "Small Interfering RNAs: A Revolutionary Tool for the Analysis of Gene Function and Gene Therapy," Molecular Interventions, 2002, pp. 158-167, vol. 2, No. 3.
Tuschl, T., et al., "Targeted mRNA Degradation by Double-Stranded RNA in Vitro," Genes & Development, 1999, pp. 3191-3197, vol. 13.
Uhlmann, E. et al. Jun. 1, 1990, "Antisense Nucleotides: A New Therapeutic Principal" Chemical Reviews, American Chemical Society, Easton, US vol. 90, No. 4, pp. 543-584, ISSN:0009-2665.
Veal et al., "Sequence-specific RNAse cleavage of gag mRNA from HIV-1 infected cells by an antisense oligonucleotide in vitro" Nucleic Acids Res. 26:5670-75, 1998.
Verma et al., "Gene therapy—promises, problems and prospects" Nature 389:239-242 (1997).
Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.
Voinnet et al., "Systemic signaling in gene silencing" Nature 389:553 (1997).
Wagner et al., "Double-stranded RNA poses puzzle" Nature 391:744-745 (1998).
Wang et al., "Circular RNA oligonucleotides. Synthesis, nucleic acid binding properties, and a comparison with circular DNAs" Nucleic Acids Res. 22:2326-2333 (1994).
Wang et al., "RNA Conformation in the Tat—TAR Complex Determined by Site-Specific Photo-Cross-Linking" Biochemistry 35:6491-6499 (1996).
Strauss, "Candidate 'Gene Silencers' Found" Science 286:886 (1999).
Waterhouse et al., "Virus resistance and gene silencing in plants can be induced by simultaneous expression of sense and antisense RNA" Proc. Natl. Acad. Sci. USA 95:13959-13964 (1998).
Watkins et al., "In vivo UV cross-linking of U snRNAs that participate in trypanosome trans-splicing" Genes Dev. 5:1859-1869 (1991).
Weil, et al (2002) "Targeting the Kinesin Eg5 to Monitor siRNA Transfection in Mammalian Cells," *Biotechniques* 33(6):1244-1248.
Wengel, "Synthesis of 3'-C- and 4'-C-Branched Oligodeoxynucleotides and the Development of Locked Nucleic Acid (LNA)" Acc. Chem. Res. 32:301-310 (1999).
Wess et al., "Early days of RNAi" BioCentury vol. 11, No. 12, 2003.
Wianny, F. et al., (2000), "Specific interference with gene function by double-stranded RNA in early mouse development", Nature Cell Biology, 2:70-75.
Wild, K. et al., (1999), "The 2 .ANG. structure of helix 6 of the human signal recognition particle RNA", Structure, (11):1345-1352.
Wu, H., et al., "Properties of Clones and Expressed Human RNase H1," The Journal of Biological Chemistry, Oct. 1, 1999, pp. 28270-28278, vol. 274, No. 40.
Yang, D. et al., (2000), "Evidence that processed small dsRNAs may mediate sequence-specific mRNA degradation during RNAi in *Drosophila* embryos", Current Biology, 10:1191-1200.
Yu, J. et al., (2002), "RNA interference by expression of short-interfering RNAs and hairpin RNAs in mammalian cells", PNAS, 99(9):6047-6052.
Zamore et al., Cell, vol. 101, pp. 25-33 (2000).
Zamore, "RNA interference: listening to the sound of silence" Nature Struc. Biol. 8:748-750, 2001.

(56) References Cited

OTHER PUBLICATIONS

Zamore, P.D. et al., (2000), "RNAi: Double-Stranded RNA Directs the ATP-Dependent Cleavage of mRNA at 21 to 23 Nucleotide Intervals", Cell, 101:25-33.
Z-Axis Connector Company, LCD Connectors, www.z-axiscc.com/prodlcd.htm, Accessed Jul. 19, 2001.
Z-Axis Connector Company, Silver STAX, www.z-axiscc.com/prodstax.htm, Accessed Jul. 19, 2001.
Zimmerman, et al. (2006) "RNAi-mediated gene silencing in non-human primates," *Nature*, vol. 441, May 4:111-114.
Zwieb et al., "Evidence for RNA-RNA cross-link formation in *Escherichia coli* ribosomes" Nucleic Acids Res. 5:2705-2720 (1978).

\* cited by examiner

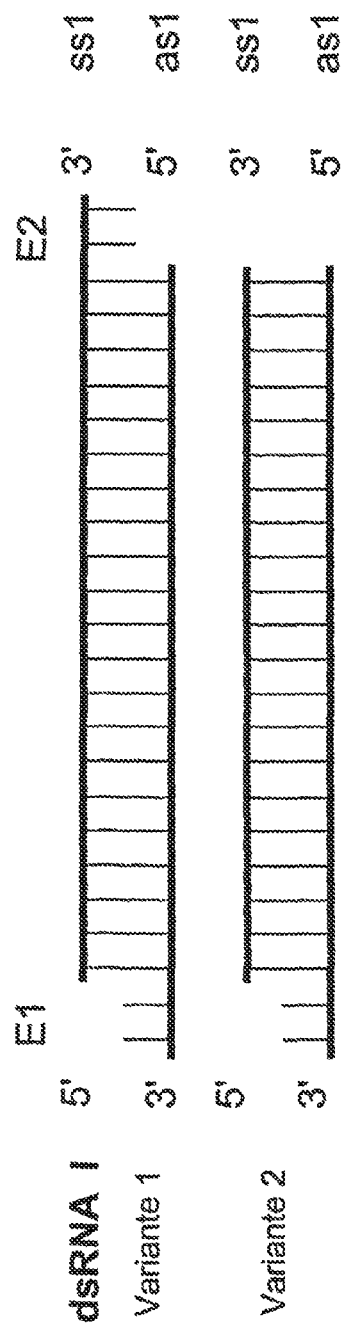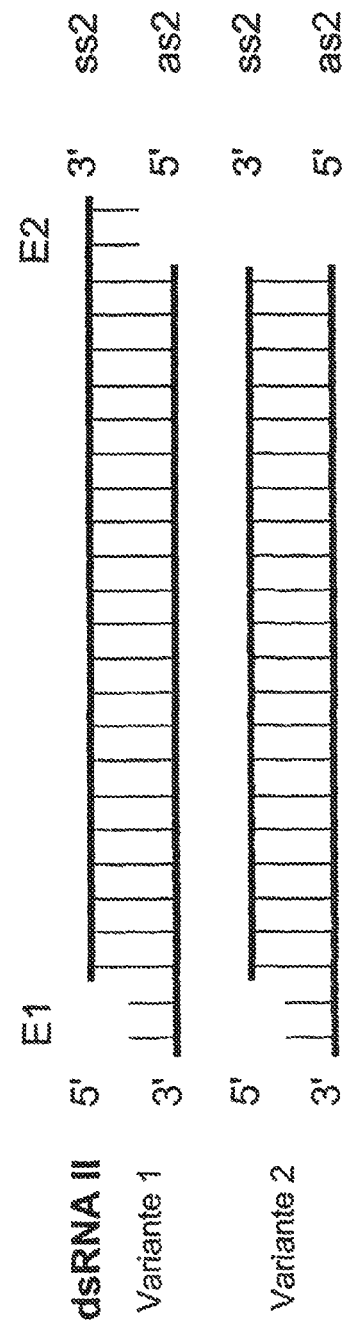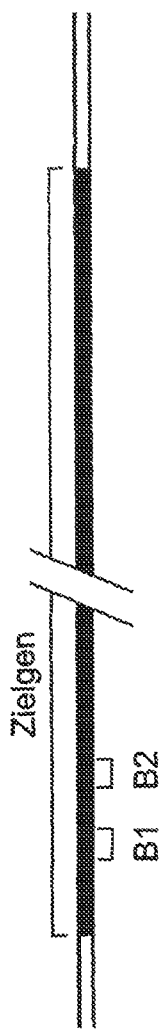

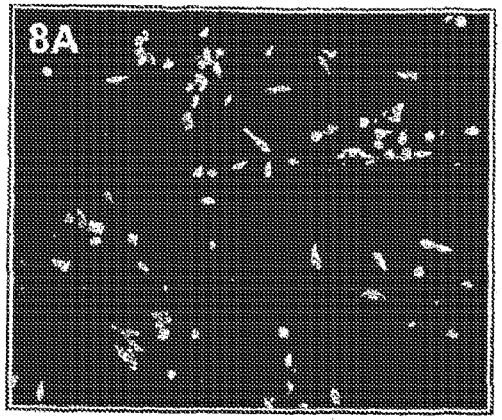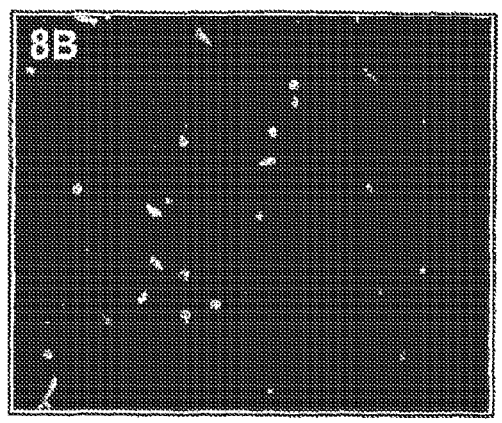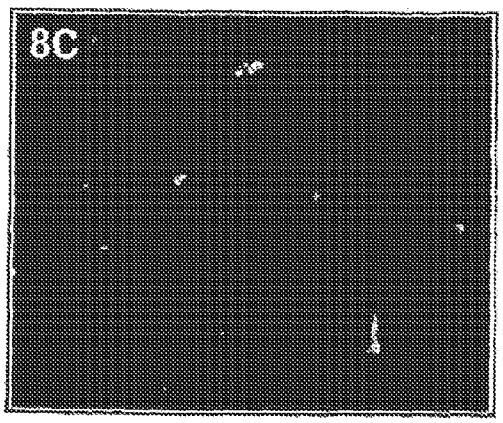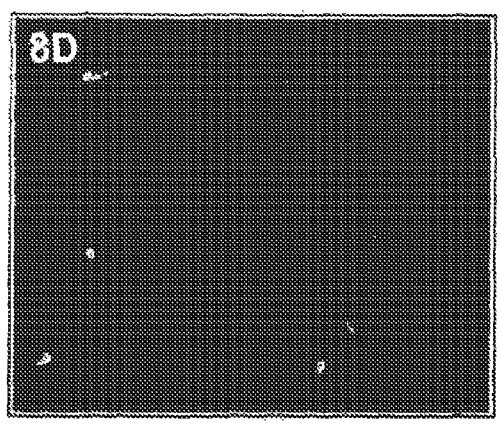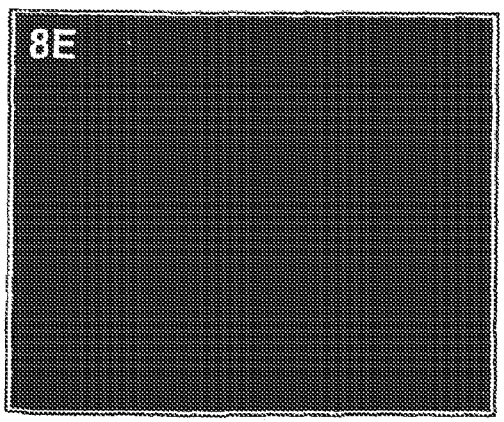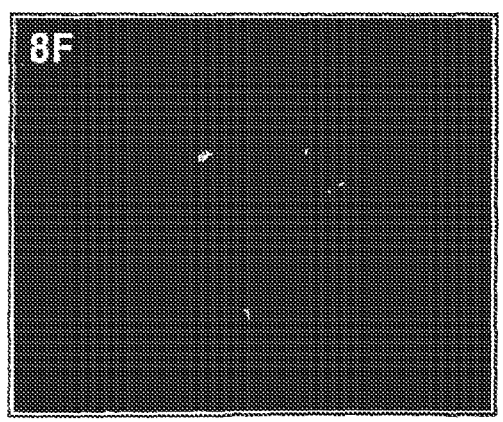
Fig. 8

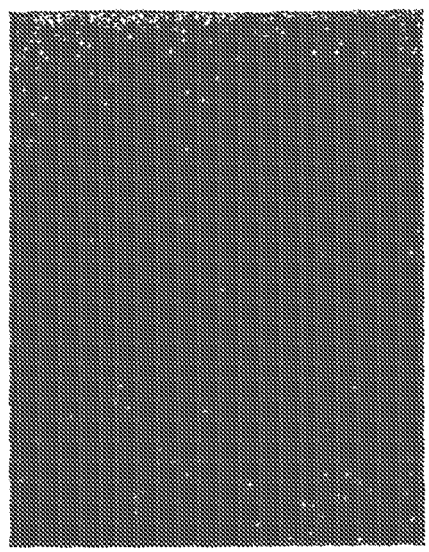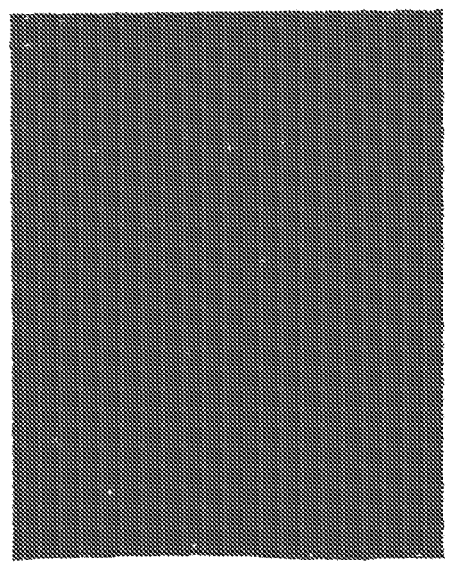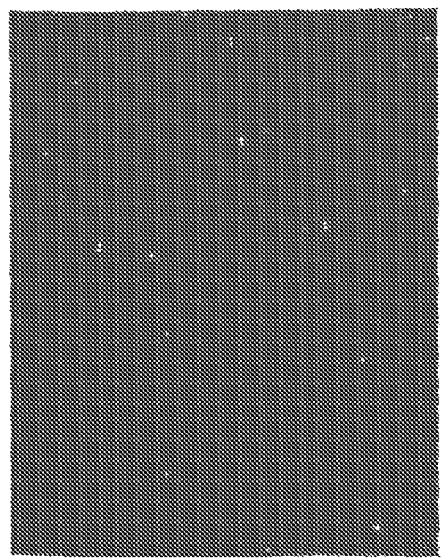
Fig. 27

COMPOSITIONS AND METHODS FOR INHIBITING EXPRESSION OF A TARGET GENE

RELATED APPLICATIONS

This application is a continuation of U.S. application Ser. No. 14/012,994 filed on Aug. 28, 2013, which is a continuation of U.S. application Ser. No. 12/894,018, filed on Sep. 29, 2010, issued as U.S. Pat. No. 8,546,143, which is a continuation of U.S. application Ser. No. 10/384,339, filed on Mar. 7, 2003, issued as U.S. Pat. No. 7,829,693, which is a continuation-in-part of International Application No. PCT/EP02/00152 (WO02/55693), which designated the United States and was filed on Jan. 9, 2002, which claims the benefit of German Patent No. 101 00 586.5, filed on Jan. 9, 2001, German patent No. 101 55 280.7, filed on Oct. 26, 2001, German Patent No. 101 58 411.3, filed Nov. 29, 2001, and German Patent No. 101 60 151.4, filed Dec. 7, 2001. The entire teachings of the above application(s) are incorporated herein by reference for all purposes.

FIELD OF THE INVENTION

This invention relates to double-stranded ribonucleic acid (dsRNA), and its use in mediating RNA interference in vitro and in vivo.

BACKGROUND OF THE INVENTION

Many diseases (e.g., cancers, hematopoietic disorders, endocrine disorders, and immune disorders) arise from the abnormal expression or activity of a particular gene or group of genes. Similarly, disease can result through expression of a mutant form of protein, as well as from expression of viral genes that have been integrated into the genome of their host. The therapeutic benefits of being able to selectively silence these abnormal or foreign genes are obvious.

A number of therapeutic agents designed to inhibit expression of a target gene have been developed, including antisense ribonucleic acid (RNA) (see, e.g., Skorski, T. et al., *Proc. Natl. Acad. Sci. USA* (1994) 91:4504-4508) and hammerhead-based ribozymes (see, e.g., James, H. A, and 1. Gibson, *Blood* (1998) 91:371). However, both of these agents have inherent limitations. Antisense approaches, using either single-stranded RNA or DNA, act in a 1:1 stoichiometric relationship and thus have low efficacy (Skorski et al., supra). For example, Jansen et al. report that, in a small percentage of patients, relatively high doses (2 mg/kg body weight per day) of antisense RNA resulted in biologically significant levels (i.e., long-term plasma concentrations above 1 mg/L) of encoded protein (Jansen, B., et al., *The Lancet* (2000) 356:1728-1733). However, no detectable level of plasma protein was observed at lower dosages (e.g., 0.6 mg). Hammerhead ribozymes, which because of their catalytic activity can degrade a higher number of target molecules, have been used to overcome the stoichiometry problem associated with antisense RNA. However, hammerhead ribozymes require specific nucleotide sequences in the target gene, which are not always present.

More recently, double-stranded RNA molecules (dsRNA) have been shown to block gene expression in a highly conserved regulatory mechanism known as RNA interference (RNAi). Briefly, the RNAse III Dicer enzyme processes dsRNA into small interfering RNAs (siRNA) of approximately 22 nucleotides, which serve as guide sequences to induce target-specific mRNA cleavage by an RNA-induced silencing complex RISC (Hammond, S. M., et al., *Nature* (2000) 404:293-296). In other words, RNAi involves a catalytic-type reaction whereby new siRNAs are generated through successive cleavage of long dsRNA. Thus, unlike antisense, RNAi degrades target RNA in a non-stoichiometric manner. When administered to a cell or organism, exogenous dsRNA has been shown to direct the sequence-specific degradation of endogenous messenger RNA (mRNA) through RNAi.

WO 99/32619 (Fire et al.) discloses the use of a dsRNA of at least 25 nucleotides in length to inhibit the expression of a target gene in *C. elegans*. dsRNA has also been shown to degrade target RNA in other organisms, including plants (see, e.g., WO 99/53050, Waterhouse et al.; and WO 99/61631, Heifetz et al.) and *Drosophila* (see, e.g., Yang, D., et al., *Curr. Biol.* (2000) 10:1191-1200). Despite successes in these organisms, until recently the general perception in the art has been that RNAi cannot be made to work in mammals. It was believed that protocols used for invertebrate and plant systems would not be effective in mammals due to the interferon response, which leads to an overall block to translation and the onset of apoptosis (see, e.g., Wianny, F., et al., *Nature Cell Biol.* (2000) 2:70-75); Fire, A., *Trends Genet.* (1999) 15:358-363; and Tuschl, T., et al., *Genes Dev.* (1999) 13(24):3191-97). At least one group of scientists believed that RNAi could only be made to work in mammals if the PKR response could be neutralized or some way avoided, although no suggestions were given as to how this might be achieved (Fire, *Trends Genet.* (1999), supra; and Montgomery and Fire, *Trends Genet.* (1998) 14:255-258). However, WO 00/44895 (Limmer) demonstrated for the first time that dsRNA can induce RNAi in mammalian cells, provided that the dsRNA meets certain structural requirements, including a defined length limitation.

Despite significant advances in the field, there remains a need for an agent that can selectively and efficiently silence a target gene using the cell's own RNAi machinery. More specifically, an agent that has both high biological activity and in vivo stability, and that can effectively inhibit expression of a target gene at a low dose, would be highly desirable. Compositions comprising such agents would be useful for treating diseases caused by abnormal expression or activity of a gene.

SUMMARY OF THE INVENTION

The present invention discloses double-stranded ribonucleic acid (dsRNA), as well as compositions and methods for inhibiting the expression of a target gene in a cell using the dsRNA. The present invention also discloses compositions and methods for treating diseases caused by the expression or activity of the target gene. The dsRNA of the invention, which is no more than 49 nucleotides in length, comprises an RNA strand (complementary RNA strand) having a region which is complementary to an RNA transcript of at least a part of a target gene. The 3'-end of the complementary RNA strand comprises a nucleotide overhang of 1 to 4 nucleotides; the 5'-end of the complementary RNA strand is blunt.

In one aspect, the invention relates to a double-stranded ribonucleic acid (dsRNA), which is no more than 49 nucleotides in length, comprises a sense RNA strand and a complementary RNA strand. The complementary RNA strand, is substantially identical to at least a part of a target gene, comprises a complementary nucleotide sequence which is complementary to an mRNA transcript of a portion of the target gene. The 3'-end of the complementary RNA has a nucleotide overhang of 1 to 4 nucleotides and the 5'-end is blunt. The dsRNA may be less than 25 nucleotides, preferably 19 to 23 nucleotides in length, and the nucleotide overhang is preferably 1 or 2 nucleotides in length. The nucleotides of the nucleotide overhang may be replaced with nucleoside thiophosphates. The dsRNA may comprise a linker between the complementary RNA strand and the sense RNA strand, preferably between the 5'-end of the complementary RNA strand and the 3'-end of the sense RNA strand. The linker may be a chemical linker, such a hexaethylene glycol linker, apoly-(oxyphosphinico-oxy-1,3-propandiol) linker, or an oligoethyleneglycol linker. The target gene may be an oncogene, a cytokine gene, an idiotype protein gene, a prion gene, a gene that encodes a protein that induces angiogenesis, a gene that encodes an adhesion protein, a gene that encodes a cell surface receptor, a gene that encodes a protein involved in a metastasizing and/or invasive process, a gene that encodes a proteinase, a gene that encodes a protein that regulates apoptosis, a gene that encodes a EGF receptor, a MDR1 gene, a gene of a human papilloma virus, a hepatitis C virus, or a human immunodeficiency virus. In one embodiment, the target gene comprises a sequence of SEQ ID NO:1-140.

In another aspect, the invention relates to a method of inhibiting the expression of a target gene in a cell. The method comprises introducing a double-stranded ribonucleic acid (dsRNA) into the cell, and maintaining the cell for a time sufficient to obtain degradation of the mRNA transcript of the target gene, thereby inhibiting expression of the target gene. The complementary RNA strand, is substantially identical to at least a part of a target gene, comprises a complementary nucleotide sequence which is complementary to an mRNA transcript of a portion of the target gene. The 3'-end of the complementary RNA has a nucleotide overhang of 1 to 4 nucleotides and the 5'-end is blunt. The dsRNA may be less than 25 nucleotides, preferably 19 to 23 nucleotides in length, and the nucleotide overhang is preferably 1 or 2 nucleotides in length. The nucleotides of the nucleotide overhang may be replaced with nucleoside thiophosphates. The dsRNA may comprise a linker between the complementary RNA strand and the sense RNA strand, preferably between the 5'-end of the complementary RNA strand and the 3'-end of the sense RNA strand. The linker may be a chemical linker, such a hexaethylene glycol linker, apoly-(oxyphosphinico-oxy-1,3-propandiol) linker, or an oligoethyleneglycol linker. The target gene may be any gene whose expression is to be inhibited, such as the target genes described above.

In yet another aspect, the invention relates to a pharmaceutical composition for inhibiting the expression of a target gene in a mammal. The pharmaceutical composition comprises a dsRNA, as described above, and a pharmaceutically acceptable carrier. The dosage unit of dsRNA may be in a range of 0.01 to 5.0 milligrams (mg), 0.1 to 200 micrograms, 0.1 to 100 micrograms, 1.0 to 50 micrograms, or 1.0 to 25 micrograms, preferably less than 25 micrograms per kilogram body weight of the mammal. The target gene may be any gene whose expression is to be inhibited, such as the target genes described above. The pharmaceutically acceptable carrier may be an aqueous solution, such as phosphate buffered saline, and may comprise a micellar structure, such as a liposome, capsid, capsoid, polymeric nanocapsule, or polymeric microcapsule. The pharmaceutical composition may be formulated to be administered by inhalation, infusion, injection, or orally, preferably by intravenous or intraperitoneal injection.

In another aspect, the invention relates to a method for treating a disease caused by the expression of a target gene in a mammal. The method comprises administering a pharmaceutical composition, as described above, comprising a double-stranded ribonucleic acid (dsRNA) and a pharmaceutically acceptable carrier. The dosage unit of dsRNA maybe in a range of 0.01 to 5.0 milligrams (mg), 0.1 to 200 micrograms, 0.1 to 100 micrograms, 1.0 to 50 micrograms, or 1.0 to 25 micrograms, preferably less than 25 micrograms per kilogram body weight of the mammal. The target gene may be any gene whose expression causes a disease in an organism, such as the target genes described elsewhere herein.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

FIG. 1a is a diagram of a first dsRNA.
FIG. 1b is a diagram of a second dsRNA.
FIG. 2 is a diagram of a target gene.
FIG. 8 fluorescence microscopic imaging of NIH/3T3 cells after transfection with pcDNA-YFP or after cotransfection with pcDNA-YFP and various dsRNAs.

FIG. 27 shows a comparison of a transmitted light- and fluorescence microscopic imaging of a transfection with 175 nM dsRNA (Sequence R1 in Table 4).

DETAILED DESCRIPTION OF THE INVENTION

Figure 3:
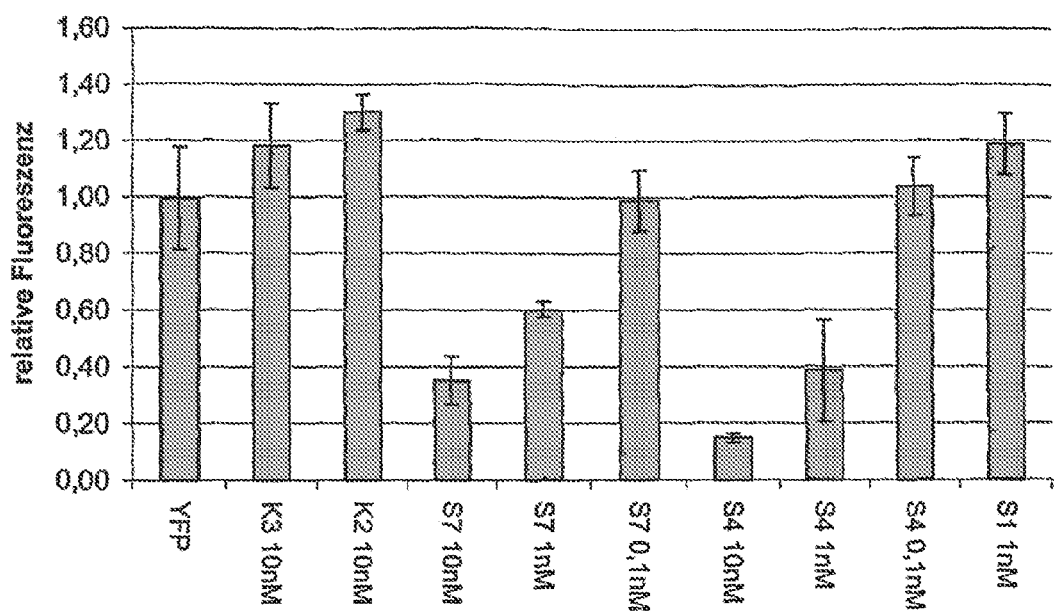
FIG. 3 relative YFP fluorescence after application of various dsRNAs in NIH/3T3 cells (first experiment).
Figure 4:
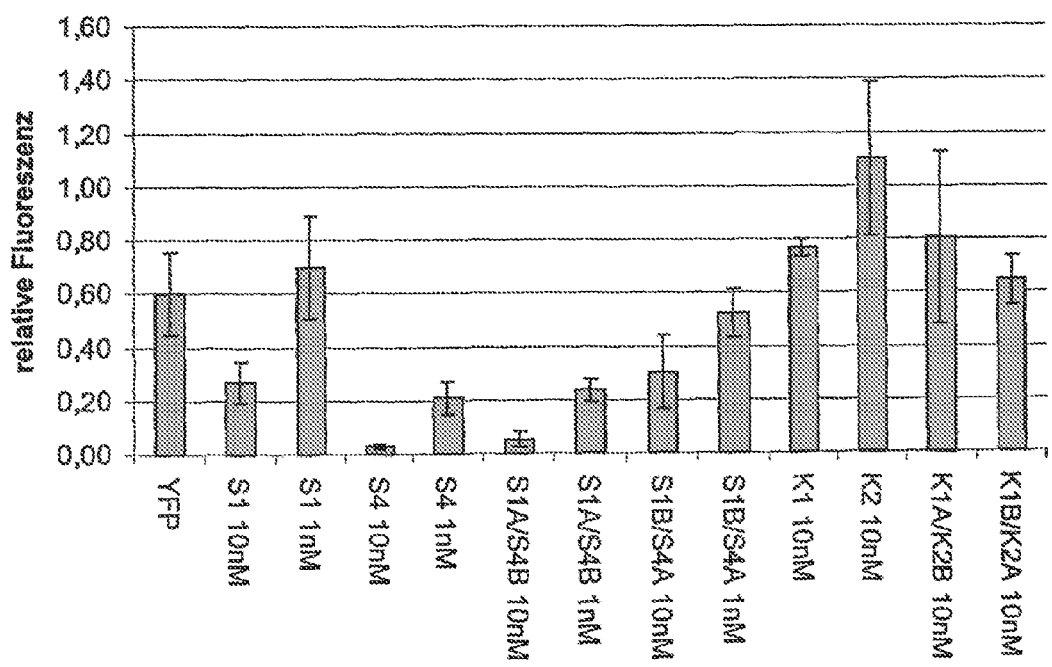
FIG. 4 relative YFP fluorescence after application of various dsRNAs in NIH/3T3 cells (second experiment).
Figure 5:
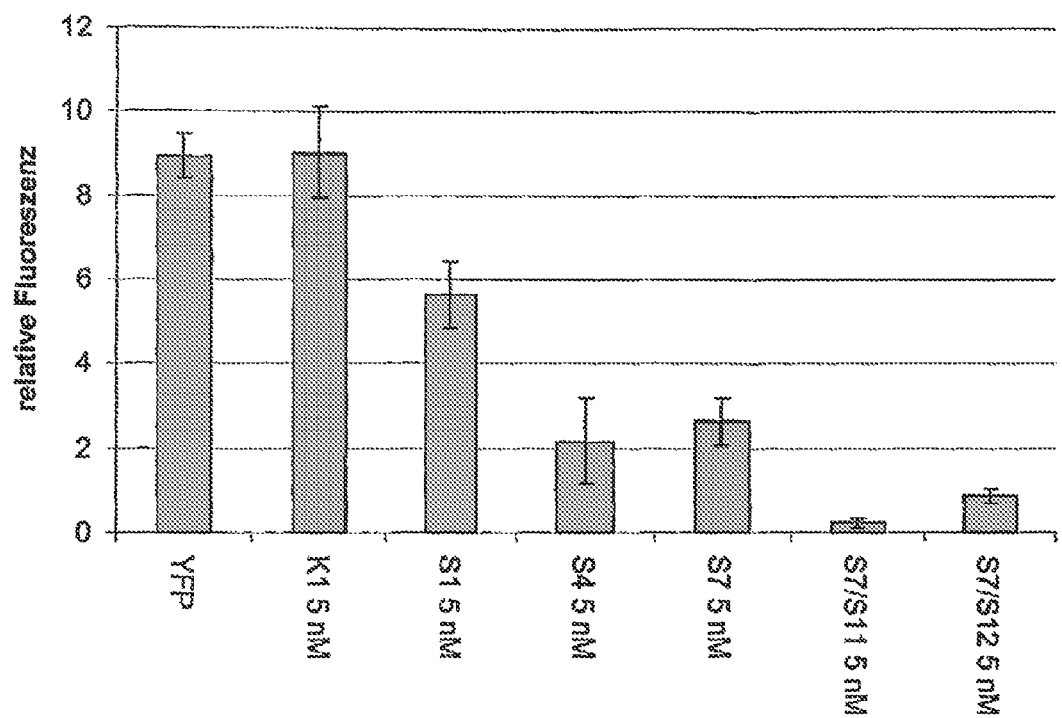
FIG. 5 relative YFP fluorescence after application of various dsRNAs in NIH/3T3 cells (third experiment).
Figure 6:
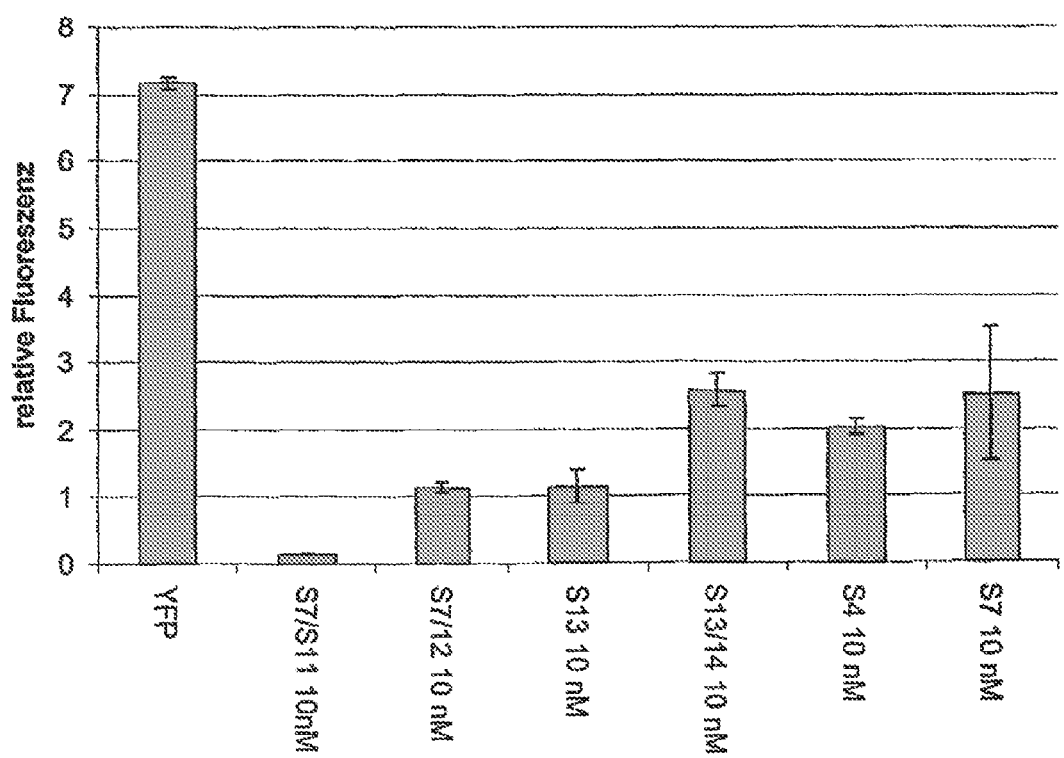
FIG. 6 relative YFP fluorescence after application of various dsRNAs in NIH/3T3 cells (fourth experiment).
Figure 7:
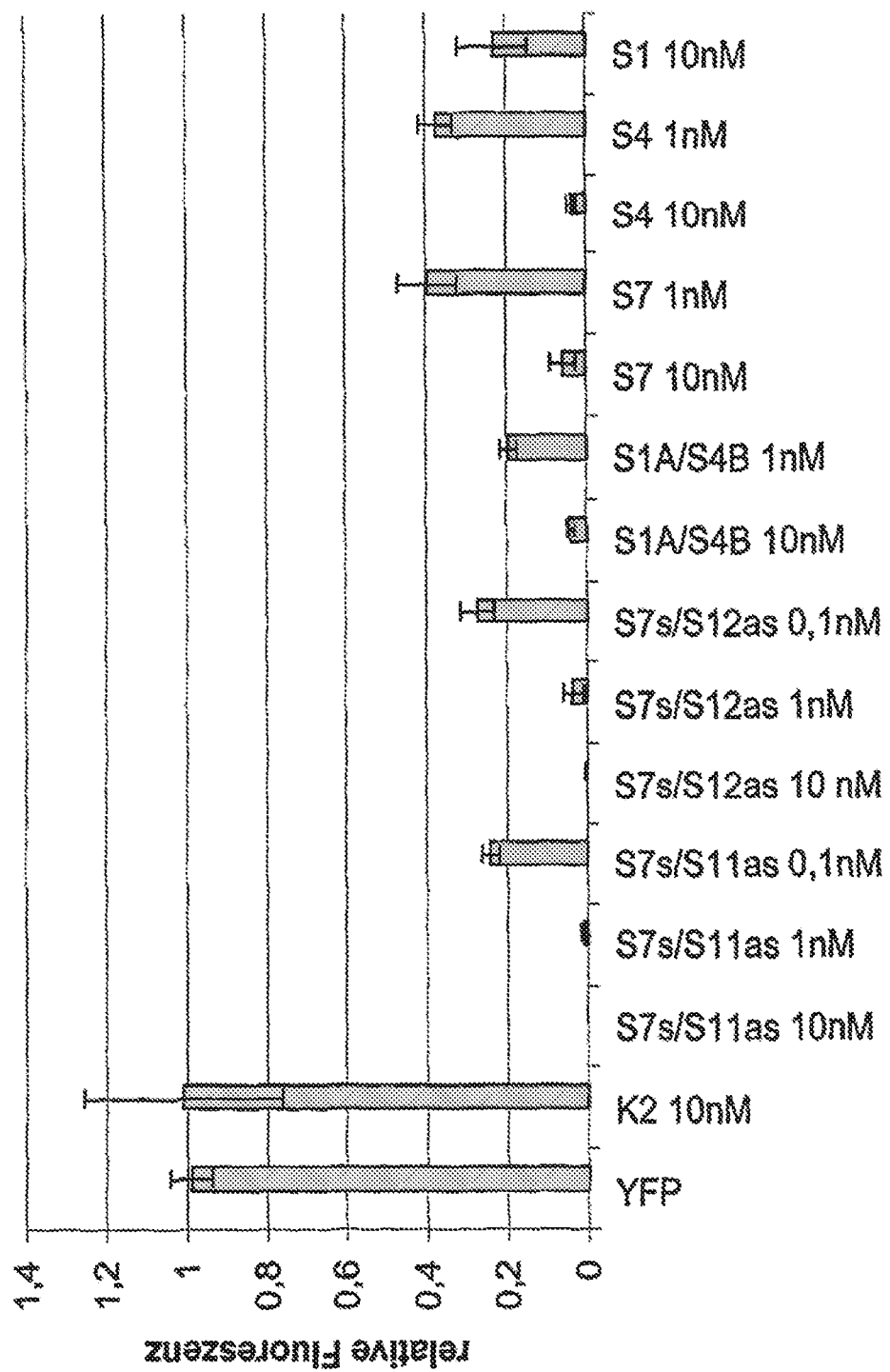
FIG. 7 relative YFP fluorescence after application of various dsRNAs in NIH/3T3 cells (fifth experiment).
Figure 9:
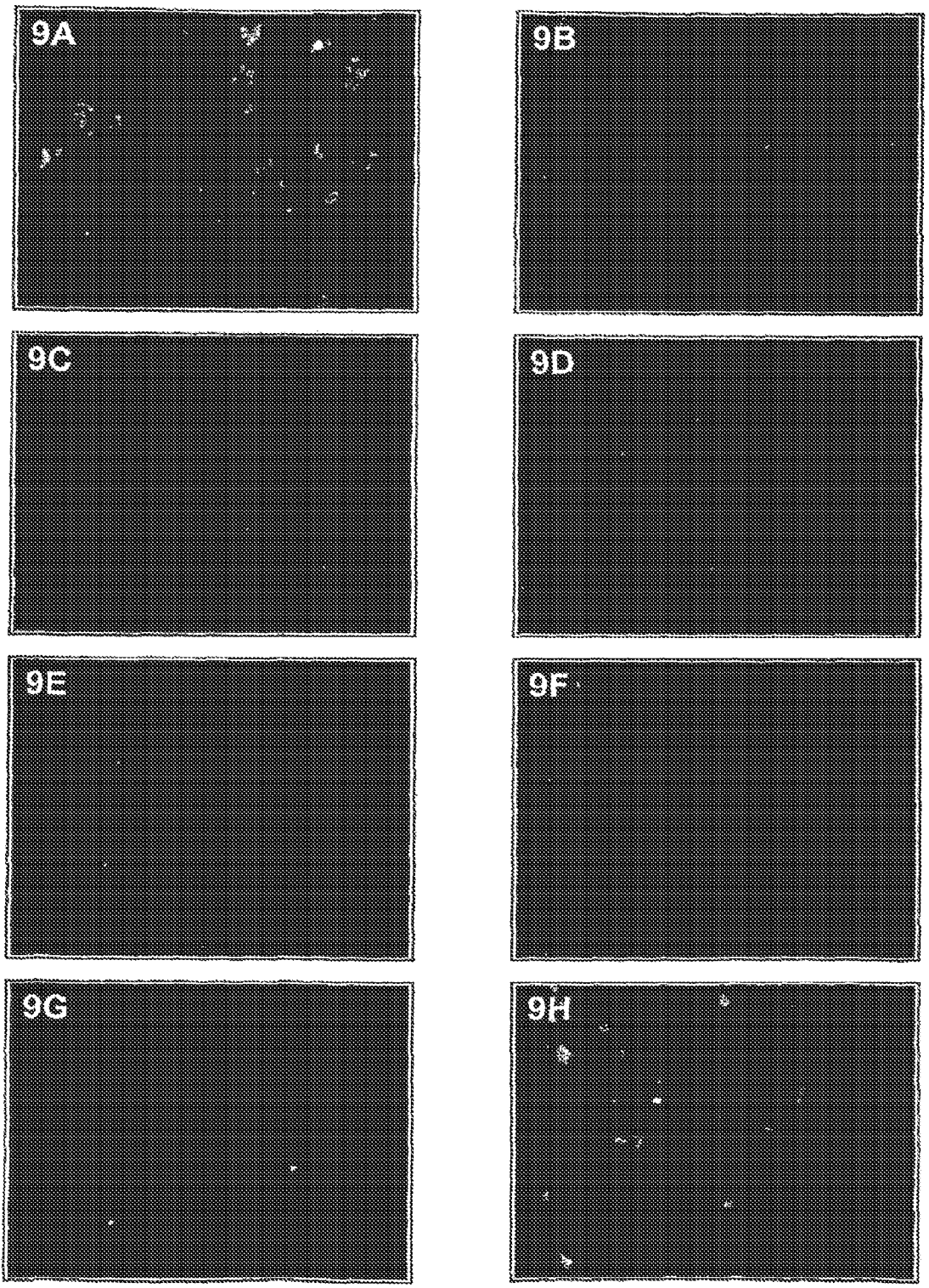
FIG. 9 fluorescence microscopic imaging of HeLa-S3 cells after transfection with pcDNA-YFP or after cotransfection with pcDNA-YFP and various dsRNAs.
Figure 10:
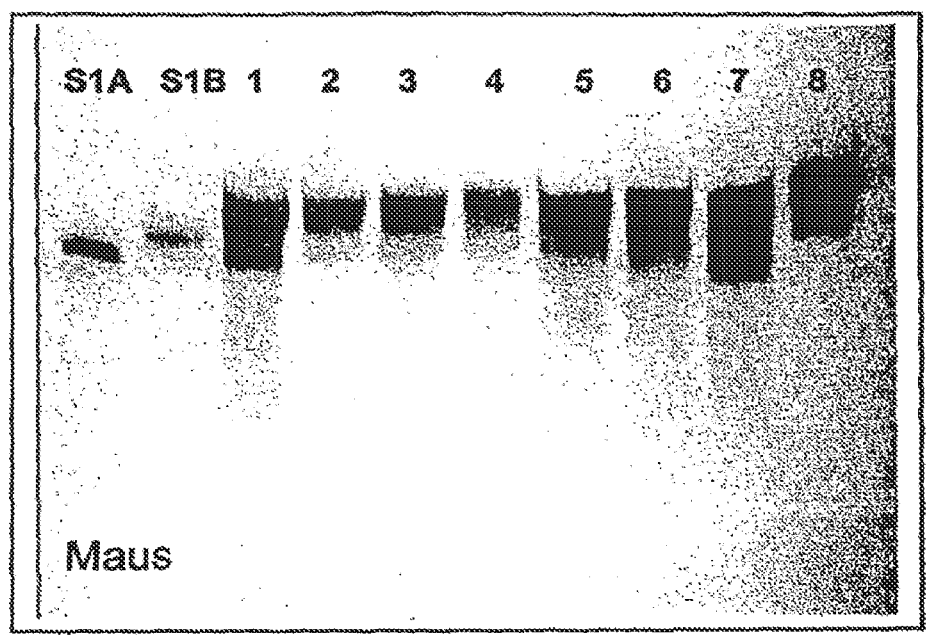
FIG. 10 is a gel electrophoretic separation of S 1 after incubation in mouse serum.
Figure 11:
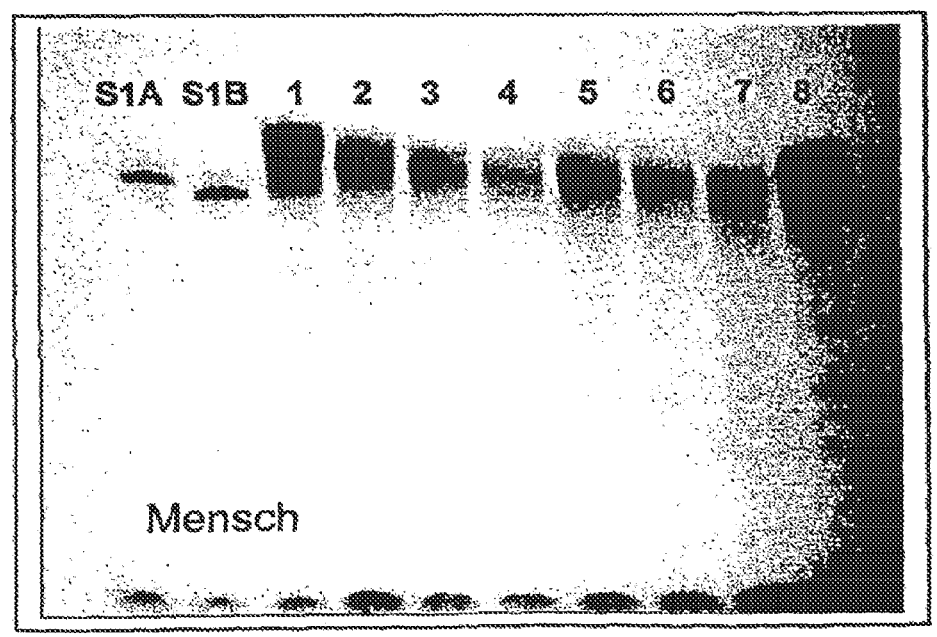
FIG. 11 is a gel electrophoretic separation of S 1 after incubation in human serum.
Figures 12, 13:
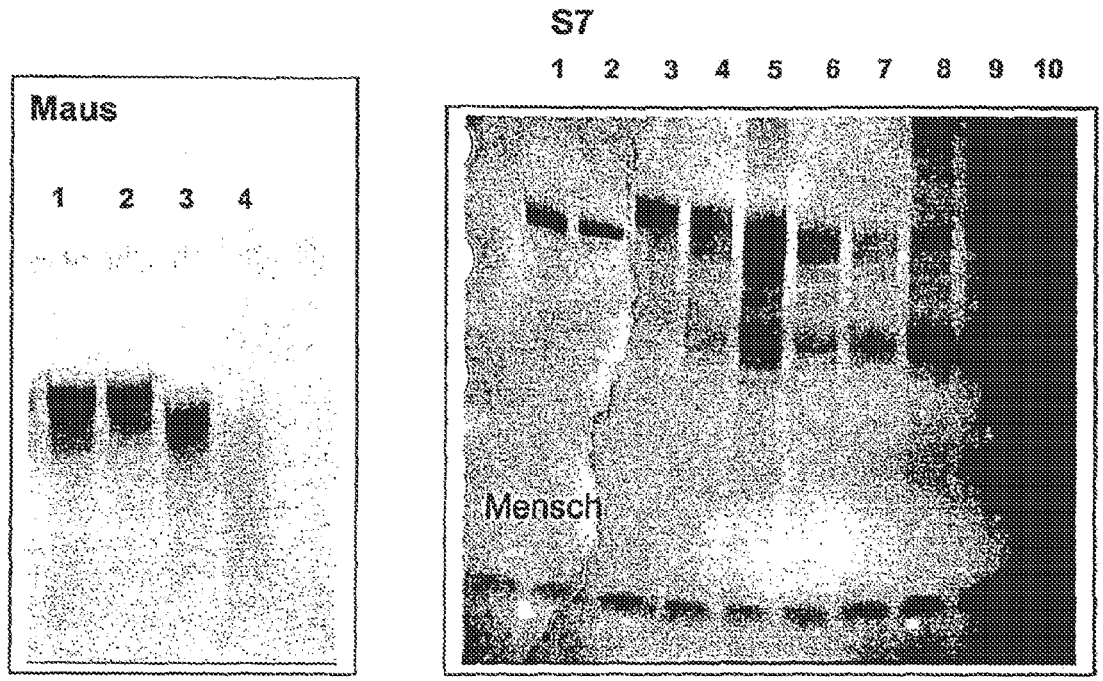
FIG. 12 is a gel electrophoretic separation of S7 after incubation in mouse serum.
FIG. 13 is a gel electrophoretic separation of S7 after incubation in human serum.
Figure 14:
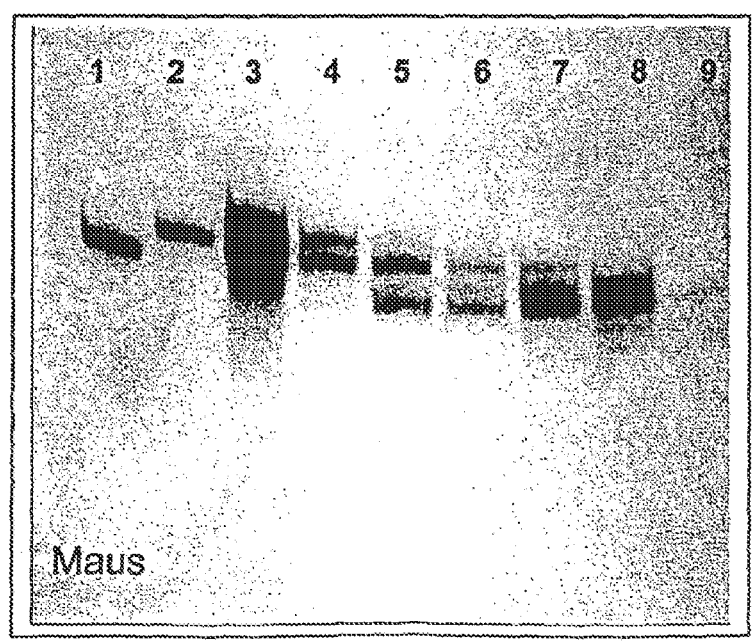
FIG. 14 is a gel electrophoretic separation of K3 after incubation in mouse serum.
Figure 15:
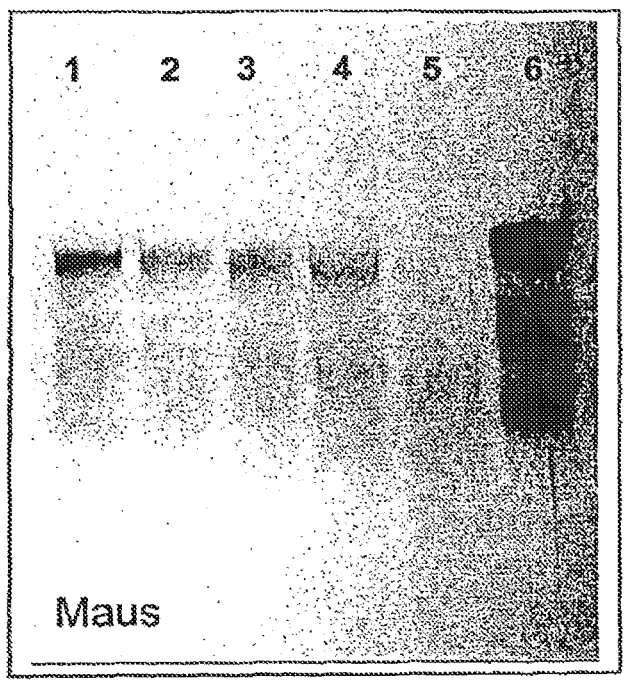
FIG. 15 is a gel electrophoretic separation of PKC112 after incubation in mouse serum.
Figure 16:
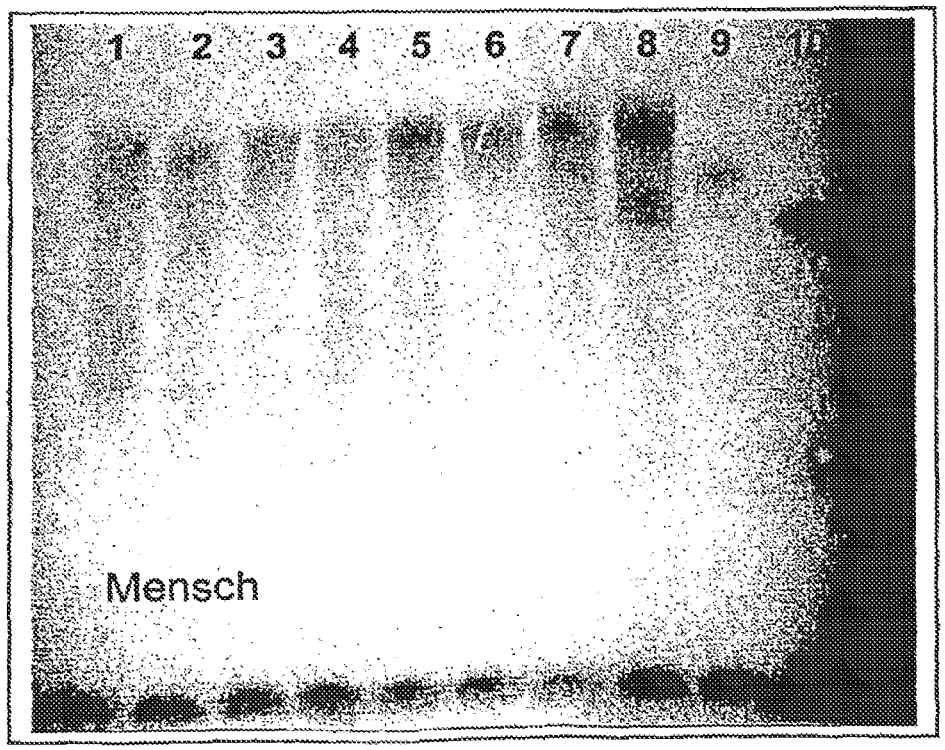
FIG. 16 is a gel electrophoretic separation of S1A/S4B after incubation in human serum.
Figure 17:
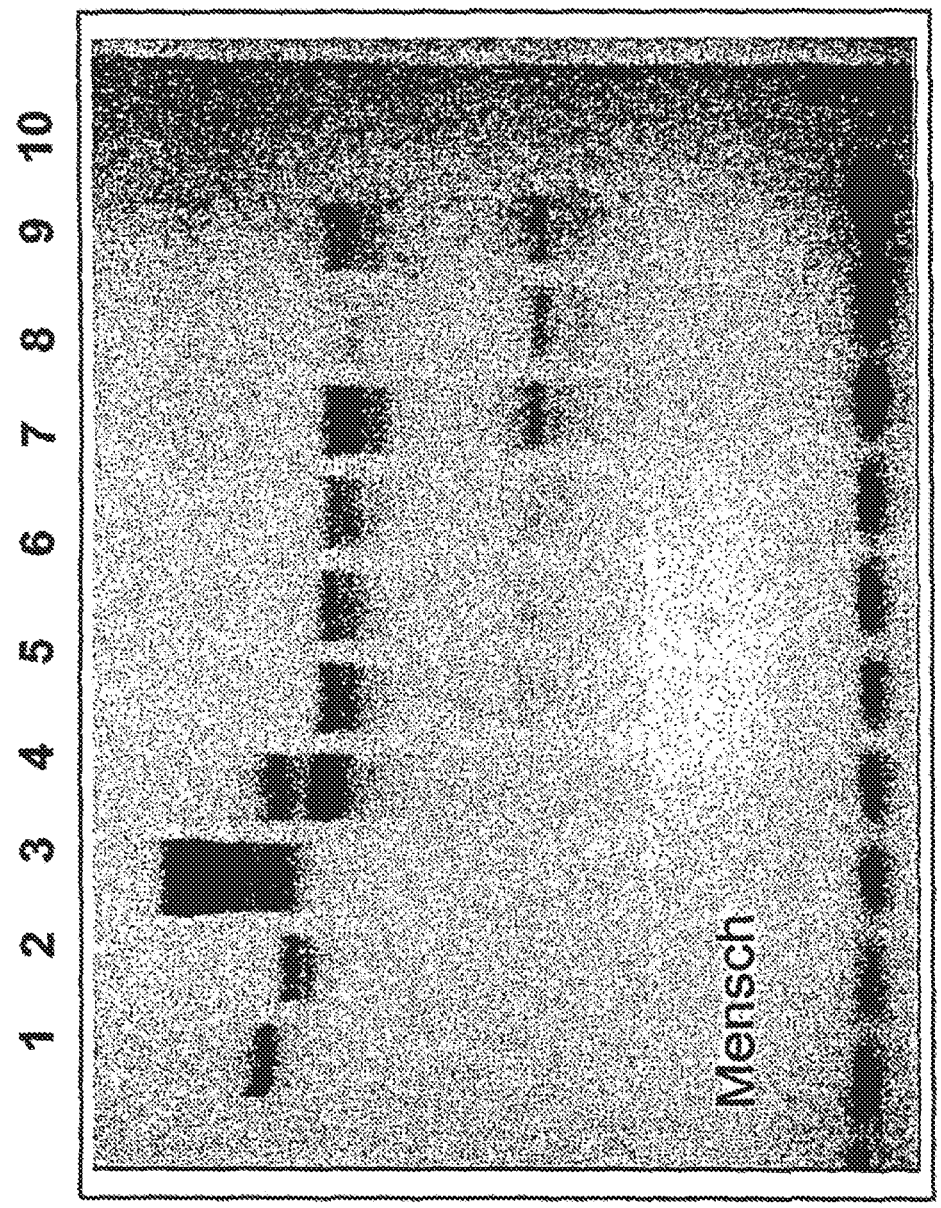
FIG. 17 is a gel electrophoretic separation of K2 after incubation in human serum.

The present invention discloses double-stranded ribonucleic acid (dsRNA), as well as compositions and methods for inhibiting the expression of a target gene in a cell using the dsRNA. The present invention also discloses compositions and methods for treating diseases in organisms caused by expression of a target gene using dsRNA. dsRNA directs the sequence-specific degradation of mRNA through a process known as RNA interference (RNAi). The process occurs in a wide variety of organisms, including mammals and other vertebrates. The dsRNA of the invention is no more than 49 nucleotides in length, and comprises an RNA strand (complementary RNA strand) having a region that is complementary to an RNA transcript of at least a portion of a target gene. The complementary RNA strand has a nucleotide overhang of 1 to 4 nucleotides at the 3'-end; the 5'-end is blunt. Using transgenic mice, the present inventors have demonstrated that very low dosages of these dsRNA can specifically and efficiently mediate RNAi, resulting in significant inhibition of expression of the target gene. The present invention encompasses these dsRNAs and compositions comprising dsRNA and their use for specifically inactivating gene function. The use of these dsRNAs enables the targeted degradation of mRNAs of genes that are implicated in a wide variety of disease processes, including cellular proliferative disorders, hematopoietic disorders, immune disorders, and certain infectious diseases. Thus, the methods and compositions of the present invention comprising these dsRNAs are useful for treating diseases and disorders caused by the expression or activity of a particular gene.

The following detailed description discloses how to make and use the dsRNA and compositions containing dsRNA to inhibit the expression of a target gene, as well as compositions and methods for treating diseases and disorders caused by the expression of the gene. The pharmaceutical compositions of the present invention comprise a dsRNA having a nucleotide sequence of no more than 49 nucleotides in length, preferably less than 25 nucleotides in length, and which is substantially identical to at least a part of the target gene, together with a pharmaceutically acceptable carrier. The dsRNA has a single-stranded nucleotide overhang of 1 to 4 nucleotides at the 3'-end of the complementary RNA strand; the 5'-end is blunt.

Accordingly, certain aspects of the present invention relate to pharmaceutical compositions comprising the dsRNA of the present invention together with a pharmaceutically acceptable carrier, methods of using the compositions to inhibit expression of a target gene, and methods of using the pharmaceutical compositions to treat diseases caused by the expression or activity of a particular gene.

I. Definitions

For convenience, the meaning of certain terms and phrases used in the specification, examples, and appended claims, are provided below.

As used herein, "target gene" refers to a section of a DNA strand of a double-stranded DNA that is complementary to a section of a DNA strand, including all transcribed regions, that serves as a matrix for transcription, as well as a section of an RNA strand of a (+) strand RNA virus. A target gene, usually the sense strand, is a gene whose expression is to be selectively inhibited or silenced through RNA interference. The term "target gene" specifically encompasses any cellular gene or gene fragment whose expression or activity is associated with a disease or disorder (e.g., an oncogene), as well as any foreign or exogenous gene or gene fragment whose expression or activity is associated with a disease, such as a gene from a pathogenic organism (e.g., a viral or pro-viral gene, viroid, or plasmodium).

Examples of genes which can be targeted for treatment include, without limitation, an oncogene (Hanahan, D. and R. A. Weinberg, Cell (2000) 100:57; and Yokota, J., Carcinogenesis (2000) 21(3):497-503); a cytokine gene (Rubinstein, M., et al., Cytokine Growth Factor Rev. (1998) 9(2): 175-81); a idiotype (Id) protein gene (Benezra, R., et al., Oncogene (2001) 20(58):8334-41; Norton, J. D., J Cell Sci. (2000) 113(22):3897-905); a prion gene (Prusiner, S. B., et al., Cell (1998) 93(3):337-48; Safar, J., and S. B. Prusiner, Prog. Brain Res. (1998) 117:421-34); a gene that expresses molecules that induce angiogenesis (Gould, V. E. and B. M. Wagner, Hum. Pathol. (2002) 33(11):1061-3); adhesion molecules (Chothia, C. and E. Y. Jones, Annu. Rev. Biochem. (1997) 66:823-62; Parise, L. V., et al., Semin. Cancer Biol. (2000) 10(6):407-14); cell surface receptors (Deller, M. C., and Y E. Jones, Curr. Opin. Struct. Biol. (2000) 10(2):213-9); genes of proteins that are involved in metastasizing and/or invasive processes (Boyd, D., Cancer Metastasis Rev. (1996) 15(1):77-89; Yokota, J., Carcinogenesis (2000) 21(3):497-503); genes of proteases as well as of molecules that regulate apoptosis and the cell cycle (Matrisian, L. M., Curr. Biol. (1999) 9(20):R776-8; Krepela, E., Neoplasma (2001) 48(5):332-49; Basbaum and Werb, Curr. Opin. Cell Biol. (1996) 8:731-738; Birkedal-Hansen, et al., Crit. Rev. Oral Biol. Med. (1993) 4:197-250; Mignatti and Rifkin, Physiol. Rev. (1993) 73:161-195; Stetler-Stevenson, et al., Annu. Rev. Cell Biol. (1993) 9:541-573; Brinkerhoff, E., and L. M. Matrisan, Nature Reviews (2002) 3:207-214; Strasser, A., et al., Annu. Rev. Biochem. (2000) 69:217-45; Chao, D. T. and S. J. Korsmeyer, Annu. Rev. Immunol. (1998) 16:395-419; Mullauer, L., et al., Mutat. Res. (2001) 488(3):211-31; Fotedar, R., et al., Prog. Cell Cycle Res. (1996) 2:147-63; Reed, J. C., Am. J Pathol. (2000) 157(5):1415-30; D'Ari, R., Bioassays (2001) 23(7):563-5); genes that express the EGF receptor; Mendelsohn, J. and J. Baselga, Oncogene (2000) 19(56):6550-65; Normanno, N., et al., Front. Biosci. (2001) 6:D685-707); and the multi-drug resistance 1 gene, MDR1 gene (Childs, S., and V. Ling, Imp. Adv. Oncol. (1994) 21-36).

The term "complementary RNA strand" (also referred to herein as the "antisense strand") refers to the strand of a dsRNA which is complementary to an mRNA transcript that is formed during expression of the target gene, or its processing products. As used herein, the term "complementary nucleotide sequence" refers to the region on the complementary RNA strand that is complementary to an mRNA transcript of a portion of the target gene. "dsRNA" refers to a ribonucleic acid molecule having a duplex structure comprising two complementary and anti-parallel nucleic acid strands. Not all nucleotides of a dsRNA must exhibit Watson-Crick base pairs; the two RNA strands may be substantially complementary (i.e., having no more than one or two nucleotide mismatches). The maximum number of base pairs is the number of nucleotides in the shortest strand of the dsRNA. The RNA strands may have the same or a different number of nucleotides. The dsRNA is no more than 49, preferably less than 25, and most preferably between 19 and 23, nucleotides in length. dsRNAs of this length are particularly efficient in inhibiting the expression of the target gene. "Introducing into" means uptake or absorption in the cell, as is understood by those skilled in the art. Absorption or uptake of dsRNA can occur through cellular processes, or by auxiliary agents or devices. For example, for in vivo delivery, dsRNA can be injected into a tissue site or administered systemically. In vitro delivery includes methods known in the art such as electroporation and lipofection.

As used herein, a "nucleotide overhang" refers to the unpaired nucleotide or nucleotides that protrude from the duplex structure when a 3'-end of one RNA strand extends beyond the 5'-end of the other strand, or vice versa.

As used herein and as known in the art, the term "identity" is the relationship between two or more polynucleotide sequences, as determined by comparing the sequences. Identity also means the degree of sequence relatedness between polynucleotide sequences, as determined by the match between strings of such sequences. Identity can be readily calculated (see, e.g., *Computation Molecular Biology*, Lesk, A. M., eds., Oxford University Press, New York (1998), and *Biocomputing: Informatics and Genome Projects*, Smith, D. W., ed., Academic Press, New York (1993), both of which are incorporated by reference herein). While there exist a number of methods to measure identity between two polynucleotide sequences, the term is well known to skilled artisans (see, e.g., *Sequence Analysis in Molecular Biology*, von Heinje, G., Academic Press (1987); and *Sequence Analysis Primer*, Gribskov., M. and Devereux, J., eds., M. Stockton Press, New York (1991)). Methods commonly employed to determine identity between sequences include, for example, those disclosed in Carillo, H., and Lipman, D., *SIAM J Applied Math*. (1988) 48:1073. "Substantially identical," as used herein, means there is a very high degree of homology (preferably 100% sequence identity) between the sense strand of the dsRNA and the corresponding part of the target gene. However, dsRNA having greater than 90%, or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base-pair random mismatches between the RNA and the target gene.

As used herein, the term "treatment" refers to the application or administration of a therapeutic agent to a patient, or application or administration of a therapeutic agent to an isolated tissue or cell line from a patient, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, the terms "pathogen" and "pathogenic organism" refer to an organism capable of producing disease, including, without limitation, a virus, viroid, or plasmodium. As used herein, the term "pathogen" includes organisms capable of causing disease in animals and/or plants.

As used herein, a "transformed cell" is a cell into which a dsRNA molecule has been introduced by means of recombinant DNA techniques.

II. Double-Stranded Ribonucleic Acid (dsRNA)

In one embodiment, the invention relates to a double-stranded ribonucleic acid (dsRNA) having a nucleotide sequence which is substantially identical to at least a portion of a target gene. The dsRNA comprises two RNA strands that are sufficiently complementary to hybridize to form the duplex structure. One strand of the dsRNA comprises the nucleotide sequence that is substantially identical to a portion of the target gene (the "sense" strand), and the other strand (the "complementary" or "antisense" strand) comprises a sequence that is complementary to an RNA transcript of the target (DNA) gene or a gene of a (+) strand RNA virus. The dsRNA has no more than 49 nucleotides, preferably less than 25 nucleotides, and most preferably 23 nucleotides in length. The dsRNA can be synthesized by standard methods known in the art, e.g., by use of an automated DNA synthesizer, such as are commercially available from Biosearch, Applied Biosystems, Inc. In specific embodiments, the dsRNA can comprise the sequence set forth in SEQ ID NO:141-173, or a complement or equivalent thereof.

At least one end of the dsRNA has a single-stranded nucleotide overhang of 1 to 4, preferably 1 or 2 nucleotides. The single-stranded overhang is located at the 3'-terminal end of the complementary (antisense) RNA strand, and the 5'-end of the complementary RNA strand is blunt (i.e., no overhang). Such dsRNAs have improved stability and inhibitory activity, thus allowing administration at low dosages, i.e., less than 5 mg/kg body weight of the recipient per day. In another embodiment, one or more of the nucleotides in the overhang is replaced with a nucleoside thiophosphate. dsRNAs having a nucleotide overhang at the 3'-end of the antisense have unexpectedly superior inhibitory properties than their blunt-ended counterparts. Moreover, the present inventors have discovered that the presence of a nucleotide overhang at the 3'-overhang of the antisense strand strengthens the interference activity of the dsRNA, without affecting its overall stability. Such dsRNAs have proven particularly stable and effective in vivo, as well as in a variety of cells, cell culture mediums, blood, and serum.

In another embodiment, the dsRNA is chemically modified for improved stability, i.e., enhanced resistance to degradation and/or strand dissociation. In this embodiment, the integrity of the duplex structure is strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. In one embodiment, the linker is a hexa-ethylene glycol linker. In this case, the dsRNAs are produced by solid phase synthesis and the hexa-ethylene glycol linker is incorporated according to standard methods (e.g., Williams, D. J., and K. B. Hall, Biochem. (1996) 35:14665-14670). In a preferred embodiment, the 5'-end of the complementary (antisense) RNA strand and the 3'-end of the second (sense) RNA strand are chemically linked via a hexa-ethylene glycol linker.

In yet another embodiment, the target gene is an oncogene; a cytokinin gene; an idiotype protein gene (Id protein gene); a prion gene; a gene that expresses a protein that induces angiogenesis, an adhesion molecule; a cell surface receptor; a gene of a protein involved in a metastasizing and/or invasive process; a gene of a proteinase; a gene of a protein that regulates apoptosis and the cell cycle; a gene that expresses the EGF receptor; or a MDR1 gene, all of which are described elsewhere herein.

In one embodiment, the target gene is the multi-drug resistance 1 gene ("MDR1"). "Multi-drug resistance" (MDR) broadly refers to a pattern of resistance to a variety of chemotherapeutic drugs with unrelated chemical structures and different mechanisms of action. Although the etiology of MDR is multifactorial, the overexpression of P-glycoprotein (Pgp), a membrane protein that mediates the transport of MDR drugs, remains the most common alteration underlying MDR in laboratory models (Childs, S., *Imp. Adv. Oncol.* (1994) 21-36). Moreover, expression of Pgp has been linked to the development of MDR in human cancer, particularly in the leukemias, lymphomas, multiple myeloma, neuroblastoma, and soft tissue sarcoma (Fan., D., et al., *Reversal of Multidrug Resistance in Cancer*, ed. Kellen, J. A. (CRC, Boca Raton, Fla.), pp. 93-125). Recent studies showed that tumor cells expressing MDR-associated protein (MRP) (Cole, S. P. C., et al., *Science* (1992) 258: 1650-1654) and lung resistance protein (LRP) (Scheffer, G. L., et al., *Nat. Med.* (1995)1:578-582) and mutation of DNA topoisomerase II (Beck, W. T., *J Natl. Cancer Inst.* (1989) 81:1683-1685) also may render MDR.

In yet another embodiment, the invention relates to a method for treating viral diseases, including but not limited to hepatitis C, hepatitis B, herpes simplex virus (HSY), HIV-AIDS, poliovirus, and smallpox virus. dsRNAs of the invention are prepared as described herein to target expressed sequences of a virus, thus ameliorating viral activity and replication. The molecules can be used in the treatment and/or diagnosis of viral infected tissue, both animal and plant. Also, such molecules can be used in the treatment of virus-associated carcinoma, such as hepatocellular cancer.

III. Pharmaceutical Compositions Comprising dsRNA

In one embodiment, the invention relates to a pharmaceutical composition comprising a dsRNA, as described in the preceding section, and a pharmaceutically acceptable carrier, as described below. The pharmaceutical composition comprising the dsRNA is useful for treating a disease or disorder associated with the expression or activity of a target gene.

In another embodiment, the invention relates to a pharmaceutical composition comprising at least two dsRNAs, both designed to target the same gene, and a pharmaceutically acceptable carrier. Because of the duplicative targeting of mRNA by a plurality of dsRNAs, pharmaceutical compositions comprising multiple dsRNAs provide improved efficiency of inhibition as compared to compositions comprising a single dsRNA. In this embodiment, the individual dsRNAs are prepared as described in the preceding section, which is incorporated by reference herein. One dsRNA (referred to herein as "dsRNA I") has a nucleotide sequence ("complementary region I") which is substantially identical to at least a portion of the target gene (referred to herein as "region A" of the target gene). Additional dsRNAs are prepared, each of which has a nucleotide sequence that is substantially identical to a different region of the target gene. For example, a second dsRNA ("dsRNA II") may have a nucleotide sequence ("complementary region II") that is substantially identical to a "region B" of the target gene. Region A and region B, which reflect distinct regions of the same target gene, may overlap each other, be adjacent to one another, or be physically separated within the target gene. dsRNA I and dsRNA II may be combined in the same pharmaceutical composition, or formulated separately. If formulated individually, the compositions containing the separate dsRNAs may comprise the same or different carriers, and may be administered using the same or different routes of administration. Moreover, the pharmaceutical compositions comprising the individual dsRNAs may be administered substantially simultaneously, sequentially, or at preset intervals throughout the day or treatment period. Although the foregoing description relates to two dsRNAs (dsRNA I and dsRNA II) which target two regions (region A and region B) of the target gene, the present invention encompasses any number of dsRNAs, each of which targets a distinct region of the target gene.

The pharmaceutical compositions of the present invention are administered in dosages sufficient to inhibit expression of the target gene. The present inventors have found that, because of their improved efficiency, compositions comprising the dsRNA of the invention can be administered at surprisingly low dosages. A maximum dosage of 5 mg dsRNA per kilogram body weight per day is sufficient to inhibit or completely suppress expression of the target gene.

In general, a suitable dose of dsRNA will be in the range of 0.01 to 5.0 milligrams per kilogram body weight of the recipient per day, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. The pharmaceutical composition may be administered once daily, or the dsRNA may be administered as two, three, four, five, six or more sub-doses at appropriate intervals throughout the day. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases. For example, mouse models are available for hematopoietic malignancies such as leukemias, lymphomas and acute myelogenous leukemia. The MMHCC (Mouse models of Human Cancer Consortium) web page (emice.nci.nih.gov), sponsored by the National Cancer Institute, provides disease-site-specific compendium of known cancer models, and has links to the searchable Cancer Models Database (cancermodels.nci.nih.gov), as well as the NCI-MMHCC mouse repository. Examples of the genetic tools that are currently available for the modeling of leukemia and lymphomas in mice, and which are useful in practicing the present invention, are described in the following references: Maru, Y, *Int. J Hematol*. (2001) 73:308-322; Pandolfi, P. P., *Oncogene* (2001) 20:5726-5735; Pollock, J. L., et al., *Curr. Opin. Hematol*. (2001) 8:206-211; Rego, E. M., et al., *Semin. in Hemat*. (2001) 38:4-70; Shannon, K. M., et al. (2001) Modeling myeloid leukemia tumors suppressor gene inactivation in the mouse, *Semin. Cancer Biol*. 11, 191-200; Van Etten, R. A., (2001) *Curr. Opin. Hematol*. 8, 224-230; Wong, S., et al. (2001) *Oncogene* 20, 5644-5659; Phillips J A., *Cancer Res*. (2000) 52(2):437-43; Harris, A W., et al, *J. Exp. Med*. (1988) 167(2):353-71; Zeng X X et al., *Blood*. (1988) 92(10):3529-36; Eriksson, B., et al., *Exp. Hematol*. (1999) 27(4):682-8; and Kovalchuk, A., et al., *J. Exp. Med*. (2000) 192(8):1183-90. Mouse repositories can also be found at: The Jackson Laboratory, Charles River Laboratories, Taconic, Harlan, Mutant Mouse Regional Resource Centers (MMRRC) National Network and at the European Mouse Mutant Archive. Such models may be used for in vivo testing of dsRNA, as well as for determining a therapeutically effective dose.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

For oral administration, the dsRNAs useful in the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of dsRNA in the cells that express the target gene. Such substances include, for example, micellar structures, such as liposomes or capsids, as described below. Surprisingly, the present inventors have discovered that compositions containing only naked dsRNA and a physiologically acceptable solvent are taken up by cells, where the dsRNA effectively inhibits expression of the target gene. Although microinjection, lipofection, viruses, viroids, capsids, capsoids, or other auxiliary agents are required to introduce dsRNA into cell cultures, surprisingly these methods and agents are not necessary for uptake of dsRNA in vivo. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions useful according to the invention also include encapsulated formulations to protect the dsRNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811;

PCT publication WO 91/06309; and European patent publication EP-A-43075, which are incorporated by reference herein.

In one embodiment, the encapsulated formulation comprises a viral coat protein. In this embodiment, the dsRNA may be bound to, associated with, or enclosed by at least one viral coat protein. The viral coat protein may be derived from or associated with a virus, such as a polyoma virus, or it may be partially or entirely artificial. For example, the coat protein may be a Virus Protein 1 and/or Virus Protein 2 of the polyoma virus, or a derivative thereof.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs useful according to the invention can be administered in combination with other known agents effective in treatment of diseases. In any event, the administering physician can adjust the amount and timing of dsRNA administration on the basis of results observed using standard measures of efficacy known in the art or described herein.

For oral administration, the dsRNAs useful in the invention will generally be provided in the form of tablets or capsules, as a powder or granules, or as an aqueous solution or suspension.

IV. Methods for Treating Diseases Caused by Expression of a Target Gene

In one embodiment, the invention relates to a method for treating a subject having a disease or at risk of developing a disease caused by the expression of a target gene. In this embodiment, the dsRNA can act as novel therapeutic agents for controlling one or more of cellular proliferative and/or differentiative disorders, disorders associated with bone metabolism, immune disorders, hematopoietic disorders, cardiovascular disorders, liver disorders, viral diseases, or metabolic disorders. The method comprises administering a pharmaceutical composition of the invention to the patient (e.g., human), such that expression of the target gene is silenced. Because of their high specificity, the dsRNAs of the present invention specifically target mRNAs of target genes of diseased cells and tissues, as described below, and at surprisingly low dosages.

In the prevention of disease, the target gene may be one which is required for initiation or maintenance of the disease, or which has been identified as being associated with a higher risk of contracting the disease. In the treatment of disease, the dsRNA can be brought into contact with the cells or tissue exhibiting the disease. For example, dsRNA substantially identical to all or part of a mutated gene associated with cancer, or one expressed at high levels in tumor cells, e.g. aurora kinase, may be brought into contact with or introduced into a cancerous cell or tumor gene.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin. As used herein, the terms "cancer," "hyperproliferative," and "neoplastic" refer to cells having the capacity for autonomous growth, i.e., an abnormal state of condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplatic cells of hematopoietic origin, e.g., arising from myeloid, lymphoid or erythroid lineages, or precursor cells thereof.

The pharmaceutical compositions of the present invention can also be used to treat a variety of immune disorders, in particular those associated with overexpression of a gene or expression of a mutant gene. Examples of hematopoietic disorders or diseases include, without limitation, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, automimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy.

Examples of genes which can be targeted for treatment include, without limitation, an oncogene; a cytokine gene; a idiotype (Id) protein; a prion gene; a gene that expresses molecules that induce angiogenesis; an adhesion molecule; a cell surface receptor; a gene of a protein involved in a metastasizing and/or invasive process; a gene of a proteases as or a protein that regulates apoptosis and the cell cycle; a gene that expresses the EGF receptor; and the multi-drug resistance 1 gene, MDR1 gene, all of which are described elsewhere herein.

In one embodiment, a pharmaceutical compositions comprising dsRNA is used to inhibit the expression of the multi-drug resistance 1 gene ("MDRI"). "Multi-drug resistance" (MDR) broadly refers to a pattern of resistance to a variety of chemotherapeutic drugs with unrelated chemical structures and different mechanisms of action. Although the etiology of MDR is multifactorial, the overexpression of P-glycoprotein (Pgp), a membrane protein that mediates the transport of MDR drugs, remains the most common alteration underlying MDR in laboratory models (Childs, S., *Imp. Adv. Oneal.* (1994) 21-36). Moreover, expression of Pgp has been linked to the development of MDR in human cancer, particularly in the leukemias, lymphomas, multiple myeloma, neuroblastoma, and soft tissue sarcoma (Fan., D., et al., *Reversal of Multidrug Resistance in Cancer*, ed. Kellen, J. A. (CRC, Boca Raton, Fla.), pp. 93-125). Recent studies showed that tumor cells expressing MDR-associated protein (MRP) (Cole, S. P. C., et al., *Science* (1992) 258: 1650-1654) and lung resistance protein (LRP) (Scheffer, G. L., et al., *Nat. Med.* (1995)1:578-582) and mutation of DNA topoisomerase II (Beck, W. T., *J Natl. Cancer Inst.* (1989) 81:1683-1685) also may render MDR.

In another embodiment, the invention relates to a method for treating viral diseases, including but not limited to human papilloma virus, hepatitis C, hepatitis B, herpes simplex virus (HSV), HIV-AIDS, poliovirus, and smallpox virus. dsRNAs of the invention are prepared as described herein to target expressed sequences of a virus, thus ameliorating viral activity and replication. The molecules can be used in the treatment and/or diagnosis of viral infected tissue, both animal and plant. Also, such molecules can be used in the treatment of virus-associated carcinoma, such as hepatocellular cancer.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

V. Methods for Inhibiting Expression of a Target Gene

In yet another aspect, the invention relates to a method for inhibiting the expression of a target gene in an organism. The method comprises administering a composition of the invention to the organism such that expression of the target gene is silenced. The organism may be an animal or a plant. Because of their high specificity, the dsRNAs of the present invention specifically target RNAs (primary or processed) of target genes, and at surprisingly low dosages. Compositions and methods for inhibiting the expression of a target gene using dsRNAs can be performed as described elsewhere herein.

In one embodiment, the invention comprises administering a composition comprising a dsRNA, wherein the dsRNA comprises a nucleotide sequence which is complementary to at least a part of an RNA transcript of the target gene of the organism to be treated. When the organism to be treated is a mammal, such as a human, the composition may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the compositions are administered by intravenous or intraparenteral infusion or injection.

The methods for inhibition the expression of a target gene can be applied to any gene one wishes to silence, thereby specifically inhibiting its expression. Examples of human genes which can be targeted for silencing include, without limitation, an oncogene; cytokinin gene; idiotype protein gene (Id protein gene); prion gene; gene that expresses molecules that induce angiogenesis, adhesion molecules, and cell surface receptors; genes of proteins that are involved in metastasizing and/or invasive processes; genes of proteases as well as of molecules that regulate apoptosis and the cell cycle; genes that express the EGF receptor; the multi-drug resistance 1 gene (MDRI gene); a gene or component of a virus, particularly a human pathogenic virus, that is expressed in pathogenic organisms, preferably in plasmodia.

The methods for inhibition the expression of a target gene can also be applied to any plant gene one wishes to silence, thereby specifically inhibiting its expression.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

RNA Interference in a Mouse Mode

In this Example, double stranded siRNAs are used to inhibit GFP gene expression in transgenic mice.

Synthesis and Preparation of dsRNAs

Oligoribonucleotides are synthesized with an RNA synthesizer (Expedite 8909, Applied Biosystems, Weiterstadt, Germany) and purified by High Pressure Liquid Chromatography (HPLC) using NucleoPac PA-100 columns, 9×250 mm (Dionex Corp.; low salt buffer: 20 mM Tris, 10 nM NaClO$_4$, pH 6.8, 10% acetonitrile; the high-salt buffer was: 20 mM Tris, 400 mM NaClO4, pH 6.S, 10% acetonitrile. flow rate: 3 ml/min). Formation of double stranded siRNAs is then achieved by heating a stoichiometric mixture of the individual complementary strands (10 M) in 10 mM sodium phosphate buffer, pH 6.8, 100 mM NaCl, to 80-90° C., with subsequent slow cooling to room temperature over 6 hours, In addition, dsRNA molecules with linkers may be produced by solid phase synthesis and addition of hexaethylene glycol as a non-nucleotide linker (D. Jeremy Williams, Kathleen B. Hall, Biochemistry, 1996, 35, 14665-14670). A Hexaethylene glycol linker phosphoramidite (Chruachem Ltd, Todd Campus, West of Scotland Science Park, Acre Road, Glasgow, G20 OUA, Scotland, UK) is coupled to the support bound oligoribonucleotide employing the same synthetic cycle as for standard nucleoside phosphoramidites (Proligo Biochemie GmbH, Georg-Hyken-Str.14, Hamburg, Germany) but with prolonged coupling times. Incorporation of linker phosphoramidite is comparable to the incorporation of nucleoside phosphoramidites.

| Name | SEQ ID NO. | DsRNA sequence | Nucleotide number (overhang at the 3'-end of the S1 double-stranded region-overhang at the 3'-end of S2) |
|---|---|---|---|
| S1 | SEQ ID NO: 148 (S2)<br>SEQ ID NO: 149 (S1) | 5'-CCACAUGAAGCAGCACGACUUC-3'<br>3'-GGUGUACUUCGUCGUGCUGAAG-5' | 0-22-0 |
| S7 | SEQ ID NO: 150 (S2)<br>SEQ ID NO: 151 (S1) | 5'-CCACAUGAAGCAGCACGACUU-3'<br>3'-CUGGUGUACUUCGUCGUGCUG-5' | 2-19-2 |
| K1 | SEQ ID NO: 153 (S2)<br>SEQ ID NO: 154 (S1) | 5'-ACAGGAUGAGGAUCGUUUCGCA-3'<br>3'-UGUCCUACUCCUAGCAAAGCGU-5' | 0-22-0 |
| K3 | SEQ ID NO: 155 (S2)<br>SEQ ID NO: 156 (S1) | 5'-GAUGAGGAUCGUUUCGCAUGA-3'<br>3'-UCCUACUCCUAGCAAAGCGUA-5' | 2-19-2 |
| K4 | SEQ ID NO: 155 (S2)<br>SEQ ID NO: 156 (S1) | 5'-GAUGAGGAUCGUUUCGCAUGA-3'<br>3'-UCCUACUCCUAGCAAAGCGUACU-5' | 2-21-0 |
| S7/S11 | SEQ ID NO: 150 (S2)<br>SEQ ID NO: 159 (S1) | 5'-CCACAUGAAGCAGCACGACUU-3'<br>3'-CUGGUGUACUUCGUCGUGCUGAA-5' | 2-21-0 |

RNAi Administration

DsRNA are administered systemically either orally, by means of inhalation, infusion, or injection, preferably by intravenous or intraperitoneal infusion or injection in combination with pharmaceutically acceptable carriers. Examples of suitable carriers are found in standard pharmaceutical texts, e.g. "Remington's Pharmaceutical Sciences", 16th edition, Mack Publishing Company, Easton, Pa., 1980. A preparation that is suitable for inhalation, infusion, or injection preferably consists of dsRNA and a physiologically tolerated solvent, preferably a physiological saline solution or a physiologically tolerated buffer, preferably a phosphate buffered saline solution. The invention anticipates the use of a double-stranded ribonucleic acid in a dosage of a maximum of 5 mg/kg body weight per day.

GFP Laboratory Mice:

The transgenic laboratory mouse strain TgN (GFPU) 5Nagy (Jackson Laboratory, Bar Harbor, Me.), which expresses GFP in all cells studied to date (with the help of a beta actin promoter and a CMV intermediate early enhancer) (Hadjantonakis A K et al., 1998, Nature Genetics 19: 220-222), was used. The GFP transgenic mice may be clearly differentiated on the basis of fluorescence (using a UV lamp) from the corresponding wild types (WT). The following experiments were carried out using GFP-heterozygote animals that were bred by mating a WT animal each with a heterozygote GFP-type animal. The animals were kept under controlled conditions in groups of 3-5 animals in Type III Makrolon cages (Ehret Co., Emmendingen, Germany) at a constant temperature of 22° C. and a light-to-dark rhythm of 12 hours. Granulated softwood (8/15, Altromin Co., Lage, Germany) was strewn on the bottom of the cages. The animals received tap water and Altromin 1324 pelleted standard feed (Altromin Co.) ad libitum.

In Vivo Experiment:

Heterozygote GFP animals were placed in cages as described above in groups of 3. DsRNA solution was injected intravenously (i.v.) into the caudal vein in 12-hour rotation (between 5:30 and 7:00 and between 17:30 and 19:00) over 5 days. Injection volume was 60 µl per 10 g body weight, and dosage was 2.5 mg dsRNA or 50 µg per kg body weight. The groups were organized as follows:

Group A: PBS (phosphate buffered saline) 60 µl per 10 g body weight each,

Group B: 2.5 mg per kg body weight of a non-specific control dsRNA (K1 control with smooth ends and a double-stranded region of 22 nucleotide pairs), Group C: 2.5 mg per kg body weight of another non-specific control dsRNA (K3 control with 2 nucleotide [nt] overhangs and both 3'-ends and a double-stranded region of 19 nucleotide pairs), Group D: 2.5 mg per kg body weight of dsRNA (directed specifically against GFP, henceforth designated as S 1, with smooth ends and a double-stranded region of 22 nucleotide pairs), Group E: 2.5 mg dsRNA per kg body weight (directed specifically against GFP, henceforth designated as S7, with 2nt overhangs and the 3'-ends of both strands, and a double-stranded region of 19 nucleotide pairs), Group F: 50 µg 51 dsRNA per kg body weight (in other words 1/50 the dosage of Group D).

After the last injection of a series of 10 injections, the animals were sacrificed after 14-20 hours, and the organs and blood were removed as described below.

Organ Removal:

Immediately after the animals were killed by C02 inhalation, the blood and various organs were removed (thymus, lungs, heart, spleen, stomach, intestines, pancreas, brain, kidneys, and liver). The organs were quickly rinsed in cold sterile PBS and dissected with a sterile scalpel. A portion was fixed for 24 hours for immunohistochemical staining in methyl Carnoy (MC, 60% methanol, 30% chloroform, 10% glacial acetic acid); another portion was immediately flash-frozen in liquid nitrogen for freeze sections and protein isolation, and stored at −80° C.; and another smaller portion was frozen for RNA isolation at −80° C. in RNAeasy Protect (QIAGEN GmbH, Max Volmer Str. 4, 40724 Hilden). Immediately after removal, the blood was kept on ice for 30 minutes, mixed, centrifuged for 5 minutes at 2000 rpm (Mini Spin, Eppendorf A G, Barkhausenweg 1, 22331, Hamburg, Germany), and the supernatant fluid was drawn off and stored at −80° C. (designated here as plasma).

Processing the Biopsies:

After fixing the tissue for 24 hours in MC, the tissue pieces were dehydrated in an ascending alcohol series at room temperature: 40 minutes each 70% methanol, 80% methanol, 2×96% methanol and 3×100% isopropanol. After that the tissue was warmed up in 100% isopropanol at 60° C. in an incubator, after which it was incubated for 1 hour in an isopropanol/paraffin mixture at 60° C. and 3× for 2 hours in paraffin, and then embedded in paraffin. Tissue sections 3 µm in thickness were prepared for immunoperoxidase staining, using a rotation microtome (Leica Microsystems Nussloch GmbH, Heidelberger Str. 17-19, 69226 Nussloch, Germany), placed on microscopic slides (Superfrost, Vogel GmbH & Co. KG, Medical Technology and Electronics, Marburger Str. 81, 35396 Giessen, Germany), and incubated for 30 minutes at 60° C.

Immunoperoxidase Staining for GFP:

The sections were deparaffinized for 3×5 minutes in xylol, rehydrated in a descending alcohol series (3×3 min. 100% ethanol, 2×2 min. 95% ethanol), and then incubated for 20 minutes in 3% $H_2O_2$/methanol to block endogenous peroxidases. Next, all incubation steps were carried out in a moist chamber. After 3×3 min. washing with PBS, the sections were incubated with a first antibody (goat anti-GFP antibody, sc-5384, Santa Cruz Biotechnology, Inc., Berheimer Str. 89-2, 69115 Heidelberg, Germany) 1:500 in 1% BSA/PBS overnight at 4° C. The sections were then incubated with the biotinylated secondary antibody (donkey anti-goat IgG; Santa Cruz Biotechnology; 1:2000 dilution) for 30 minutes at room temperature, after which they were incubated for 30 minutes with Avidin D peroxidase (1:2000 dilution, Vector Laboratories, 30 Ingold Road, Burlingame, Calif. 94010). After each antibody incubation, the sections were washed in PBS for 3×3 min., and buffer residue was removed from the sections along with cell material. All antibodies were diluted with 1% bovine serum albumin (BSA)/PBS. The sections were stained with 3,3'-diamino benzidine (DAB) using the DAB Substrate Kit (Vector Laboratories) in accordance with the manufacturer's instructions. Gill's Hematoxylin III (Merck KgaA, Frankfurter Str. 250, 64293 Darmstadt) was used as the nuclear counterstain. After dehydration in an ascending alcohol series and 3×5 minutes xylol, the sections were covered with Entellan (Merck). Microscopic evaluation of the stains was accomplished using a IX50 microscope from OLYMPUS Optical Co. (Europe) GmbH, Wendenstr. 14-18 20097 Hamburg, Germany, fitted with a CCD camera (Hamamatsu Photonics K.K., Systems Division, 8012 Joko-cho Hamamatsu City, 431-3196 Japan).

Protein Isolation from Tissue Pieces:

Frozen tissue samples were added to 800 µl isolation buffer (50 m HEPES, pH 7.5; 150 mM NaCl; 1 mM EDTA; 2.5 mM EGTA; 10% glycerol; 0.1% Tween; 1 mM DTT; 10 mM β-glycerol phosphate; 1 mM NaF; 0.1 mM Na3VO4 with a "complete" protease inhibitor tablet from Roche Diagnostics GmbH, Roche Applied Science, Sandhofer Str. 116, 68305 Mannheim), and homogenized for 2×30 seconds with an ultraturrax (DIAX 900, Dispersion Tool 6G, HEIDOLPH Instruments GmbH & Co. KG, Walpersdorfer Str. 12, 91126 Schwabach), and cooled on ice in between steps. After incubation for 30 minutes on ice, the homogenate was mixed and centrifuged for 20 minutes at 10,000 g, 4° C. (3K30, SIGMA Laboratory Centrifuge GmbH, An der Unteren Söse 50,37507 Osterode am Harz). The supernatant fluid was again incubated for 10 minutes on ice, mixed, and centrifuged for 20 minutes at 15,000 g, 4° C. Protein determination of the supernatant fluid was determined according to Bradford, 1976, modified according to Zor & Selinger, 1996, using the Roti-Nanoquant system (Carl Roth GmbH & Co., Schoemperlenstr. 1-5, 76185 Karlsruhe, Germany) in accordance with manufacturer's instructions. BSA was used for protein calibration in a concentration range of 10 to 100 µg/ml.

SDS Gel Electrophoresis:

Denaturing, discontinuous 15% SDS-PAGE (polyacrylamide gel electrophoresis) according to Läemmli (Nature 277: 680-685, 1970) was carried out in a Multigel-Long electrophoresis chamber (Whatman Biometra GmbH, Rudolf Wissell Str. 30, 37079 Göttingen). The separation gel was poured on to a thickness of 1.5 mm: 7.5 ml acrylamide/bisacrylamide (30%, 0.9%); 3.8 ml 1.5 M Tris/HCl, pH 8.4; 150 µl 10% SDS; 3.3 ml distilled water; 250 µl ammonium persulfate (10%); 9 µl TEMED (N,N,N',N'-tetramethylendiamine), and covered over with 0.1% SDS until polymerization occurred. A collection gel was then poured on: 0.83 µl acrylamide/bisacrylamide (30%, 0.9%), 630 µl M tris/HCl, pH 6.8; 3.4 ml distilled water; 50 µl 10% SDS; 50 µl 10% ammonium persulfate; 5 µl TEMED.

A corresponding quantity of 4× sample buffer (200 mM Tris, pH 6.8, 4% SDS, 100 mM DTT (dithiotreithol), 0.02% bromophenol blue, 20% glycerin) was then added to the proteins, which were then denatured on a heat block at 100° C., centrifuged on ice after cooling off, and then applied to the gel. The same plasma and protein quantities were used in each lane (3 µl plasma or 25 µg total protein each). Protein electrophoresis was carried out at room temperature at a constant 50V. The protein gel marker Kaleidoscope Prestained Standard (Bio-Rad Laboratories GmbH, Heidemannstr. 164, 80939 Munich) was used as molecular marker.

Western Blot and Immunodetection:

Proteins separated by SDS-PAGE were transferred to a PVDF (polyvinyl difluoride) membrane (Hybond-P, Amersham Biosciences Europe GmbH, Munzinger Str. 9, 79111 Freiburg, Germany) using the semidry transfer method according to Kyhse-Anderson (J. Biochem. Biophys. Methods 10: 203-210, 1984) at room temperature and constant amperage of 0.8 mA/cm2 for 1.5 hours in Tris/Glycerin transfer buffer (39 mM glycerin, 46 mM tris, 0.1% SDS, and 20% methanol). After immunodetection both the gels and the blots, as well as the blot membranes, were stained with Coomassie (0.1% Coomassie G250, 45% methanol, 10% glacial acetic acid) in order to check for electrophoretic transfer. The blot membranes were incubated after transfer in 1% skim milk powder/PBS for 1 hour at room temperature to saturate nonspecific bonds. Next, each membrane was washed three times for 3 minutes with 0.1% Tween-20/PBS. All subsequent antibody incubations and wash steps were done in 0.1% Tween-20/PBS. The primary antibody (goat anti-GFP antibody, sc-5384, Santa Cruz Biotechnology) was incubated for one hour at room temperature at a dilution of 1:1000. After washing 3×5 minutes, the membranes were incubated with a horseradish peroxidase coupled secondary antibody (donkey anti-goat IgG, Santa Cruz Biotechnology), at a dilution of 1:10,000. Detection of horseradish peroxidase was then achieved using the ECL system (Amersham) in accordance with the manufacturer's instructions.

Figure 18:
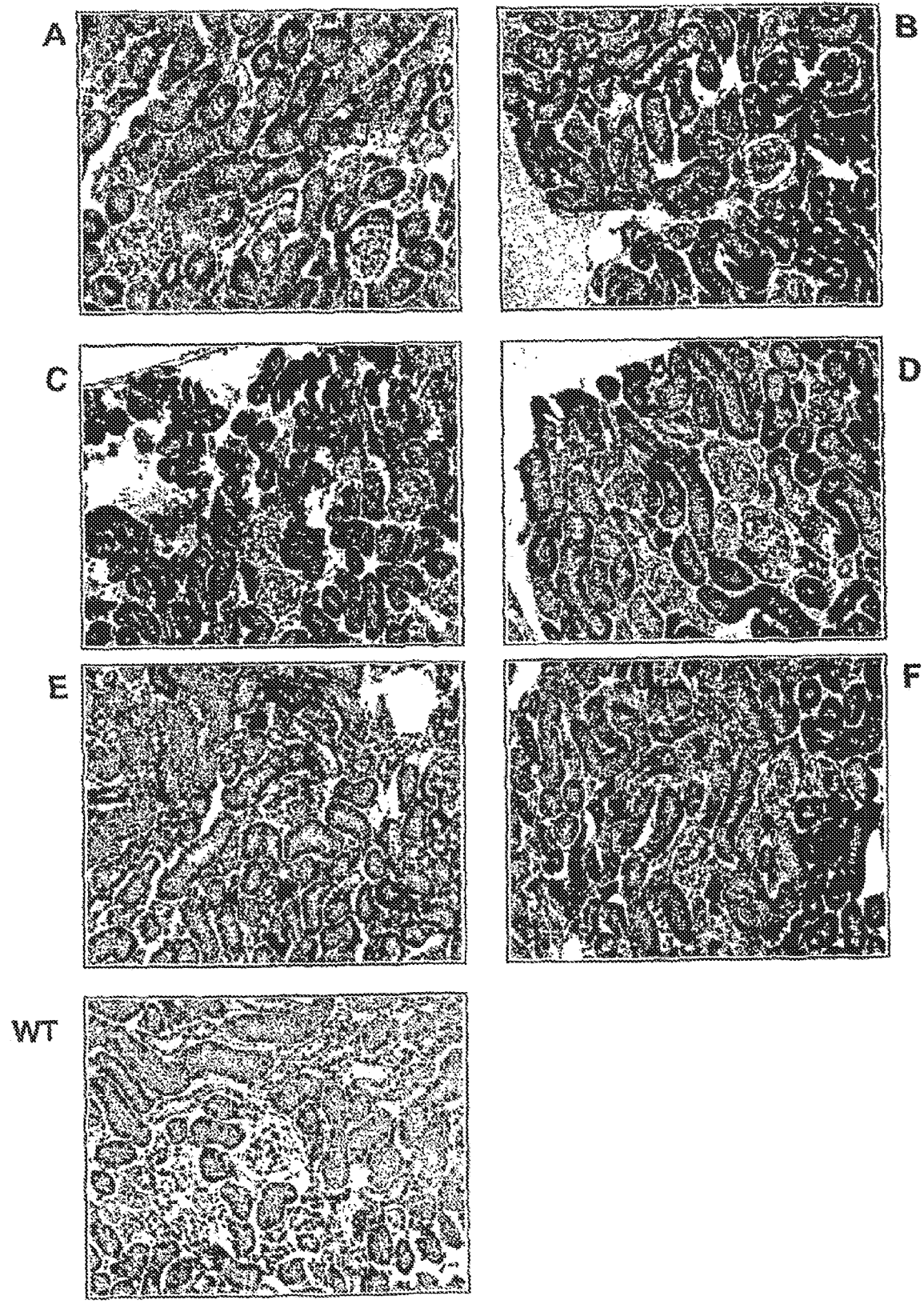
FIG. 18 is a GFP-specific immunoperoxidase staining of kidney paraffin sections from transgenic GFP mice.
Figure 19:
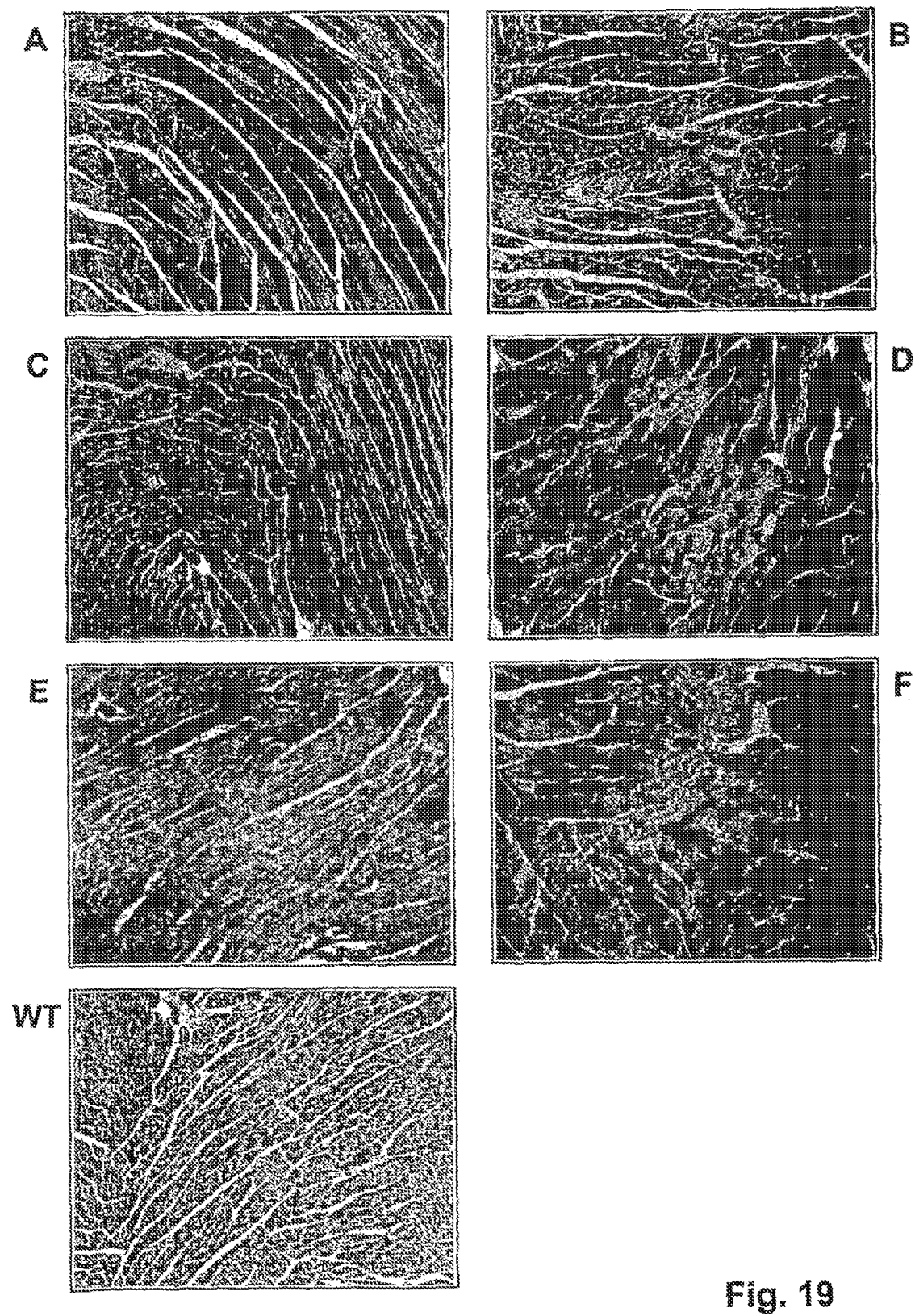
FIG. 19 is a GFP-specific immunoperoxidase staining of heart paraffin sections from transgenic GFP mice.
Figure 20:
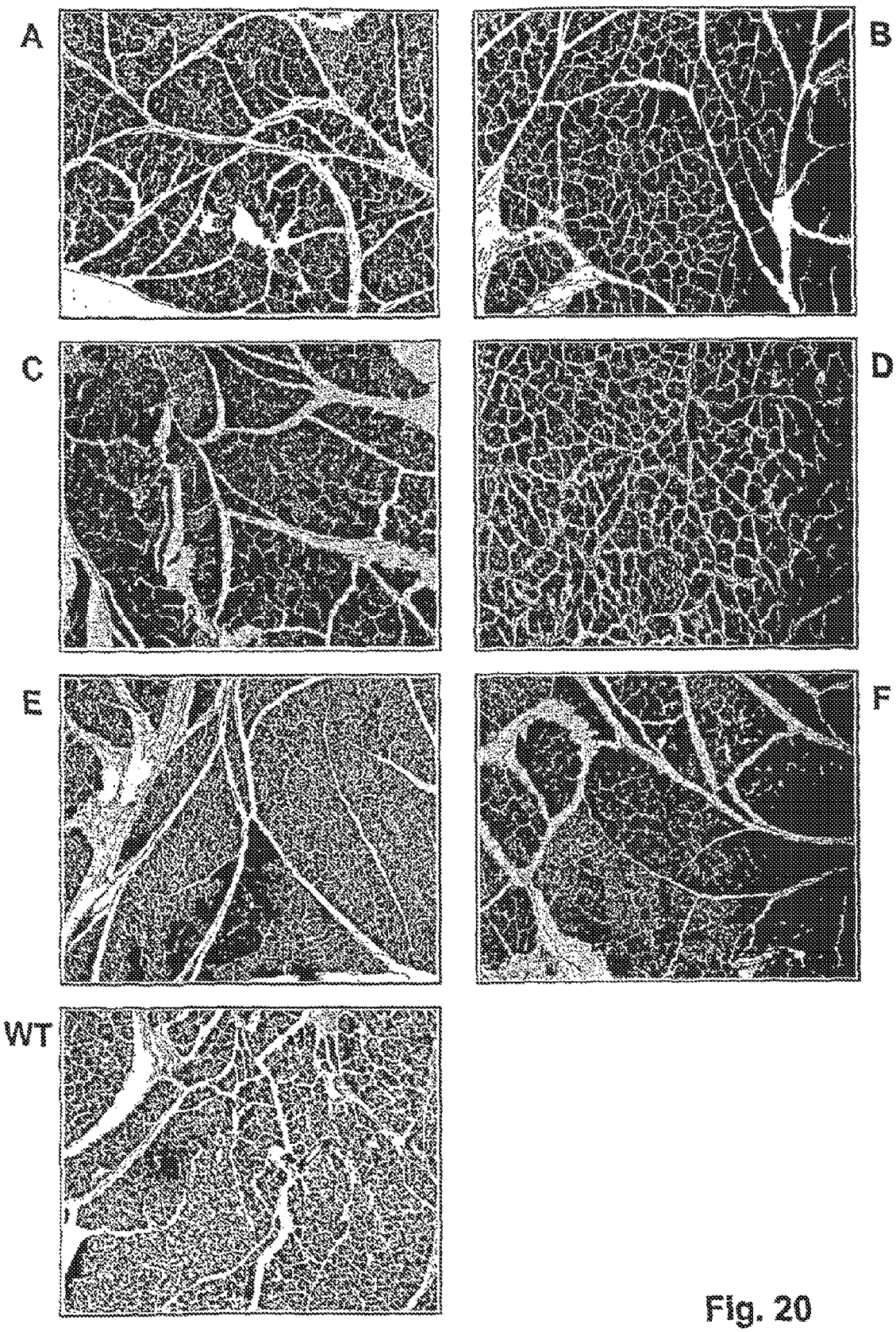
FIG. 20 is a GFP-specific immunoperoxidase staining of pancreas paraffin sections from transgenic GFP mice.
Figure 21:
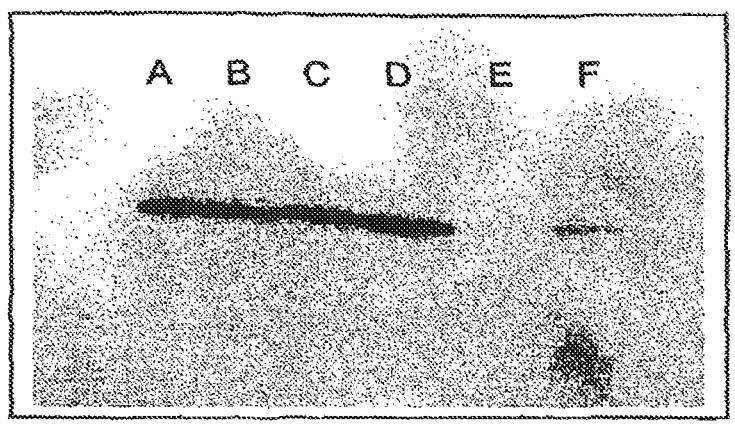
FIG. 21 is a Western blot analysis of GFP expression in plasma.
Figure 22:
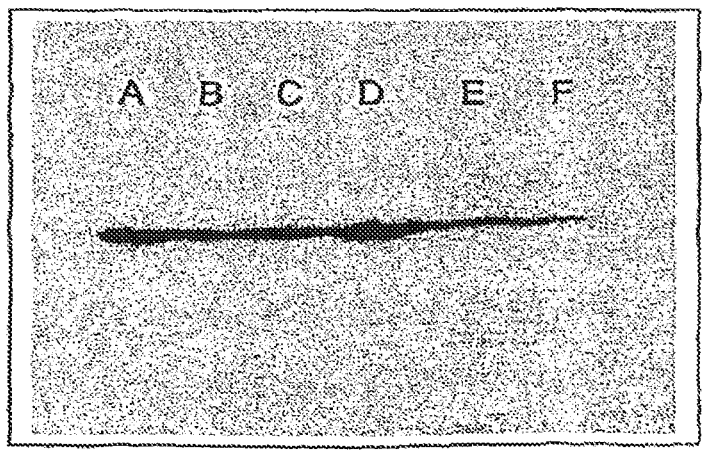
FIG. 22 is a Western blot analysis of GFP expression in kidney.
Figure 23:
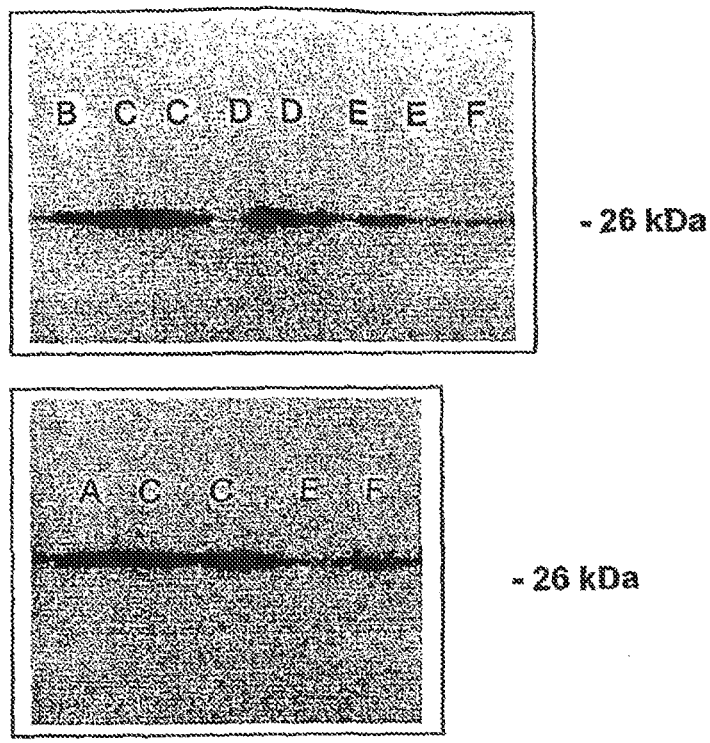
FIG. 23 is a Western blot analysis of GFP expression in heart.

FIGS. 18 to 20 show inhibition of GFP expression after intravenous injection of specific anti-GFP dsRNA, by means of immunoperoxidase GFP staining of 3 µm paraffin sections. Over the course of the experiment, the anti-GFP dsRNA, with a double-stranded region of 22 nucleotide (nt) pairs without overhangs at the 3'-ends (D) and the corresponding non-specific control dsRNA (B), as well as the specific anti-GFP dsRNA, with a double-stranded region consisting of 19 nucleotide pairs with 2nt overhangs at the 3'-ends (E), and the corresponding non-specific control dsRNA (C) were applied in 12-hour rotation over 5 days. (F) received 1/50 the dosage of Group (D). Animals not administered dsRNA (A) and WT animals were used as further controls. FIG. 18 shows the inhibition of GFP expression in kidney sections; FIG. 19 in heart sections; and FIG. 20 in pancreas tissue. FIGS. 21 to 23 show Western blot analyses of GFP expression in plasma and tissues. FIG. 21 shows the inhibition of GFP expression in plasma; FIG. 22 in kidney; and FIG. 23 in heart. FIG. 23 shows the total protein isolate from various animals. The same quantities of total protein were used for each track. In the animals that were given non-specific control dsRNA (animals in Groups B and C), GFP is not reduced in comparison with animals that received no dsRNA. Animals that received the specific anti-GFP dsRNA with 2nt overhangs at the 3'-ends of both strands and a double-stranded region consisting of 19 nucleotide pairs showed significantly inhibited GFP expression in the tissues studied (heart, kidneys, pancreas, and blood), compared with untreated animals (FIGS. 18-23). Of the animals in Groups D and F, who were given specific anti-GFP dsRNA, with blunt ends and a double-stranded region consisting of 22 nucleotide pairs, only those animals that received the dsRNA at a dosage of 50 µg/kg body weight per day demonstrated specific inhibition of GFP expression. However, the degree of inhibition was less marked than that seen with the animals in Group E.

A summary evaluation of GFP expression in tissue sections and Western blot shows that the inhibition of GFP expression is greatest in blood and in kidneys (FIGS. 18, 21 and 22).

Example 2

Inhibition of EGFR Gene Expression with EFFR-Specific siRNA

The epidermal growth factor (=EGF) receptor (=EGFR) belongs to the tyrosine kinase receptors, transmembrane proteins with an intrinsic tyrosin kinase activity that are involved in the control of a series of cellular processes such as cell growth, cell differentiation, migratory processes, and cell vitality (reviewed in: Van der Geer et al., 1994). The EGFR family consists of 4 members, EGFR (ErbB1), HER2 (ErbB2), HER3 (ErbB3), and HER4 (ErbB4) with a transmembrane domain, a cysteine-rich extracellular domain, and a catalytic intracellular domain. The EGFR sequence, a 170-kDa protein, was first described by Ullrich et al., 1984.

EGFR is activated by peptide growth factors such as EGF, TGFα (transforming growth factor), amphiregulin, betacellulin, HB-EGF (heparin binding EGF-like growth factor), and neuregulins. Ligand binding induces the formation of homodimers or heterodimers with subsequent autophosphorylation of cytoplasmic tyrosine (Ullrich & Schlessinger, 1990; Alroy & Yarden, 1997). The phosphorylated amino acids form the binding sites of numerous proteins that are involved in the initial steps of a complex signal transduction pathway. EGFR is involved in many cancers, and is therefore an appropriate target for therapeutic approaches (Huang & Harari, 1999). The mechanisms that lead to aberrant EGFR activity may be related to overexpression, amplification, constitutive activation of mutant receptor forms, or autocrine loops (Voldberg et al., 1997). Overexpression of EGFR has been described for a series of tumors such as breast cancer (Walker & Dearing, 1999), non-minor lung cancer (Fontaninii et al., 1998), pancreatic cancer, colon cancer (Salomon et al., 1995), and glioblastoma (Rieske et al., 1998). For malignant glioblastoma, in particular, there have to date been no effective and specific therapeutic agents.

Example 3

Efficacy of Inhibition of EGFR Gene Expression

To test the effectiveness of dsRNA for the specific inhibition of EGFR gene expression, U-87 MG cells (human glioblastoma cells), ECCAC (European Collection of Animal Cell Culture) No. 89081402 were transfected with the specific anti-EGF-receptor-directed dsRNA (SEQ ID NO:51). After approximately 72 hours of incubation, the cells were harvested, the protein was isolated, and EGFR expression was analyzed by Western blot.

Test Protocol:
Synthesis and Preparation of dsRNAs

Oligoribonucleotides were synthesized with an RNA synthesizer (Expedite 8909, Applied Biosystems, Weiterstadt, Germany) and purified by High Pressure Liquid Chromatography (HPLC) using NucleoPac PA-100 columns, 9×250 mm (Dionex Corp.; low salt buffer: 20 mM tris, 10 mM NaClO$_4$, pH 6.8, 10% acetonitrile; flow rate: 3 ml/min). Formation of double stranded siRNAs was then achieved by heating a stoichiometric mixture of the individual complementary strands (10 M) to 95° C. for 5 minutes in 25 mM Tris-HCl, pH 7.5, and 100 mM NaCl, followed by subsequent cooling for 6 hours to room temperature.

dsRNA molecules with linkers were produced by solid phase synthesis and addition of hexaethylene glycol as a non-nucleotide linker (D. Jeremy Williams, Kathleen B. Hall, Biochemistry, 1996, 35, 14665-14670). A Hexaethylene glycol linker phosphoramidite (Chruachem Ltd, Todd Campus, West of Scotland Science Park, Acre Road, Glasgow, G20 OUA, Scotland, UK) was coupled to the support bound oligoribonucleotide employing the same synthetic cycle as for standard nucleoside phosphoramidites (Proligo Biochemie GmbH, Georg-Hyken-Str.14, Hamburg, Germany) but with prolonged coupling times. Incorporation of linker phosphoramidite was comparable to the incorporation of nucleoside phosphoramidites.

Seeding the Cells:

All cells were cultured under sterile conditions at an appropriate workstation (HS 18/Hera Safe, Kendro, Heraeus). U-87 MG cells were incubated in a CO$_2$-incubator (T20, Hera Cell, Kendro, Heraeus) at 37° C., 5% CO$_2$ and saturated atmospheric humidity in DMEM (Dulbecco's modified eagle medium, Biochrom) with 10% FCS (fetal calf serum, Biochrom), 2 mM L-glutamine (Biochromone) mM sodium pyruvate (Biochrom), 1×NEAA (nonessential amino acids, Biochrom), and penicillin/streptomycin (100 IU/100 µg/ml, Biochrom). In order to maintain the cells in an exponential growth state, the cells were passaged every 3 days. 24 hours before dsRNA application by means of transfection, the cells were trypsinized (10× trypsin/EDTA, Biochrom, Germany) and placed in a 6-well plate (6-well plates, Schubert & Weiss Laboratories, GmbH) in 1.5 µl growth medium.

DsRNA Application in Cultured U-87 MG Cells:
Cells were transfected with dsRNA using the OLIGOFECTAMINE™ reagent (Life Technologies) in accordance with the manufacturer's instructions. Total transfection volume was 1 ml. First, the dsRNA was diluted in serum-free medium: 0.5 µl of a 20 µM stock solution of specific anti-EGFR directed dsRNA and 9.5 µl of a 20 µM stock solution of nonspecific dsRNA (K1A/K2B) diluted with 175 µl serum-free medium (200 nM dsRNA in the transfection incubate or 10 nM specific EGFR-dsRNA) per well. The OLIGOFECTAMINE™ reagent was also diluted in serum-free medium: 3 µl with 12 µl medium per well and then incubated for 10 minutes at room temperature. Then the diluted OLIGOFECTAMINE™ reagent was added to the medium of diluted dsRNA, mixed, and incubated for a further 20 minutes at room temperature. The medium was changed during incubation. The cells were washed 1× with 1 ml serum-free medium and further incubated with 800 µl serum-free medium until the dsRNA/OLIGO-FECTAMINE™ reagent was added. After the addition of 200 µl dsRNA/OLIGOFECTAMINE™ reagent per well, the cells incubated up until protein isolation.

Protein Isolation:

Approximately 72 hours after transfection, the cells were harvested and total protein was isolated. The medium was removed, and the cell monolayer was washed once with PBS. After the addition of 200 µl protein isolation buffer (1× "Complete" protease inhibitor, Roche, 50 mM HEPES, pH 7.5, 150 mM NaCl, 1 mM EDTA, 2.5 mM EGTA, 10% glycerin, 0.1% Tween-20, 1 mM DTT, 10 mM β-glycerine phosphate, 1 mM NaF, 0.1 mM $Na_3VO_4$) the cells were removed with the help of a cell scraper, incubated for 10 minutes on ice, transferred to an Eppendorf reagent vessel, and stored at −80° C. for at least 30 minutes. After thawing, the lysate was homogenized at the third setting for 10 seconds with a disperser (DIAX 900, 6G disperser, Heidolph Instruments GmbH, Schwabach), incubated on ice for 10 minutes, and then centrifuged for 15 minutes at 14,000×g at 4° C. (3K30, Sigma). Quantitation of total protein in the supernatant was determined according to Bradford using the Roti-Nanoquant system from Roth (Roth GmbH, Karlsruhe) in accordance with the manufacturer's instructions. 200 µl protein solution at a suitable dilution is mixed with 800 µl 1× working solution, and extinction was measured in semi-microcuvettes at 450 nm and 590 nm against distilled water in a Beckman spectrophotometer (DU 250). BSA dilutions were used for calibration (beaded BSA, Sigma).

SDS Gel Electrophoresis:

Denaturing, discontinuous 15% SDS-PAGE (polyacrylamide gel electrophoresis) according to Läemmli (Nature 277: 680-685, 1970) was carried out in a Multigel-Long electrophoresis chamber (Whatman Biometra GmbH, Rudolf Wissell Str. 30, 37079 Gottingen). The separation gel was poured on to a thickness of 1.5 mm: 7.5 ml acrylamide/bisacrylamide (30%, 0.9%); 3.8 ml 1.5 M Tris/HCl, pH 8.4; 150 µl 10% SDS; 3.3 ml distilled water; 250 µl ammonium persulfate (10%); 9 µl TEMED (N,N,N',N'-tetramethylendiamine), and covered over with 0.1% SDS until polymerization occurred. A collection gel was then poured on: 0.83 µl acrylamide/bisacrylamide (30%, 0.9%), 630 µl M tris/Hel, pH 6.8; 3.4 ml distilled water; 50 µl 10% SDS; 50 µl 10% ammonium persulfate; 5 µl TEMED.

A corresponding quantity of 4× sample buffer (200 mM Tris, pH 6.8, 4% SDS, 100 mM DIT (dithiotreithol), 0.02% bromophenol blue, 20% glycerin) was then added to the proteins, which were then denatured on a heat block at 100° C., centrifuged on ice after cooling off, and then applied to the gel (35 µg total protein/lane). Protein electrophoresis was carried out at room temperature at a constant 50V. The protein gel marker Kaleidoscope Prestained Standard (Bio-Rad Laboratories GmbH, Heidemannstr. 164, 80939 Munich) was used as molecular marker.

Western Blot and Immunodetection:

Transfer of the proteins from SDS-PAGE to a PVDF (polyvinyl difluoride) membrane (Hybond-P, Amersham) was done using a semidry method according to Kyhse-Anderson (J. Biochem. Biophys. Methods 10:203-210, 1984) at room temperature and a constant 0.8 $mA/cm^2$ for 1.5 hours. A cathode buffer (30 mM Tris, 40 mM glycine, 10% methanol, and 0.1% SDS, pH 9.4), anode buffer I (300 mM Tris, pH 10.4, 10% methanol), and anode buffer II (30 mM Tris, pH 10.4, 10% methanol) were used as the transfer buffers. Before assembling the blot stack with 3 MM Whatman paper (Schleicher & Schüll) the gel was incubated in cathode buffer, and the PVDF membrane (previously for 30 seconds in 100% methanol) in anode buffer II (5 minutes): 2 layers of 3 MM paper (anode buffer I), 1 layer 3 MM paper (anode buffer II), PVDF membrane, gel, 3 layers 3 MM paper (cathode buffer). To analyze electrophoretic transfer, both the post-blot gels and the blot membranes were stained after immunodetection using Coomassie (0.1% Coomassie G250, 45% methanol, 10% glacial acetic acid).

After transfer, the blot membrane was incubated in 1% skim milk powder/PBS/0.1% Tween-20 for one hour at room temperature. After that, the membrane was washed three times for 3 minutes with 0.1% Tween-20/PBS. All subsequent antibody incubations and washings were done using 0.1% Tween-20/PBS. The primary antibody (human EGFR extracellular domain, specific goat IgG, Catalogue No. AF231, R&D Systems) was incubated with shaking for two hours at room temperature at a concentration of 1.5 µg/ml. After washing 3×5 minutes, the membrane was incubated for one hour at room temperature with the secondary antibody (labeled donkey anti-goat IgG horseradish peroxidase, Santa Cruz Biotechnology) at a dilution of 1:10,000. After washing (3×3 minutes in PBS/0.1% Tween-20) horseradish peroxidase was detected by ECL reaction (enhanced chemoluminescence). To 18 ml of distilled water, 200 µl Solution A (250 mM luminol, Roth, dissolved in DMSO), 89 µl Solution B (90 mM pcoumaric acid, Sigma, dissolved in DMSO), and 2 ml 30% $H_2O_2$ solution were added. Depending on membrane size, 4-6 ml were pipetted directly onto the membrane, incubated for 1 minute at room temperature, and then placed immediately on X-Ray film (Biomax MS, Kodak).

The sequences used here are depicted in Table 3 below, as well as in SEQ ID NOS:153, 157, 158, 168-173.

TABLE 3

```
ES-7  SEQ ID NO: 168 (A) 5'-AACACCGCAGCAUGUCAAGAU-3'    2-19-2
      SEQ ID NO: 169 (B) 3'-UUUUGUGGCGUCGUACAGUUC-5'

ES-8  SEQ ID NO: 170 (A) 5'-AAGUUAAAAUUCCCGUCGCUAU-3'   2⁵-19-2⁵
      SEQ ID NO: 171 (B) 3'-CAAUUUUAAGGGCAGCGAUAGU-5'

ES2A/ SEQ ID NO: 172 (A) 5'-AGUGUGAUCCAAGCUGUCCCAA-3'   0-22-0
```

TABLE 3-continued

```
ES5B  SEQ ID NO: 173  (B) 3'-UUUCACACUAGGUUCGACAGGGUU-5'

K2    SEQ ID NO: 157  (A) 5'-ACAGGAUGAGGAUCGUUUCGCAUG-3'  2-22-2
      SEQ ID NO: 158  (B) 3'-UCUGUCCUACUCCUAGCAAAGCGU-5'

K1A/  SEQ ID NO: 153  (A) 5'-ACAGGAUGAGGAUCGUUUCGCA-3'    0-22-2
KWB   SEQ ID NO: 158  (B) 3'-UCUGUCCUACUCCUAGCAAAGCGU-5'
```

Example 4

Figure 24:
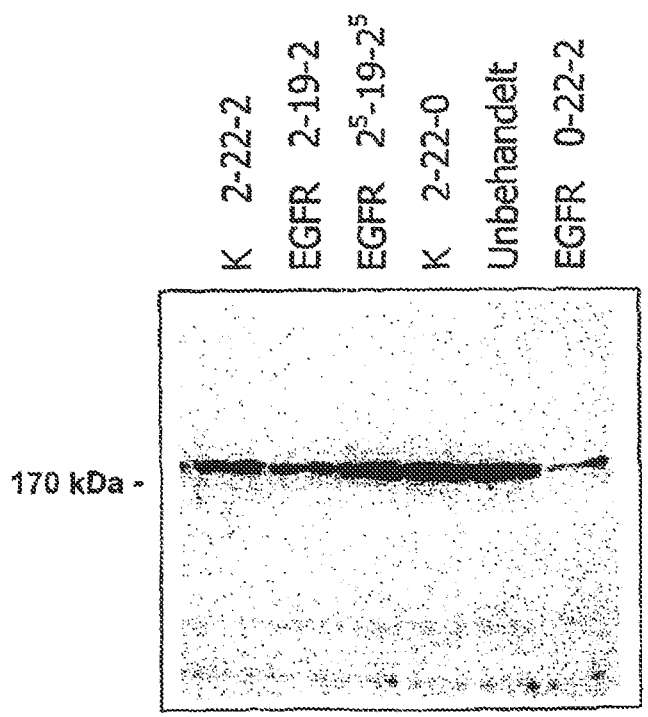
FIG. 24 is a Western blot analysis of EGFR expression in U-87 MG glioblastoma cells.

Inhibition of EGFR Expression in U-87 MG Glioblastoma Cells 24 hours after seeding the cells, U-87 MG glioblastoma cells were transfected with 10 nM dsRNA and oligofectamine. After 72 hours, the cells were harvested and total protein isolated and loaded on to a 7.5% SDS-PAGE gel. 35 µg total protein was applied to each lane. The corresponding Western blot analysis (see FIG. 24) shows that with the specific anti-EGFR-directed dsRNA with a 2nt overhang at the 3'-end of the antisense strand, EGFR expression in U-87 MG cells is significantly inhibited in comparison to the corresponding controls. This inhibition of expression of an endogenous gene by means of specific dsRNA confirms the results noted in Example II. The inhibition of EGFR expression mediated by ES-7 and ES-8 is notably smaller. The dsRNAs used in FIG. 24 are shown in Table 3.

Example 5

Treatment of a Breast Cancer Patient with EGFR siRNA

In this Example, EGFR-specific double stranded siRNA is injected into a breast cancer patient and shown to specifically inhibit EGFR gene expression.

SiRNA Synthesis

EGFR-specific siRNAs directed against the fusion sequence of EGFR are chemically synthesized with or without a hexaethylene glycol linker as described above siRNA Administration and Dosage The present example provides for pharmaceutical compositions for the treatment of human breast cancer patients comprising a therapeutically effective amount of a EGFR-specific siRNA as disclosed herein, in combination with a pharmaceutically acceptable carrier or excipient. SiRNAs useful according to the invention may be formulated for oral or parenteral administration. The pharmaceutical compositions may be administered in any effective, convenient manner including, for instance, administration by topical, oral, anal, vaginal, intravenous, intraperitoneal, intramuscular, subcutaneous, intranasal or intradermal routes among others. One of skill in the art can readily prepare siRNAs for injection using such carriers that include, but are not limited to, saline, buffered saline, dextrose, water, glycerol, ethanol, and combinations thereof. Additional examples of suitable carriers are found in standard pharmaceutical texts, e.g. "Remington's Pharmaceutical Sciences", 16th edition, Mack Publishing Company, Easton, Pa., 1980.

The dosage of the siRNAs will vary depending on the form of administration. In the case of an injection, the therapeutically effective dose of siRNA per injection is in a dosage range of approximately 1-500 g/kg body weight, preferably 100 g/kg body weight. In addition to the active ingredient, the compositions usually also contain suitable buffers, for example phosphate buffer, to maintain an appropriate pH and sodium chloride, glucose or mannitol to make the solution isotonic. The administering physician will determine the daily dosage which will be most suitable for an individual and will vary with the age, gender, weight and response of the particular individual, as well as the severity of the patient's symptoms. The above dosages are exemplary of the average case. There can, of course, be individual instances where higher or lower dosage ranges are merited, and such are within the scope of this invention. The siRNAs of the present invention may be administered alone or with additional siRNA species or in combination with other pharmaceuticals.

RNA Purification and Analysis

Efficacy of the siRNA treatment is determined at defined intervals after the initiation of treatment using real time PCR or RNAse protection assays on total RNA extracted tissue biopsies. Cytoplasmic RNA from whole blood, taken prior to and during treatment, is purified with the help of the RNeasy Kit (Qiagen, Hilden) and Bcr-abl mRNA levels are quantitated by real time RT-PCR. Real-time Taqman-RT-PCR is performed as described previously (Eder M et al. Leukemia 1999; 13: 1383-1389; Scherr M et al. BioTechniques. 2001; 31: 520-526). Analysis by real time PCR at regular intervals, for example every 1-2 weeks, provides the attending physician with a rapid and accurate assessment of treatment efficacy as well as the opportunity to modify the treatment regimen in response to the patient's symptoms and disease progression.

Example 6

EGFR-Specific siRNA Expression Vectors

In another aspect of the invention, siRNA molecules that interact with target RNA molecules and modulate gene expression activity are expressed from transcription units inserted into DNA or RNA vectors (see for example Couture et A, 1996, TIG., 12, 5 1 0, Skillern et A, International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann et al., 1995, Proc. Natl. Acad. Sci. USA 92:1292).

The individual strands of a siRNA can be transcribed by promoters on two separate expression vectors and cotransfected into a target cell. Alternatively each individual strand of the siRNA can be transcribed by promoters both of which are located on the same expression plasmid. In a preferred embodiment, the siRNA is expressed as an inverted repeat joined by a linker polynucleotide sequence such that the siRNA has a stem and loop structure.

The recombinant siRNA expression vectors are preferably DNA plasmids or viral vectors. siRNA expressing viral vectors can be constructed based on, but not limited to, adeno-associated virus (for a review, see Muzyczka et al. (1992, Curr. Topics in Micro. and Immunol. 158:97-129)), adenovirus (see, for example, Berkner et al. (1988, BioTechniques 6:616), Rosenfeld et al. (1991, Science 252:431-434), and Rosenfeld et al. (1992, Cell 68:143-155)), or alphavirus as well as others known in the art. Retroviruses have been used to introduce a variety of genes into many different cell types, including epithelial cells, in vitro and/or in vivo (see for example Eglitis, et al., 1985, Science 230:1395-1398; Danos and Mulligan, 1988, Proc. Natl. Acad. Sci. USA 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Natl. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

The promoter driving siRNA expression in either a DNA plasmid or viral vector of the invention may be a eukaryotic RNA polymerase I (e.g. ribosomal RNA promoter), RNA polymerase II (e.g. CMV early promoter or actin promoter or U1 snRNA promoter) or preferably RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to specific organs or cell types (see, e.g., Lasko et al., 1992, Proc. Natl. Acad. Sci. USA 89:6232). Several tissue-specific regulatory sequences are known in the art including the albumin regulatory sequence for liver (Pinkert et al., 1987, Genes Dev. 1:268276); the endothelin regulatory sequence for endothelial cells (Lee, 1990, J. Biol. Chem. 265:10446-50); the keratin regulatory sequence for epidennis; the myosin light chain-2 regulatory sequence for heart (Lee et al., 1992, J. Biol. Chem. 267:15875-85), and the insulin regulatory sequence for pancreas (Bucchini et al., 1986, Proc. Natl. Acad. Sci. USA 83:2511-2515), or the vav regulatory sequence for hematopoietic cells (Oligvy et al., 1999, Proc. Natl. Acad. Sci. USA 96:14943-14948). Another suitable regulatory sequence, which directs constitutive expression of transgenes in cells of hematopoietic origin, is the murine MHC class I regulatory sequence (Morello et al., 1986, EMBO J. 5:1877-1882). Since NMC expression is induced by cytokines, expression of a test gene operably linked to this promoter can be upregulated in the presence of cytokines.

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et at, 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the siRNA transgene.

Preferably, recombinant vectors capable of expressing siRNA molecules are delivered as described below, and persist in target cells. Alternatively, viral vectors can be used that provide for transient expression of siRNA molecules. Such vectors can be repeatedly administered as necessary. Once expressed, the siRNAs bind to target RNA and modulate its function or expression. Delivery of siRNA expressing vectors can be systemic, such as by intravenous or intramuscular administration, by administration to target cells ex-planted from the patient followed by reintroduction into the patient, or by any other means that allows for introduction into a desired target cell.

SiRNA expression DNA plasmids are typically transfected into target cells as a complex with cationic lipid carriers (e.g. Oligofectamine) or non-cationic lipid-based carriers (e.g. Transit-TKO™). Multiple lipid transfections for siRNA-mediated knockdowns targeting different regions of a single target gene or multiple target genes over a period of a week or more are also contemplated by the present invention. Successful introduction of the vectors of the invention into host cells can be monitored using various known methods. For example, transient transfection. can be signaled with a reporter, such as a fluorescent marker, such as Green Fluorescent Protein (GFP). Stable transfection. of ex vivo cells can be ensured using markers that provide the transfected cell with resistance to specific environmental factors (e.g., antibiotics and drugs), such as hygromycin B resistance.

For a review of techniques that can be used to generate and assess transgenic animals, skilled artisans can consult Gordon (IwL Rev. CytoL 1 1 5:171-229, 1989), and may obtain additional guidance from, for example: Hogan et al. "Manipulating the Mouse Embryo" (Cold Spring Harbor Press, Cold Spring Harbor, N.Y., 1986; Krimpenfort et al., BiolTechnology 9:86, 1991; Palmiter et al., Cell 41:343, 1985; Kraemer et al., "Genetic Manipulation of the Early Mammalian Embryo," Cold Spring Harbor Press, Cold Spring Harbor, N.Y., 1985; Hammer et al., Nature 315:680, 1985; Purcel et al., Science, 244:1281, 1986; Wagner et al., U.S. Pat. No. 5,175,385; and Krimpenfort et al., U.S. Pat. No. 5,175,384.

The EGFR-specific siRNAs described above can also be generally inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Example 7

Method of Determining an Effective Dose of a siRNA

A therapeutically effective amount of a composition containing a sequence that encodes an EGFR-specific siRNA, (i.e., an effective dosage), is an amount that inhibits expression of the polypeptide encoded by the EGFR target gene by at least 10 percent. Higher percentages of inhibition, e.g., 15, 20, 30, 40, 50, 75, 85, 90 percent or higher may be preferred in certain embodiments. Exemplary doses include milligram or microgram amounts of the molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). The compositions can be administered one time per week for between about 1 to 10 weeks, e.g., between 2 to 8 weeks, or between about 3 to 7 weeks, or for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. In some cases transient expression of the siRNA may be desired. When an inducible promoter is included in the construct encoding an siRNA, expression is assayed upon delivery to the subject of an appropriate dose of the substance used to induce expression.

Appropriate doses of a composition depend upon the potency of the molecule (the sequence encoding the siRNA) with respect to the expression or activity to be modulated. One or more of these molecules can be administered to an animal (e.g., a human) to modulate expression or activity of one or more target polypeptides. A physician may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The efficacy of treatment can be monitored either by measuring the amount of the target gene mRNA (e.g. using real time PCR) or the amount of polypeptide encoded by the target gene mRNA (Western blot analysis). In addition, the attending physician will monitor the symptoms associated with the disease or disorder afflicting the patient and compare with those symptoms recorded prior to the initiation of siRNA treatment.

Example 8

Inhibiting Expression of Multi-Drug Resistance Gene 1 (MDR1) Using a MDR-1 Specific siRNA Inhibition of MDR1 expression by MDR-1 specific siRNA was tested using the colon cancer cell line LS174T (ATCC—American Type Culture Collection; Tom et al., 1976). Expression of MDR1 in this cell line is inducible by adding rifampicin to the culture medium (Geick et al., 2001). Cells were transfected with MDR-1 specific siRNA using a variety of commercially available transfection kits (Lipofectamine, Oligofectamine, both from Invitrogen; TransMessenger, Qiagen), of which the TransMessenger kit proved to be the most suitable for this cell line.

Four short double-stranded ribonucleic acids (R1-R4) were tested (see Table 4). The ribonucleic acids are homologous with segments of the coding sequence of MDR1 (SEQ ID NO:30). Sequences R1-R3 consist of a 22-mer sense strand and a 24-mer antisense strand, whereby the resulting double strand exhibits a 2-nucleotide overhang at its 3'-end (0-22-2).

Sequence R4 corresponds to R1; however it consists of a 19-mer double-stranded, each with 2-nucleotide overhangs at each 3'-end (2-19-2).

TABLE 4

| Name | SEQ ID NO. | Sequence | Position in Data bank-# AF016535 |
|------|------------|----------|-----------------------------------|
| Seq R1 | SEQ ID NO: 141 | 5'-CCA UCU CGA AAA GAA GUU AAG A-3' | 1320-1342 |
|        | SEQ ID NO: 142 | 3'-UG GGU AGA CGU UUU CUU CAA UUC U-5' | 1335-1318 |
| Seq R2 | SEQ ID NO: 143 | 5'-UAU AGG UUC CAG GCU UGC UGU A-3' | 2599-2621 |
|        | SEQ ID NO: 152 | 3'-CG AUA UCC AAG GUC CGA ACG ACA U-5' | 2621-2597 |
| Seq R3 | SEQ ID NO: 144 | 5'-CCA GAG AAG GCC GCA CCU GCA U-3' | 3778-3799 |
|        | SEQ ID NO: 145 | 3'-UC GGU CUC UUC CGG CGU GGA CGU A-5' | 3799-3776 |
| Seq R4 | SEQ ID NO: 146 | 5'-CCA UUC CGA AAA GAA GUU AAG-3' | 1320-1341 |
|        | SEQ ID NO: 147 | 3'-UG GGU AGA GCU UUU CUU CAA U -5' | 1339-1318 |
|        |            |          | Position in Data bank-# AF402779 |
| KIA/ | SEQ ID NO: 153 | 5'-ACA GGA UGA GGA UCG UUU CGC A-3' | 2829-2808 |
| K2B  | SEQ ID NO: 158 | 3'-UC UGU CCU ACU CCU AGC AAA GCG U-5' | 2808-2831 |

The sequences shown in Table 4 are designated as sequences SEQ ID NOS:141-147, 152, 153, and 158 in the sequence listing. Cells were first seeded in 12-well plates at $3.8 \times 10^5$ cells/well. A day later, dsRNA was transfected into the cells in duplicate at a concentration of 175 nM. For each transfection assay, 93.3 μl EC-R buffer (TransMessenger kits, Qiagen, Hilden) was mixed with 3.2 μl Enhancer R prior to the addition of 3.5 μl of the particular 20 μM dsRNA, mixed well, and incubated for 5 minutes at room temperature. After the addition of 6 μl TransMessenger transfection reagent, the transfection assay was mixed vigorously for 10 seconds, and then incubated for a further 10 minutes at room temperature. The cells were then washed once with PBS (phosphate-buffered saline), and 200 μl fresh medium without FCS was added to the cells in each well. After 10-minute incubation, 100 μl FCS-free medium was pipetted into each transfection assay, mixed, and the mixture was then pipetted drop by drop onto the cells (the dsRNA concentration of 175 μM relates to 400 μl medium total volume). The dsRNA/TransMessenger complexes were incubated with the cells for 4 hours at 37° C. in FCS-free medium. The medium was then changed and replaced with fresh medium containing 10 μM rifampin and 10% FCS. A non-specific dsRNA sequence that exhibits no homologies with the MDR1 gene sequence was used (K) as a control, and a MOCK transfection was conducted that contained all reagents except for dsRNA.

The cells were harvested after 24, 48, and 72 hours, and total RNA was extracted with the RNeasy mini kit from Qiagen. 10 μg total protein from each sample was then separated by electrophoresis on a 1% agarose-formaldehyde gel, blotted on a nylon membrane, and then hybridized as an internal control with specific probes that had been randomly marked with $5'$-$\alpha^{32}$p-dCTP, first against MDR1, and after the blot had been stripped, against GAPDH, and then exposed on x-ray film. The x-ray film was digitized (Image Master, VDS, Pharmacia) and quantified using Image-Quant software and standardized against the GAPDH signal.

Figure 25A:
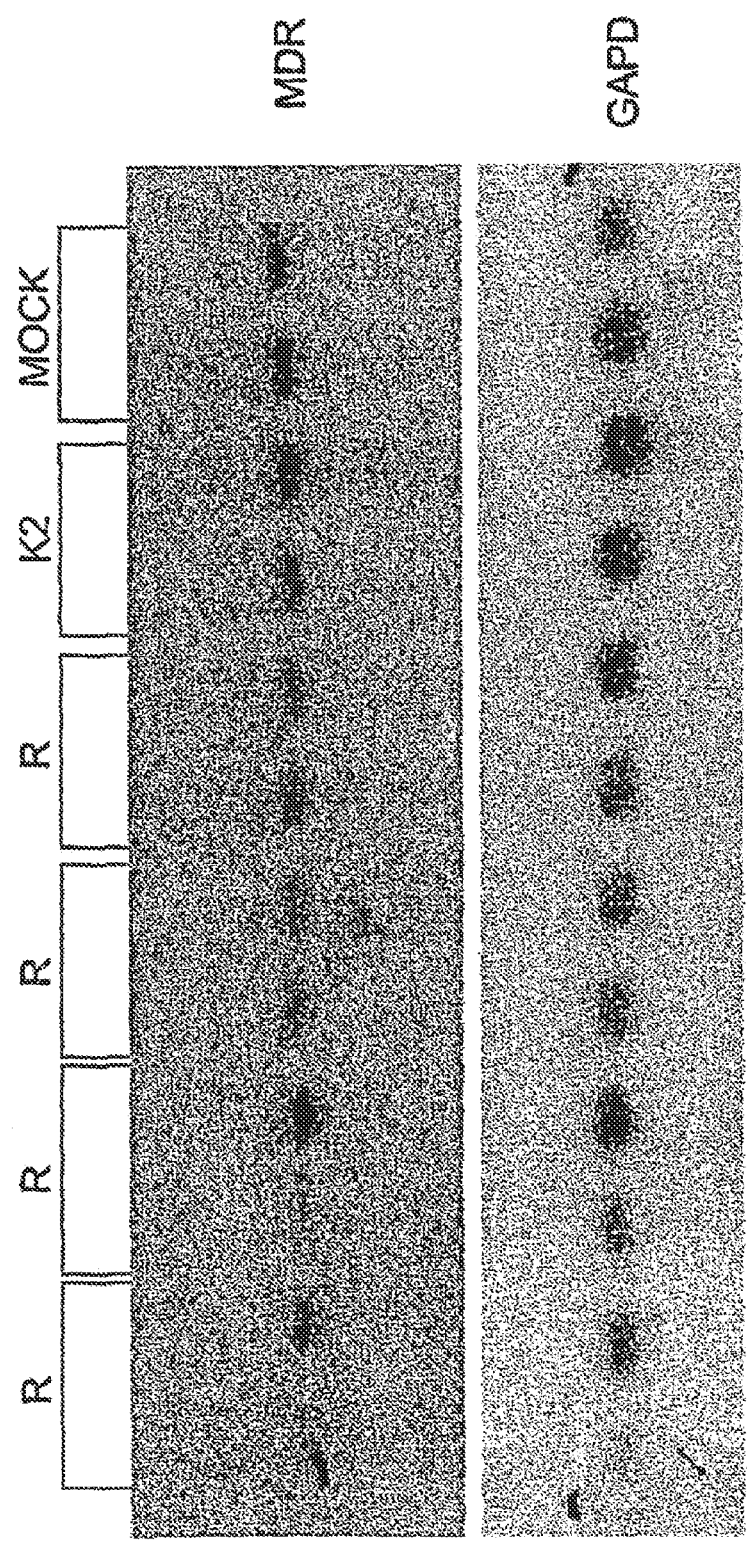
FIG. 25a shows a Northern blot analysis of the MDRI mRNA level in colon carcinoma cell line LSI74T, whereby the cells were harvested after 74 hours.
Figure 25B:
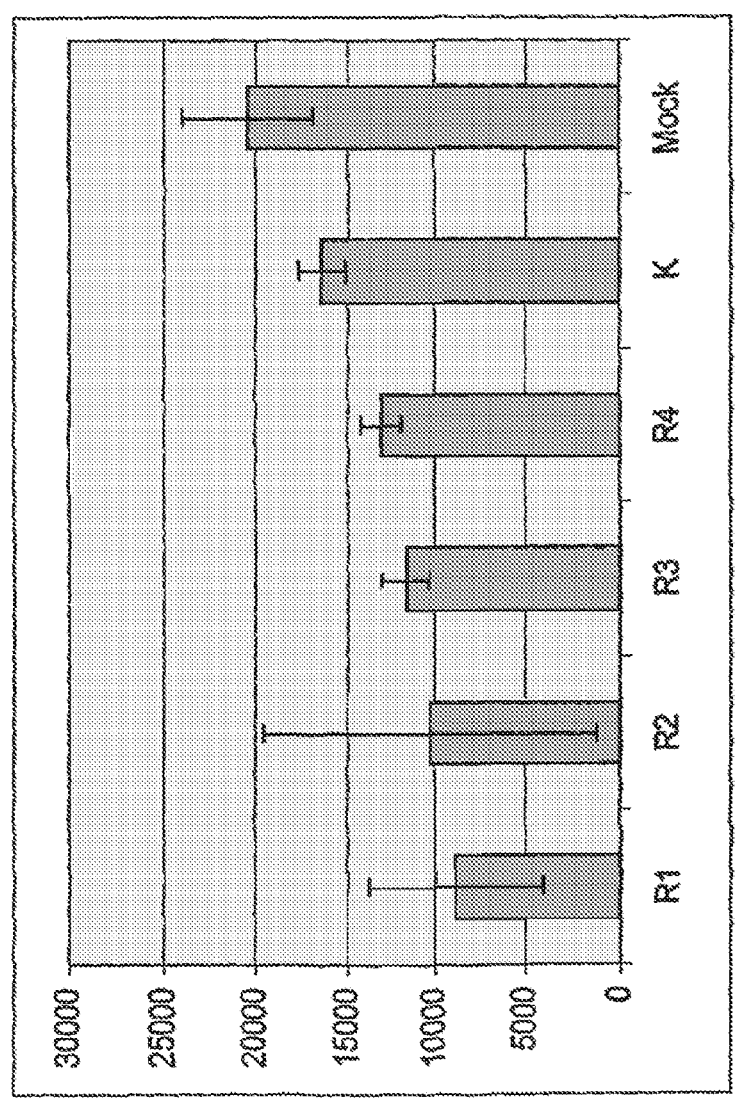
FIG. 25b shows quantification of the bands in FIG. 25a, whereby the averages are represented by two values.
Figure 26A:
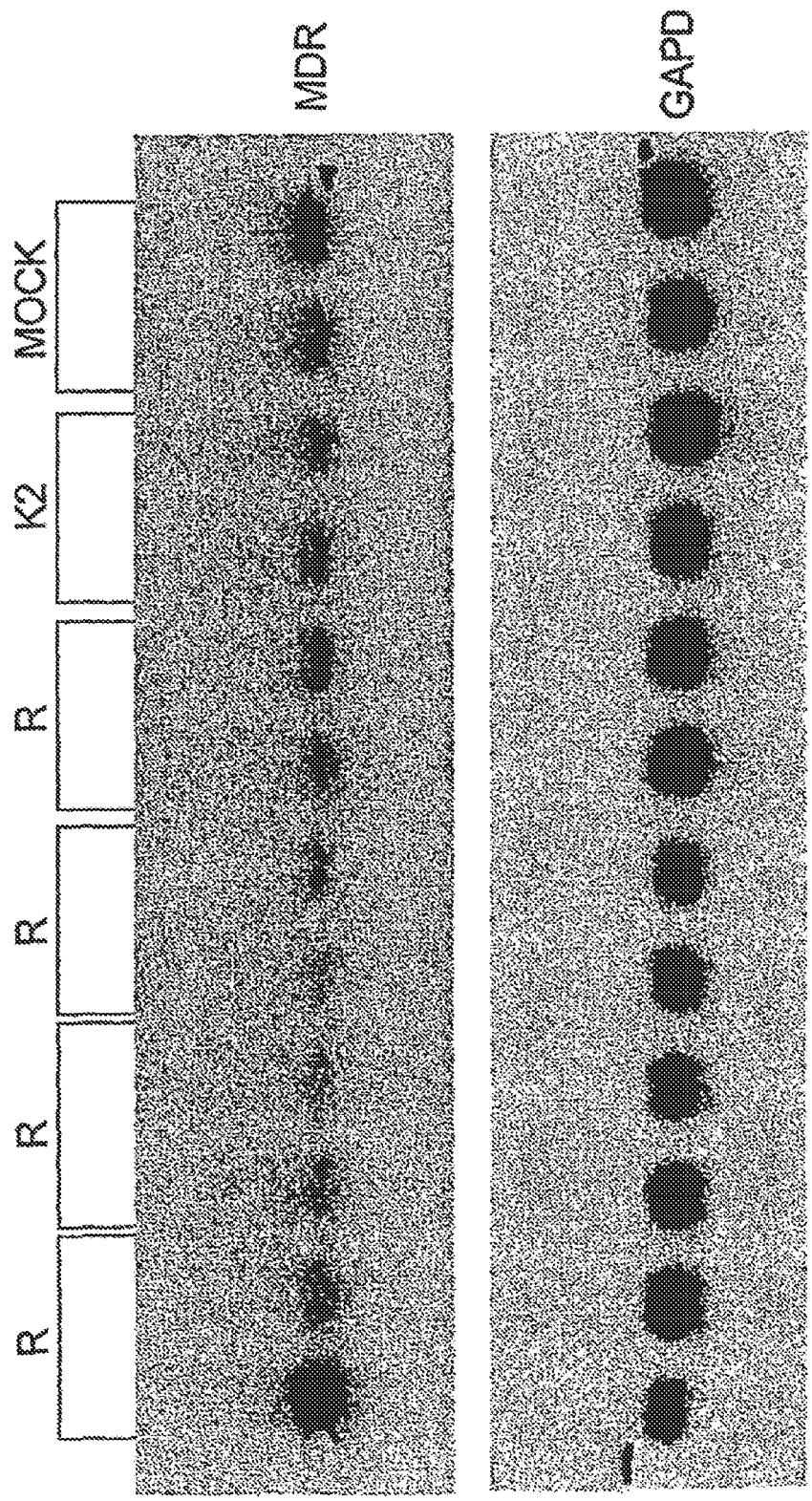
FIG. 26a shows a Northern blot analysis of the MDRI mRNA level in colon carcinoma cell line LS174T, whereby the cells were harvested after 48 hours.
Figure 26B:
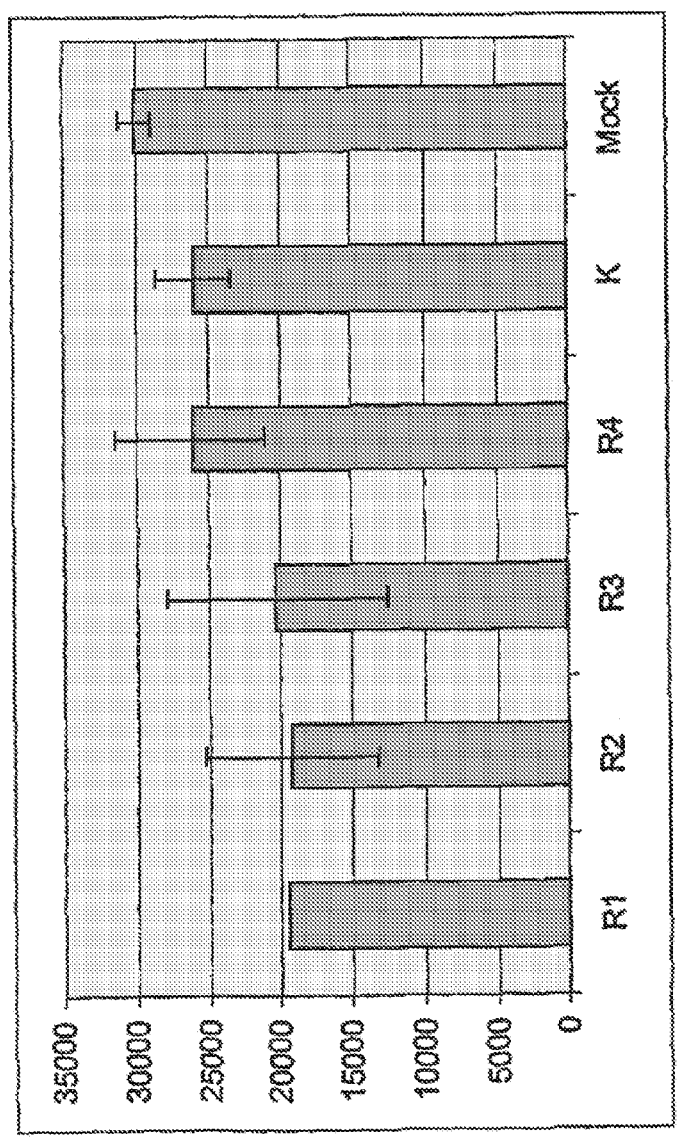
FIG. 26b shows quantification of the bands in FIG. 26a, whereby the averages are represented by two values.

FIGS. 25 and 26 show Northern blots (FIGS. 26a, 26a) with quantitative analysis of the MDR1-specific signal after adjustment with the corresponding GAPDH values (FIGS. 25b, 26p). A reduction in the MDR1-mRNA by as much as 55% was observed in comparison to the MOCK transfection, and by as much as 45% in comparison to the nonspecific control transfection. After 48 hours there was a significant reduction in the MDR1-mRNA level in the dsRNA constructs designated as R1, R2, and R3 (Table 4). With the R4 dsRNA constructs, no significant reduction compared to controls was observed after 48 hours (FIGS. 26a and 26b). After 74 hours, there was an even stronger reduction in MDR1-mRNA levels in the presence of R1, R2, and R3 as compared to the values observed at 48 hours (FIGS. 25a and 26b). A significant decrease in the MDR1-mRNA level was seen at this time with R4 as well. Thus, the constructs with a 2nt overhang at the 3'-end of the antisense strand and a double-stranded region consisting of 22 nucleotide pairs reduces the MDR1-mRNA level more efficiently than do constructs with 2nt overhangs at the 3'-end of both strands (antisense strand and sense strand) and a double-stranded region consisting of 19 nucleotide pairs, apparently independent of the sequence region homologous to the MDR1 gene in each case (after 48 hours; FIG. 26b). The results strengthen the findings in Example IV, which describe the inhibition of EGFR gene expression by means of specific dsRNAs after transfection in U-87 MG cells.

Transfection efficiency was determined in a separate experiment with the help of a DNA oligonucleotide marked with Texas red (TexRed-A[GATC]$_5$T; also transfected with 175 nM) (FIGS. 27a, 27b; 400× enlargement, 48 hours after transfection). Transfection efficiency was approximately 50% on the basis of red fluorescent cells in comparison to total cell number. If one takes the transfection rate of cells of approximately 50% into consideration, then the observed decrease in the MDR1-mRNA level by approximately 45-55% (compared with the controls) indicates that MDR1-mRNA was almost completely and specifically broken down in all cells that were successfully transfected with specific dsRNA.

SEQUENCE LISTING

```
<160> NUMBER OF SEQ ID NOS: 173

<210> SEQ ID NO 1
<211> LENGTH: 2955
<212> TYPE: DNA
<213> ORGANISM: Homo sapiens
<300> PUBLICATION INFORMATION:
<302> TITLE: Eph A1
<310> PATENT DOCUMENT NUMBER: NM00532

<400> SEQUENCE: 1
atggagcggc gctggcccct ggggctaggg ctggtgctgc tgctctgcgc cccgctgccc        60 ccggggcgc gcgccaagga agttactctg atggacacaa gcaaggcaca gggagagctg       120
ggctggctgc tggatccccc aaaagatggg tggagtgaac agcaacagat actgaatggg       180 acaccctct acatgtacca ggactgccca atgcaaggac gcagagacac tgaccactgg       240
cttcgctcca attggatcta ccgcggggag gaggcttccc gcgtccacgt ggagctgcag       300
ttcaccgtgc gggactgcaa gagtttccct ggggagccg ggcctctggg ctgcaaggag       360
accttcaacc ttctgtacat ggagagtgac caggatgtgg gcattcagct ccgacggccc       420
ttgttccaga aggtaaccac ggtggctgca gaccagagct tcaccattcg agaccttgcg       480
```

-continued

```
tctggctccg tgaagctgaa tgtggagcgc tgctctctgg gccgcctgac ccgccgtggc    540
ctctacctcg ctttccacaa cccgggtgcc tgtgtggccc tggtgtctgt ccgggtcttc    600
taccagcgct gtcctgagac cctgaatggc ttggcccaat cccagacac tctgcctggc     660
cccgctgggt tggtggaagt ggcgggcacc tgcttgcccc acgcgcgggc cagccccagg    720
ccctcaggtg caccccgcat gcactgcagc cctgatggcg agtggctggt gcctgtagga    780
cggtgccact gtgagcctgg ctatgaggaa ggtggcagtg gcgaagcatg tgttgcctgc    840
cctagcggct cctaccggat ggacatggac acccccatt gtctcacgtg ccccagcag     900
agcactgctg agtctgaggg ggccaccatc tgtacctgtg agagcggcca ttacagagct    960
cccggggagg gcccccaggt ggcatgcaca ggtccccct cggcccccg aaacctgagc     1020
ttctctgcct cagggactca gctctccctg cgttgggaac ccccagcaga tacgggggga    1080
cgccaggatg tcagatacag tgtgaggtgt tcccagtgtc agggcacagc acaggacggg    1140
gggccctgcc agccctgtgg ggtgggcgtg cacttctcgc cggggggccg ggcgctcacc    1200
acacctgcag tgcatgtcaa tggccttgaa ccttatgcca actacacctt taatgtggaa    1260
gcccaaaatg gagtgtcagg gctgggcagc tctggccatg ccagcacctc agtcagcatc    1320
agcatggggc atgcagagtc actgtcaggc ctgtctctga ctggtgaa gaaagaaccg      1380
aggcaactag agctgacctg ggcggggtcc cggccccgaa gccctggggc gaacctgacc    1440
tatgagctgc acgtgctgaa ccaggatgaa gaacggtacc agatggttct agaacccagg    1500
gtcttgctga cagagctgca gcctgacacc acatacatcg tcagagtccg aatgctgacc    1560
ccactgggtc ctggccctt ctcccctgat catgagtttc ggaccagccc accagtgtcc     1620
aggggcctga ctggaggaga gattgtagcc gtcatctttg ggctgctgct tggtgcagcc    1680
ttgctgcttg ggattctcgt tttccggtcc aggagagccc agcggcagag gcagcagagg    1740
cacgtgaccg cgccaccgat gtggatcgag aggacaagct gtgctgaagc cttatgtggt    1800
acctccaggc atacgaggac cctgcacagg gagccttgga cttcacccgg aggctggtct    1860
aattttcctt cccgggagct tgatccagcg tggctgatgg tggacactgt cataggagaa    1920
ggagagtttg gggaagtgta tcagggacc ctcaggctcc ccagccagga ctgcaagact     1980
gtggccatta agaccttaaa agacacatcc ccaggtggcc agtggtggaa cttccttcga    2040
gaggcaacta tcatgggcca gtttagccac ccgcatattc tgcatctgga aggcgtcgtc    2100
acaaagcgaa agccgatcat gatcatcaca gaatttatgg agaatgcagc cctggatgcc    2160
ttcctgaggg agcgggagga ccagctggtc cctgggcagc tagtggccat gctgcagggc    2220
atagcatctg gcatgaacta cctcagtaat cacaattatg tccaccggga cctggctgcc    2280
agaaacatct tggtgaatca aaacctgtgc tgcaaggtgt ctgactttgg cctgactcgc    2340
ctcctggatg actttgatgg cacatacgaa acccaggag gaaagatccc tatccgttgg    2400
acagcccctg aagccattgc ccatcggatc ttcaccacag ccagcgatgt gtggagccttt   2460
gggattgtga tgtgggaggt gctgagcttt ggggacaagc cttatgggga gatgagcaat    2520
caggaggtta tgaagagcat tgaggatggg taccggttgc cccctcctgt ggactgccct    2580
gccctctgt atgagctcat gaagaactgc tgggcatatg accgtgcccg ccggccacac    2640
ttccagaagc ttcaggcaca tctggagcaa ctgcttgcca ccccactc cctgcggacc      2700
attgccaact tgacccccag ggtgactctt cgcctgccca gcctgagtgg ctcagatggg    2760
atcccgtatc gaaccgtctc tgagtggctc gagtccatac gcatgaaacg ctacatcctg    2820
cacttccact cggctgggct ggacaccatg gagtgtgtgc tggagctgac cgctgaggac    2880
```

```
ctgacgcaga tgggaatcac actgcccggg caccagaagc gcattctttg cagtattcag   2940
ggattcaagg actga                                                    2955

<210> SEQ ID NO 2
<211> LENGTH: 3042
<212> TYPE: DNA
<213> ORGANISM: Homo sapiens
<300> PUBLICATION INFORMATION:
<302> TITLE: ephrin A2
<310> PATENT DOCUMENT NUMBER: XM002088

<400> SEQUENCE: 2
gaagttgcgc gcaggccggc gggcgggagc ggacaccgag gccggcgtgc aggcgtgcgg     60
gtgtgcggga ccgggctcg  gggggatcgg accgagagcg agaagcgcgg catggagctc    120
caggcagccc gcgcctgctt cgccctgctg tggggctgtg cgctggccgc ggccgcggcg    180
gcgcagggca aggaagtggt actgctggac tttgctgcag ctggagggga gctcggctgg    240
ctcacacacc cgtatggcaa agggtgggac ctgatgcaga acatcatgaa tgacatgccg    300
atctacatgt actccgtgtg caacgtgatg tctggcgacc aggacaactg gctccgcacc    360
aactgggtgt accgaggaga ggctgagcgt atcttcattg agctcaagtt tactgtacgt    420
gactgcaaca gcttccctgg tggcgccagc tcctgcaagg agactttcaa cctctactat    480
gccgagtcgg acctggacta cggcaccaac ttccagaagc gcctgttcac caagattgac    540
accattgcgc ccgatgagat caccgtcagc agcgacttcg aggcacgcca cgtgaagctg    600
aacgtggagg agcgctccgt ggggccgctc acccgcaaag gcttctacct ggccttccag    660
gatatcggtg cctgtgtggc gctgctctcc gtccgtgtct actacaagaa gtgccccgag    720
ctgctgcagg gctggccca  cttccctgag accatcgccg gctctgatgc accttccctg    780
gccactgtgg ccggcacctg tgtggaccat gccgtggtgc accgggggg  tgaagagccc    840 cgtatgcact gtgcagtgga tggcgagtgg ctggtgccca ttgggcagtg cctgtgccag    900
gcaggctacg agaaggtgga ggatgcctgc caggcctgct cgcctggatt ttttaagttt    960
gaggcatctg agagcccctg cttggagtgc cctgagcaca cgctgccatc ccctgagggt   1020
gccacctcct gcgagtgtga ggaaggcttc ttccggggcac ctcaggaccc agcgtcgatg   1080
ccttgcacac gaccccccctc cgccccacac tacctcacag ccgtgggcat gggtgccaag   1140
gtggagctgc gctggacgcc ccctcaggac agcgggggcc gcgaggacat tgtctacagc   1200
gtcacctgcg aacagtgctg gcccgagtct ggggaatgcg gccgtgtga  ggccagtgtg   1260 cgctactcgg agcctcctca cggactgacc cgcaccagtg tgacagtgag cgacctggag   1320
ccccacatga actacacctt caccgtggag gcccgcaatg gcgtctcagg cctggtaacc   1380
agccgcagct tccgtactgc cagtgtcagc atcaaccaga cagagccccc caaggtgagg   1440
ctggagggcc gcagcaccac ctcgcttagc gtctcctgga gcatcccccc gccgcagcag   1500
agccgagtgt ggaagtacga ggtcacttac cgcaagaagg gagactccaa cagctacaat   1560
gtgcgccgca ccgagggttt ctccgtgacc ctggacgacc tggcccccaga caccacctac   1620 ctggtccagg tgcaggcact gacgcaggag ggccagggg  ccggcagcaa ggtgcacgaa   1680
ttccagacgc tgtccccgga gggatctggc aacttggcgg tgattggcgg cgtggctgtc   1740
ggtgtggtcc tgcttctggt gctggcagga gttggcttct ttatccaccg caggaggaag   1800
aaccagcgtg cccgccagtc cccggaggac gtttacttct ccaagtcaga acaactgaag   1860
cccctgaaga catacgtgga cccccacaca tatgaggacc ccaaccaggc tgtgttgaag   1920
```

| | |
|---|---|
| ttcactaccg agatccatcc atcctgtgtc actcggcaga aggtgatcgg agcaggagag | 1980 |
| tttggggagg tgtacaaggg catgctgaag acatcctcgg ggaagaagga ggtgccggtg | 2040 |
| gccatcaaga cgctgaaagc cggctacaca gagaagcagc gagtggactt cctcggcgag | 2100 |
| gccggcatca tgggccagtt cagccaccac aacatcatcc gcctagaggg cgtcatctcc | 2160 |
| aaatacaagc ccatgatgat catcactgag tacatggaga tgggggccct ggacaagttc | 2220 |
| cttcgggaga aggatggcga gttcagcgtg ctgcagctgg tgggcatgct gcggggcatc | 2280 |
| gcagctggca tgaagtacct ggccaacatg aactatgtgc accgtgacct ggctgcccgc | 2340 |
| aacatcctcg tcaacagcaa cctggtctgc aaggtgtctg actttggcct gtcccgcgtg | 2400 |
| ctggaggacg accccgaggc cacctacacc accagtggcg gcaagatccc catccgctgg | 2460 |
| accgccccgg aggccatttc ctaccggaag ttcacctctg ccagcgacgt gtggagcttt | 2520 |
| ggcattgtca tgtgggaggt gatgacctat ggcgagcggc cctactggga gttgtccaac | 2580 |
| cacgaggtga tgaaagccat caatgatggc ttccggctcc ccacacccat ggactgcccc | 2640 |
| tccgccatct accagctcat gatgcagtgc tggcagcagg agcgtgcccg ccgccccaag | 2700 |
| ttcgctgaca tcgtcagcat cctggacaag ctcattcgtg cccctgactc cctcaagacc | 2760 |
| ctggctgact ttgaccccgc gtgtctatc cggctcccca gcacgagcgg ctcggagggg | 2820 |
| gtgcccttcc gcacggtgtc cgagtggctg gagtccatca gatgcagca gtatacggag | 2880 |
| cacttcatgg cggccggcta cactgccatc gagaaggtgg tgcagatgac caacgacgac | 2940 |
| atcaagagga ttggggtgcg gctgcccggc caccagaagc gcatcgccta cagcctgctg | 3000 |
| ggactcaagg accaggtgaa cactgtgggg atccccatct ga | 3042 |

<210> SEQ ID NO 3
<211> LENGTH: 2953
<212> TYPE: DNA
<213> ORGANISM: Homo sapiens
<300> PUBLICATION INFORMATION:
<302> TITLE: ephrin A3
<310> PATENT DOCUMENT NUMBER: NM005233

<400> SEQUENCE: 3

| | |
|---|---|
| atggattgtc agctctccat cctcctcctt ctcagctgct ctgttctcga cagcttcggg | 60 |
| gaactgattc cgcagccttc caatgaagtc aatctactgg attcaaaaac aattcaaggg | 120 |
| gagctgggct ggatctctta tccatcacat gggtgggaag agatcagtgg tgtggatgaa | 180 |
| cattacacac ccatcaggac ttaccaggtg tgcaatgtca tggaccacag tcaaaacaat | 240 |
| tggctgagaa caaactgggt ccccaggaac tcagctcaga gatttatgt ggagctcaag | 300 |
| ttcactctac gagactgcaa tagcattcca ttggttttag aacttgcaa ggagacattc | 360 |
| aacctgtact acatggagtc tgatgatgat catggggtga atttcgaga gcatcagttt | 420 |
| acaaagattg acaccattgc agctgatgaa agtttcactc aaatggatct tggggaccgt | 480 |
| attctgaagc tcaacactga gattagaaa gtaggtcctg tcaacaagaa gggatttat | 540 |
| ttggcatttc aagatgttgg tgcttgtgtt gccttggtgt ctgtgagagt atacttcaaa | 600 |
| aagtgcccat ttcagtgaa gaatctggct atgtttccag acacggtacc catgactcc | 660 |
| cagtccctgg tggaggttag agggtcttgt gtcaacaatt ctaaggagga agatcctcca | 720 |
| aggatgtact gcagtacaga aggcgaatgg cttgtaccca ttggcaagtg ttcctgcaat | 780 |
| gctggctatg aagaagagg ttttatgtgc caagcttgtc gaccaggttt ctacaaggca | 840 |
| ttggatggta atatgaagtg tgctaagtgc ccgcctcaca gttctactca ggaagatggt | 900 |

```
tcaatgaact gcaggtgtga gaataattac ttccgggcag acaaagaccc tccatccatg    960
gcttgtaccc gacctccatc ttcaccaaga aatgttatct ctaatataaa cgagacctca   1020
gttatcctgg actggagttg gcccctggac acaggaggcc ggaaagatgt taccttcaac   1080
atcatatgta aaaaatgtgg gtggaatata aacagtgtg agccatgcag cccaaatgtc    1140
cgcttcctcc ctcgacagtt tggactcacc aacaccacgg tgacagtgac agaccttctg   1200
gcacatacta actacacctt tgagattgat gccgttaatg gggtgtcaga gctgagctcc   1260
ccaccaagac agtttgctgc ggtcagcatc acaactaatc aggctgctcc atcacctgtc   1320
ctgacgatta agaaagatcg gacctccaga aatagcatct ctttgtcctg caagaacct    1380 gaacatccta atgggatcat attggactac gaggtcaaat actatgaaaa gcaggaacaa   1440
gaaacaagtt ataccattct gagggcaaga ggcacaaatg ttaccatcag tagcctcaag   1500
cctgacacta tatacgtatt ccaaatccga gcccgaacag ccgctggata tgggacgaac   1560
agccgcaagt ttgagtttga aactagtcca gactctttct ccatctctgg tgaaagtagc   1620
caagtggtca tgatcgccat ttcagcggca gtagcaatta ttctcctcac tgttgtcatc   1680
tatgttttga ttgggaggtt ctgtggctat aagtcaaaac atggggcaga tgaaaaaaga   1740
cttcattttg gcaatgggca tttaaaactt ccaggtctca ggacttatgt tgacccacat   1800
acatatgaag accctaccca agctgttcat gagtttgcca aggaattgga tgccaccaac   1860
atatccattg ataaagttgt tggagcaggt gaatttggag aggtgtgcag tggtcgctta   1920
aaacttcctt caaaaaaaga gatttcagtg gccattaaaa ccctgaaagt tggctacaca   1980
gaaaagcaga ggagagactt cctgggagaa gcaagcatta tgggacagtt tgaccacccc   2040
aatatcattc gactggaagg agttgttacc aaaagtaagc cagttatgat tgtcacagaa   2100
tacatggaga atggttcctt ggatagtttc ctacgtaaac acgatgccca gtttactgtc   2160
attcagctag tggggatgct tcgagggata gcatctggca tgaagtacct gtcagacatg   2220
ggctatgttc accgagacct cgctgctcgg aacatcttga tcaacagtaa cttggtgtgt   2280
aaggtttctg atttcggact ttcgcgtgtc ctggaggatg acccagaagc tgcttataca   2340
acaagaggag ggaagatccc aatcaggtgg acatcaccag aagctatagc ctaccgcaag   2400
ttcacgtcag ccagcgatgt atggagttat gggattgttc tctgggaggt gatgtcttat   2460
ggagagagac atactgggga gatgtccaat caggatgtaa ttaaagctgt agatgagggc   2520
tatcgactgc caccccccat ggactgccca gctgccttgt atcagctgat gctggactgc   2580
tggcagaaaa acaggaacaa cagacccaag tttgagcaga ttgttagtat tctgacaag    2640 cttatccgga atcccggcag cctgaagatc atcaccagtg cagccgcaag gccatcaaac   2700
cttcttctgg accaaagcaa tgtggatatc tctaccttcc gcacaacagg tgactggctt   2760
aatggtgtcc ggacagcaca ctgcaaggaa atcttcacgg gcgtggagta cagttcttgt   2820
gacacaatag ccaagatttc cacagatgac atgaaaaagg ttggtgtcac cgtggttggg   2880
ccacagaaga agatcatcag tagcattaaa gctctagaaa cgcaatcaaa gaatggccca   2940
gttcccgtgt aaa                                                     2953
```

<210> SEQ ID NO 4
<211> LENGTH: 2784
<212> TYPE: DNA
<213> ORGANISM: Homo sapiens
<300> PUBLICATION INFORMATION:
<302> TITLE: ephrin A4
<310> PATENT DOCUMENT NUMBER: XM002578

<400> SEQUENCE: 4

```
atggatgaaa aaaatacacc aatccgaacc taccaagtgt gcaatgtgat ggaacccagc      60
cagaataact ggctacgaac tgattggatc acccgagaag gggctcagag ggtgtatatt     120
gagattaaat tcaccttgag ggactgcaat agtcttccgg cgtcatggg gacttgcaag      180
gagacgttta acctgtacta ctatgaatca gacaacgaca agagcgtttt catcagagag     240
aaccagtttg tcaaaattga caccattgct gctgatgaga gcttcaccca gtggacatt      300
ggtgacagaa tcatgaagct gaacaccgag atccgggatg tagggccatt aagcaaaaag     360
gggttttacc tggcttttca ggatgtgggg gcctgcatcg ccctggtatc agtccgtgtg     420
ttctataaaa agtgtccact cacagtccgc aatctggccc agtttcctga caccatcaca     480
ggggctgata cgtcttccct ggtggaagtt cgaggctcct gtgtcaacaa ctcagaagag     540
aaagatgtgc aaaaatgta ctgtggggca gatggtgaat ggctggtacc cattggcaac     600
tgcctatgca cgctgggca tgaggagcgg agcggagaat gccaagcttg caaaattgga    660
tattacaagg ctctctccac ggatgccacc tgtgccaagt gcccacccca gctactct      720
gtctgggaag gagccacctc gtgcacctgt gaccgaggct ttttcagagc tgacaacgat     780
gctgcctcta tgccctgcac ccgtccacca tctgctcccc tgaacttgat ttcaaatgtc     840
aacgagacat ctgtgaactt ggaatggagt agccctcaga atacaggtgg ccgccaggac     900
atttcctata atgtggtatg caagaaatgt ggagctggtg accccagcaa gtgccgaccc     960
tgtggaagtg gggtccacta cacccccacag cagaatggct tgaagaccac caaagtctcc    1020
atcactgacc tcctagctca taccaattac acctttgaaa tctggctgt gaatggagtg     1080
tccaaatata accctaaccc agaccaatca gtttctgtca ctgtgaccac caaccaagca     1140
gcaccatcat ccattgcttt ggtccaggct aaagaagtca aagatacag tgtggcactg     1200
gcttggctgg aaccagatcg gcccaatggg gtaatcctgg aatatgaagt caagtattat    1260
gagaaggatc agaatgagcg aagctatcgt atagttcgga cagctgccag gaacacagat    1320
atcaaaggcc tgaaccctct cacttcctat gtttttccacg tgcgagccag acagcagct    1380
ggctatggag acttcagtga gcccttggag gttacaacca acacagtgcc ttcccggatc    1440
attggagatg ggctaactc cacagtcctt ctggtctctg tctcgggcag tgtggtgctg    1500
gtggtaattc tcattgcagc ttttgtcatc agccggagac gggagtaaata cagtaaagcc    1560
aaacaagaag cggatgaaga gaaacatttg aatcaaggtg taagaacata tgtggacccc    1620
tttacgtacg aagatcccaa ccaagcagtg cgagagtttg ccaaagaaat tgacgcatcc    1680
tgcattaaga ttgaaaaagt tataggagtt ggtgaatttg gtgaggtatg cagtgggcgt    1740
ctcaaagtgc ctggcaagag agatctgt gtggctatca agactctgaa agctggttat    1800
acagacaaac agaggagaga cttcctgagt gaggccagca tcatgggaca gtttgaccat    1860
ccgaacatca ttcacttgga aggcgtggtc actaaatgta aaccagtaat gatcataaca    1920
gagtacatgg agaatggctc cttggatgca ttcctcagga aaaatgatgg cagatttaca    1980
gtcattcagc tggtgggcat gcttcgtggc attgggtctg gatgaagta tttatctgat    2040
atgagctatg tgcatcgtga tctggccgca cggaacatcc tggtgaacag caacttggtc    2100
tgcaaagtgt ctgattttgg catgtcccga gtgcttgagg atgatccgga agcagcttac    2160
accaccaggg gtggcaagat tcctatccgg tggactgcgc cagaagcaat tgcctatcgt    2220
aaattcacat cagcaagtga tgtatggagc tatggaatcg ttatgtggga agtgatgtcg    2280
```

-continued

| | |
|---|---|
| tacggggaga ggccctattg ggatatgtcc aatcaagatg tgattaaagc cattgaggaa | 2340 |
| ggctatcggt tacccctcc aatggactgc cccattgcgc tccaccagct gatgctagac | 2400 |
| tgctggcaga aggagaggag cgacaggcct aaatttgggc agattgtcaa catgttggac | 2460 |
| aaactcatcc gcaaccccaa cagcttgaag aggacaggga cggagagctc cagacctaac | 2520 |
| actgccttgt tggatccaag ctcccctgaa ttctctgctg tggtatcagt gggcgattgg | 2580 |
| ctccaggcca ttaaaatgga ccggtataag gataacttca cagctgctgg ttataccaca | 2640 |
| ctagaggctg tggtgcacgt gaaccaggag gacctggcaa gaattggtat cacagccatc | 2700 |
| acgcaccaga ataagatttt gagcagtgtc caggcaatgc gaacccaaat gcagcagatg | 2760 |
| cacggcagaa tggttcccgt ctga | 2784 |

<210> SEQ ID NO 5
<211> LENGTH: 2997
<212> TYPE: DNA
<213> ORGANISM: Homo sapiens
<300> PUBLICATION INFORMATION:
<302> TITLE: ephrin A7
<310> PATENT DOCUMENT NUMBER: XM004485

<400> SEQUENCE: 5

| | |
|---|---|
| atggttttc aaactcggta cccttcatgg attattttat gctacatctg gctgctccgc | 60 |
| tttgcacaca caggggaggc gcaggctgcg aaggaagtac tactgctgga ttctaaagca | 120 |
| caacaaacag agttggagtg gatttcctct ccacccaatg ggtgggaaga aattagtggt | 180 |
| ttggatgaga actataccc gatacgaaca taccaggtgt gccaagtcat ggagcccaac | 240 |
| caaaacaact ggctgcggac taactggatt tccaaaggca atgcacaaag gattttttgta | 300 |
| gaattgaaat tcaccctgag ggattgtaac agtcttcctg gagtactggg aacttgcaag | 360 |
| gaaacatttta atttgtacta ttatgaaaca gactatgaca ctggcaggaa ataagagaa | 420 |
| aacctctatg taaaaataga caccattgct gcagatgaaa gtttacccca aggtgacctt | 480 |
| ggtgaaagaa agatgaagct taacactgag gtgagagaga ttggacctt gtccaaaaag | 540 |
| ggattctatc ttgcctttca ggatgtaggg gcttgcatag cttggttttc tgtcaaagtg | 600 |
| tactacaaga agtgctggtc cattattgag aacttagcta tctttccaga tacagtgact | 660 |
| ggttcagaat tttcctcttt agtcgaggtt cgagggacat gtgtcagcag tgcagaggaa | 720 |
| gaagcggaaa acgcccccag gatgcactgc agtgcagaag gagaatggtt agtgcccatt | 780 |
| ggaaaatgta tctgcaaagc aggctaccag caaaaggag acacttgtga accctgtggc | 840 |
| cgtgggttct acaagtcttc ctctcaagat cttcagtgct ctcgttgtcc aactcacagt | 900 |
| ttttctgata agaaggctc ctccagatgt gaatgtgaag atgggtatta cagggctcca | 960 |
| tctgacccac catacgttgc atgcacaagg cctccatctg caccacagaa cctcattttc | 1020 |
| aacatcaacc aaaccacagt aagtttggaa tggagtcctc ctgcagacaa tgggggaaga | 1080 |
| aacgatgtga cctacagaat attgtgtaag cggtgcagtt gggagcaggg cgaatgtgtt | 1140 |
| ccctgtggga gtaacattgg atacatgccc cagcagactg gattagagga taactatgtc | 1200 |
| actgtcatgg acctgctagc ccacgctaat tatactttg aagttgaagc tgtaaatgga | 1260 |
| gtttctgact taagccgatc ccagaggctc tttgctgctg tcagtatcac cactggtcaa | 1320 |
| gcagctccct cgcaagtgag tggagtaatg aaggagagag tactgcagcg gagtgtcgag | 1380 |
| ctttcctggc aggaaccaga gcatcccaat ggagtcatca cagaatatga aatcaagtat | 1440 |
| tacgagaaag atcaagggga acggacctac tcaacagtaa aaaccaagtc tacttcagcc | 1500 |

```
tccattaata atctgaaacc aggaacagtg tatgttttcc agattcgggc ttttactgct    1560
gctggttatg gaaattacag tcccagactt gatgttgcta cactagagga agctacaggt    1620
aaaatgtttg aagctacagc tgtctccagt gaacagaatc ctgttattat cattgctgtg    1680
gttgctgtag ctgggaccat cattttggtg ttcatggtct ttggcttcat cattgggaga    1740
aggcactgtg gttatagcaa agctgaccaa gaaggcgatg aagagcttta ctttcatttt    1800
aaatttccag gcaccaaaac ctacattgac cctgaaacct atgaggaccc aaatagagct    1860
gtccatcaat tcgccaagga gctagatgcc tcctgtatta aaattgagcg tgtgattggt    1920
gcaggagaat tcggtgaagt ctgcagtggc cgtttgaaac ttccagggaa agagatgtt    1980 gcagtagcca taaaaaccct gaaagttggt tacacagaaa acaaaggag agactttttg    2040 tgtgaagcaa gcatcatggg gcagtttgac cacccaaatg ttgtccattt ggaaggggtt    2100
gttacaagag ggaaaccagt catgatagta atagagttca tggaaaatgg agccctagat    2160
gcatttctca ggaaacatga tgggcaattt acagtcattc agttagtagg aatgctgaga    2220
ggaattgctg ctggaatgag atatttggct gatatgggat atgttcacag gaccttgca    2280 gctcgcaata ttcttgtcaa cagcaatctc gtttgtaaag tgtcagattt tggcctgtcc    2340
cgagttatag aggatgatcc agaagctgtc tatacaacta ctggtggaaa aattccagta    2400
aggtggacag cacccgaagc catccagtac cggaaattca catcagccag tgatgtatgg    2460
agctatggaa tagtcatgtg ggaagttatg tcttatggag aaagacctta ttgggacatg    2520
tcaaatcaag atgttataaa agcaatagaa gaaggttatc gtttaccagc acccatggac    2580
tgcccagctg gccttcacca gctaatgttg gattgttggc aaaaggagcg tgctgaaagg    2640
ccaaaatttg aacagatagt tggaattcta gacaaaatga ttcgaaaccc aaatagtctg    2700
aaaactcccc tgggaacttg tagtaggcca ataagccctc ttctggatca aaacactcct    2760
gatttcacta ccttttgttc agttggagaa tggctacaag ctattaagat ggaaagatat    2820
aaagataatt tcacggcagc tggctacaat tcccttgaat cagtagccag gatgactatt    2880
gaggatgtga tgagtttagg gatcacactg gttggtcatc aaaagaaaat catgagcagc    2940
attcagacta tgagagcaca aatgctacat ttacatggaa ctggcattca agtgtga     2997
```

<210> SEQ ID NO 6
<211> LENGTH: 3018
<212> TYPE: DNA
<213> ORGANISM: Homo sapiens
<220> FEATURE:
<221> NAME/KEY: CDS
<222> LOCATION: (1)..(3018)

<400> SEQUENCE: 6

```
atg gcc ccc gcc cgg ggc cgc ctg ccc cct gcg ctc tgg gtc gtc acg         48
Met Ala Pro Ala Arg Gly Arg Leu Pro Pro Ala Leu Trp Val Val Thr
1               5                   10                  15 gcc gcg gcg gcg gcg gcc acc tgc gtg tcc gcg gcg cgc ggc gaa gtg         96
Ala Ala Ala Ala Ala Ala Thr Cys Val Ser Ala Ala Arg Gly Glu Val
            20                  25                  30 aat ttg ctg gac acg tcg acc atc cac ggg gac tgg ggc tgg ctc acg        144
Asn Leu Leu Asp Thr Ser Thr Ile His Gly Asp Trp Gly Trp Leu Thr
        35                  40                  45 tat ccg gct cat ggg tgg gac tcc atc aac gag gtg gac gag tcc ttc        192
Tyr Pro Ala His Gly Trp Asp Ser Ile Asn Glu Val Asp Glu Ser Phe
    50                  55                  60 cag ccc atc cac acg tac cag gtt tgc aac gtc atg agc ccc aac cag        240
Gln Pro Ile His Thr Tyr Gln Val Cys Asn Val Met Ser Pro Asn Gln
```

```
                     65                    70                    75                    80
aac aac tgg ctg cgc acg agc tgg gtc ccc cga gac ggc gcc cgg cgc      288
Asn Asn Trp Leu Arg Thr Ser Trp Val Pro Arg Asp Gly Ala Arg Arg
                         85                    90                    95 gtc tat gct gag atc aag ttt acc ctg cgc gac tgc aac agc atg cct      336
Val Tyr Ala Glu Ile Lys Phe Thr Leu Arg Asp Cys Asn Ser Met Pro
            100                   105                   110 ggt gtg ctg ggc acc tgc aag gag acc ttc aac ctc tac tac ctg gag      384
Gly Val Leu Gly Thr Cys Lys Glu Thr Phe Asn Leu Tyr Tyr Leu Glu
                    115                   120                   125 tcg gac cgc gac ctg ggg gcc agc aca caa gaa agc cag ttc ctc aaa      432
Ser Asp Arg Asp Leu Gly Ala Ser Thr Gln Glu Ser Gln Phe Leu Lys
        130                   135                   140 atc gac acc att gcg gcc gac gag agc ttc aca ggt gcc gac ctt ggt      480
Ile Asp Thr Ile Ala Ala Asp Glu Ser Phe Thr Gly Ala Asp Leu Gly
145                   150                   155                   160 gtg cgg cgt ctc aag ctc aac acg gag gtg cgc agt gtg ggt ccc ctc      528
Val Arg Arg Leu Lys Leu Asn Thr Glu Val Arg Ser Val Gly Pro Leu
                    165                   170                   175 agc aag cgc ggc ttc tac ctg gcc ttc cag gac ata ggt gcc tgc ctg      576
Ser Lys Arg Gly Phe Tyr Leu Ala Phe Gln Asp Ile Gly Ala Cys Leu
                180                   185                   190 gcc atc ctc tct ctc cgc atc tac tat aag aag tgc cct gcc atg gtg      624
Ala Ile Leu Ser Leu Arg Ile Tyr Tyr Lys Lys Cys Pro Ala Met Val
            195                   200                   205 cgc aat ctg gct gcc ttc tcg gag gca gtg acg ggg gcc gac tcg tcc      672
Arg Asn Leu Ala Ala Phe Ser Glu Ala Val Thr Gly Ala Asp Ser Ser
        210                   215                   220 tca ctg gtg gag gtg agg ggc cag tgc gtg cgg cac tca gag gag cgg      720
Ser Leu Val Glu Val Arg Gly Gln Cys Val Arg His Ser Glu Glu Arg
225                   230                   235                   240 gac aca ccc aag atg tac tgc agc gcg gag ggc gag tgg ctc gtg ccc      768
Asp Thr Pro Lys Met Tyr Cys Ser Ala Glu Gly Glu Trp Leu Val Pro
                    245                   250                   255 atc ggc aaa tgc gtg tgc agt gcc ggc tac gag gag cgg cgg gat gcc      816
Ile Gly Lys Cys Val Cys Ser Ala Gly Tyr Glu Glu Arg Arg Asp Ala
                260                   265                   270 tgt gtg gcc tgt gag ctg ggc ttc tac aag tca gcc cct ggg gac cag      864
Cys Val Ala Cys Glu Leu Gly Phe Tyr Lys Ser Ala Pro Gly Asp Gln
            275                   280                   285 ctg tgt gcc cgc tgc cct ccc cac agc cac tcc gca gct cca gcc gcc      912
Leu Cys Ala Arg Cys Pro Pro His Ser His Ser Ala Ala Pro Ala Ala
        290                   295                   300 caa gcc tgc cac tgt gac ctc agc tac tac cgt gca gcc ctg gac ccg      960
Gln Ala Cys His Cys Asp Leu Ser Tyr Tyr Arg Ala Ala Leu Asp Pro
305                   310                   315                   320 ccg tcc tca gcc tgc acc cgg cca ccc tcg gca cca gtg aac ctg atc     1008
Pro Ser Ser Ala Cys Thr Arg Pro Pro Ser Ala Pro Val Asn Leu Ile
                    325                   330                   335 tcc agt gtg aat ggg aca tca gtg act ctg gag tgg gcc cct ccc ctg     1056
Ser Ser Val Asn Gly Thr Ser Val Thr Leu Glu Trp Ala Pro Pro Leu
                340                   345                   350 gac cca ggt ggc cgc agt gac atc acc tac aat gcc gtg tgc cgc cgc     1104
Asp Pro Gly Gly Arg Ser Asp Ile Thr Tyr Asn Ala Val Cys Arg Arg
            355                   360                   365 tgc ccc tgg gca ctg agc cgc tgc gag gca tgt ggg agc ggc acc cgc     1152
Cys Pro Trp Ala Leu Ser Arg Cys Glu Ala Cys Gly Ser Gly Thr Arg
        370                   375                   380 ttt gtg ccc cag cag aca agc ctg gtg cag gcc agc ctg ctg gtg gcc     1200
```

```
                Phe Val Pro Gln Gln Thr Ser Leu Val Gln Ala Ser Leu Leu Val Ala
                385                 390                 395                 400 aac ctg ctg gcc cac atg aac tac tcc ttc tgg atc gag gcc gtc aat       1248
Asn Leu Leu Ala His Met Asn Tyr Ser Phe Trp Ile Glu Ala Val Asn
                        405                 410                 415 ggc gtg tcc gac ctg agc ccc gag ccc cgc cgg gcc gct gtg gtc aac       1296
Gly Val Ser Asp Leu Ser Pro Glu Pro Arg Arg Ala Ala Val Val Asn
                420                 425                 430 atc acc acg aac cag gca gcc ccg tcc cag gtg gtg gtg atc cgt caa       1344
Ile Thr Thr Asn Gln Ala Ala Pro Ser Gln Val Val Val Ile Arg Gln
                435                 440                 445 gag cgg gcg ggg cag acc agc gtc tcg ctg ctg tgg cag gag ccc gag       1392
Glu Arg Ala Gly Gln Thr Ser Val Ser Leu Leu Trp Gln Glu Pro Glu
            450                 455                 460 cag ccg aac ggc atc atc ctg gag tat gag atc aag tac tac gag aag       1440
Gln Pro Asn Gly Ile Ile Leu Glu Tyr Glu Ile Lys Tyr Tyr Glu Lys
465                 470                 475                 480 gac aag gag atg cag agc tac tcc acc ctc aag gcc gtc acc acc aga       1488
Asp Lys Glu Met Gln Ser Tyr Ser Thr Leu Lys Ala Val Thr Thr Arg
                        485                 490                 495 gcc acc gtc tcc ggc ctc aag ccg ggc acc cgc tac gtg ttc cag gtc       1536
Ala Thr Val Ser Gly Leu Lys Pro Gly Thr Arg Tyr Val Phe Gln Val
                500                 505                 510 cga gcc cgc acc tca gca ggc tgt ggc cgc ttc agc cag gcc atg gag       1584
Arg Ala Arg Thr Ser Ala Gly Cys Gly Arg Phe Ser Gln Ala Met Glu
                515                 520                 525 gtg gag acc ggg aaa ccc cgg ccc cgc tat gac acc agg acc att gtc       1632
Val Glu Thr Gly Lys Pro Arg Pro Arg Tyr Asp Thr Arg Thr Ile Val
            530                 535                 540 tgg atc tgc ctg acg ctc atc acg ggc ctg gtg gtg ctt ctg ctc ctg       1680
Trp Ile Cys Leu Thr Leu Ile Thr Gly Leu Val Val Leu Leu Leu Leu
545                 550                 555                 560 ctc atc tgc aag aag agg cac tgt ggc tac agc aag gcc ttc cag gac       1728
Leu Ile Cys Lys Lys Arg His Cys Gly Tyr Ser Lys Ala Phe Gln Asp
                        565                 570                 575 tcg gac gag gag aag atg cac tat cag aat gga cag gca ccc cca cct       1776
Ser Asp Glu Glu Lys Met His Tyr Gln Asn Gly Gln Ala Pro Pro Pro
                580                 585                 590 gtc ttc ctg cct ctg cat cac ccc ccg gga aag ctc cca gag ccc cag       1824
Val Phe Leu Pro Leu His His Pro Pro Gly Lys Leu Pro Glu Pro Gln
                595                 600                 605 ttc tat gcg gaa ccc cac acc tac gag gag cca ggc cgg gcg ggc cgc       1872
Phe Tyr Ala Glu Pro His Thr Tyr Glu Glu Pro Gly Arg Ala Gly Arg
            610                 615                 620 agt ttc act cgg gag atc gag gcc tct agg atc cac atc gag aaa atc       1920
Ser Phe Thr Arg Glu Ile Glu Ala Ser Arg Ile His Ile Glu Lys Ile
625                 630                 635                 640 atc ggc tct gga gac tcc ggg gaa gtc tgc tac ggg agg ctg cgg gtg       1968
Ile Gly Ser Gly Asp Ser Gly Glu Val Cys Tyr Gly Arg Leu Arg Val
                        645                 650                 655 cca ggg cag cgg gat gtg ccc gtg gcc atc aag gcc ctc aaa gcc ggc       2016
Pro Gly Gln Arg Asp Val Pro Val Ala Ile Lys Ala Leu Lys Ala Gly
                660                 665                 670 tac acg gag aga cag agg cgg gac ttc ctg agc gag gcg tcc atc atg       2064
Tyr Thr Glu Arg Gln Arg Arg Asp Phe Leu Ser Glu Ala Ser Ile Met
                675                 680                 685 ggg caa ttc gac cat ccc aac atc atc cgc ctc gag ggt gtc gtc acc       2112
Gly Gln Phe Asp His Pro Asn Ile Ile Arg Leu Glu Gly Val Val Thr
690                 695                 700
```

| | | | | | | | | | | | | | | | | |
|---|---|---|---|---|---|---|---|---|---|---|---|---|---|---|---|---|
| cgt | ggc | cgc | ctg | gca | atg | att | gtg | act | gag | tac | atg | gag | aac | ggc | tct | 2160 |
| Arg | Gly | Arg | Leu | Ala | Met | Ile | Val | Thr | Glu | Tyr | Met | Glu | Asn | Gly | Ser | |
| 705 | | | | 710 | | | | | 715 | | | | | 720 | | |

| | | | | | | | | | | | | | | | | |
|---|---|---|---|---|---|---|---|---|---|---|---|---|---|---|---|---|
| ctg | gac | acc | ttc | ctg | agg | acc | cac | gac | ggg | cag | ttc | acc | atc | atg | cag | 2208 |
| Leu | Asp | Thr | Phe | Leu | Arg | Thr | His | Asp | Gly | Gln | Phe | Thr | Ile | Met | Gln | |
| | | | | 725 | | | | | 730 | | | | | 735 | | |

| | | | | | | | | | | | | | | | | |
|---|---|---|---|---|---|---|---|---|---|---|---|---|---|---|---|---|
| ctg | gtg | ggc | atg | ctg | aga | gga | gtg | ggt | gcc | ggc | atg | cgc | tac | ctc | tca | 2256 |
| Leu | Val | Gly | Met | Leu | Arg | Gly | Val | Gly | Ala | Gly | Met | Arg | Tyr | Leu | Ser | |
| | | | 740 | | | | | 745 | | | | | 750 | | | |

| | | | | | | | | | | | | | | | | |
|---|---|---|---|---|---|---|---|---|---|---|---|---|---|---|---|---|
| gac | ctg | ggc | tat | gtc | cac | cga | gac | ctg | gcc | gcc | cgc | aac | gtc | ctg | gtt | 2304 |
| Asp | Leu | Gly | Tyr | Val | His | Arg | Asp | Leu | Ala | Ala | Arg | Asn | Val | Leu | Val | |
| | | | 755 | | | | | 760 | | | | | 765 | | | |

| | | | | | | | | | | | | | | | | |
|---|---|---|---|---|---|---|---|---|---|---|---|---|---|---|---|---|
| gac | agc | aac | ctg | gtc | tgc | aag | gtg | tct | gac | ttc | ggg | ctc | tca | cgg | gtg | 2352 |
| Asp | Ser | Asn | Leu | Val | Cys | Lys | Val | Ser | Asp | Phe | Gly | Leu | Ser | Arg | Val | |
| | | 770 | | | | | 775 | | | | | 780 | | | | |

| | | | | | | | | | | | | | | | | |
|---|---|---|---|---|---|---|---|---|---|---|---|---|---|---|---|---|
| ctg | gag | gac | gac | ccg | gat | gct | gcc | tac | acc | acc | acg | ggc | ggg | aag | atc | 2400 |
| Leu | Glu | Asp | Asp | Pro | Asp | Ala | Ala | Tyr | Thr | Thr | Thr | Gly | Gly | Lys | Ile | |
| 785 | | | | 790 | | | | | 795 | | | | | 800 | | |

| | | | | | | | | | | | | | | | | |
|---|---|---|---|---|---|---|---|---|---|---|---|---|---|---|---|---|
| ccc | atc | cgc | tgg | acg | gcc | cca | gag | gcc | atc | gcc | ttc | cgc | acc | ttc | tcc | 2448 |
| Pro | Ile | Arg | Trp | Thr | Ala | Pro | Glu | Ala | Ile | Ala | Phe | Arg | Thr | Phe | Ser | |
| | | | | 805 | | | | | 810 | | | | | 815 | | |

| | | | | | | | | | | | | | | | | |
|---|---|---|---|---|---|---|---|---|---|---|---|---|---|---|---|---|
| tcg | gcc | agc | gac | gtg | tgg | agc | ttc | ggc | gtg | gtc | atg | tgg | gag | gtg | ctg | 2496 |
| Ser | Ala | Ser | Asp | Val | Trp | Ser | Phe | Gly | Val | Val | Met | Trp | Glu | Val | Leu | |
| | | | 820 | | | | | 825 | | | | | 830 | | | |

| | | | | | | | | | | | | | | | | |
|---|---|---|---|---|---|---|---|---|---|---|---|---|---|---|---|---|
| gcc | tat | ggg | gag | cgg | ccc | tac | tgg | aac | atg | acc | aac | cgg | gat | gtc | atc | 2544 |
| Ala | Tyr | Gly | Glu | Arg | Pro | Tyr | Trp | Asn | Met | Thr | Asn | Arg | Asp | Val | Ile | |
| | | | 835 | | | | | 840 | | | | | 845 | | | |

| | | | | | | | | | | | | | | | | |
|---|---|---|---|---|---|---|---|---|---|---|---|---|---|---|---|---|
| agc | tct | gtg | gag | gag | ggg | tac | cgc | ctg | ccc | gca | ccc | atg | ggc | tgc | ccc | 2592 |
| Ser | Ser | Val | Glu | Glu | Gly | Tyr | Arg | Leu | Pro | Ala | Pro | Met | Gly | Cys | Pro | |
| 850 | | | | | 855 | | | | | 860 | | | | | | |

| | | | | | | | | | | | | | | | | |
|---|---|---|---|---|---|---|---|---|---|---|---|---|---|---|---|---|
| cac | gcc | ctg | cac | cag | ctc | atg | ctc | gac | tgt | tgg | cac | aag | gac | cgg | gcg | 2640 |
| His | Ala | Leu | His | Gln | Leu | Met | Leu | Asp | Cys | Trp | His | Lys | Asp | Arg | Ala | |
| 865 | | | | 870 | | | | | 875 | | | | | 880 | | |

| | | | | | | | | | | | | | | | | |
|---|---|---|---|---|---|---|---|---|---|---|---|---|---|---|---|---|
| cag | cgg | cct | cgc | ttc | tcc | cag | att | gtc | agt | gtc | ctc | gat | gcg | ctc | atc | 2688 |
| Gln | Arg | Pro | Arg | Phe | Ser | Gln | Ile | Val | Ser | Val | Leu | Asp | Ala | Leu | Ile | |
| | | | | 885 | | | | | 890 | | | | | 895 | | |

| | | | | | | | | | | | | | | | | |
|---|---|---|---|---|---|---|---|---|---|---|---|---|---|---|---|---|
| cgc | agc | cct | gag | agt | ctc | agg | gcc | acc | gcc | aca | gtc | agc | agg | tgc | cca | 2736 |
| Arg | Ser | Pro | Glu | Ser | Leu | Arg | Ala | Thr | Ala | Thr | Val | Ser | Arg | Cys | Pro | |
| | | | 900 | | | | | 905 | | | | | 910 | | | |

| | | | | | | | | | | | | | | | | |
|---|---|---|---|---|---|---|---|---|---|---|---|---|---|---|---|---|
| ccc | cct | gcc | ttc | gtc | cgg | agc | tgc | ttt | gac | ctc | cga | ggg | ggc | agc | ggt | 2784 |
| Pro | Pro | Ala | Phe | Val | Arg | Ser | Cys | Phe | Asp | Leu | Arg | Gly | Gly | Ser | Gly | |
| | | | 915 | | | | | 920 | | | | | 925 | | | |

| | | | | | | | | | | | | | | | | |
|---|---|---|---|---|---|---|---|---|---|---|---|---|---|---|---|---|
| ggc | ggt | ggg | ggc | ctc | acc | gtg | ggg | gac | tgg | ctg | gac | tcc | atc | cgc | atg | 2832 |
| Gly | Gly | Gly | Gly | Leu | Thr | Val | Gly | Asp | Trp | Leu | Asp | Ser | Ile | Arg | Met | |
| | | 930 | | | | | 935 | | | | | 940 | | | | |

| | | | | | | | | | | | | | | | | |
|---|---|---|---|---|---|---|---|---|---|---|---|---|---|---|---|---|
| ggc | cgg | tac | cga | gac | cac | ttc | gct | gcg | ggc | gga | tac | tcc | tct | ctg | ggc | 2880 |
| Gly | Arg | Tyr | Arg | Asp | His | Phe | Ala | Ala | Gly | Gly | Tyr | Ser | Ser | Leu | Gly | |
| 945 | | | | | 950 | | | | | 955 | | | | | 960 | |

| | | | | | | | | | | | | | | | | |
|---|---|---|---|---|---|---|---|---|---|---|---|---|---|---|---|---|
| atg | gtg | cta | cgc | atg | aac | gcc | cag | gac | gtg | cgc | gcc | ctg | ggc | atc | acc | 2928 |
| Met | Val | Leu | Arg | Met | Asn | Ala | Gln | Asp | Val | Arg | Ala | Leu | Gly | Ile | Thr | |
| | | | | 965 | | | | | 970 | | | | | 975 | | |

| | | | | | | | | | | | | | | | | |
|---|---|---|---|---|---|---|---|---|---|---|---|---|---|---|---|---|
| ctc | atg | ggc | cac | cag | aag | aag | atc | ctg | ggc | agc | att | cag | acc | atg | cgg | 2976 |
| Leu | Met | Gly | His | Gln | Lys | Lys | Ile | Leu | Gly | Ser | Ile | Gln | Thr | Met | Arg | |
| | | | 980 | | | | | 985 | | | | | 990 | | | |

| | | | | | | | | | | | | | | | |
|---|---|---|---|---|---|---|---|---|---|---|---|---|---|---|---|
| gcc | cag | ctg | acc | agc | acc | cag | ggg | ccc | cgc | cgg | cac | ctc | tga | | 3018 |
| Ala | Gln | Leu | Thr | Ser | Thr | Gln | Gly | Pro | Arg | Arg | His | Leu | | | |
| | | | 995 | | | | | 1000 | | | | 1005 | | | |

<210> SEQ ID NO 7
<211> LENGTH: 1497

<212> TYPE: DNA
<213> ORGANISM: Homo sapiens
<300> PUBLICATION INFORMATION:
<308> DATABASE ACCESSION NUMBER: U83508
<309> DATABASE ENTRY DATE: 1996-12-31
<300> PUBLICATION INFORMATION:
<302> TITLE: angiopoietin 2
<310> PATENT DOCUMENT NUMBER: U83508

<400> SEQUENCE: 7

```
atgacagttt tcctttcctt tgctttcctc gctgccattc tgactcacat agggtgcagc    60
aatcagcgcc gaagtccaga aaacagtggg agaagatata accggattca acatgggcaa   120
tgtgcctaca ctttcattct tccagaacac gatggcaact gtcgtgagag tacgacagac   180
cagtacaaca caaacgctct gcagagagat gctccacacg tggaaccgga tttctcttcc   240
cagaaacttc aacatctgga acatgtgatg aaaattata ctcagtggct gcaaaaactt   300
gagaattaca ttgtggaaaa catgaagtcg agatggccc agatacagca gaatgcagtt   360
cagaaccaca cggctaccat gctggagata ggaaccagcc tcctctctca gactgcagag   420
cagaccagaa agctgacaga tgttgagacc caggtactaa atcaaacttc tcgacttgag   480
atacagctgc tggagaattc attatccacc tacaagctag agaagcaact tcttcaacag   540
acaaatgaaa tcttgaagat ccatgaaaaa acagtttat tagaacataa atcttagaa   600
atggaaggaa acacaagga gagttggac accttaaagg aagagaaaga gaaccttcaa   660
ggcttggtta ctcgtcaaac atatataatc caggagctgg aaaagcaatt aaacagagct   720
accaccaaca acagtgtcct tcagaagcag caactggagc tgatggacac agtccacaac   780
cttgtcaatc tttgcactaa agaaggtgtt ttactaaagg gaggaaaaag agaggaagag   840
aaaccattta gagactgtgc agatgtatat caagctggtt ttaataaaag tggaatctac   900
actatttata ttaataatat gccagaaccc aaaaaggtgt tttgcaatat ggatgtcaat   960
gggggagggt tggactgtaa taacatcgt gaagatggaa gtctagattt ccaaagaggc  1020
tggaaggaat ataaaatggg ttttggaaat ccctccggtg aatattggct ggggaatgag  1080
tttatttttg ccattaccag tcagaggcag tacatgctaa gaattgagtt aatggactgg  1140
gaagggaacc gagcctattc acagtatgac agattccaca taggaaatga aaagcaaaac  1200
tataggttgt atttaaaagg tcacactggg acagcaggaa aacagagcag cctgatctta  1260
cacggtgctg atttcagcac taaagatgct gataatgaca actgtatgtg caaatgtgcc  1320
ctcatgttaa caggaggatg gtggtttgat gcttgtggcc cctccaatct aaatggaatg  1380
ttctatactg cgggacaaaa ccatggaaaa ctgaatggga taaagtggca ctacttcaaa  1440
gggcccagtt actccttacg ttccacaact atgatgattc gacctttaga tttttga    1497
```

<210> SEQ ID NO 8
<211> LENGTH: 3417
<212> TYPE: DNA
<213> ORGANISM: Homo sapiens
<300> PUBLICATION INFORMATION:
<310> PATENT DOCUMENT NUMBER: XM001924
<300> PUBLICATION INFORMATION:
<302> TITLE: Tie1

<400> SEQUENCE: 8

```
atggtctggc gggtgccccc tttcttgctc cccatcctct tcttggcttc tcatgtgggc    60
gcggcggtgg acctgacgct gctggccaac ctgcggctca cggaccccca gcgcttcttc   120
ctgacttgcg tgtctgggga ggccggggcg ggaggggct cggacgcctg ggccccgccc   180
```

```
ctgctgctgg agaaggacga ccgtatcgtg cgcaccccgc ccgggccacc cctgcgcctg    240
gcgcgcaacg gttcgcacca ggtcacgctt cgcggcttct ccaagccctc ggacctcgtg    300
ggcgtcttct cctgcgtggg cggtgctggg gcgcggcgca cgcgcgtcat ctacgtgcac    360
aacagccctg gagcccacct gcttccagac aaggtcacac acactgtgaa caaaggtgac    420
accgctgtac tttctgcacg tgtgcacaag gagaagcaga cagacgtgat ctggaagagc    480
aacggatcct acttctacac cctggactgg catgaagccc aggatgggcg gttcctgctg    540
cagctcccaa atgtgcagcc accatcgagc ggcatctaca gtgccactta cctggaagcc    600 agcccctgg gcagcgcctt ctttcggctc atcgtgcggg gttgtggggc tgggcgctgg    660
gggccaggct gtaccaagga gtgcccaggt tgcctacatg gaggtgtctg ccacgaccat    720
gacggcgaat gtgtatgccc ccctggcttc actggcaccc gctgtgaaca ggcctgcaga    780
gagggccgtt ttgggcagag ctgccaggag cagtgcccag gcatatcagg ctgccggggc    840
ctcaccttct gcctcccaga cccctatggc tgctcttgtg gatctggctg gagaggaagc    900
cagtgccaag aagcttgtgc ccctggtcat tttgggggctg attgccgact ccagtgccag    960
tgtcagaatg gtggcacttg tgaccggttc agtggttgtg tctgcccctc tgggtggcat   1020
ggagtgcact gtgagaagtc agaccggatc ccccagatcc tcaacatggc tcagaactg   1080 gagttcaact agagacgat gccccggatc aactgtgcag ctgcaggaa ccccttcccc   1140 gtgcggggca gcatagagct acgcaagcca cgacggcactg tgctcctgtc caccaaggcc   1200
attgtggagc cagagaagac cacagctgag ttcgaggtgc ccgcttggt tcttgcggac   1260 agtgggttct gggagtgccg tgtgtccaca tctggcggcc aagacagccg gcgcttcaag   1320
gtcaatgtga aagtgccccc cgtgcccctg gctgcacctc ggctcctgac caagcagagc   1380
cgccagcttg tggtctcccc gctggtctcg ttctctgggg atggacccat ctccactgtc   1440
cgcctgcact accggcccca ggacagtacc atggactggt cgaccattgt ggtggacccc   1500
agtgagaacg tgacgttaat gaacctgagg ccaaagacag gatacagtgt tcgtgtgcag   1560
ctgagccggc caggggaagg aggagagggg gcctggggc ctcccacct catgaccaca   1620 gactgtcctg agcctttgtt gcagccgtgg ttggagggct ggcatgtgga aggcactgac   1680
cggctgcgag tgagctggtc cttgccttg gtgcccgggc cactggtggg cgacggtttc   1740
ctgctgcgcc tgtgggacgg gacacggggg caggagcggg gggagaacgt ctcatccccc   1800
caggcccgca ctgccctcct gacgggactc acgcctggca cccactacca gctggatgtg   1860
cagctctacc actgcaccct cctgggcccg gcctcgcccc ctgcacacgt gcttctgccc   1920
cccagtgggc ctccagcccc ccgacacctc cacgcccagg ccctctcaga ctccgagatc   1980
cagctgacat ggaagcaccc ggaggctctg cctgggccaa tatccaagta cgttgtggag   2040
gtgcaggtgg ctgggggtgc aggagaccca ctgtggatag acgtggacag gcctgaggag   2100
acaagcacca tcatccgtgg cctcaacgcc agcacgcgct acctcttccg catgcgggcc   2160
agcattcagg ggctcgggga ctggagcaac acagtagaag agtccaccct gggcaacggg   2220
ctgcaggctg agggcccagt ccaagagagc cgggcagctg aagagggcct ggatcagcag   2280
ctgatcctgg cggtggtggg ctccgtgtct gccacctgcc tccatcct ggctgccctt   2340 ttaaccctgg tgtgcatccg cagaagctgc ctgcatcgga gacgcacctt cacctaccag   2400
tcaggctcgg gcgaggagac catcctgcag ttcagctcag ggaccttgac acttaccccgg   2460 cggccaaaac tgcagcccga gccctgagc tacccagtgc tagagtggga ggacatcacc   2520
tttgaggacc tcatcgggga ggggaacttc ggccaggtca tccgggccat gatcaagaag   2580
```

| | |
|---|---|
| gacgggctga agatgaacgc agccatcaaa atgctgaaag agtatgcctc tgaaaatgac | 2640 |
| catcgtgact ttgcgggaga actggaagtt ctgtgcaaat tggggcatca ccccaacatc | 2700 |
| atcaacctcc tgggggcctg taagaaccga ggttacttgt atatcgctat tgaatatgcc | 2760 |
| ccctacggga acctgctaga ttttctgcgg aaaagccggg tcctagagac tgacccagct | 2820 |
| tttgctcgag agcatgggac agcctctacc cttagctccc ggcagctgct gcgtttcgcc | 2880 |
| agtgatgcgg ccaatggcat gcagtacctg agtgagaagc agttcatcca cagggacctg | 2940 |
| gctgcccgga atgtgctggt cggagagaac ctggcctcca agattgcaga cttcggcctt | 3000 |
| tctcggggag aggaggttta tgtgaagaag acgatgggc gtctccctgt gcgctggatg | 3060 |
| gccattgagt ccctgaacta cagtgtctat accaccaaga gtgatgtctg gtcctttgga | 3120 |
| gtccttcttt gggagatagt gagccttgga ggtacaccct actgtggcat gacctgtgcc | 3180 |
| gagctctatg aaaagctgcc ccagggctac cgcatggagc agcctcgaaa ctgtgacgat | 3240 |
| gaagtgtacg agctgatgcg tcagtgctgg cgggaccgtc cctatgagcg acccccctt | 3300 |
| gcccagattg cgctacagct aggccgcatg ctggaagcca ggaaggccta tgtgaacatg | 3360 |
| tcgctgtttg agaacttcac ttacgcgggc attgatgcca cagctgagga ggcctga | 3417 |

<210> SEQ ID NO 9
<211> LENGTH: 3375
<212> TYPE: DNA
<213> ORGANISM: Homo sapiens
<300> PUBLICATION INFORMATION:
<302> TITLE: TEK
<310> PATENT DOCUMENT NUMBER: L06139

<400> SEQUENCE: 9

| | |
|---|---|
| atggactctt tagccagctt agttctctgt ggagtcagct tgctcctttc tggaactgtg | 60 |
| gaaggtgcca tggacttgat cttgatcaat tccctacctc ttgtatctga tgctgaaaca | 120 |
| tctctcacct gcattgcctc tgggtggcgc cccatgagc ccatcaccat aggaagggac | 180 |
| tttgaagcct taatgaacca gcaccaggat ccgctggaag ttactcaaga gtgtgaccga | 240 |
| gaatgggcta aaaagttgt ttggaagaga aaaaggcta gtaagatcaa tggtgcttat | 300 |
| ttctgtgaag gcgagttcg aggagaggca atcaggatac gaaccatgaa gatgcgtcaa | 360 |
| caagcttcct tcctaccagc tactttaact atgactgtgg acaagggaga taacgtgaac | 420 |
| atatctttca aaaggtatt gattaaagaa gaagatgcag tgatttacaa aaatggttcc | 480 |
| ttcatccatt cagtgccccg gcatgaagta cctgatattc tagaagtaca cctgcctcat | 540 |
| gctcagcccc aggatgctgg agtgtactcg gccaggtata taggaggaaa cctcttcacc | 600 |
| tcggccttca ccaggctgat agtccggaga tgtgaagccc agaagtgggg acctgaatgc | 660 |
| aaccatctct gtactgcttg tatgaacaat ggtgtctgcc atgaagatac tggagaatgc | 720 |
| atttgccctc ctgggttat gggaaggacg tgtgagaagg cttgtgaact gcacacgttt | 780 |
| ggcagaactt gtaaagaaag gtgcagtgga caagaggat gcaagtctta tgtgttctgt | 840 |
| ctccctgacc cctatgggtg ttcctgtgcc acaggctgga aaggtctgca gtgcaatgaa | 900 |
| gcatgccacc tggttttta cgggccagat tgtaagctta ggtgcagctg caacaatggg | 960 |
| gagatgtgtg atcgcttcca aggatgtctc tgctctccag atggcagggg ctccagtgt | 1020 |
| gagagagaag gcataccgag gatgaccca aagatagtgg atttgccaga tcatatagaa | 1080 |
| gtaaacagtg gtaaatttaa tcccatttgc aaagcttctg ctggccgct acctactaat | 1140 |
| gaagaaatga cctggtgaa gccggatggg acagtgctcc atccaaaaga ctttaaccat | 1200 |

```
acggatcatt tctcagtagc catattcacc atccaccgga tcctccccc tgactcagga      1260 gtttgggtct gcagtgtgaa cacagtggct gggatggtgg aaaagcccct caacatttct      1320
gttaaagttc ttccaaagcc cctgaatgcc ccaaacgtga ttgacactgg acataacttt      1380
gctgtcatca acatcagctc tgagccttac tttggggatg gaccaatcaa atccaagaag      1440
cttctataca aacccgttaa tcactatgag gcttggcaac atattcaagt gacaaatgag      1500
attgttacac tcaactattt ggaacctcgg acagaatatg aactctgtgt gcaactggtc      1560
cgtcgtggag agggtgggga agggcatcct ggacctgtga gacgcttcac aacagcttct      1620
atcggactcc ctcctccaag aggtctaaat ctcctgccta aagtcagac cactctaaat      1680 ttgacctggc aaccaatatt tccaagctcg aagatgact tttatgttga agtggagaga      1740
aggtctgtgc aaaaaagtga tcagcagaat attaaagttc aggcaacttt gacttcggtg      1800
ctacttaaca acttacatcc cagggagcag tacgtggtcc gagctagagt caacaccaag      1860 gcccagggg aatggagtga agatctcact gcttggaccc ttagtgacat tcttcctcct      1920
caaccagaaa acatcaagat tccaacatt acacactcct cggctgtgat tcttggaca       1980 atattggatg ctattctat ttcttctatt actatccgtt acaaggttca aggcaagaat      2040
gaagaccagc acgttgatgt gaagataaag aatgccacca tcattcagta tcagctcaag      2100
ggcctagagc ctgaaacagc ataccaggtg acattttttg cagagaacaa catagggtca      2160
agcaacccag ccttttctca tgaactggtg accctcccag aatctcaagc accagcggac      2220
ctcggagggg ggaagatgct gcttatagcc atccttggct ctgctggaat gacctgcctg      2280
actgtgctgt tggccttct gatcatattg caattgaaga gggcaaatgt gcaaaggaga      2340
atggcccaag ccttccaaaa cgtgagggaa gaaccagctg tgcagttcaa ctcagggact      2400
ctggccctaa acaggaaggt caaaaacaac ccagatccta caatttatcc agtgcttgac      2460
tggaatgaca tcaaatttca agatgtgatt gggagggca attttggcca agttcttaag      2520
gcgcgcatca agaaggatgg gttacggatg gatgctgcca tcaaaagaat gaaagaatat      2580
gcctccaaag atgatcacag ggactttgca ggagaactgg aagttctttg taaacttgga      2640
caccatccaa acatcatcaa tctcttagga gcatgtgaac atcgaggcta cttgtacctg      2700
gccattgagt acgcgcccca tggaaacctt ctggacttcc ttcgcaagag ccgtgtgctg      2760
gagacggacc cagcatttgc cattgccaat agcaccgcgt ccacactgtc ctcccagcag      2820
ctccttcact tcgctgccga cgtggcccgg gcatggact acttgagcca aaaacagttt      2880
atccacaggg atctggctgc cagaaacatt ttagttggtg aaaactatgt ggcaaaaata      2940
gcagattttg gattgtcccg aggtcaagag gtgtacgtga aaagacaat gggaaggctc      3000 ccagtgcgct ggatggccat cgagtcactg aattacagtg tgtacacaac caacagtgat      3060
gtatggtcct atggtgtgtt actatgggag attgttagct taggaggcac accctactgc      3120
gggatgactt gtgcagaact ctacgagaag ctgccccagg gctacagact ggagaagccc      3180
ctgaactgtg atgatgaggt gtatgatcta atgagacaat gctggcggga agccttat       3240 gagaggccat catttgccca gatattggtg tccttaaaca gaatgttaga ggagcgaaag      3300
acctacgtga ataccacgct ttatgagaag tttacttatg caggaattga ctgttctgct      3360
gaagaagcgg cctag                                                     3375

<210> SEQ ID NO 10
<211> LENGTH: 2400
<212> TYPE: DNA
```

```
<213> ORGANISM: Homo sapiens
<220> FEATURE:
<221> NAME/KEY: CDS
<222> LOCATION: (1)..(2397)
<300> PUBLICATION INFORMATION:
<300> PUBLICATION INFORMATION:
<302> TITLE: beta5 integrin
<310> PATENT DOCUMENT NUMBER: X53002

<400> SEQUENCE: 10 atg ccg cgg gcc ccg gcg ccg ctg tac gcc tgc ctc ctg ggg ctc tgc      48
Met Pro Arg Ala Pro Ala Pro Leu Tyr Ala Cys Leu Leu Gly Leu Cys
1               5                   10                  15 gcg ctc ctg ccc cgg ctc gca ggt ctc aac ata tgc act agt gga agt      96
Ala Leu Leu Pro Arg Leu Ala Gly Leu Asn Ile Cys Thr Ser Gly Ser
                20                  25                  30 gcc acc tca tgt gaa gaa tgt cta cta atc cac cca aaa tgt gcc tgg     144
Ala Thr Ser Cys Glu Glu Cys Leu Leu Ile His Pro Lys Cys Ala Trp
            35                  40                  45 tgc tcc aaa gag gac ttc gga agc cca cgg tcc atc acc tct cgg tgt     192
Cys Ser Lys Glu Asp Phe Gly Ser Pro Arg Ser Ile Thr Ser Arg Cys
        50                  55                  60 gat ctg agg gca aac ctt gtc aaa aat ggc tgt gga ggt gag ata gag     240
Asp Leu Arg Ala Asn Leu Val Lys Asn Gly Cys Gly Gly Glu Ile Glu
65                  70                  75                  80 agc cca gcc agc agc ttc cat gtc ctg agg agc ctg ccc ctc agc agc     288
Ser Pro Ala Ser Ser Phe His Val Leu Arg Ser Leu Pro Leu Ser Ser
                85                  90                  95 aag ggt tcg ggc tct gca ggc tgg gac gtc att cag atg aca cca cag     336
Lys Gly Ser Gly Ser Ala Gly Trp Asp Val Ile Gln Met Thr Pro Gln
                100                 105                 110 gag att gcc gtg aac ctc cgg ccc ggt gac aag acc acc ttc cag cta     384
Glu Ile Ala Val Asn Leu Arg Pro Gly Asp Lys Thr Thr Phe Gln Leu
            115                 120                 125 cag gtt cgc cag gtg gag gac tat cct gtg gac ctg tac tac ctg atg     432
Gln Val Arg Gln Val Glu Asp Tyr Pro Val Asp Leu Tyr Tyr Leu Met
        130                 135                 140 gac ctc tcc ctg tcc atg aag gat gac ttg gac aat atc cgg agc ctg     480
Asp Leu Ser Leu Ser Met Lys Asp Asp Leu Asp Asn Ile Arg Ser Leu
145                 150                 155                 160 ggc acc aaa ctc gcg gag gag atg agg aag ctc acc agc aac ttc cgg     528
Gly Thr Lys Leu Ala Glu Glu Met Arg Lys Leu Thr Ser Asn Phe Arg
                165                 170                 175 ttg gga ttt ggg tct ttt gtt gat aag gac atc tct cct ttc tcc tac     576
Leu Gly Phe Gly Ser Phe Val Asp Lys Asp Ile Ser Pro Phe Ser Tyr
                180                 185                 190 acg gca ccg agg tac cag acc aat ccg tgc att ggt tac aag ttg ttt     624
Thr Ala Pro Arg Tyr Gln Thr Asn Pro Cys Ile Gly Tyr Lys Leu Phe
            195                 200                 205 cca aat tgc gtc ccc tcc ttt ggg ttc cgc cat ctg ctg cct ctc aca     672
Pro Asn Cys Val Pro Ser Phe Gly Phe Arg His Leu Leu Pro Leu Thr
        210                 215                 220 gac aga gtg gac agc ttc aat gag gaa gtt cgg aaa cag agg gtg tcc     720
Asp Arg Val Asp Ser Phe Asn Glu Glu Val Arg Lys Gln Arg Val Ser
225                 230                 235                 240 cgg aac cga gat gcc cct gag ggg ggc ttt gat gca gta ctc cag gca     768
Arg Asn Arg Asp Ala Pro Glu Gly Gly Phe Asp Ala Val Leu Gln Ala
                245                 250                 255 gcc gtc tgc aag gag aag att ggc tgg cga aag gat gca ctg cat ttg     816
Ala Val Cys Lys Glu Lys Ile Gly Trp Arg Lys Asp Ala Leu His Leu
                260                 265                 270
```

```
ctg gtg ttc aca aca gat gat gtg ccc cac atc gca ttg gat gga aaa    864
Leu Val Phe Thr Thr Asp Asp Val Pro His Ile Ala Leu Asp Gly Lys
            275                 280                 285 ttg gga ggc ctg gtg cag cca cac gat ggc cag tgc cac ctg aac gag    912
Leu Gly Gly Leu Val Gln Pro His Asp Gly Gln Cys His Leu Asn Glu
        290                 295                 300 gcc aac gag tac aca gca tcc aac cag atg gac tat cca tcc ctt gcc    960
Ala Asn Glu Tyr Thr Ala Ser Asn Gln Met Asp Tyr Pro Ser Leu Ala
305                 310                 315                 320 ttg ctt gga gag aaa ttg gca gag aac aac atc aac ctc atc ttt gca   1008
Leu Leu Gly Glu Lys Leu Ala Glu Asn Asn Ile Asn Leu Ile Phe Ala
                325                 330                 335 gtg aca aaa aac cat tat atg ctg tac aag aat ttt aca gcc ctg ata   1056
Val Thr Lys Asn His Tyr Met Leu Tyr Lys Asn Phe Thr Ala Leu Ile
            340                 345                 350 cct gga aca acg gtg gag att tta gat gga gac tcc aaa aat att att   1104
Pro Gly Thr Thr Val Glu Ile Leu Asp Gly Asp Ser Lys Asn Ile Ile
        355                 360                 365 caa ctg att att aat gca tac aat agt atc cgg tct aaa gtg gag ttg   1152
Gln Leu Ile Ile Asn Ala Tyr Asn Ser Ile Arg Ser Lys Val Glu Leu
370                 375                 380 tca gtc tgg gat cag cct gag gat ctt aat ctc ttc ttt act gct acc   1200
Ser Val Trp Asp Gln Pro Glu Asp Leu Asn Leu Phe Phe Thr Ala Thr
385                 390                 395                 400 tgc caa gat ggg gta tcc tat cct ggt cag agg aag tgt gag ggt ctg   1248
Cys Gln Asp Gly Val Ser Tyr Pro Gly Gln Arg Lys Cys Glu Gly Leu
                405                 410                 415 aag att ggg gac acg gca tct ttt gaa gta tca ttg gag gcc cga agc   1296
Lys Ile Gly Asp Thr Ala Ser Phe Glu Val Ser Leu Glu Ala Arg Ser
            420                 425                 430 tgt ccc agc aga cac acg gag cat gtg ttt gcc ctg cgg ccg gtg gga   1344
Cys Pro Ser Arg His Thr Glu His Val Phe Ala Leu Arg Pro Val Gly
        435                 440                 445 ttc cgg gac agc ctg gag gtg ggg gtc acc tac aac tgc acg tgc ggc   1392
Phe Arg Asp Ser Leu Glu Val Gly Val Thr Tyr Asn Cys Thr Cys Gly
450                 455                 460 tgc agc gtg ggg ctg gaa ccc aac agc gcc agg tgc aac ggg agc ggg   1440
Cys Ser Val Gly Leu Glu Pro Asn Ser Ala Arg Cys Asn Gly Ser Gly
465                 470                 475                 480 acc tat gtc tgc ggc ctg tgt gag tgc agc ccc ggc tac ctg ggc acc   1488
Thr Tyr Val Cys Gly Leu Cys Glu Cys Ser Pro Gly Tyr Leu Gly Thr
                485                 490                 495 agg tgc gag tgc cag gat ggg gag aac cag agc gtg tac cag aac ctg   1536
Arg Cys Glu Cys Gln Asp Gly Glu Asn Gln Ser Val Tyr Gln Asn Leu
            500                 505                 510 tgc cgg gag gca gag ggc aag cca ctg tgc agc ggg cgt ggg gac tgc   1584
Cys Arg Glu Ala Glu Gly Lys Pro Leu Cys Ser Gly Arg Gly Asp Cys
        515                 520                 525 agc tgc aac cag tgc tcc tgc ttc gag agc gag ttt ggc aag atc tat   1632
Ser Cys Asn Gln Cys Ser Cys Phe Glu Ser Glu Phe Gly Lys Ile Tyr
530                 535                 540 ggg cct ttc tgt gag tgc gac aac ttc tcc tgt gcc agg aac aag gga   1680
Gly Pro Phe Cys Glu Cys Asp Asn Phe Ser Cys Ala Arg Asn Lys Gly
545                 550                 555                 560 gtc ctc tgc tca ggc cat ggc gag tgt cac tgc ggg gaa tgc aag tgc   1728
Val Leu Cys Ser Gly His Gly Glu Cys His Cys Gly Glu Cys Lys Cys
                565                 570                 575 cat gca ggt tac atc ggg gac aac tgt aac tgc tcg aca gac atc agc   1776
His Ala Gly Tyr Ile Gly Asp Asn Cys Asn Cys Ser Thr Asp Ile Ser
            580                 585                 590
```

| | | | | | | | | | | | | | | |
|---|---|---|---|---|---|---|---|---|---|---|---|---|---|---|
| aca | tgc | cgg | ggc | aga | gat | ggc | cag | atc | tgc | agc | gag | cgt | ggg | cac tgt | 1824 |
| Thr | Cys | Arg | Gly | Arg | Asp | Gly | Gln | Ile | Cys | Ser | Glu | Arg | Gly | His Cys | |
| | | 595 | | | | 600 | | | | 605 | | | | | |

| ctc | tgt | ggg | cag | tgc | caa | tgc | acg | gag | ccg | ggg | gcc | ttt | ggg | gag atg | 1872 |
| Leu | Cys | Gly | Gln | Cys | Gln | Cys | Thr | Glu | Pro | Gly | Ala | Phe | Gly | Glu Met | |
| 610 | | | | | 615 | | | | | 620 | | | | | |

| tgt | gag | aag | tgc | ccc | acc | tgc | ccg | gat | gca | tgc | agc | acc | aag | aga gat | 1920 |
| Cys | Glu | Lys | Cys | Pro | Thr | Cys | Pro | Asp | Ala | Cys | Ser | Thr | Lys | Arg Asp | |
| 625 | | | | 630 | | | | | 635 | | | | | 640 | |

| tgc | gtc | gag | tgc | ctg | ctg | ctc | cac | tct | ggg | aaa | cct | gac | aac | cag acc | 1968 |
| Cys | Val | Glu | Cys | Leu | Leu | Leu | His | Ser | Gly | Lys | Pro | Asp | Asn | Gln Thr | |
| | | | | 645 | | | | | 650 | | | | | 655 | |

| tgc | cac | agc | cta | tgc | agg | gat | gag | gtg | atc | aca | tgg | gtg | gac | acc atc | 2016 |
| Cys | His | Ser | Leu | Cys | Arg | Asp | Glu | Val | Ile | Thr | Trp | Val | Asp | Thr Ile | |
| | | | 660 | | | | | 665 | | | | | 670 | | |

| gtg | aaa | gat | gac | cag | gag | gct | gtg | cta | tgt | ttc | tac | aaa | acc | gcc aag | 2064 |
| Val | Lys | Asp | Asp | Gln | Glu | Ala | Val | Leu | Cys | Phe | Tyr | Lys | Thr | Ala Lys | |
| | | 675 | | | | | 680 | | | | | 685 | | | |

| gac | tgc | gtc | atg | atg | ttc | acc | tat | gtg | gag | ctc | ccc | agt | ggg | aag tcc | 2112 |
| Asp | Cys | Val | Met | Met | Phe | Thr | Tyr | Val | Glu | Leu | Pro | Ser | Gly | Lys Ser | |
| 690 | | | | | 695 | | | | | 700 | | | | | |

| aac | ctg | acc | gtc | ctc | agg | gag | cca | gag | tgt | gga | aac | acc | ccc | aac gcc | 2160 |
| Asn | Leu | Thr | Val | Leu | Arg | Glu | Pro | Glu | Cys | Gly | Asn | Thr | Pro | Asn Ala | |
| 705 | | | | 710 | | | | | 715 | | | | | 720 | |

| atg | acc | atc | ctc | ctg | gct | gtg | gtc | ggt | agc | atc | ctc | ctt | gtt | ggg ctt | 2208 |
| Met | Thr | Ile | Leu | Leu | Ala | Val | Val | Gly | Ser | Ile | Leu | Leu | Val | Gly Leu | |
| | | | | 725 | | | | | 730 | | | | | 735 | |

| gca | ctc | ctg | gct | atc | tgg | aag | ctg | ctt | gtc | acc | atc | cac | gac | cgg agg | 2256 |
| Ala | Leu | Leu | Ala | Ile | Trp | Lys | Leu | Leu | Val | Thr | Ile | His | Asp | Arg Arg | |
| | | | 740 | | | | | 745 | | | | | 750 | | |

| gag | ttt | gca | aag | ttt | cag | agc | gag | cga | tcc | agg | gcc | cgc | tat | gaa atg | 2304 |
| Glu | Phe | Ala | Lys | Phe | Gln | Ser | Glu | Arg | Ser | Arg | Ala | Arg | Tyr | Glu Met | |
| | | 755 | | | | | 760 | | | | | 765 | | | |

| gct | tca | aat | cca | tta | tac | aga | aag | cct | atc | tcc | acg | cac | act | gtg gac | 2352 |
| Ala | Ser | Asn | Pro | Leu | Tyr | Arg | Lys | Pro | Ile | Ser | Thr | His | Thr | Val Asp | |
| 770 | | | | | 775 | | | | | 780 | | | | | |

| ttc | acc | ttc | aac | aag | ttc | aac | aaa | tcc | tac | aat | ggc | act | gtg | gac tga | 2400 |
| Phe | Thr | Phe | Asn | Lys | Phe | Asn | Lys | Ser | Tyr | Asn | Gly | Thr | Val | Asp | |
| 785 | | | | | 790 | | | | | 795 | | | | | |

```
<210> SEQ ID NO 11
<211> LENGTH: 2367
<212> TYPE: DNA
<213> ORGANISM: Homo sapiens
<300> PUBLICATION INFORMATION:
<302> TITLE: beta3 integrin
<310> PATENT DOCUMENT NUMBER: NM000212

<400> SEQUENCE: 11
```

| | | | | | |
|---|---|---|---|---|---|
| atgcgagcgc | ggccgcggcc | ccggccgctc | tgggcgactg | tgctggcgct | ggggcgctg | 60 |
| gcgggcgttg | gcgtaggagg | gcccaacatc | tgtaccacgc | gaggtgtgag | ctcctgccag | 120 |
| cagtgcctgg | ctgtgagccc | catgtgtgcc | tggtgctctg | atgaggccct | gcctctgggc | 180 |
| tcacctcgct | gtgacctgaa | ggagaatctg | ctgaaggata | ctgtgcccc | agaatccatc | 240 |
| gagttcccag | tgagtgaggc | ccgagtacta | gaggacaggc | ccctcagcga | caagggctct | 300 |
| ggagacagct | cccaggtcac | tcaagtcagt | ccccagagga | ttgcactccg | gctccggcca | 360 |
| gatgattcga | gaatttctc | catccaagtg | cggcaggtgg | aggattaccc | tgtggacatc | 420 |
| tactacttga | tggacctgtc | ttactccatg | aaggatgatc | tgtggagcat | ccagaacctg | 480 |

```
ggtaccaagc tggccaccca gatgcgaaag ctcaccagta acctgcggat tggcttcggg      540
gcatttgtgg acaagcctgt gtcaccatac atgtatatct ccccaccaga ggccctcgaa      600
aacccctgct atgatatgaa gaccacctgc ttgcccatgt ttggctacaa acacgtgctg      660
acgctaactg accaggtgac ccgcttcaat gaggaagtga agaagcagag tgtgtcacgg      720
aaccgagatg ccccagaggg tggctttgat gccatcatgc aggctacagt ctgtgatgaa      780
aagattggct ggaggaatga tgcatcccac ttgctggtgt ttaccactga tgccaagact      840
catatagcat tggacggaag gctggcaggc attgtccagc taatgacgg gcagtgtcat      900 gttggtagtg acaatcatta ctctgcctcc actaccatgg attatccctc tttggggctg      960
atgactgaga agctatccca gaaaaacatc aatttgatct ttgcagtgac tgaaaatgta     1020
gtcaatctct atcagaacta tagtgagctc atcccaggga ccacagttgg ggttctgtcc     1080
atggattcca gcaatgtcct ccagctcatt gttgatgctt atgggaaaat ccgttctaaa     1140
gtagagctgg aagtgcgtga cctccctgaa gagttgtctc tatccttcaa tgccacctgc     1200
ctcaacaatg aggtcatccc tggcctcaag tcttgtatgg gactcaagat tggagacacg     1260
gtgagcttca gcattgaggc caaggtgcga ggctgtcccc aggagaagga gaagtccttt     1320
accataaagc ccgtgggctt caaggacagc ctgatcgtcc aggtcaccct tgattgtgac     1380
tgtgcctgcc aggcccaagc tgaacctaat agccatcgct gcaacaatgg caatgggacc     1440
tttgagtgtg gggtatgccg ttgtgggcct ggctggctgg atcccagtg tgagtgctca     1500 gaggaggact atcgcccttc ccagcaggac gaatgcagcc ccggagggg tcagcccgtc     1560 tgcagccagc ggggcgagtg cctctgtggt caatgtgtct gccacagcag tgactttggc     1620
aagatcacgg gcaagtactg cgagtgtgac gacttctcct gtgtccgcta caaggggag     1680 atgtgctcag ccatggcca gtgcagctgt gggactgcc tgtgtgactc cgactggacc     1740
ggctactact gcaactgtac cacgcgtact gacacctgca tgtccagcaa tgggctgctg     1800
tgcagcggcc gcggcaagtg tgaatgtggc agctgtgtct gtatccagcc gggctcctat     1860
ggggacacct gtgagaagtg ccccacctgc ccagatgcct gcacctttaa gaaagaatgt     1920
gtggagtgta agaagtttga ccgggagccc tacatgaccg aaaatacctg caaccgttac     1980
tgccgtgacg agattgagtc agtgaaagag cttaaggaca ctggcaagga tgcagtgaat     2040
tgtacctata gaatgagga tgactgtgtc gtcagattcc agtactatga agattctagt     2100
ggaaagtcca tcctgtatgt ggtagaagag ccagagtgtc caagggccc tgacatcctg     2160 gtggtcctgc tctcagtgat gggggccatt ctgctcattg ccttgccgc cctgctcatc     2220 tggaaactcc tcatcaccat ccacgaccga aaagaattcg ctaaatttga ggaagaacgc     2280
gccagagcaa aatgggacac agccaacaac ccactgtata agaggccac gtctaccttc     2340 accaatatca cgtaccgggg cacttaa                                          2367
```

<210> SEQ ID NO 12
<211> LENGTH: 3147
<212> TYPE: DNA
<213> ORGANISM: Homo sapiens
<300> PUBLICATION INFORMATION:
<302> TITLE: alpha v intergrin
<310> PATENT DOCUMENT NUMBER: NM0022210

<400> SEQUENCE: 12

```
atggctttc cgccgcggcg acggctgcgc ctcggtcccc gcggcctccc gcttcttctc       60
tcgggactcc tgctacctct gtgccgcgcc ttcaacctag acgtggacag tcctgccgag      120
```

```
tactctggcc ccgagggaag ttacttcggc ttcgccgtgg atttcttcgt gcccagcgcg    180
tcttcccgga tgtttcttct cgtgggagct cccaaagcaa acaccaccca gcctgggatt    240
gtggaaggag ggcaggtcct caaatgtgac tggtcttcta cccgccggtg ccagccaatt    300
gaatttgatg caacaggcaa tagagattat gccaaggatg atccattgga atttaagtcc    360
catcagtggt ttggagcatc tgtgaggtcg aaacaggata aaattttggc ctgtgcccca    420
ttgtaccatt ggagaactga gatgaaacag gagcgagagc ctgttggaac atgctttctt    480
caagatggaa caaagactgt tgagtatgct ccatgtagat cacaagatat tgatgctgat    540
ggacagggat tttgtcaagg aggattcagc attgatttta ctaaagctga cagagtactt    600
cttggtggtc ctggtagctt ttattggcaa ggtcagctta tttcggatca agtggcagaa    660
atcgtatcta aatacgaccc caatgtttac agcatcaagt ataataacca attagcaact    720
cggactgcac aagctatttt tgatgacagc tatttgggtt attctgtggc tgtcggagat    780
ttcaatggtg atggcataga tgactttgtt tcaggagttc aagagcagc aaggactttg     840
ggaatggttt atatttatga tgggaagaac atgtcctcct tatacaattt tactggcgag    900
cagatggctg catatttcgg attttctgta gctgccactg acattaatgg agatgattat    960
gcagatgtgt ttattggagc acctctcttc atggatcgtg gctctgatgg caaactccaa   1020
gaggtggggc aggtctcagt gtctctacag agagcttcag gagacttcca gacgacaaag   1080
ctgaatggat ttgaggtctt tgcacggttt ggcagtgcca tagctccttt gggagatctg   1140
gaccaggatg gtttcaatga tattgcaatt gctgctccat atgggggtga agataaaaaa   1200
ggaattgttt atatcttcaa tggaagatca acaggcttga acgcagtccc atctcaaatc   1260
cttgaagggc agtgggctgc tcgaagcatg ccaccaagct ttggctattc aatgaaagga   1320
gccacagata tagacaaaaa tggatatcca gacttaattg taggagcttt tggtgtagat   1380
cgagctatct tatacagggc cagaccagtt atcactgtaa atgctggtct tgaagtgtac   1440
cctagcattt taaatcaaga caataaaacc tgctcactgc ctggaacagc tctcaaagtt   1500
tcctgtttta atgttaggtt ctgcttaaag gcagatggca aggagtact cccaggaaa     1560
cttaatttcc aggtggaact tcttttggat aaactcaagc aaaagggagc aattcgacga   1620
gcactgtttc tctacagcag gtcccccaagt cactccaaga acatgactat ttcaaggggg   1680
ggactgatgc agtgtgagga attgatagcg tatctgcggg atgaatctga atttagagac   1740
aaactcactc caattactat ttttatggaa tatcggttgg attatagaac agctgctgat   1800
acaacaggct tgcaacccat tcttaaccag ttcacgcctg ctaacattag tcgacaggct   1860
cacattctac ttgactgtgg tgaagacaat gtctgtaaac ccaagctgga agtttctgta   1920
gatagtgatc aaaagaagat ctatattggg gatgacaacc ctctgacatt gattgttaag   1980
gctcagaatc aaggagaagg tgcctacgaa gctgagctca tcgtttccat tccactgcag   2040
gctgatttca tcgggttgt ccgaaacaat gaagccttag caagactttc ctgtgcattt     2100
aagacagaaa accaaactcg ccaggtggta tgtgaccttg aaacccaat gaaggctgga   2160
actcaactct tagctggtct tcgtttcagt gtgcaccagc agtcagagat ggatacttct   2220
gtgaaatttg acttacaaat ccaaagctca aatctatttg acaaagtaag cccagttgta   2280
tctcacaaag ttgatcttgc tgttttagct gcagttgaga taagaggagt ctcgagtcct   2340
gatcatatct ttcttccgat tccaaactgg gagcacaagg agaaccctga gactgaagaa   2400
gatgttgggc cagttgttca gcacatctat gagctgagaa acaatggtcc aagttcattc   2460
```

| | |
|---|---|
| agcaaggcaa tgctccatct tcagtggcct tacaaatata ataataacac tctgttgtat | 2520 |
| atccttcatt atgatattga tggaccaatg aactgcactt cagatatgga gatcaaccct | 2580 |
| ttgagaatta agatctcatc tttgcaaaca actgaaaaga atgacacggt tgccgggcaa | 2640 |
| ggtgagcggg accatctcat cactaagcgg gatcttgccc tcagtgaagg agatattcac | 2700 |
| actttgggtt gtggagttgc tcagtgcttg aagattgtct gccaagttgg gagattagac | 2760 |
| agaggaaaga gtgcaatctt gtacgtaaag tcattactgt ggactgagac ttttatgaat | 2820 |
| aaagaaaatc agaatcattc ctattctctg aagtcgtctg cttcatttaa tgtcatagag | 2880 |
| tttccttata agaatcttcc aattgaggat atcaccaact ccacattggt taccactaat | 2940 |
| gtcacctggg gcattcagcc agcgcccatg cctgtgcctg tgtgggtgat cattttagca | 3000 |
| gttctagcag gattgttgct actggctgtt ttggtatttg taatgtacag gatgggcttt | 3060 |
| tttaaacggg tccggccacc tcaagaagaa caagaaaggg agcagcttca acctcatgaa | 3120 |
| aatggtgaag gaaactcaga aacttaa | 3147 |

<210> SEQ ID NO 13
<211> LENGTH: 402
<212> TYPE: DNA
<213> ORGANISM: Homo sapiens
<300> PUBLICATION INFORMATION:
<302> TITLE: CaSm (cancer associated SM-like oncogene)
<310> PATENT DOCUMENT NUMBER: AF000177

<400> SEQUENCE: 13

| | |
|---|---|
| atgaactata tgcctggcac cgccagcctc atcgaggaca ttgacaaaaa gcacttggtt | 60 |
| ctgcttcgag atggaaggac acttataggc ttttttaagaa gcattgatca atttgcaaac | 120 |
| ttagtgctac atcagactgt ggagcgtatt catgtgggca aaaaatacgg tgatattcct | 180 |
| cgagggattt ttgtggtcag aggagaaaat gtggtcctac taggagaaat agacttggaa | 240 |
| aaggagagtg acacacccct ccagcaagta tccattgaag aaattctaga gaacaaagg | 300 |
| gtggaacagc agaccaagct ggaagcagag aagttgaaag tgcaggccct gaaggaccga | 360 |
| ggtctttcca ttcctcgagc agatactctt gatgagtact aa | 402 |

<210> SEQ ID NO 14
<211> LENGTH: 1923
<212> TYPE: DNA
<213> ORGANISM: Homo sapiens
<300> PUBLICATION INFORMATION:
<302> TITLE: c-myb
<310> PATENT DOCUMENT NUMBER: NM005375

<400> SEQUENCE: 14

| | |
|---|---|
| atggcccgaa gacccggca cagcatatat agcagtgacg aggatgatga ggactttgag | 60 |
| atgtgtgacc atgactatga tgggctgctt cccaagtctg gaaagcgtca cttggggaaa | 120 |
| acaaggtgga cccgggaaga ggatgaaaaa ctgaagaagc tggtggaaca gaatggaaca | 180 |
| gatgactgga aagttattgc caattatctc ccgaatcgaa cagatgtgca gtgccagcac | 240 |
| cgatggcaga aagtactaaa ccctgagctc atcaagggtc cttggaccaa agaagaagat | 300 |
| cagagagtga tagagcttgt acagaaatac ggtccgaaac gttggtctgt tattgccaag | 360 |
| cacttaaagg ggagaattgg aaaacaatgt agggagaggt ggcataacca cttgaatcca | 420 |
| gaagttaaga aaacctcctg gacagaagag gaagacagaa ttatttacca ggcacacaag | 480 |
| agactgggga cagatggggc agaaatcgca aagctactgc ctggacgaac tgataatgct | 540 |
| atcaagaacc actggaattc tacaatgcgt cggaaggtcg aacaggaagg ttatctgcag | 600 |

```
gagtcttcaa aagccagcca gccagcagtg ccacaagct tccagaagaa cagtcatttg      660
atgggttttg ctcaggctcc gcctacagct caactccctg ccactggcca gcccactgtt    720
aacaacgact attcctatta ccacatttct gaagcacaaa atgtctccag tcatgttcca    780 tacccctgtag cgttacatgt aaatatagtc aatgtccctc agccagctgc cgcagccatt   840
cagagacact ataatgatga agaccctgag aaggaaaagc gaataaagga attagaattg    900
ctcctaatgt caaccgagaa tgagctaaaa ggacagcagg tgctaccaac acagaaccac    960
acatgcagct accccgggtg gcacagcacc accattgccg accacaccag acctcatgga   1020
gacagtgcac ctgtttcctg tttgggagaa caccactcca ctccatctct gccagcggat   1080
cctggctccc tacctgaaga aagcgcctcg ccagcaaggt gcatgatcgt ccaccagggc   1140
accattctgg ataatgttaa gaacctctta gaatttgcag aaacactcca atttatagat   1200
tctttcttaa acacttccag taaccatgaa aactcagact tggaaatgcc ttctttaact   1260
tccacccccc tcattggtca caaattgact gttacaacac catttcatag agaccagact   1320
gtgaaaactc aaaaggaaaa tactgttttt agaacccccag ctatcaaaag gtcaatctta   1380
gaaagctctc caagaactcc tacaccattc aaacatgcac ttgcagctca agaaattaaa   1440
tacggtcccc tgaagatgct acctcagaca ccctctcatc tagtagaaga tctgcaggat   1500
gtgatcaaac aggaatctga tgaatctgga tttgttgctg agtttcaaga aaatggacca   1560
cccttactga gaaaatcaa acaagaggtg gaatctccaa ctgataaatc aggaaacttc    1620
ttctgctcac accactggga aggggacagt ctgaataccc aactgttcac gcagacctcg   1680
cctgtgcgag atgcaccgaa tattcttaca agctccgttt taatggcacc agcatcagaa   1740
gatgaagaca atgttctcaa agcatttaca gtacctaaaa acaggtccct ggcgagcccc   1800
ttgcagcctt gtagcagtac ctgggaacct gcatcctgtg gaaagatgga ggagcagatg   1860
acatcttcca gtcaagctcg taaatacgtg aatgcattct cagcccggac gctggtcatg   1920
tga                                                                 1923

<210> SEQ ID NO 15
<211> LENGTH: 544
<212> TYPE: DNA
<213> ORGANISM: Homo sapiens
<300> PUBLICATION INFORMATION:
<302> TITLE: c-myc
<310> PATENT DOCUMENT NUMBER: J00120

<400> SEQUENCE: 15 gaccccgag ctgtgctgct cgcggccgcc accgccgggc cccggccgtc cctggctccc     60
ctcctgcctc gagaagggca gggcttctca gaggcttggc gggaaaaaga acggaggggag  120 ggatcgcgct gagtataaaa gccggttttc ggggctttat ctaactcgct gtagtaattc   180
cagcgagagg cagagggagc gagcgggcgg ccggctaggg tggaagagcc gggcgagcag   240
agctgcgctg cgggcgtcct gggaagggag atccggagcg aatagggggc ttcgcctctg   300
gcccagccct cccgctgatc ccccagccag cggtccgcaa ccctttgccgc atccacgaaa  360 ctttgcccat agcagcgggc gggcactttg cactggaact acaacacccc gagcaaggac   420
gcgactctcc cgacgcgggg aggctattct gcccatttgg ggacacttcc ccgccgctgc   480
caggacccgc ttctctgaaa ggctctcctt gcagctgctt agacgctgga ttttttcgg    540 gtag                                                                544
```

```
<210> SEQ ID NO 16
<211> LENGTH: 618
<212> TYPE: DNA
<213> ORGANISM: Homo sapiens
<300> PUBLICATION INFORMATION:
<302> TITLE: ephrin-A1
<310> PATENT DOCUMENT NUMBER: NM004428

<400> SEQUENCE: 16
atggagttcc tctgggcccc tctcttgggt ctgtgctgca gtctggccgc tgctgatcgc      60
cacaccgtct tctggaacag ttcaaatccc aagttccgga atgaggacta caccatacat     120
gtgcagctga atgactacgt ggacatcatc tgtccgcact atgaagatca ctctgtggca     180
gacgctgcca tggagcagta catactgtac ctggtggagc atgaggagta ccagctgtgc     240
cagccccagt ccaaggacca agtccgctgg cagtgcaacc ggcccagtgc caagcatggc     300
ccggagaagc tgtctgagaa gttccagcgc ttcacacctt tcaccctggg caaggagttc     360
aaagaaggac acagctacta ctacatctcc aaacccatcc accagcatga agaccgctgc     420
ttgaggttga aggtgactgt cagtggcaaa atcactcaca gtcctcaggc ccatgtcaat     480
ccacaggaga gagacttgc agcagatgac ccagaggtgc gggttctaca tagcatcggt     540
cacagtgctg ccccacgcct cttcccactt gcctggactg tgctgctcct tccacttctg     600
ctgctgcaaa ccccgtga                                                   618

<210> SEQ ID NO 17
<211> LENGTH: 642
<212> TYPE: DNA
<213> ORGANISM: Homo sapiens

<400> SEQUENCE: 17
atggcgcccg cgcagcgccc gctgctcccg ctgctgctcc tgctgttacc gctgccgccg      60
ccgcccttcg cgcgcgccga ggacgccgcc cgcgccaact cggaccgcta cgccgtctac     120
tggaaccgca gcaaccccag gttccacgca ggcgcggggg acgacggcgg gggctacacg     180
gtggaggtga gcatcaatga ctacctggac atctactgcc cgcactatgg ggcgccgctg     240
ccgccggccg agcgcatgga gcgctacgtg ctgtacatgg tcaacggcga gggccacgcc     300
tcctgcgacc accgccagcg cggcttcaag cgctgggagt gcaacggcc cgcggcgccc     360 gggggggccgc tcaagttctc ggagaagttc cagctcttca cgcccttctc cctgggcttc     420
gagttccggc ccggccacga gtattactac atctctgcca cgcctcccaa tgctgtggac     480
cggccctgcc tgcgactgaa ggtgtacgtg cggccgacca cgagaccct gtacgaggct     540 cctgagccca tcttcaccag caataactcg tgtagcagcc cgggcggctg ccgcctcttc     600
ctcagcacca tccccgtgct ctggacctc ctgggttcct ag                         642

<210> SEQ ID NO 18
<211> LENGTH: 717
<212> TYPE: DNA
<213> ORGANISM: Homo sapiens
<300> PUBLICATION INFORMATION:
<302> TITLE: ephrin-A3
<310> PATENT DOCUMENT NUMBER: XM001787

<400> SEQUENCE: 18
atggcggcgg ctccgctgct gctgctgctg ctgctcgtgc ccgtgccgct gctgccgctg      60
ctggcccaag ggccggagg ggcgctggga aacggcatg cggtgtactg aacagctcc        120 aaccagcacc tgcggcgaga gggctacacc gtgcaggtga acgtgaacga ctatctggat    180
```

```
atttactgcc cgcactacaa cagctcgggg gtgggccccg ggcgggacc ggggcccgga    240 ggcggggcag agcagtacgt gctgtacatg gtgagccgca acggctaccg cacctgcaac    300
gccagccagg gcttcaagcg ctgggagtgc aaccggccgc acgccccgca cagccccatc    360
aagttctcgg agaagttcca gcgctacagc gccttctctc tgggctacga gttccacgcc    420
ggccacgagt actactacat ctccacgccc actcacaacc tgcactggaa gtgtctgagg    480
atgaaggtgt tcgtctgctg cgcctccaca tcgcactccg gggagaagcc ggtccccact    540
ctcccccagt tcaccatggg ccccaatatg aagatcaacg tgctggaaga ctttgaggga    600
gagaaccctc aggtgcccaa gcttgagaag agcatcagcg ggaccagccc caaacgggaa    660
cacctgcccc tggccgtggg catcgccttc ttcctcatga cgttcttggc ctcctag      717
```

<210> SEQ ID NO 19
<211> LENGTH: 606
<212> TYPE: DNA
<213> ORGANISM: Homo sapiens
<300> PUBLICATION INFORMATION:
<302> TITLE: ephrin-A3
<310> PATENT DOCUMENT NUMBER: XM001784

<400> SEQUENCE: 19

```
atgcggctgc tgcccctgct gcggactgtc ctctgggccg cgttcctcgg ctcccctctg    60
cgcgggggct ccagcctccg ccacgtagtc tactggaact ccagtaaccc caggttgctt    120
cgaggagacg ccgtggtgga gctgggcctc aacgattacc tagacattgt ctgcccccac    180
tacgaaggcc cagggccccc tgagggcccc gagacgtttg cttttgtacat ggtggactgg    240 ccaggctatg agtcctgcca ggcagagggc ccccgggcct acaagcgctg ggtgtgctcc    300 ctgcccttttg ccatgttcca attctcagag aagattcagc gcttcacacc cttctccctc    360
ggctttgagt tcttacctgg agagacttac tactacatct cggtgcccac tccagagagt    420
tctggccagt gcttgaggct ccaggtgtct gtctgctgca aggagaggaa gtctgagtca    480
gcccatcctg ttgggagccc tggagagagt ggcacatcag ggtggcgagg gggggacact    540
cccagccccc tctgtctctt gctattactg ctgcttctga ttcttcgtct tctgcgaatt    600
ctgtga                                                              606
```

<210> SEQ ID NO 20
<211> LENGTH: 687
<212> TYPE: DNA
<213> ORGANISM: Homo sapiens
<300> PUBLICATION INFORMATION:
<302> TITLE: ephrin-A5
<310> PATENT DOCUMENT NUMBER: NM001962

<400> SEQUENCE: 20

```
atgttgcacg tggagatgtt gacgctggtg tttctggtgc tctggatgtg tgtgttcagc    60
caggacccgg gctccaaggc cgtcgccgac cgctacgctg tctactggaa cagcagcaac    120
cccagattcc agagggtgga ctaccatatt gatgtctgta tcaatgacta cctggatgtt    180
ttctgccctc actatgagga ctccgtccca gaagataaga ctgagcgcta tgtcctctac    240
atggtgaact tgatggcta cagtgcctgc gaccacactt ccaaagggtt caagagatgg    300
gaatgtaacc ggcctcactc tccaaatgga ccgctgaagt tctctgaaaa attccagctc    360
ttcactccct ttctctagg atttgaattc aggccaggcc gagaatattt ctacatctcc    420
tctgcaatcc cagataatgg aagaaggtcc tgtctaaagc tcaaagtctt tgtgagacca    480
acaaatagct gtatgaaaac tataggtgtt catgatcgtg ttttcgatgt aacgacaaa    540
```

| | |
|---|---|
| gtagaaaatt cattagaacc agcagatgac accgtacatg agtcagccga gccatcccgc | 600 |
| ggcgagaacg cggcacaaac accaaggata cccagccgcc tttttggcaat cctactgttc | 660 |
| ctcctggcga tgcttttgac attatag | 687 |

<210> SEQ ID NO 21
<211> LENGTH: 2955
<212> TYPE: DNA
<213> ORGANISM: Homo sapiens

<400> SEQUENCE: 21

| | |
|---|---|
| atggccctgg attatctact actgctcctc ctggcatccg cagtggctgc gatggaagaa | 60 |
| acgttaatgg acaccagaac ggctactgca gagctgggct ggacggccaa tcctgcgtcc | 120 |
| gggtgggaag aagtcagtgg ctacgatgaa aacctgaaca ccatccgcac ctaccagqtg | 180 |
| tgcaatgtct tcgagcccaa ccagaacaat tggctgctca ccaccttcat caaccggcgg | 240 |
| ggggcccatc gcatctacac agagatgcgc ttcactgtga gagactgcag cagcctccct | 300 |
| aatgtcccag atcctgcaa ggagaccttc aacttgtatt actatgagac tgactctgtc | 360 |
| attgccacca agaagtcagc cttctggtct gaggccccct acctcaaagt agacaccatt | 420 |
| gctgcagatg agagcttctc ccaggtggac tttgggggaa ggctgatgaa ggtaaacaca | 480 |
| gaagtcagga gctttgggcc tcttactcgg aatggttttt acctcgcttt tcaggattat | 540 |
| ggagcctgta tgtctcttct ttctgtccgt gtcttcttca aaaagtgtcc cagcattgtg | 600 |
| caaaattttg cagtgtttcc agagactatg acaggggcag agagcacatc tctggtgatt | 660 |
| gctcggggca catgcatccc caacgcagag gaagtggacg tgcccatcaa actctactgc | 720 |
| aacgggatg gggaatggat ggtgcctatt ggcgcgatgca cctgcaagcc tggctatgag | 780 |
| cctgagaaca gcgtggcatg caaggcttgc cctgcaggga cattcaaggc cagccaggaa | 840 |
| gctgaaggct gctcccactg cccctccaac agccgctccc ctgcagaggc gtctcccatc | 900 |
| tgcacctgtc ggaccggtta ttaccgagcg gactttgacc tccagaagt ggcatgcact | 960 |
| agcgtcccat caggtccccg caatgttatc tccatcgtca atgagacgtc catcattctg | 1020 |
| gagtggcacc ctccaaggga gacaggtggg cgggatgatg tgacctacaa catcatctgc | 1080 |
| aaaaagtgcc gggcagaccg ccggagctgc tcccgctgtg acgacaatgt ggagtttgtg | 1140 |
| cccaggcagc tgggcctgac ggagtgccgc gtctccatca gcagcctgtg ggcccacacc | 1200 |
| ccctacacct ttgacatcca ggccatcaat ggagtctcca gcaagagtcc cttcccccca | 1260 |
| cagcacgtct ctgtcaacat caccacaaac caagccgccc cctccaccgt tcccatcatg | 1320 |
| caccaagtca gtgccactat gaggagcatc accttgtcat ggccacagcc ggagcagccc | 1380 |
| aatggcatca tcctggacta tgagatccgg tactatgaga aggaacacaa tgagttcaac | 1440 |
| tcctccatgg ccaggagtca gaccaacaca gcaaggattg atgggctgcg gcctggcatg | 1500 |
| gtatatgtgg tacaggtgcg tgcccgcact gttgctggct acggcaagtt cagtggcaag | 1560 |
| atgtgcttcc agactctgac tgacgatgat tacaagtcag agctgaggga gcagctgccc | 1620 |
| ctgattgctg gctcggcagc ggccggggtc gtgttcgttg tgtccttggt ggccatctct | 1680 |
| atcgtctgta gcaggaaacg ggcttatagc aaagaggctg tgtacagcga taagctccag | 1740 |
| cattacagca caggccgagg ctccccaggg atgaagatct acattgaccc cttcacttat | 1800 |
| gaggatccca acgaagctgt ccgggagttt gccaaggaga ttgatgtatc ttttgtgaaa | 1860 |
| attgaagagg tcatcggagc agggggagtt tggagaagtgt acaaggggcg tttgaaactg | 1920 |

| | |
|---|---|
| ccaggcaaga gggaaatcta cgtggccatc aagaccctga aggcagggta ctcggagaag | 1980 |
| cagcgtcggg actttctgag tgaggcgagc atcatgggcc agttcgacca tcctaacatc | 2040 |
| attcgcctgg agggtgtggt caccaagagt cggcctgtca tgatcatcac agagttcatg | 2100 |
| gagaatggtg cattggattc tttcctcagg caaaatgacg gcagttcac cgtgatccag | 2160 |
| cttgtgggta tgctcagggg catcgctgct ggcatgaagt acctggctga gatgaattat | 2220 |
| gtgcatcggg acctggctgc taggaacatt ctggtcaaca gtaacctggt gtgcaaggtg | 2280 |
| tccgactttg gcctctcccg ctacctccag gatgacacct cagatcccac ctacaccagc | 2340 |
| tccttgggag ggaagatccc tgtgagatgg acagctccag aggccatcgc ctaccgcaag | 2400 |
| ttcacttcag ccagcgacgt ttggagctat gggatcgtca tgtgggaagt catgtcattt | 2460 |
| ggagagagac cctattggga tatgtccaac caagatgtca tcaatgccat cgagcaggac | 2520 |
| taccggctgc ccccacccat ggactgtcca gctgctctac accagctcat gctggactgt | 2580 |
| tggcagaagg accggaacag ccggcccgg tttgcggaga ttgtcaacac cctagataag | 2640 |
| atgatccgga cccggcaag tctcaagact gtggcaacca tcaccgccgt gccttcccag | 2700 |
| cccctgctcg accgctccat cccagacttc acggccttta ccaccgtgga tgactggctc | 2760 |
| agcgccatca aaatggtcca gtacagggac agcttcctca ctgctggctt cacctcccct | 2820 |
| cagctggtca cccagatgac atcagaagac ctcctgagaa taggcatcac cttggcaggc | 2880 |
| catcagaaga agatcctgaa cagcattcat tctatgaggg tccagataag tcagtcacca | 2940 |
| acggcaatgg catga | 2955 |

<210> SEQ ID NO 22
<211> LENGTH: 3168
<212> TYPE: DNA
<213> ORGANISM: Homo sapiens

<400> SEQUENCE: 22

| | |
|---|---|
| atggctctgc ggaggctggg ggccgcgctg ctgctgctgc cgctgctcgc cgccgtggaa | 60 |
| gaaacgctaa tggactccac tacagcgact gctgagctgg gctggatggt gcatcctcca | 120 |
| tcagggtggg aagaggtgag tggctacgat gagaacatga acacgatccg cacgtaccag | 180 |
| gtgtgcaacg tgtttgagtc aagccagaac aactggctac ggaccaagtt tatccggcgc | 240 |
| cgtggcgccc accgcatcca cgtggagatg aagttttcgg tgcgtgactg cagcagcatc | 300 |
| cccagcgtgc ctggctcctg caaggagacc ttcaacctct attactatga ggctgacttt | 360 |
| gactcggcca ccaagaccct tccccaactgg atggagaatc catgggtgaa ggtggatacc | 420 |
| attgcagccg acgagagctt ctcccaggtg gacctgggtg gccgcgtcat gaaaatcaac | 480 |
| accgaggtgc ggagcttcgg acctgtgtcc cgcagcggct tctacctggc cttccaggac | 540 |
| tatggcggct gcatgtccct catcgccgtg cgtgtcttct accgcaagtg cccccgcatc | 600 |
| atccagaatg cgccatcttc caggaaacc ctgtcggggg ctgagagcac atcgctggtg | 660 |
| gctgccgggg gcagctgcat cgccaatgcg gaagaggtga tgtacccat caagctctac | 720 |
| tgtaacgggg acggcgagtg gctggtgccc atcgggcgct gcatgtgcaa gcaggcttc | 780 |
| gaggccgttg agaatggcac cgtctgccga ggttgtccat ctgggacttt caaggccaac | 840 |
| caaggggatg aggcctgtac ccactgtccc atcaacagcc ggaccacttc tgaaggggcc | 900 |
| accaactgtg tctgccgcaa tggctactac agagcagacc tggaccccct ggacatgccc | 960 |
| tgcacaacca tccctccgc gccccaggct gtgattccca gtgtcaatga cctcccctc | 1020 |
| atgctggagt ggacccctcc ccgcgactcc ggaggccgag aggacctcgt ctacaacatc | 1080 |

```
atctgcaaga gctgtggctc gggccggggt gcctgcaccc gctgcgggga caatgtacag    1140
tacgcaccac gccagctagg cctgaccgag ccacgcattt acatcagtga cctgctggcc    1200
cacacccagt acaccttcga gatccaggct gtgaacggcg ttactgacca gagccccttc    1260
tcgcctcagt tcgcctctgt gaacatcacc accaaccagg cagctccatc ggcagtgtcc    1320
atcatgcatc aggtgagccg caccgtggac agcattaccc tgtcgtggtc ccagccagac    1380
cagcccaatg gcgtgatcct ggactatgag ctgcagtact atgagaagga gctcagtgag    1440
tacaacgcca cagccataaa aagccccacc aacacggtca ccgtgcaggg cctcaaagcc    1500
ggcgccatct atgtcttcca ggtgcgggca cgcaccgtgg caggctacgg cgctacagc     1560 ggcaagatgt acttccagac catgacagaa gccgagtacc agacaagcat ccaggagaag    1620
ttgccactca tcatcggctc ctcggccgct ggcctggtct tcctcattgc tgtggttgtc    1680
atcgccatcg tgtgtaacag acggggggttt gagcgtgctg actcggagta cacggacaag    1740
ctgcaacact acaccagtgg ccacatgacc ccaggcatga agatctacat cgatcctttc    1800
acctacgagg accccaacga ggcagtgcgg gagtttgcca aggaaattga catctcctgt    1860
gtcaaaattg agcaggtgat cggagcaggg gagtttggcg aggtctgcag tggccacctg    1920
aagctgccag gcaagagaga gatctttgtg gccatcaaga cgctcaagtc gggctacacg    1980
gagaagcagc gccgggactt cctgagcgaa gcctccatca tgggccagtt cgaccatccc    2040
aacgtcatcc acctggaggg tgtcgtgacc aagagcacac ctgtgatgat catcaccgag    2100
ttcatggaga atggctccct ggactccttt ctccggcaaa acgatgggca gttcacagtc    2160
atccagctgg tgggcatgct tcggggcatc gcagctggca tgaagtacct ggcagacatg    2220
aactatgttc accgtgacct ggctgcccgc aacatcctcg tcaacagcaa cctggtctgc    2280
aaggtgtcgg acttttgggct ctcacgcttt ctagaggacg atacctcaga ccccacctac    2340
accagtgccc tgggcggaaa gatccccatc cgctggacag ccccggaagc catccagtac    2400
cggaagttca cctcggccag tgatgtgtgg agctacggca ttgtcatgtg ggaggtgatg    2460
tcctatgggg agcggcccta ctgggacatg accaaccagg atgtaatcaa tgccattgag    2520
caggactatc ggctgccacc gcccatggac tgccgagcg ccctgcacca actcatgctg    2580
gactgttggc agaaggaccg caaccaccgg cccaagttcg ccaaattgt caacacgcta    2640 gacaagatga tccgcaatcc caacagcctc aaagccatgg cgcccctctc ctctggcatc    2700
aacctgccgc tgctggaccg cacgatcccc gactacacca gctttaacac ggtggacgag    2760
tggctggagg ccatcaagat ggggcagtac aaggagagct cgccaatgc cggcttcacc    2820 tcctttgacg tcgtgtctca gatgatgatg gaggacattc tccgggttgg ggtcactttg    2880
gctggccacc agaaaaaaat cctgaacagt atccaggtga tgcgggcgca gatgaaccag    2940
attcagtctg tggagggcca gccactcgcc aggaggccac gggccacggg aagaaccaag    3000
cggtgccagc cacgagacgt caccaagaaa acatgcaact caaacgacgg aaaaaaaaag    3060
ggaatgggaa aaagaaaac agatcctggg aggggcggg aaatacaagg aatatttttt    3120
aaagaggatt ctcataagga aagcaatgac tgttcttgcg ggggataa              3168
```

<210> SEQ ID NO 23
<211> LENGTH: 2997
<212> TYPE: DNA
<213> ORGANISM: Homo sapiens

<400> SEQUENCE: 23

```
atggccagag cccgcccgcc gccgccgccg tcgccgccgc cggggcttct gccgctgctc    60
cctccgctgc tgctgctgcc gctgctgctg ctcccgccg gctgccgggc gctggaagag    120
accctcatgg acacaaaatg ggtaacatct gagttggcgt ggacatctca tccagaaagt    180
gggtgggaag aggtgagtgg ctacgatgag gccatgaatc ccatccgcac ataccaggtg    240
tgtaatgtgc gcgagtcaag ccagaacaac tggcttcgca cggggttcat ctggcggcgg    300
gatgtgcagc gggtctacgt ggagctcaag ttcactgtgc gtgactgcaa cagcatcccc    360
aacatccccg gctcctgcaa ggagaccttc aacctcttct actacgaggc tgacagcgat    420
gtggcctcag cctcctcccc cttctggatg agaacccct acgtgaaagt ggacaccatt    480
gcacccgatg agagcttctc gcggctggat gccggccgtg tcaacaccaa ggtgcgcagc    540
tttgggccac tttccaaggc tggcttctac ctggccttcc aggaccaggg cgcctgcatg    600
tcgctcatct ccgtgcgcgc cttctacaag aagtgtgcat ccaccaccgc aggcttcgca    660
ctcttcccg agaccctcac tggggcggag cccacctcgc tggtcattgc tcctggcacc    720
tgcatcccta acgccgtgga ggtgtcggtg ccactcaagc tctactgcaa cggcgatggg    780
gagtggatgg tgcctgtggg tgcctgcacc tgtgccaccg ccatgagcc agctgccaag    840
gagtcccagt gccgccctg tcccctgggg agctacaagg cgaagcaggg agaggggccc    900
tgcctcccat gtcccccaa cagccgtacc acctccccag ccgccagcat ctgcacctgc    960
cacaataact tctaccgtgc agactcggac tctgcggaca gtgcctgtac caccgtgcca   1020
tctccacccc gaggtgtgat ctccaatgtg aatgaaacct cactgatcct cgagtggagt   1080
gagccccggg acctgggtgt ccgggatgac ctcctgtaca atgtcatctg caagaagtgc   1140
catggggctg gaggggcctc agcctgctca cgctgtgatg acaacgtgga gtttgtgcct   1200
cggcagctgg gcctgtcgga gccccgggtc cacaccagcc atctgctggc ccacacgcgc   1260
tacacctttg aggtgcaggc ggtcaacggt gtctcgggca gagccctct gccgcctcgt   1320
tatgcggccg tgaatatcac cacaaaaccag gctgccccgt ctgaagtgcc cacactacgc   1380
ctgcacagca gctcaggcag cagcctcacc ctatcctggg caccccaga gcggcccaac   1440
ggagtcatcc tggactacga gatgaagtac tttgagaaga gcgagggcat cgcctccaca   1500
gtgaccagcc agatgaactc cgtgcagctg gacgggcttc ggcctgacgc ccgctatgtg   1560
gtccaggtcc gtgcccgcac agtagctggc tatgggcagt acagccgccc tgccgagttt   1620
gagaccacaa gtgagagagg ctctggggcc cagcagctcc aggagcagct tcccctcatc   1680
gtgggctccg ctacagctgg gcttgtcttc gtggtggctg tcgtggtcat cgctatcgtc   1740
tgcctcagga agcagcgaca cggctctgat tcggagtaca cggagaagct gcagcagtac   1800
attgctcctg gaatgaaggt ttatattgac ccttttacct acgaggaccc taatgaggct   1860
gttcgggagt ttgccaagga gatcgacgtg tcctgcgtca agatcgagga ggtgatcgga   1920
gctggggaat ttggggaagt gtgccgtggt cgactgaaac agcctggccg ccagaggtg   1980
tttgtggcca tcaagacgct gaaggtgggc tacaccgaga ggcagcggcg ggacttccta   2040
agcgaggcct ccatcatggg tcagtttgat caccccaata taatccggct cgagggcgtg   2100
gtcaccaaaa gtcggccagt tatgatcctc actgagttca tggaaaactg cgccctggac   2160
tccttcctcc ggctcaacga tgggcagttc acggtcatcc agctggtggg catgttgcgg   2220
ggcattgctg ccggcatgaa gtacctgtcc gagatgaact atgtgcaccg cgacctggct   2280
gctcgcaaca tccttgtcaa cagcaacctg gtctgcaaag tctcagactt ggccctctcc   2340
cgcttcctgg aggatgaccc ctccgatcct acctacacca gttccctggg cgggaagatc   2400
```

| cccatccgct ggactgcccc agaggccata gcctatcgga agttcacttc tgctagtgat | 2460 |
| gtctggagct acggaattgt catgtgggag gtcatgagct atggagagcg accctactgg | 2520 |
| gacatgagca accaggatgt catcaatgcc gtggagcagg attaccggct gccaccaccc | 2580 |
| atggactgtc ccacagcact gcaccagctc atgctggact gctgggtgcg ggaccggaac | 2640 |
| ctcaggccca aattctccca gattgtcaat accctggaca agctcatccg caatgctgcc | 2700 |
| agcctcaagg tcattgccag cgctcagtct ggcatgtcac agcccctcct ggaccgcacg | 2760 |
| gtcccagatt acacaacctt cacgacagtt ggtgattggc tggatgccat caagatgggg | 2820 |
| cggtacaagg agagcttcgt cagtgcgggg tttgcatctt ttgacctggt ggcccagatg | 2880 |
| acggcagaag acctgctccg tattggggtc accctggccg ccaccagaa gaagatcctg | 2940 |
| agcagtatcc aggacatgcg gctgcagatg aaccagacgc tgcctgtgca ggtctga | 2997 |

<210> SEQ ID NO 24
<211> LENGTH: 2964
<212> TYPE: DNA
<213> ORGANISM: Homo sapiens
<400> SEQUENCE: 24

| atggagctcc gggtgctgct ctgctgggct tcgttggccg cagctttgga agagaccctg | 60 |
| ctgaacacaa aattggaaac tgctgatctg aagtgggtga cattccctca ggtggacggg | 120 |
| cagtgggagg aactgagcgg cctggatgag aacagcaca gcgtgcgcac ctacgaagtg | 180 |
| tgtgaagtgc agcgtgcccc gggccaggcc cactggcttc gcacaggttg ggtcccacgg | 240 |
| cggggcgccg tccacgtgta cgccacgctg cgcttcacca tgctcgagtg cctgtccctg | 300 |
| cctcgggctg ggcgctcctg caaggagacc ttcaccgtct tctactatga gagcgatgcg | 360 |
| gacacggcca cggccctcac gccagcctgg atggagaacc cctacatcaa ggtggacacg | 420 |
| gtggccgcgg agcatctcac ccggaagcgc cctggggccg aggccaccgg aaggtgaat | 480 |
| gtcaagacgc tgcgtctggg accgctcagc aaggctggct tctacctggc cttccaggac | 540 |
| cagggtgcct gcatggccct gctatccctg cacctcttct acaaaaagtg cgcccagctg | 600 |
| actgtgaacc tgactcgatt cccggagact gtgcctcggg agctggttgt gcccgtggcc | 660 |
| ggtagctgcg tggtggatgc cgtccccgcc cctggcccca gcccagcct ctactgccgt | 720 |
| gaggatggcc agtgggccga acagccggtc acgggctgca gctgtgctcc ggggttcgag | 780 |
| gcagctgagg ggaacaccaa gtgccgagcc tgtgcccagg gcaccttcaa gccctgtca | 840 |
| ggagaagggt cctgccagcc atgcccagcc aatagccact ctaacaccat ggatctgcc | 900 |
| gtctgccagt ccgcgtcgg ggacttccgg gcacgcacag acccccgggg tgcaccctgc | 960 |
| accacccctc cttcggctcc gcggagcgtg gtttcccgcc tgaacggctc ctccctgcac | 1020 |
| ctggaatgga gtgccccct ggagtctggt ggccgagagg acctcaccta cgccctccgc | 1080 |
| tgccgggagt gccgacccgg aggctcctgt gcgccctgcg gggagacct gacttttgac | 1140 |
| cccggccccc gggacctggt ggagccctgg gtggtggttc gagggctacg tccggacttc | 1200 |
| acctatacct ttgaggtcac tgcattgaac gggtatcct ccttagccac ggggcccgtc | 1260 |
| ccatttgagc ctgtcaatgt caccactgac cgagaggtac ctcctgcagt gtctgacatc | 1320 |
| cgggtgacgc ggtcctcacc cagcagcttg agcctggcct gggctgttcc ccgggcaccc | 1380 |
| agtggggcgt ggctggacta cgaggtcaaa taccatgaga agggcgccga gggtcccagc | 1440 |
| agcgtgcggt tcctgaagac gtcagaaaac cgggcagagc tgcgggggct gaagcgggga | 1500 |

```
gccagctacc tggtgcaggt acgggcgcgc tctgaggccg gctacgggcc cttcggccag     1560
gaacatcaca gccagaccca actgatgag agcgagggct ggcggagca gctggccctg      1620 attgcgggca cggcagtcgt gggtgtggtc ctggtcctgg tggtcattgt ggtcgcagtt     1680
ctctgcctca ggaagcagag caatgggaga gaagcagaat attcggacaa acacggacag     1740
tatctcatcg acatggtac taaggtctac atcgaccct tcacttatga agaccctaat      1800
gaggctgtga gggaatttgc aaaagagatc gatgtctcct acgtcaagat tgaagaggtg     1860
attggtgcag gtgagtttgg cgaggtgtgc cgggggcggc tcaaggcccc agggaagaag     1920
gagagctgtg tggcaatcaa gaccctgaag gtggctaca cggagcggca gcggcgtgag     1980
tttctgagcg aggcctccat catgggccag ttcgagcacc ccaatatcat ccgcctggag     2040
ggcgtggtca ccaacagcat gcccgtcatg attctcacag agttcatgga gaacggcgcc     2100
ctggactcct tcctgcggct aaacgacgga cagttcacag tcatccagct cgtgggcatg     2160
ctgcggggca tcgcctcggg catgcggtac cttgccgaga tgagctacgt ccaccgagac     2220
ctggctgctc gcaacatcct agtcaacagc aacctcgtct gcaaagtgtc tgactttggc     2280 cttttcccgat tcctggagga gaactcttcc gatcccacct acacgagctc cctgggagga     2340
aagattccca tccgatggac tgccccgcag gccattgcct tccggaagtt cacttccgcc     2400
agtgatgcct ggagttacgg gattgtgatg tgggaggtga tgtcatttgg ggagaggccg     2460
tactgggaca tgagcaatca ggacgtgatc aatgccattg aacaggacta ccggctgccc     2520 ccgccccag actgtcccac ctccctccac cagctcatgc tggactgttg gcagaaagac     2580
cggaatgccc ggccccgctt cccccaggtg gtcagcgccc tggacaagat gatccggaac     2640
cccgccagcc tcaaaatcgt ggcccgggag aatggcgggg cctcacaccc tctcctggac     2700
cagcggcagc tcactactc agcttttggc tctgtgggcg agtggcttcg ggccatcaaa     2760
atgggaagat acgaagcccg tttcgcagcc gctggctttg gctccttcga gctggtcagc     2820
cagatctctg ctgaggacct gctccgaatc ggagtcactc tggcgggaca ccagaagaaa     2880
atcttggcca gtgtccagca catgaagtcc caggccaagc cgggaacccc gggtgggaca     2940
ggaggaccgg ccccgcagta ctga                                           2964

<210> SEQ ID NO 25
<211> LENGTH: 1041
<212> TYPE: DNA
<213> ORGANISM: Homo sapiens
<300> PUBLICATION INFORMATION:
<302> TITLE: ephrin-B1
<310> PATENT DOCUMENT NUMBER: NM004429

<400> SEQUENCE: 25
atggctcggc ctgggcagcg ttggctcggc aagtggcttg tggcgatggt cgtgtgggcg       60
ctgtgccggc tcgccacacc gctggccaag aacctggagc ccgtatcctg gagctccctc      120
aaccccaagt cctgagtgg aagggcttg tgatctatc cgaaaattgg agacaagctg        180
gacatcatct gcccccgagc agaagcaggg cggccctatg agtactacaa gctgtacctg     240
gtgcggcctg agcaggcagc tgcctgtagc acagttctcg accccaacgt gttggtcacc     300
tgcaataggc cagagcagga atacgctttt accatcaagt ccaggagtt cagccccaac     360 tacatgggcc tggagttcaa gaagcaccat gattactaca ttacctcaac atccaatgga     420
agcctggagg gctggaaaa ccgggagggc ggtgtgtgcc gcacacgcac catgaagatc     480
atcatgaagg ttgggcaaga tcccaatgct gtgacgcctg agcagctgac taccagcagg     540
```

```
cccagcaagg aggcagacaa cactgtcaag atggccacac aggcccctgg tagtcgggc      600 tccctgggtg actctgatgg caagcatgag actgtgaacc aggaagagaa gagtggccca      660
ggtgcaagtg ggggcagcag cggggaccct gatggcttct tcaactccaa ggtggcattg      720
ttcgcggctc tcggtgccgg ttgcgtcatc ttcctgctca tcatcatctt cctgacggtc      780
ctactactga agctacgcaa gcggcaccgc aagcacacac agcagcgggc ggctgccctc      840
tcgctcagta ccctggccag tcccaagggg ggcagtggca cagcgggcac cgagcccagc      900
gacatcatca ttcccttacg gactacagag aacaactact gcccccacta tgagaaggtg      960
agtggggact acgggcaccc tgtctacatc gtccaagaga tgccgcccca gagcccggcg     1020
aacatctact acaaggtctg a                                               1041

<210> SEQ ID NO 26
<211> LENGTH: 1002
<212> TYPE: DNA
<213> ORGANISM: Homo sapiens
<300> PUBLICATION INFORMATION:

<400> SEQUENCE: 26
atggctgtga aagggactc cgtgtggaag tactgctggg gtgttttgat ggttttatgc        60
agaactgcga tttccaaatc gatagtttta gagcctatct attggaattc ctcgaactcc      120
aaatttctac ctggacaagg actggtacta tacccacaga taggagacaa attggatatt      180
atttgcccca agtggactc taaaactgtt ggccagtatg aatattataa agtttatatg       240
gttgataaag accaagcaga cagatgcact attaagaagg aaaatacccc tctcctcaac      300
tgtgccaaac cagaccaaga tatcaaattc accatcaagt ttcaagaatt cagccctaac      360
ctctggggtc tagaatttca gaagaacaaa gattattaca ttatatctac atcaaatggg      420
tctttggagg gcctggataa ccaggaggga ggggtgtgcc agacaagagc catgaagatc      480
ctcatgaaag ttggacaaga tgcaagttct gctggatcaa ccaggaataa agatccaaca      540
agacgtccag aactagaagc tggtacaaat ggaagaagtt cgacaacaag tccctttgta      600
aaaccaaatc caggttctag cacagacggc aacagcgccg acattcggg gaacaacatc      660 ctcggttccg aagtggcctt atttgcaggg attgcttcag gatgcatcat cttcatcgtc      720
atcatcatca cgctggtggt cctcttgctg aagtaccgga ggagacacag gaagcactcg      780
ccgcagcaca cgaccacgct gtcgctcagc acactggcca cccaagcg cagcggcaac       840 aacaacggct cagagcccag tgacattatc atcccgctaa ggactgcgga cagcgtcttc      900
tgccctcact acgagaaggt cagcggcgac tacgggcacc cggtgtacat cgtccaggag      960
atgcccccgc agagcccggc gaacatttac tacaaggtct ga                       1002

<210> SEQ ID NO 27
<211> LENGTH: 1023
<212> TYPE: DNA
<213> ORGANISM: Homo sapiens

<400> SEQUENCE: 27
atggggcccc cccattctgg gccgggggc gtgcgagtcg ggccctgct gctgctgggg         60 gttttggggc tggtgtctgg gctcagcctg gagcctgtct actggaactc ggcgaataag      120
aggttccagg cagagggtgg ttatgtgctg taccctcaga tcggggaccg gctagacctg      180
ctctgccccc gggcccggcc tcctggccct cactcctctc ctaattatga gttctacaag      240
ctgtacctgg taggggtgc tcagggccgg cgctgtgagg caccccctgc cccaaacctc      300
```

| | |
|---|---|
| cttctcactt gtgatcgccc agacctggat ctccgcttca ccatcaagtt ccaggagtat | 360 |
| agccctaatc tctggggcca cgagttccgc tcgcaccacg attactacat cattgccaca | 420 |
| tcggatggga cccggagggg cctggagagc ctgcagggag gtgtgtgcct aaccagaggc | 480 |
| atgaaggtgc ttctccgagt gggacaaagt ccccgaggag gggctgtccc cgaaaacct | 540 |
| gtgtctgaaa tgcccatgga aagagaccga ggggcagccc acagcctgga gcctgggaag | 600 |
| gagaacctgc caggtgaccc caccagcaat gcaacctccc ggggtgctga aggcccctg | 660 |
| cccctccca gcatgcctgc agtggctggg gcagcagggg ggctggcgct gctcttgctg | 720 |
| ggcgtggcag gggctggggg tgccatgtgt tggcggagac ggcgggccaa gccttcggag | 780 |
| agtcgccacc ctggtcctgg ctccttcggg aggggagggt ctctgggcct ggggggtgga | 840 |
| ggtgggatgg gacctcggga ggctgagcct ggggagctag ggatagctct gcggggtggc | 900 |
| ggggctgcag atcccccctt ctgcccccac tatgagaagg tgagtggtga ctatgggcat | 960 |
| cctgtgtata tcgtgcagga tgggcccccc cagagccctc aaacatcta ctacaaggta | 1020 |
| tga | 1023 |

<210> SEQ ID NO 28
<211> LENGTH: 3399
<212> TYPE: DNA
<213> ORGANISM: Homo sapiens
<300> PUBLICATION INFORMATION:
<302> TITLE: telomerase reverse transcriptase
<310> PATENT DOCUMENT NUMBER: AF015950

<400> SEQUENCE: 28

| | |
|---|---|
| atgccgcgcg ctccccgctg ccgagccgtg cgctccctgc tgcgcagcca ctaccgcgag | 60 |
| gtgctgccgc tggccacgtt cgtgcggcgc ctggggcccc agggctggcg gctggtgcag | 120 |
| cgcggggacc cggcggcttt ccgcgcgctg gtggcccagt gcctggtgtg cgtgccctgg | 180 |
| gacgcacggc cgcccccgc cgccccctcc ttccgccagg tgtcctgcct gaaggagctg | 240 |
| gtggcccgag tgctgcagag gctgtgcgag cgcggcgcga agaacgtgct ggccttcggc | 300 |
| ttcgcgctgc tggacggggc cgcgggggc ccccccgagg ccttcaccac cagcgtgcgc | 360 |
| agctacctgc ccaacacggt gaccgacgca ctgcggggga cgggggcgtg ggggctgctg | 420 |
| ctgcgccgcg tgggcgacga cgtgctggtt cacctgctgg cacgctgcgc gctctttgtg | 480 |
| ctggtggctc ccagctgcgc ctaccaggtg tgcgggccgc cgctgtacca gctcggcgct | 540 |
| gccactcagg cccggccccc gccacacgct agtggacccc gaaggcgtct gggatgcgaa | 600 |
| cgggcctgga accatagcgt cagggaggcc ggggtccccc tgggcctgcc agccccgggt | 660 |
| gcgaggaggc gcggggcag tgccagccga agtctgccgt tgcccaagag gcccaggcgt | 720 |
| ggcgctgccc ctgagccgga gcggacgccc gttgggcagg ggtcctgggc caccccgggc | 780 |
| aggacgcgtg gaccgagtga ccgtggtttc tgtgtggtgt cacctgccag acccgccgaa | 840 |
| gaagccacct ctttggaggg tgcgctctct ggcacgcgcc actcccaccc atccgtgggc | 900 |
| cgccagcacc acgcgggccc cccatccaca tcgcggccac cacgtccctg ggacacgcct | 960 |
| tgtcccccgg tgtacgccga gaccaagcac ttcctctact cctcaggcga caaggagcag | 1020 |
| ctgcggccct ccttcctact cagctctctg aggcccagcc tgactggcgc tcggaggctc | 1080 |
| gtggagacca tctttctggg ttccaggccc tggatgccag ggactccccg caggttgccc | 1140 |
| cgcctgcccc agcgctactg gcaaatgcgg ccctgtttc tggagctgct tgggaaccac | 1200 |
| gcgcagtgcc cctacgggt gctcctcaag acgcactgcc cgctgcgagc tgcggtcacc | 1260 |

```
ccagcagccg gtgtctgtgc ccgggagaag ccccagggct ctgtggcggc ccccgaggag    1320
gaggacacag accccgtcg cctggtgcag ctgctccgcc agcacagcag ccctggcag     1380 gtgtacggct tcgtgcgggc ctgcctgcgc cggctggtgc ccccaggcct ctggggctcc    1440
aggcacaacg aacgccgctt cctcaggaac accaagaagt tcatctccct ggggaagcat    1500
gccaagctct cgctgcagga gctgacgtgg aagatgagcg tgcgggactg cgcttggctg    1560
cgcaggagcc caggggttgg ctgtgttccg gccgcagagc accgtctgcg tgaggagatc    1620
ctggccaagt tcctgcactg gctgatgagt gtgtacgtcg tcgagctgct caggtctttc    1680
ttttatgtca cggagaccac gtttcaaaag aacaggctct ttttctaccg gaagagtgtc    1740
tggagcaagt tgcaaagcat tggaatcaga cagcacttga agagggtgca gctgcgggag    1800
ctgtcggaag cagaggtcag gcagcatcgg gaagccaggc ccgccctgct gacgtccaga    1860
ctccgcttca tccccaagcc tgacgggctg cggccgattg tgaacatgga ctacgtcgtg    1920
ggagccagaa cgttccgcag agaaaagagg gccgagcgtc tcacctcgag ggtgaaggca    1980
ctgttcagcg tgctcaacta cgagcgggcg cggcgccccg gcctcctggg cgcctctgtg    2040
ctgggcctgg acgatatcca cagggcctgg cgcaccttcg tgctgcgtgt gcgggcccag    2100
gacccgccgc ctgagctgta cttttgtcaag gtggatgtga cgggcgcgta cgacaccatc    2160
ccccaggaca ggctcacgga ggtcatcgcc agcatcatca accccagaa cacgtactgc     2220 gtgcgtcggt atgccgtggt ccagaaggcc gcccatgggc acgtccgcaa ggccttcaag    2280
agccacgtct ctaccttgac agacctccag ccgtacatgc gacagttcgt ggctcacctg    2340
caggagacca gcccgctgag ggatgccgtc gtcatcgagc agagctcctc cctgaatgag    2400
gccagcagtg gcctcttcga cgtcttccta cgcttcatgt gccaccacgc cgtgcgcatc    2460
aggggcaagt cctacgtcca gtgccagggg atcccgcagg gctccatcct ctccacgctg    2520
ctctgcagcc tgtgctacgg cgacatggag aacaagctgt ttgcggggat tcggcgggac    2580
gggctgctcc tgcgtttggt ggatgatttc ttgttggtga cacctcacct cacccacgcg    2640
aaaaccttcc tcaggaccct ggtccgaggt gtccctgagt atggctgcgt ggtgaacttg    2700
cggaagacag tggtgaactt ccctgtagaa gacgaggccc tgggtggcac ggcttttgtt    2760
cagatgccgg cccacggcct attcccctgg tgcggcctgc tgctggatac ccggaccctg    2820
gaggtgcaga gcgactactc cagctatgcc cggacctcca tcagagccag tctcaccttc    2880
aaccgcggct tcaaggctgg gaggaacatg cgtcgcaaac tctttggggt cttgcggctg    2940
aagtgtcaca gcctgtttct ggatttgcag gtgaacagcc tccagacggt gtgcaccaac    3000
atctacaaga tcctcctgct gcaggcgtac aggtttcacg catgtgtgct gcagctccca    3060
tttcatcagc aagtttggaa gaaccccaca tttttcctgc gcgtcatctc tgacacggcc    3120
tccctctgct actccatcct gaaagccaag aacgcaggga tgtcgctggg ggccaagggc    3180
gccgccggcc ctctgccctc cgaggccgtg cagtggctgt gccaccaagc attcctgctc    3240
aagctgactc gacaccgtgt cacctacgtg ccactcctgg ggtcactcag gacagcccag    3300
acgcagctga gtcggaagct cccggggacg acgctgactg ccctggaggc cgcagccaac    3360
ccggcactgc cctcagactt caagaccatc ctggactga                          3399
```

<210> SEQ ID NO 29
<211> LENGTH: 567
<212> TYPE: DNA
<213> ORGANISM: Homo sapiens
<300> PUBLICATION INFORMATION:
<302> TITLE: K-ras

| <310> PATENT DOCUMENT NUMBER: M54968 | |
|---|---|
| <400> SEQUENCE: 29 | |

| | |
|---|---:|
| atgactgaat ataaacttgt ggtagttgga gcttgtggcg taggcaagag tgccttgacg | 60 |
| atacagctaa ttcagaatca ttttgtggac gaatatgatc caacaataga ggattcctac | 120 |
| aggaagcaag tagtaattga tggagaaacc tgtctcttgg atattctcga cacagcaggt | 180 |
| caagaggagt acagtgcaat gagggaccag tacatgagga ctggggaggg ctttctttgt | 240 |
| gtatttgcca taataatac taaatcattt gaagatattc accattatag agaacaaatt | 300 |
| aaaagagtta aggactctga agatgtacct atggtcctag taggaaataa atgtgatttg | 360 |
| ccttctagaa cagtagacac aaaacaggct caggacttag caagaagtta tggaattcct | 420 |
| tttattgaaa catcagcaaa gacaagacag ggtgttgatg atgccttcta tacattagtt | 480 |
| cgagaaattc gaaaacataa agaaaagatg agcaaagatg gtaaaagaa gaaaagaag | 540 |
| tcaaagacaa agtgtgtaat tatgtaa | 567 |

<210> SEQ ID NO 30
<211> LENGTH: 3840
<212> TYPE: DNA
<213> ORGANISM: Homo sapiens
<300> PUBLICATION INFORMATION:
<302> TITLE: mdr-1
<310> PATENT DOCUMENT NUMBER: AF016535

<400> SEQUENCE: 30

| | |
|---|---:|
| atggatcttg aaggggaccg caatggagga gcaaagaaga gaacttttt taaactgaac | 60 |
| aataaaagtg aaaagataa gaaggaaaag aaaccaactg tcagtgtatt ttcaatgttt | 120 |
| cgctattcaa attggcttga caagttgtat atggtggtgg aactttggc tgccatcatc | 180 |
| catgggctg acttcctct catgatgctg gtgtttggag aaatgacaga tatctttgca | 240 |
| aatgcaggaa atttagaaga tctgatgtca aacatcacta tagaagtga tatcaatgat | 300 |
| acagggttct tcatgaatct ggaggaagac atgaccaggt atgcctatta ttacagtgga | 360 |
| attggtgctg gggtgctggt tgctgcttac attcaggttt cattttggtg cctggcagct | 420 |
| ggaagacaaa tacacaaaat tagaaaacag ttttttcatg ctataatgcg acaggagata | 480 |
| ggctggtttg atgtgcacga tgttggggag cttaacaccc gacttacaga tgatgtctcc | 540 |
| aagattaatg aaggaattgg tgacaaaatt ggaatgttct ttcagtcaat ggcaacattt | 600 |
| ttcactgggt ttatagtagg atttacacgt ggttggaagc taaccettgt gattttggcc | 660 |
| atcagtcctg ttcttggact gtcagctgct gtctgggcaa agatactatc ttcatttact | 720 |
| gataaagaac tcttagcgta tgcaaagct ggagcagtag ctgaagaggt cttggcagca | 780 |
| attagaactg tgattgcatt tggaggacaa aagaaagaac ttgaaggta acaaaaat | 840 |
| ttagaagaag ctaaaagaat tgggataaag aaagctatta cagccaatat ttctataggt | 900 |
| gctgcttttcc tgctgatcta tgcatcttat gctctggcct tctggtatgg gaccaccttg | 960 |
| gtcctctcag gggaatattc tattggacaa gtactcactg tattttctgt attaattggg | 1020 |
| gcttttagtg ttggacaggc atctccaagc attgaagcat tgcaaatgc aagaggagca | 1080 |
| gcttatgaaa tcttcaagat aattgataat aagccaagta ttgacagcta ttcgaagagt | 1140 |
| gggcacaaac cagataatat taagggaaat ttggaattca gaaatgttca cttcagttac | 1200 |
| ccatctcgaa aagaagttaa gatcttgaag ggtctgaacc tgaaggtgca gagtgggcag | 1260 |
| acggtggccc tggttggaaa cagtggctgt gggaagagca acagtccag ctgatgcag | 1320 |

```
aggctctatg accccacaga ggggatggtc agtgttgatg acaggatat taggaccata    1380
aatgtaaggt ttctacggga aatcattggt gtggtgagtc aggaacctgt attgtttgcc    1440
accacgatag ctgaaaacat tcgctatggc cgtgaaaatg tcaccatgga tgagattgag    1500
aaagctgtca aggaagccaa tgcctatgac tttatcatga aactgcctca taaatttgac    1560
accctggttg gagagagagg ggcccagttg agtggtgggc agaagcagag gatcgccatt    1620
gcacgtgccc tggttcgcaa ccccaagatc ctcctgctgg atgaggccac gtcagccttg    1680
gacacagaaa gcgaagcagt ggttcaggtg gctctggata aggccagaaa aggtcggacc    1740
accattgtga tagctcatcg tttgtctaca gttcgtaatg ctgacgtcat cgctggtttc    1800
gatgatggag tcattgtgga gaaaggaaat catgatgaac tcatgaaaga gaaaggcatt    1860
tacttcaaac ttgtcacaat gcagacagca ggaaatgaag ttgaattaga aaatgcagct    1920
gatgaatcca aaagtgaaat tgatgccttg gaaatgtctt caaatgattc aagatccagt    1980
ctaataagaa aaagatcaac tcgtaggagt gtccgtggat cacaagccca agacagaaag    2040
cttagtacca aagaggctct ggatgaaagt atacctccag tttccttttg gaggattatg    2100
aagctaaatt taactgaatg gccttatttt gttgttggtg tattttgtgc cattataaat    2160
ggaggcctgc aaccagcatt tgcaataata ttttcaaaga ttatagggt ttttacaaga    2220
attgatgatc ctgaaacaaa acgacagaat agtaacttgt tttcactatt gtttctagcc    2280
cttggaatta tttcttttat tacatttttc cttcagggtt tcacatttgg caaagctgga    2340
gagatcctca ccaagcggct ccgatacatg gttttccgat ccatgctcag acaggatgtg    2400
agttggtttg atgaccctaa aaacaccact ggagcattga ctaccaggct cgccaatgat    2460
gctgctcaag ttaaagggc tataggttcc aggcttgctg taattaccca gaatatagca    2520
aatcttggga caggaataat tatatccttc atctatggtt ggcaactaac actgttactc    2580
ttagcaattg tacccatcat tgcaatagca ggagttgttg aaatgaaaat gttgtctgga    2640
caagcactga aagataagaa agaactagaa ggtgctggga agatcgctac tgaagcaata    2700
gaaaacttcc gaaccgttgt ttctttgact caggagcaga gtttgaaca tatgtatgct    2760
cagagtttgc aggtaccata cagaaactct ttgaggaaag cacacatctt tggaattaca    2820
ttttccttca cccaggcaat gatgtatttt tcctatgctg gatgtttccg gtttggagcc    2880
tacttggtgg cacataaact catgagcttt gaggatgttc tgttagtatt ttcagctgtt    2940
gtctttggtg ccatggccgt ggggcaagtc agttcatttg ctcctgacta tgccaaagcc    3000
aaaatatcag cagcccacat catcatgatc attgaaaaaa ccccttttgat tgacagctac    3060
agcacggaag gcctaatgcc gaacacattg gaaggaaatg tcacatttgg tgaagttgta    3120
ttcaactatc ccaccgacc ggacatccca gtgcttcagg gactgagcct ggaggtgaag    3180
aagggccaga cgctggctct ggtgggcagc agtggctgtg gaagagcac agtggtccag    3240
ctcctggagc ggttctacga ccccttggca gggaaagtgc tgcttgatgg caaagaaata    3300
aagcgactga atgttcagtg gctccgagca cacctgggca tcgtgtccca ggagcccatc    3360
ctgtttgact gcagcattgc tgagaacatt gcctatggag acaacagccg ggtggtgtca    3420
caggaagaga ttgtgagggc agcaaaggag gccaacatac atgccttcat cgagtcactg    3480
cctaataaat atagcactaa agtaggagac aaaggaactc agctctctgg tggccagaaa    3540
caacgcattg ccatagctcg tgcccttgtt agacagcctc atattttgct tttggatgaa    3600
gccacgtcag ctctgataca agaaagtgaa aaggttgtcc aagaagccct ggacaaagcc    3660
agagaaggcc gcacctgcat tgtgattgct caccgcctgt ccaccatcca gaatgcagac    3720
```

```
ttaatagtgg tgtttcagaa tggcagagtc aaggagcatg gcacgcatca gcagctgctg   3780
gcacagaaag gcatctattt ttcaatggtc agtgtccagg ctggaacaaa gcgccagtga   3840
```

<210> SEQ ID NO 31
<211> LENGTH: 1318
<212> TYPE: DNA
<213> ORGANISM: Homo sapiens
<300> PUBLICATION INFORMATION:
<302> TITLE: UPAR (urokinase-type plasminogen activator receptor)
<310> PATENT DOCUMENT NUMBER: XM009232

<400> SEQUENCE: 31

```
atgggtcacc cgccgctgct gccgctgctg ctgctgctcc acacctgcgt cccagcctct    60
tggggcctgc ggtgcatgca gtgtaagacc aacggggatt gccgtgtgga agagtgcgcc   120
ctgggacagg acctctgcag gaccacgatc gtgcgcttgt gggaagaagg agaagagctg   180
gagctggtgg agaaaagctg tacccactca gagaagacca caggaccct gagctatcgg   240 actggcttga agatcaccag ccttaccgag gttgtgtgtg ggttagactt gtgcaaccag   300
ggcaactctg gccgggctgt cacctattcc cgaagccgtt acctcgaatg catttcctgt   360
ggctcatcag acatgagctg tgagagggc cggcaccaga gcctgcagtg ccgcagccct   420
gaagaacagt gcctggatgt ggtgacccac tggatccagg aaggtgaaga agggcgtcca   480
aaggatgacc gccacctccg tggctgtggc taccttcccg gctgcccggg ctccaatggt   540
ttccacaaca cgacaccctt ccacttcctg aaatgctgca acaccaccaa atgcaacgag   600
ggcccaatcc tggagcttga aaatctgccg cagaatggcc gccagtgtta cagctgcaag   660
gggaacagca cccatggatg ctcctctgaa gagactttcc tcattgactg ccgaggcccc   720
atgaatcaat gtctggtagc caccggcact cacgaaccga aaaaccaaag ctatatggta   780
agaggctgtg caaccgcctc aatgtgccaa catgcccacc tgggtgacgc cttcagcatg   840
aaccacattg atgtctcctg ctgtactaaa agtggctgta accacccaga cctggatgtc   900
cagtaccgca gtgggctgc tcctcagcct ggccctgccc atctcagcct caccatcacc   960
ctgctaatga ctgccagact gtggggaggc actctcctct ggacctaaac ctgaaatccc  1020
cctctctgcc ctggctggat ccgggggacc cctttgccct tccctcggct cccagcccta  1080
cagacttgct gtgtgacctc aggccagtgt gccgacctct ctgggcctca gttttcccag  1140
ctatgaaaac agctatctca caaagttgtg tgaagcagaa gagaaaagct ggaggaaggc  1200
cgtgggccaa tgggagagct cttgttatta ttaatattgt tgccgctgtt gtgttgttgt  1260
tattaattaa tattcatatt atttattttta tacttacata aagattttgt accagtgg   1318
```

<210> SEQ ID NO 32
<211> LENGTH: 636
<212> TYPE: DNA
<213> ORGANISM: Homo sapiens
<300> PUBLICATION INFORMATION:
<302> TITLE: Bak
<310> PATENT DOCUMENT NUMBER: U16811

<400> SEQUENCE: 32

```
atggcttcgg ggcaaggccc aggtcctccc aggcaggagt gcggagagcc tgccctgccc    60
tctgcttctg aggagcaggt agcccaggac acagaggagg ttttccgcag ctacgttttt   120
taccgccatc agcaggaaca ggaggctgaa ggggtggctg cccctgccga cccagagatg   180
gtcaccttac ctctgcaacc tagcagcacc atggggcagg tgggacggca gctcgccatc   240
```

```
atcgggacg acatcaaccg acgctatgac tcagagttcc agaccatgtt gcagcacctg    300
cagcccacgg cagagaatgc ctatgagtac ttcaccaaga ttgccaccag cctgtttgag    360
agtggcatca attggggccg tgtggtggct cttctgggct tcggctaccg tctggcccta    420
cacgtctacc agcatggcct gactggcttc ctaggccagg tgacccgctt cgtggtcgac    480
ttcatgctgc atcactgcat tgcccggtgg attgcacaga ggggtggctg ggtggcagcc    540
ctgaacttgg gcaatggtcc catcctgaac gtgctggtgg ttctgggtgt ggttctgttg    600
ggccagtttg tggtacgaag attcttcaaa tcatga                              636
```

```
<210> SEQ ID NO 33
<211> LENGTH: 579
<212> TYPE: DNA
<213> ORGANISM: Homo sapiens
<300> PUBLICATION INFORMATION:
<302> TITLE: Bax alpha
<310> PATENT DOCUMENT NUMBER: L22473

<400> SEQUENCE: 33
```

```
atggacgggt ccggggagca gcccagaggc ggggggccca ccagctctga gcagatcatg     60
aagacagggg ccttttttgct tcagggtttc atccaggatc gagcagggcg aatgggggg    120 gaggcacccg agctggccct ggacccggtg cctcaggatg cgtccaccaa gaagctgagc    180
gagtgtctca gcgcatcgg ggacgaactg gacagtaaca tggagctgca gaggatgatt    240
gccgccgtgg acacagactc cccccgagag gtcttttttcc gagtggcagc tgacatgttt    300
tctgacggca acttcaactg gggccgggtt gtcgcccttt tctactttgc cagcaaactg    360
gtgctcaagg ccctgtgcac caaggtgccg gaactgatca gaaccatcat gggctggaca    420
ttggacttcc tccgggagcg gctgttgggc tggatccaag accagggtgg ttgggacggc    480
ctcctctcct actttgggac gcccacgtgg cagaccgtga ccatctttgt ggcgggagtg    540
ctcaccgcct cgctcaccat ctggaagaag atgggctga                           579
```

```
<210> SEQ ID NO 34
<211> LENGTH: 657
<212> TYPE: DNA
<213> ORGANISM: Homo sapiens
<300> PUBLICATION INFORMATION:
<302> TITLE: Bax beta
<310> PATENT DOCUMENT NUMBER: L22474

<400> SEQUENCE: 34
```

```
atggacgggt ccggggagca gcccagaggc ggggggccca ccagctctga gcagatcatg     60
aagacagggg ccttttttgct tcagggtttc atccaggatc gagcagggcg aatgggggg    120 gaggcacccg agctggccct ggacccggtg cctcaggatg cgtccaccaa gaagctgagc    180
gagtgtctca gcgcatcgg ggacgaactg gacagtaaca tggagctgca gaggatgatt    240
gccgccgtgg acacagactc cccccgagag gtcttttttcc gagtggcagc tgacatgttt    300
tctgacggca acttcaactg gggccgggtt gtcgcccttt tctactttgc cagcaaactg    360
gtgctcaagg ccctgtgcac caaggtgccg gaactgatca gaaccatcat gggctggaca    420
ttggacttcc tccgggagcg gctgttgggc tggatccaag accagggtgg ttgggtgaga    480
ctcctcaagc ctcctcaccc ccaccaccgc gccctcacca ccgccctgc cccaccgtcc    540 ctgcccccccg ccactcctct gggaccctgg gccttctgga gcaggtcaca gtggtgccct    600
ctccccatct tcagatcatc agatgtggtc tataatgcgt tttccttacg tgtctga       657
```

```
<210> SEQ ID NO 35
<211> LENGTH: 432
<212> TYPE: DNA
<213> ORGANISM: Homo sapiens
<300> PUBLICATION INFORMATION:
<302> TITLE: Bax delta
<310> PATENT DOCUMENT NUMBER: U19599

<400> SEQUENCE: 35
atggacgggt ccggggagca gcccagaggc ggggggccca ccagctctga gcagatcatg        60
aagacagggg ccctttttgct tcaggggatg attgccgccg tggacacaga ctccccccga      120
gaggtctttt tccgagtggc agctgacatg ttttctgacg gcaacttcaa ctggggccgg       180
gttgtcgccc ttttctactt tgccagcaaa ctggtgctca aggccctgtg caccaaggtg       240
ccggaactga tcagaaccat catgggctgg acattggact cctccggga gcggctgttg        300 ggctggatcc aagaccaggg tggttgggac ggcctcctct cctactttgg gacgcccacg       360
tggcagaccg tgaccatctt tgtggcggga gtgctcaccg cctcgctcac catctggaag       420
aagatgggct ga                                                           432

<210> SEQ ID NO 36
<211> LENGTH: 495
<212> TYPE: DNA
<213> ORGANISM: Homo sapiens
<300> PUBLICATION INFORMATION:
<302> TITLE: Bax epsolin
<310> PATENT DOCUMENT NUMBER: AF007826

<400> SEQUENCE: 36
atggacgggt ccggggagca gcccagaggc ggggggccca ccagctctga gcagatcatg        60
aagacagggg cccttttgct tcagggtttc atccaggatc gagcagggcg aatgggggga       120
gaggcacccg agctggccct ggaccccgtg cctcaggatg cgtccaccaa gaagctgagc       180
gagtgtctca agcgcatcgg ggacgaactg gacagtaaca tggagctgca gaggatgatt      240
gccgccgtgg acacagactc cccccgagag gtctttttcc gagtggcagc tgacatgttt      300
tctgacggca acttcaactg ggccgggtt gtcgcccttt tctactttgc cagcaaactg       360
gtgctcaagg ctggcgtgaa atggcgtgat ctgggctcac tgcaacctct gcctcctggg       420
ttcaagcgat tcacctgcct cagcatccca aggagctggg attacaggcc ctgtgcacca      480
aggtgccgga actga                                                        495

<210> SEQ ID NO 37
<211> LENGTH: 582
<212> TYPE: DNA
<213> ORGANISM: Homo sapiens
<300> PUBLICATION INFORMATION:
<302> TITLE: bcl-w
<310> PATENT DOCUMENT NUMBER: U59747

<400> SEQUENCE: 37
atggcgaccc cagcctcggc cccagacaca cgggctctgg tggcagactt tgtaggttat        60
aagctgaggc agaagggtta tgtctgtgga gctggccccg ggagggccc agcagctgac       120 ccgctgcacc aagccatgcg ggcagctgga gatgagttcg agaccgcctt ccggcgcacc       180
ttctctgatc tggcggctca gctgcatgtg accccaggct cagcccagca acgcttcacc      240
caggtctccg acgaactttt tcaaggggc cccaactggg ccgccttgt agccttcttt         300 gtctttgggg ctgcactgtg tgctgagagt gtcaacaagg agatgaacc actggtggga        360 caagtgcagg agtggatggt ggcctacctg gagacgcggc tggctgactg gatccacagc      420
```

```
agtgggggct gggcggagtt cacagctcta tacggggacg gggccctgga ggaggcgcgg    480
cgtctgcggg aggggaactg ggcatcagtg aggacagtgc tgacggggc cgtggcactg     540 ggggccctgg taactgtagg ggcctttttt gctagcaagt ga                      582
```

<210> SEQ ID NO 38
<211> LENGTH: 2481
<212> TYPE: DNA
<213> ORGANISM: Homo sapiens
<300> PUBLICATION INFORMATION:
<302> TITLE: HIF-alpha
<310> PATENT DOCUMENT NUMBER: U22431

<400> SEQUENCE: 38

```
atggagggcg ccggcggcgc gaacgacaag aaaaagataa gttctgaacg tcgaaaagaa    60
aagtctcgag atgcagccag atctcggcga agtaaagaat ctgaagtttt ttatgagctt   120
gctcatcagt tgccacttcc acataatgtg agttcgcatc ttgataaggc ctctgtgatg   180
aggcttacca tcagctattt gcgtgtgagg aaacttctgg atgctggtga tttgatatt    240 gaagatgaca tgaaagcaca gatgaattgc ttttatttga agccttgga tggttttgtt   300 atggttctca cagatgatgg tgacatgatt tacatttctg ataatgtgaa caaatacatg   360
ggattaactc agtttgaact aactggacac agtgtgtttg attttactca tccatgtgac   420
catgaggaaa tgagagaaat gcttacacac agaaatggcc ttgtgaaaaa gggtaaagaa   480
caaaacacac agcgaagctt tttttctcaga atgaagtgta ccctaactag ccgaggaaga   540
actatgaaca taaagtctgc aacatggaag gtattgcact gcacaggcca cattcacgta   600
tatgatacca acagtaacca acctcagtgt gggtataaga accacctat gacctgcttg   660 gtgctgattt gtgaacccat tcctcaccca tcaaatattg aaattccttt agatagcaag   720
actttcctca gtcgacacag cctggatatg aaattttctt attgtgatga agaattacc    780 gaattgatgg gatatgagcc agaagaactt ttaggccgct caatttatga atattatcat   840
gctttggact ctgatcatct gaccaaaact catcatgata tgtttactaa aggacaagtc   900
accacaggac agtacaggat gcttgccaaa agaggtggaa atgtctgggt tgaaactcaa   960
gcaactgtca tatataacac caagaattct caaccacagt gcattgtatg tgtgaattac  1020
gttgtgagtg gtattattca gcacgacttg atttttctcc ttcaacaaac agaatgtgtc  1080
cttaaaccgg ttgaatcttc agatatgaaa atgactcagc tattccacca agttgaatca  1140
gaagatacaa gtagcctctt tgacaaactt aagaaggaac ctgatgcttt aactttgctg  1200
gccccagccg ctggagacac aatcatatct ttagattttg gcagcaacga cacagaaact  1260
gatgaccagc aacttgagga agtaccatta tataatgatg taatgctccc ctcacccaac  1320
gaaaaattac agaatataaa tttggcaatg tctccattac ccaccgctga acgccaaag   1380 ccacttcgaa gtagtgctga ccctgcactc aatcaagaag ttgcattaaa attagaacca  1440
aatccagagt cactggaact ttcttttacc atgcccagga tcaggatca gacacctagt   1500 ccttccgatg gaagcactag acaaagttca cctgagccta atagtccag tgaatattgt   1560 ttttatgtgg atagtgatat ggtcaatgaa ttcaagttgg aattggtaga aaacttttt   1620 gctgaagaca cagaagcaaa gaacccattt tctactcagg acacagattt agacttggag  1680
atgttagctc cctatatccc aatggatgat gacttccagt tacgttcctt cgatcagttg  1740
tcaccattag aaagcagttc cgcaagccct gaaagcgcaa gtcctcaaag cacagttaca  1800
gtattccagc agactcaaat acaagaacct actgctaatg ccaccactac cactgccacc  1860
```

```
actgatgaat taaaaacagt gacaaaagac cgtatggaag acattaaaat attgattgca    1920
tctccatctc ctacccacat acataaagaa actactagtg ccacatcatc accatataga    1980
gatactcaaa gtcggacagc ctcaccaaac agagcaggaa aaggagtcat agaacagaca    2040
gaaaaatctc atccaagaag ccctaacgtg ttatctgtcg ctttgagtca agaactaca     2100 gttcctgagg aagaactaaa tccaaagata ctagctttgc agaatgctca gagaaagcga    2160
aaaatggaac atgatggttc acttttcaa gcagtaggaa ttggaacatt attacagcag     2220
ccagacgatc atgcagctac tacatcactt tcttggaaac gtgtaaaagg atgcaaatct    2280
agtgaacaga atgaatgga gcaaaagaca attattttaa taccctctga tttagcatgt     2340
agactgctgg ggcaatcaat ggatgaaagt ggattaccac agctgaccag ttatgattgt    2400
gaagttaatg ctcctataca aggcagcaga aacctactgc agggtgaaga attactcaga    2460
gctttggatc aagttaactg a                                              2481

<210> SEQ ID NO 39
<211> LENGTH: 481
<212> TYPE: DNA
<213> ORGANISM: Homo sapiens
<300> PUBLICATION INFORMATION:
<302> TITLE: ID1
<310> PATENT DOCUMENT NUMBER: X77956

<400> SEQUENCE: 39
atgaaagtcg ccagtggcag caccgccacc gccgccgcgg cccccagctg cgcgctgaag    60
gccggcaaga cagcgagcgg tgcgggcgag gtggtgcgct gtctgtctga gcagagcgtg    120
gccatctcgc gctgccgggg cgccggggcg cgcctgcctg ccctgctgga cgagcagcag    180
gtaaacgtgc tgctctacga catgaacggc tgttactcac gcctcaagga gctggtgccc    240
accctgcccc agaaccgcaa ggtgagcaag gtggagattc tccagcacgt catcgactac    300
atcagggacc ttcagttgga gctgaactcg gaatccgaag ttgggacccc cggggggccga   360 gggctgccgg tccgggctcc gctcagcacc ctcaacggcg agatcagcgc cctgacggcc    420
gaggcggcat gcgttcctgc ggacgatcgc atcttgtgtc gctgaatggt gaaaaaaaaa    480
a                                                                    481

<210> SEQ ID NO 40
<211> LENGTH: 110
<212> TYPE: DNA
<213> ORGANISM: Homo sapiens
<300> PUBLICATION INFORMATION:
<302> TITLE: ID2B
<310> PATENT DOCUMENT NUMBER: M96843

<400> SEQUENCE: 40
tgaaagcctt cagtcccgtg aggtccatta ggaaaaacag cctgttggac caccgcctgg    60
gcatctccca gagcaaaacc ccggtggatg acctgatgag cctgctgtaa               110

<210> SEQ ID NO 41
<211> LENGTH: 486
<212> TYPE: DNA
<213> ORGANISM: Homo sapiens
<300> PUBLICATION INFORMATION:
<302> TITLE: ID4
<310> PATENT DOCUMENT NUMBER: Y07958

<400> SEQUENCE: 41
atgaaggcgg tgagcccggt gcgcccctcg ggccgcaagg cgccgtcggg ctgcggcggc    60
```

-continued

```
ggggagctgg cgctgcgctg cctggccgag cacggccaca gcctgggtgg ctccgcagcc    120
gcggcggcgg cggcggcggc agcgcgctgt aaggcggccg aggcggcggc cgacgagccg    180
gcgctgtgcc tgcagtgcga tatgaacgac tgctatagcc gcctgcggag gctggtgccc    240
accatcccgc ccaacaagaa agtcagcaaa gtggagatcc tgcagcacgt tatcgactac    300
atcctggacc tgcagctggc gctggagacg cacccggccc tgctgaggca gccaccaccg    360
cccgcgccgc acaccaccc ggccgggacc tgtccagccg cgccgccgcg gaccccgctc     420
actgcgctca acaccgaccc ggccggcgcg gtgaacaagc agggcgacag cattctgtgc    480
cgctga                                                                486

<210> SEQ ID NO 42
<211> LENGTH: 462
<212> TYPE: DNA
<213> ORGANISM: Homo sapiens
<300> PUBLICATION INFORMATION:
<302> TITLE: IGF1
<310> PATENT DOCUMENT NUMBER: NM000618

<400> SEQUENCE: 42
atgggaaaaa tcagcagtct tccaacccaa ttatttaagt gctgcttttg tgatttcttg     60
aaggtgaaga tgcacaccat gtcctcctcg catctcttct acctggcgct gtgcctgctc    120
accttcacca gctctgccac ggctggaccg gagacgctct gcggggctga gctggtggat    180
gctcttcagt tcgtgtgtgg agacaggggc ttttatttca acaagcccac agggtatggc    240
tccagcagtc ggagggcgcc tcagacaggc atcgtggatg agtgctgctt ccggagctgt    300
gatctaagga ggctggagat gtattgcgca cccctcaagc ctgccaagtc agctcgctct    360
gtccgtgccc agcgccacac cgacatgccc aagacccaga aggaagtaca tttgaagaac    420
gcaagtagag ggagtgcagg aaacaagaac tacaggatgt ag                        462

<210> SEQ ID NO 43
<211> LENGTH: 591
<212> TYPE: DNA
<213> ORGANISM: Homo sapiens
<300> PUBLICATION INFORMATION:
<302> TITLE: PDGFA
<310> PATENT DOCUMENT NUMBER: NM002607

<400> SEQUENCE: 43
atgaggacct tggcttgcct gctgctcctc ggctgcggat acctcgccca tgttctggcc     60
gaggaagccg agatcccccg cgaggtgatc gagaggctgg cccgcagtca gatccacagc    120
atccgggacc tccagcgact cctggagata gactccgtag ggagtgagga ttctttggac    180
accagcctga gagctcacgg ggtccacgcc actaagcatg tgcccgagaa gcggcccctg    240
cccattcgga ggaagagaag catcgaggaa gctgtccccg ctgtctgcaa gaccaggacg    300
gtcatttacg agattcctcg gagtcaggtc gaccccacgt ccgccaactt cctgatctgg    360 ccccgtgcg tggaggtgaa acgctgcacc ggctgctgca cacgagcag tgtcaagtgc     420 cagcccctccc gcgtccacca ccgcagcgtc aaggtggcca aggtggaata cgtcaggaag    480
aagccaaaat taaagaagt ccaggtgagg ttagaggagc atttggagtg cgcctgcgcg    540
accacaagcc tgaatccgga ttatcgggaa gaggacacgg atgtgaggtg a              591

<210> SEQ ID NO 44
<211> LENGTH: 528
<212> TYPE: DNA
```

<213> ORGANISM: Homo sapiens
<300> PUBLICATION INFORMATION:
<302> TITLE: PDGFRA
<310> PATENT DOCUMENT NUMBER: XM003568

<400> SEQUENCE: 44

```
atggccaagc ctgaccacgc taccagtgaa gtctacgaga tcatggtgaa atgctggaac      60
agtgagccgg agaagagacc ctccttttac cacctgagtg agattgtgga gaatctgctg     120
cctggacaat ataaaagag ttatgaaaaa attcacctgg acttcctgaa gagtgaccat     180
cctgctgtgg cacgcatgcg tgtggactca gacaatgcat acattggtgt cacctacaaa     240
aacgaggaag acaagctgaa ggactgggag ggtggtctgg atgagcagag actgagcgct     300
gacagtggct acatcattcc tctgcctgac attgaccctg ccctgagga ggaggacctg     360
ggcaagagga cagacacag ctcgcagacc tctgaagaga gtgccattga cgggttcc     420
agcagttcca ccttcatcaa gagagaggac gagaccattg aagacatcga catgatggat     480
gacatcggca tagactcttc agacctggtg gaagacagct cctgtaa               528
```

<210> SEQ ID NO 45
<211> LENGTH: 1911
<212> TYPE: DNA
<213> ORGANISM: Homo sapiens
<300> PUBLICATION INFORMATION:
<302> TITLE: PDGFRB
<310> PATENT DOCUMENT NUMBER: XM003790

<400> SEQUENCE: 45

```
atgcggcttc cgggtgcgat gccagctctg gccctcaaag cgagctgct gttgctgtct       60
ctcctgttac ttctggaacc acagatctct cagggcctgg tcgtcacacc cccggggcca     120
gagcttgtcc tcaatgtctc cagcaccttc gttctgacct gctcgggttc agctccggtg     180
gtgtgggaac ggatgtccca ggagccccca caggaaatgg ccaaggccca ggatggcacc     240
ttctccagcg tgctcacact gaccaacctc actgggctag acacgggaga atacttttgc     300
acccacaatg actcccgtgg actggagacc gatgagcgga acggctcta catctttgtg     360
ccagatccca ccgtgggctt cctccctaat gatgccgagg aactattcat ctttctcacg     420
gaaataactg agatcaccat tccatgccga gtaacagacc cacagctggt ggtgacactg     480
cacgagaaga aggggacgt tgcactgcct gtccctatg atcaccaacg tggctttct     540
ggtatctttg aggacagaag ctacatctgc aaaaccacca ttggggacag ggaggtggat     600
tctgatgcct actatgtcta cagactccag gtgtcatcca tcaacgtctc tgtgaacgca     660
gtgcagactg tggtccgcca gggtgagaac atcaccctca tgtgcattgt gatcgggaat     720
gaggtggtca acttcgagtg gacatacccc cgcaaagaaa gtgggcggct ggtggagccg     780
gtgactgact tcctcttgga tatgccttac cacatccgct ccatcctgca catcccagt     840
gccgagttag aagactcggg gacctacacc tgcaatgtga cggagagtgt gaatgaccat     900
caggatgaaa aggccatcaa catcaccgtg gttgagagcg gctacgtgcg ctcctgggga     960
gaggtgggca cactacaatt tgctgagctg catcggagcc ggacactgca ggtagtgttc    1020
gaggcctacc caccgcccac tgtcctgtgg ttcaaagaca accgcaccct gggcgactcc    1080
agcgctggcg aaatcgccct gtccacgcgc aacgtgtcgg agacccggta tgtgtcagag    1140
ctgacactgg ttcgcgtgaa ggtggcagag ctggccact acaccatgcg ggccttccat    1200
gaggatgctg aggtccagct ctccttccag ctacagatca atgtccctgt ccagagtgctg    1260
gagctaagtg agagccaccc tgacagtggg gaacagacag tccgctgtcg tggccgggc    1320
```

```
atgcccagc cgaacatcat ctggtctgcc tgcagagacc tcaaaaggtg tccacgtgag      1380
ctgccgccca cgctgctggg aacagttcc gaagaggaga gccagctgga gactaacgtg      1440
acgtactggg aggaggagca ggagtttgag gtggtgagca cactgcgtct gcagcacgtg     1500
gatcggccac tgtcggtgcg ctgcacgctg cgcaacgctg tgggccagga cacgcaggag     1560
gtcatcgtgg tgccacactc cttgcccttt aaggtggtgg tgatctcagc catcctggcc    1620
ctggtggtgc tcaccatcat ctcccttatc atcctcatca tgctttggca gaagaagcca    1680
cgttacgaga tccgatggaa ggtgattgag tctgtgagct ctgacggcca tgagtacatc    1740
tacgtggacc ccatgcagct gccctatgac tcccgtgggg agctgccgcg ggaccagctt    1800
gtgctgggac gcaccctcgg ctctggggcc tttgggcagg tggtggaggc cacggttcat    1860
ggcctgagcc attttcaagc cccaatgaaa gtggccgtca aaaatgctta a             1911
```

<210> SEQ ID NO 46
<211> LENGTH: 1176
<212> TYPE: DNA
<213> ORGANISM: Homo sapiens
<300> PUBLICATION INFORMATION:
<302> TITLE: TGFbeta1
<310> PATENT DOCUMENT NUMBER: NM000660

<400> SEQUENCE: 46

```
atgccgccct ccgggctgcg gctgctgccg ctgctgctac cgctgctgtg gctactggtg      60
ctgacgcctg gccgccggc cgcgggacta tccacctgca agactatcga catggagctg      120
gtgaagcgga gcgcatcga ggccatccgc ggccagatcc tgtccaagct gcggctcgcc     180 agcccccga gccaggggga ggtgccgccc ggcccgctgc ccgaggccgt gctcgccctg     240
tacaacagca cccgcgaccg ggtggccggg gagagtgcag aaccggagcc cgagcctgag    300
gccgactact acgccaagga ggtcacccgc gtgctaatgg tggaaaccca acgaaaatc    360 tatgacaagt tcaagcagag tacacacagc atatatatgt tcttcaacac atcagagctc    420
cgagaagcgg tacctgaacc cgtgttgctc tcccgggcag agctgcgtct gctgaggagg    480
ctcaagttaa aagtggagca gcacgtggag ctgtaccaga aatacagcaa caattcctgg    540
cgatacctca gcaaccggct gctggcaccc agcgactcgc cagagtggtt atcttttgat    600
gtcaccggag ttgtgcggca gtggttgagc cgtggagggg aaattgaggg cttccgcctt    660
agcgcccact gctcctgtga cagcagggat aacacactgc aagtggacat caacgggttc    720
actaccggcc gccgaggtga cctggccacc attcatggca tgaaccggcc tttcctgctt    780
ctcatggcca ccccgctgga gagggcccag catctgcaaa gctcccggca ccgccgagcc    840
ctggacacca actattgctt cagctccacg gagaagaact gctgcgtgcg gcagctgtac    900
attgacttcc gcaaggacct cggctggaag tggatccacg agcccaaggg ctaccatgcc    960
aacttctgcc tcgggccctg cccctacatt tggagcctgg acacgcagta cagcaaggtc    1020
ctggccctgt acaaccagca taaccccggc gcctcggcgg cgccgtgctg cgtgccgcag    1080
gcgctggagc cgctgcccat cgtgtactac gtgggccgca agcccaaggt ggagcagctg    1140
tccaacatga tcgtgcgctc ctgcaagtgc agctga                              1176
```

<210> SEQ ID NO 47
<211> LENGTH: 1245
<212> TYPE: DNA
<213> ORGANISM: Homo sapiens
<300> PUBLICATION INFORMATION:
<302> TITLE: TGFbeta2

<310> PATENT DOCUMENT NUMBER: NM003238

<400> SEQUENCE: 47

```
atgcactact gtgtgctgag cgcttttctg atcctgcatc tggtcacggt cgcgctcagc      60
ctgtctacct gcagcacact cgatatggac cagttcatgc gcaagaggat cgaggcgatc     120
cgcgggcaga tcctgagcaa gctgaagctc accagtcccc agaagactaa tcctgagccc     180
gaggaagtcc ccccggaggt gatttccatc tacaacagca ccaggacttg ctccaggag      240
aaggcgagcc ggagggcggc cgcctgcgag cgcgagagga gcgacgaaga gtactacgcc     300
aaggaggttt acaaaataga catgccgccc ttcttcccct ccgaaaatgc catcccgccc     360
actttctaca gaccctactt cagaattgtt cgatttgacg tctcagcaat ggagaagaat     420
gcttccaatt tggtgaaagc agagttcaga gtctttcgtt tgcagaaccc aaaagccaga     480
gtgcctgaac aacggattga gctatatcag attctcaagt ccaaagattt aacatctcca     540
acccagcgct acatcgacag caaagttgtg aaaacaagag cagaaggcga atggctctcc     600
ttcgatgtaa ctgatgctgt tcatgaatgg cttcaccata aagacaggaa cctgggattt     660
aaaataagct acactgtcc ctgctgcact tttgtaccat ctaataatta catcatccca      720
aataaaagtg aagaactaga agcaagattt gcaggtattg atggcacctc cacatatacc     780
agtggtgatc agaaaactat aaagtccact aggaaaaaaa acagtgggaa gacccacat      840
ctcctgctaa tgttattgcc ctcctacaga cttgagtcac aacagaccaa ccggcggaag     900
aagcgtgctt tggatgcggc ctattgcttt agaaatgtgc aggataattg ctgcctacgt     960
ccactttaca ttgatttcaa gagggatcta gggtggaaat ggatacacga acccaaaggg    1020
tacaatgcca acttctgtgc tggagcatgc ccgtatttat ggagttcaga cactcagcac    1080
agcagggtcc tgagcttata ataccataa atccagaag catctgcttc ccttgctgc       1140
gtgtcccaag atttagaacc tctaaccatt ctctactaca ttggcaaaac acccaagatt    1200
gaacagcttt ctaatatgat tgtaaagtct tgcaaatgca gctaa                    1245
```

<210> SEQ ID NO 48
<211> LENGTH: 1239
<212> TYPE: DNA
<213> ORGANISM: Homo sapiens
<300> PUBLICATION INFORMATION:
<302> TITLE: TGFbeta3
<310> PATENT DOCUMENT NUMBER: XM007417

<400> SEQUENCE: 48

```
atgaagatgc acttgcaaag ggctctggtg gtcctggccc tgctgaactt tgccacggtc      60
agcctctctc tgtccacttg caccaccttg gacttcggcc acatcaagaa gaagagggtg     120
gaagccatta gggacagat cttgagcaag ctcaggctca ccagcccccc tgagccaacg      180
gtgatgaccc acgtcccta tcaggtcctg gcccttaca acagcacccg ggagctgctg      240
gaggagatgc atgggagag ggaggaaggc tgcacccagg aaaacaccga gtcggaatac     300
tatgccaaag aaatccataa attcgacatg atccaggggc tggcggagca acgaactg      360
gctgtctgcc ctaaaggaat tacctccaag gttttccgct tcaatgtgtc ctcagtggag     420
aaaaatagaa ccaacctatt ccgagcagaa ttccgggtct gcgggtgcc caaccccagc     480
tctaagcgga atgagcagag gatcgagctc ttccagatcc ttcggccaga tgagcacatt     540
gccaaacagc gctatatcgg tggcaagaat ctgcccacac ggggcactgc cgagtggctg     600
tcctttgatg tcactgacac tgtgcgtgag tggctgttga agagagtc caacttaggt     660
```

| | |
|---|---|
| ctagaaatca gcattcactg tccatgtcac acctttcagc ccaatggaga tatcctggaa | 720 |
| aacattcacg aggtgatgga aatcaaattc aaaggcgtgg acaatgagga tgaccatggc | 780 |
| cgtggagatc tggggcgcct caagaagcag aaggatcacc acaaccctca tctaatcctc | 840 |
| atgatgattc ccccacaccg gctcgacaac ccgggccagg ggggtcagag gaagaagcgg | 900 |
| gctttggaca ccaattactg cttccgcaac ttggaggaga actgctgtgt gcgcccctc | 960 |
| tacattgact ccgacagga tctgggctgg aagtgggtcc atgaacctaa ggctactat | 1020 |
| gccaacttct gctcaggccc ttgcccatac ctccgcagtg cagacacaac ccacagcacg | 1080 |
| gtgctgggac tgtacaacac tctgaaccct gaagcatctg cctcgccttg ctgcgtgccc | 1140 |
| caggacctgg agccctgac catcctgtac tatgttggga ggaccccca agtggagcag | 1200 |
| ctctccaaca tggtggtgaa gtcttgtaaa tgtagctga | 1239 |

<210> SEQ ID NO 49
<211> LENGTH: 1704
<212> TYPE: DNA
<213> ORGANISM: Homo sapiens
<300> PUBLICATION INFORMATION:
<302> TITLE: TGFbetaR2
<310> PATENT DOCUMENT NUMBER: XM003094

<400> SEQUENCE: 49

| | |
|---|---|
| atgggtcggg ggctgctcag gggcctgtgg ccgctgcaca tcgtcctgtg gacgcgtatc | 60 |
| gccagcacga tcccaccgca cgttcagaag tcggttaata cgacatgat agtcactgac | 120 |
| aacaacggtg cagtcaagtt ccacaactg tgtaaatttt gtgatgtgag attttccacc | 180 |
| tgtgacaacc agaaatcctg catgagcaac tgcagcatca cctccatctg tgagaagcca | 240 |
| caggaagtct gtgtggctgt atggagaaag aatgacgaga acataacact agagacagtt | 300 |
| tgccatgacc ccaagctccc ctaccatgac tttattctgg aagatgctgc ttctccaaag | 360 |
| tgcattatga aggaaaaaaa aaagcctggt gagactttct tcatgtgttc ctgtagctct | 420 |
| gatgagtgca atgacaacat catcttctca gaagaatata caccagcaa tcctgacttg | 480 |
| ttgctagtca tatttcaagt gacaggcatc agcctcctgc caccactggg agttgccata | 540 |
| tctgtcatca tcatcttcta ctgctaccgc gttaaccggc agcagaagct gagttcaacc | 600 |
| tgggaaaccg gcaagacgcg gaagctcatg gagttcagcg agcactgtgc catcatcctg | 660 |
| gaagatgacc gctctgacat cagctccacg tgtgccaaca catcaaccaa caacacagag | 720 |
| ctgctgccca ttgagctgga caccctggtg gggaaaggtc gctttgctga ggtctataag | 780 |
| gccaagctga gcagaacac ttcagagcag tttgagacag tggcagtcaa gatctttccc | 840 |
| tatgaggagt atgcctcttg gaagacagag aaggacatct ctcagacat caatctgaag | 900 |
| catgagaaca tactccagtt cctgacggct gaggagcgga gacggagtt ggggaaacaa | 960 |
| tactggctga tcaccgcctt ccacgccaag gcaacctac aggagtacct gacgcggcat | 1020 |
| gtcatcagct gggaggacct gcgcaagctg ggcagctccc tcgcccgggg gattgctcac | 1080 |
| ctccacagtg atcacactcc atgtgggagg cccaagatgc ccatcgtgca cagggacctc | 1140 |
| aagagctcca atatcctcgt gaagaacgac ctaacctgct gcctgtgtga ctttgggctt | 1200 |
| tccctgcgtc tggaccctac tctgtctgtg atgacctgg ctaacagtgg caggtggga | 1260 |
| actgcaagat acatggctcc agaagtccta gaatccagga tgaatttgga gaatgttgag | 1320 |
| tccttcaagc agaccgatgt ctactccatg gctctggtgc tctgggaaat gacatctcgc | 1380 |
| tgtaatgcag tgggagaagt aaaagattat gagcctccat ttggttccaa ggtgcgggag | 1440 |

```
cacccctgtg tcgaaagcat gaaggacaac gtgttgagag atcgagggcg accagaaatt    1500
cccagcttct ggctcaacca ccagggcatc cagatggtgt gtgagacgtt gactgagtgc    1560
tgggaccacg acccagaggc ccgtctcaca gcccagtgtg tggcagaacg cttcagtgag    1620
ctggagcatc tggacaggct ctcggggagg agctgctcgg aggagaagat tcctgaagac    1680
ggctccctaa acactaccaa atag                                          1704

<210> SEQ ID NO 50
<211> LENGTH: 609
<212> TYPE: DNA
<213> ORGANISM: Homo sapiens
<300> PUBLICATION INFORMATION:
<302> TITLE: TGFbeta3
<310> PATENT DOCUMENT NUMBER: XM001924

<400> SEQUENCE: 50
atgtctcatt acaccattat tgagaatatt tgtcctaaag atgaatctgt gaaattctac     60
agtcccaaga gagtgcactt tcctatcccg caagctgaca tggataagaa gcgattcagc    120
tttgtcttca agcctgtctt caacacctca ctgctctttc tacagtgtga gctgacgctg    180
tgtacgaaga tggagaagca cccccagaag ttgcctaagt gtgtgcctcc tgacgaagcc    240
tgcacctcgc tggacgcctc gataatctgg gccatgatgc agaataagaa gacgttcact    300
aagccccttg ctgtgatcca ccatgaagca gaatctaaag aaaaaggtcc aagcatgaag    360
gaaccaaatc caatttctcc accaattttc catggtctgg acccctaacc gtgatgggc    420 attgcgtttg cagcctttgt gatcggagca ctcctgacgg ggccttgtg gtacatctat    480 tctcacacag gggagacagc aggaaggcag caagtcccca cctcccgcc agcctcggaa    540 aacagcagtg ctgcccacag catcggcagc acgcagagca cgccttgctc agcagcagc    600 acggcctag                                                           609

<210> SEQ ID NO 51
<211> LENGTH: 3633
<212> TYPE: DNA
<213> ORGANISM: Homo sapiens
<300> PUBLICATION INFORMATION:
<302> TITLE: EGFR
<310> PATENT DOCUMENT NUMBER: X00588

<400> SEQUENCE: 51
atgcgaccct ccgggacggc cggggcagcg ctcctggcgc tgctggctgc gctctgcccg     60
gcgagtcggg ctctggagga aaagaaagtt tgccaaggca cgagtaacaa gctcacgcag    120
ttgggcactt ttgaagatca tttttctcagc ctccagagga tgttcaataa ctgtgaggtg    180
gtccttggga atttggaaat tacctatgtg cagaggaatt atgatctttc cttcttaaag    240
accatccagg aggtggctgg ttatgtcctc attgcccctca acacagtgga gcgaattcct    300
ttggaaaacc tgcagatcat cagaggaaat atgtactacg aaaattccta tgccttagca    360
gtcttatcta actatgatgc aaataaaacc ggactgaagg agctgccat gagaaattta    420 caggaaatcc tgcatggcgc cgtgcggttc agcaacaacc ctgccctgtg caacgtggag    480
agcatccagt ggcgggacat agtcagcagt gactttctca gcaacatgtc gatggacttc    540
cagaaccacc tgggcagctg ccaaaagtgt gatccaagct gtcccaatgg agctgctgg    600 ggtgcaggag aggagaactg ccagaaactg accaaaatca tctgtgccca gcagtgctcc    660
gggcgctgcc gtggcaagtc ccccagtgac tgctgccaca accagtgtgc tgcaggctgc    720
acaggccccc gggagagcga ctgcctggtc tgccgcaaat tccgagacga agccacgtgc    780
```

```
aaggacacct gcccccact  catgctctac aaccccacca cgtaccagat ggatgtgaac    840
cccgagggca aatacagctt tggtgccacc tgcgtgaaga agtgtccccg taattatgtg    900
gtgacagatc acggctcgtg cgtccgagcc tgtggggccg acagctatga gatggaggaa    960
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag gggtgactcc   1140
ttcacacata ctcctcctct ggatccacag gaactggata ttctgaaaac cgtaaaggaa   1200
atcacagggt ttttgctgat tcaggcttgg cctgaaaaca ggacggacct ccatgccttt   1260
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc aggtctgcca tgccttgtgc tcccccgagg gctgctgggg cccggagccc   1560
agggactgcg tctcttgccg gaatgtcagc cgaggcaggg aatgcgtgga caagtgcaag   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgcccggc aggagtcatg   1800
ggagaaaaca cacctggt  ctggaagtac gcagacgccg gccatgtgtg ccacctgtgc   1860
catccaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
ggtgcgttcg gcacggtgta taagggactc tggatcccag aaggtgagaa agttaaaatt   2220
cccgtcgcta tcaaggaatt aagagaagca acatctccga aagccaacaa ggaaatcctc   2280
gatgaagcct acgtgatggc cagcgtggac aaccccacg  tgtgccgcct gctgggcatc   2340
tgcctcacct ccaccgtgca actcatcacg cagctcatgc ccttcggctg cctcctggac   2400
tatgtccggg aacacaaaga caatattggc tcccagtacc tgctcaactg gtgtgtgcag   2460
atcgcaaagg gcatgaacta cttggaggac cgtcgcttgg tgcaccgcga cctggcagcc   2520
aggaacgtac tggtgaaaac accgcagcat gtcaagatca cagattttgg gctggccaaa   2580
ctgctgggtg cggaagagaa agaataccat gcagaaggag gcaaagtgcc tatcaagtgg   2640
atggcattgg aatcaatttt cacacagaatc tatacccacc agagtgatgt ctggagctac   2700
ggggtgaccg tttgggagtt gatgaccttt ggatccaagc catatgacgg aatccctgcc   2760
agcgagatct cctccatcct ggagaaagga gaacgcctcc ctcagccacc catatgtacc   2820
atcgatgtct acatgatcat ggtcaagtgc tggatgatag acgcagatag tcgcccaaag   2880
ttccgtgagt tgatcatcga attctccaaa atggcccgag accccagcg  ctaccttgtc   2940
attcagggggg atgaaagaat gcatttgcca agtcctacag actccaactt ctaccgtgcc   3000
ctgatggatg aagaagacat ggacgacgtg tggatgccg  acgagtacct catcccacag   3060
cagggcttct tcagcagccc ctccacgtca cggactcccc tcctgagctc tctgagtgca   3120
```

| | |
|---|---|
| accagcaaca attccaccgt ggcttgcatt gatagaaatg ggctgcaaag ctgtcccatc | 3180 |
| aaggaagaca gcttcttgca gcgatacagc tcagacccca caggcgcctt gactgaggac | 3240 |
| agcatagacg acaccttcct cccagtgcct gaatacataa accagtccgt tcccaaaagg | 3300 |
| cccgctggct ctgtgcagaa tcctgtctat acaatcagc ctctgaaccc cgcgcccagc | 3360 |
| agagacccac actaccagga cccccacagc actgcagtgg gcaaccccga gtatctcaac | 3420 |
| actgtccagc ccacctgtgt caacagcaca ttcgacagcc ctgcccactg ggcccagaaa | 3480 |
| ggcagccacc aaattagcct ggacaaccct gactaccagc aggacttctt cccaaggaa | 3540 |
| gccaagccaa atggcatctt taagggctcc acagctgaaa atgcagaata cctaagggtc | 3600 |
| gcgccacaaa gcagtgaatt tattggagca tga | 3633 |

<210> SEQ ID NO 52
<211> LENGTH: 3768
<212> TYPE: DNA
<213> ORGANISM: Homo sapiens
<300> PUBLICATION INFORMATION:
<302> TITLE: ERBB2
<310> PATENT DOCUMENT NUMBER: NM004448

<400> SEQUENCE: 52

| | |
|---|---|
| atggagctgg cggccttgtg ccgctggggg ctcctcctcg ccctcttgcc ccccggagcc | 60 |
| gcgagcaccc aagtgtgcac cggcacagac atgaagctgc ggctccctgc cagtcccgag | 120 |
| acccacctgg acatgctccg ccacctctac cagggctgcc aggtggtgca gggaaacctg | 180 |
| gaactcacct acctgcccac caatgccagc ctgtccttcc tgcaggatat ccaggaggtg | 240 |
| cagggctacg tgctcatcgc tcacaaccaa gtgaggcagg tcccactgca gaggctgcgg | 300 |
| attgtgcgag gcacccagct ctttgaggac aactatgccc tggccgtgct agacaatgga | 360 |
| gacccgctga acaataccac ccctgtcaca ggggcctccc caggaggcct gcgggagctg | 420 |
| cagcttcgaa gcctcacaga gatcttgaaa ggaggggtct tgatccagcg gaaccccag | 480 |
| ctctgctacc aggacacgat tttgtggaag gacatcttcc acaagaacaa ccagctggct | 540 |
| ctcacactga tagacaccaa ccgctctcgg gcctgccacc ctgttctcc gatgtgtaag | 600 |
| ggctcccgct gctgggggaga gagttctgag gattgtcaga gcctgacgcg cactgtctgt | 660 |
| gccggtggct gtgcccgctg caagggccca ctgcccactg actgctgcca tgagcagtgt | 720 |
| gctgccggct gcacgggccc caagcactct gactgcctgg cctgcctcca cttcaaccac | 780 |
| agtggcatct gtgagctgca ctgcccagcc ctggtcacct acaacacaga cacgtttgag | 840 |
| tccatgccca atccccgaggg ccggtataca ttcggcgcca gctgtgtgac tgcctgtccc | 900 |
| tacaactacc tttctacgga cgtgggatcc tgcaccctcg tctgccccct gcacaaccaa | 960 |
| gaggtgacag cagaggatgg aacacagcgg tgtgagaagt gcagcaagcc ctgtgcccga | 1020 |
| gtgtgctatg gtctgggcat ggagcacttg cgagaggtga gggcagttac cagtgccaat | 1080 |
| atccaggagt tgctggctg caagaagatc tttgggagcc tggcatttct gccggagagc | 1140 |
| tttgatgggg acccagcctc caacactgcc cgctccagc agagcagct ccaagtgttt | 1200 |
| gagactctgg aagagatcac aggttaccta tacatctcag catggccgga cagcctgcct | 1260 |
| gacctcagcg tcttccagaa cctgcaagta atccggggac gaattctgca caatggcgcc | 1320 |
| tactcgctga cccctgcaagg gctgggcatc agctggctgg gctgcgctc actgagggaa | 1380 |
| ctgggcagtg gactggccct catccaccat aacacccacc tctgcttcgt gcacacggtg | 1440 |
| ccctgggacc agctctttcg gaacccgcac caagctctgc tccacactgc caaccggcca | 1500 |

```
gaggacgagt gtgtgggcga gggcctggcc tgccaccagc tgtgcgcccg agggcactgc    1560
tggggtccag ggcccaccca gtgtgtcaac tgcagccagt tccttcgggg ccaggagtgc    1620
gtggaggaat gccgagtact gcaggggctc cccagggagt atgtgaatgc caggcactgt    1680
ttgccgtgcc accctgagtg tcagcccag aatggctcag tgacctgttt tggaccggag    1740
gctgaccagt gtgtggcctg tgcccactat aaggaccctc ccttctgcgt ggcccgctgc    1800
cccagcggtg tgaaacctga cctctcctac atgcccatct ggaagtttcc agatgaggag    1860
ggcgcatgcc agccttgccc catcaactgc acccactcct gtgtggacct ggatgacaag    1920
ggctgccccg ccgagcagag agccagccct ctgacgtcca tcgtctctgc ggtggttggc    1980
attctgctgg tcgtggtctt ggggtgtc tttgggatcc tcatcaagcg acggcagcag    2040
aagatccgga gtacacgat gcggagactg ctgcaggaaa cggagctggt ggagccgctg    2100
acacctagcg gagcgatgcc caaccaggcg cagatgcgga tcctgaaaga gacggagctg    2160
aggaaggtga aggtgcttgg atctggcgct tttggcacag tctacaaggg catctggatc    2220
cctgatgggg agaatgtgaa aattccagtg gccatcaaag tgttgaggga aaacacatcc    2280
cccaaagcca acaaagaaat cttagacgaa gcatacgtga tggctggtgt gggctcccca    2340
tatgtctccc gccttctggg catctgcctg acatccacgg tgcagctggt gacacagctt    2400
atgccctatg gctgcctctt agaccatgtc cgggaaaacc gcggacgcct gggctcccag    2460
gacctgctga actggtgtat gcagattgcc aaggggatga gctacctgga ggatgtgcgg    2520
ctcgtacaca gggacttggc cgctcggaac gtgctggtca agagtcccaa ccatgtcaaa    2580
attacagact tcgggctggc tcggctgctg gacattgacg agacagagta ccatgcagat    2640
gggggcaagg tgcccatcaa gtggatggcg ctggagtcca ttctccgccg gcggttcacc    2700
caccagagtg atgtgtggag ttatggtgtg actgtgtggg agctgatgac ttttggggcc    2760
aaaccttacg atgggatccc agcccgggag atccctgacc tgctggaaaa gggggagcgg    2820
ctgccccagc cccccatctg caccattgat gtctacatga tcatggtcaa atgttggatg    2880
attgactctg aatgtcggcc aagattccgg gagttggtgt ctgaattctc ccgcatggcc    2940
agggaccccc agcgctttgt ggtcatccag aatgaggact gggcccagc cagtcccttg    3000 gacagcacct tctaccgctc actgctggag gacgatgaca tgggggacct ggtggatgct    3060
gaggagtatc tggtacccca gcagggcttc ttctgtccag accctgcccc gggcgctggg    3120
ggcatggtcc accacaggca ccgcagctca tctaccagga gtggcggtgg ggacctgaca    3180
ctagggctgg agccctctga agaggaggcc cccaggtctc cactggcacc ctccgaaggg    3240
gctggctccg atgtatttga tggtgacctg ggaatggggg cagccaaggg gctgcaaagc    3300
ctccccacac atgaccccag ccctctacag cggtacagtg aggaccccac agtacccctg    3360
ccctctgaga ctgatggcta cgttgccccc ctgacctgca gccccagcc tgaatatgtg    3420 aaccagccag atgttcggcc ccagcccct tcgccccgag agggccctct gcctgctgcc    3480
cgacctgctg gtgccactct ggaaagggcc aagactctct cccagggaa gaatgggggtc    3540 gtcaaagacg ttttgccctt tgggggtgcc gtggagaacc ccgagtactt gacaccccag    3600
ggaggagctg cccctcagcc ccaccctcct cctgccttca gcccagcctt cgacaacctc    3660
tattactggg accaggaccc accagagcgg ggggctccac ccagcacctt caaagggaca    3720
cctacggcag agaacccaga gtacctgggt ctggacgtgc cagtgtga                3768
```

<210> SEQ ID NO 53  
<211> LENGTH: 1986

<212> TYPE: DNA
<213> ORGANISM: Homo sapiens
<300> PUBLICATION INFORMATION:
<302> TITLE: ERBB3
<310> PATENT DOCUMENT NUMBER: XM006723

<400> SEQUENCE: 53

```
atgcacaact tcagtgtttt ttccaatttg acaaccattg gaggcagaag cctctacaac      60
cggggcttct cattgttgat catgaagaac ttgaatgtca catctctggg cttccgatcc     120
ctgaaggaaa ttagtgctgg gcgtatctat ataagtgcca ataggcagct ctgctaccac     180
cactctttga actggaccaa ggtgcttcgg gggcctacgg aagagcgact agacatcaag     240
cataatcggc cgcgcagaga ctgcgtggca gagggcaaag tgtgtgaccc actgtgctcc     300
tctgggggat gctggggccc aggccctggt cagtgcttgt cctgtcgaaa ttatagccga     360
ggaggtgtct gtgtgaccca ctgcaacttt ctgaatgggg agcctcgaga atttgcccat     420
gaggccgaat gcttctcctg ccacccggaa tgccaaccca tggagggcac tgccacatgc     480
aatggctcgg gctctgatac ttgtgctcaa tgtgcccatt tcgagatgg gccccactgt      540
gtgagcagct gccccatgg agtcctaggt gccagggcc aatctacaa gtacccagat        600
gttcagaatg aatgtcggcc ctgccatgag aactgcaccc aggggtgtaa aggaccagag     660
cttcaagact gtttaggaca aacactggtg ctgatcggca aaacccatct gacaatggct     720
ttgacagtga tagcaggatt ggtagtgatt ttcatgatgc tgggcggcac ttttctctac     780
tggcgtgggc gccggattca gaataaaagg gctatgaggc gatacttgga acggggtgag     840
agcatagagc ctctggaccc cagtgagaag gctaacaaag tcttggccag aatcttcaaa     900
gagacagagc taaggaagct taaagtgctt ggctcgggtg tctttggaac tgtgcacaaa     960
ggagtgtgga tccctgaggg tgaatcaatc aagattccag tctgcattaa agtcattgag    1020
gacaagagtg gacggcagag ttttcaagct gtgacagatc atatgctggc cattggcagc    1080
ctggaccatg cccacattgt aaggctgctg ggactatgcc agggtcatc tctgcagctt     1140
gtcactcaat atttgcctct gggttctctg ctggatcatg tgagacaaca ccggggggca    1200
ctggggccac agctgctgct caactgggga gtacaaattg ccaagggaat gtactacctt    1260
gaggaacatg gtatggtgca tagaaacctg gctgcccgaa acgtgctact caagtcaccc    1320
agtcaggttc aggtggcaga ttttggtgtg gctgacctgc tgcctcctga tgataagcag    1380
ctgctataca gtgaggccaa gactccaatt aagtggatgg cccttgagag tatccacttt    1440
gggaaataca caccagagtg tgatgtctgg agctatggtg tgacagtttg ggagttgatg    1500
accttcgggg cagagcccta tgcagggcta cgattggctg aagtaccaga cctgctagag    1560
aagggggagc ggttggcaca gcccagatc tgcacaattg atgtctacat ggtgatggtc     1620
aagtgttgga tgattgatga aacattcgc ccaaccttta agaactagc caatgagttc      1680
accaggatgg cccgagaccc accacggtat ctggtcataa agagagagag tgggcctgga    1740
atagcccctg ggccagagcc ccatggtctg acaaacaaga agctagagga agtagagctg    1800
gagccagaac tagacctaga cctagacttg gaagcagagg aggacaacct ggcaaccacc    1860
acactgggct ccgccctcag cctaccagtt ggaaacactt atcggccacg tgggagccag    1920
agccttttaa gtccatcatc tggatacatg cccatgaacc agggtaatct tgggggttctt   1980
ccttag                                                               1986
```

<210> SEQ ID NO 54
<211> LENGTH: 1437

```
<212> TYPE: DNA
<213> ORGANISM: Homo sapiens
<300> PUBLICATION INFORMATION:
<302> TITLE: ERBB4
<310> PATENT DOCUMENT NUMBER: XM002260

<400> SEQUENCE: 54
atgatgtacc tggaagaaag acgactcgtt catcgggatt tggcagcccg taatgtctta      60
gtgaaatctc caaaccatgt gaaaatcaca gattttgggc tagccagact cttggaagga     120
gatgaaaaag agtacaatgc tgatggagga agatgccaa ttaaatggat ggctctggag      180
tgtatacatt acaggaaatt cacccatcag agtgacgttt ggagctatgg agttactata     240
tgggaactga tgacctttgg aggaaaaccc tatgatgaa ttccaacgcg agaaatccct      300
gatttattag agaaaggaga acgtttgcct cagcctccca tctgcactat tgacgtttac     360
atggtcatgg tcaaatgttg gatgattgat gctgacagta gacctaaatt taaggaactg     420
gctgctgagt tttcaaggat ggctcgagac cctcaaagat acctagttat tcagggtgat     480
gatcgtatga agcttcccag tccaaatgac agcaagttct ttcagaatct cttggatgaa     540
gaggatttgg aagatatgat ggatgctgag gagtacttgg tccctcaggc tttcaacatc     600
ccacctccca tctatacttc cagagcaaga attgactcga ataggagtga aattggacac     660
agccctcctc ctgcctacac ccccatgtca ggaaaccagt ttgtataccg agatggaggt     720
tttgctgctg aacaaggagt gtctgtgccc tacagagccc caactagcac aattccagaa     780
gctcctgtgg cacagggtgc tactgctgag attttttgatg actcctgctg taatggcacc     840
ctacgcaagc cagtggcacc ccatgtccaa gaggacagta gcacccagag gtacagtgct     900
gaccccaccg tgtttgcccc agaacggagc ccacgaggag agctggatga ggaaggttac     960
atgactccta tgcgagacaa acccaaacaa gaatacctga tccagtgga ggagaaccct     1020 tttgtttctc ggagaaaaaa tggagacctt caagcattgg ataatcccga atatcacaat    1080
gcatccaatg gtcccaccaa ggccgaggat gagtatgtga atgagccact gtacctcaac    1140
acctttgcca cacccttggg aaaagctgag tacctgaaga caacatact gtcaatgcca    1200 gagaaggcca gaaagcgtt tgacaaccct gactactgga ccacagcct gccacctcgg    1260 agcaccttc agcacccaga ctacctgcag gagtacagca caaaatattt ttataaacag    1320
aatgggcgga tccggcctat tgtggcagag aatcctgaat acctctctga ttctccctg    1380 aagccaggca ctgtgctgcc gcctccacct tacagacacc ggaatactgt ggtgtaa      1437

<210> SEQ ID NO 55
<211> LENGTH: 627
<212> TYPE: DNA
<213> ORGANISM: Homo sapiens
<300> PUBLICATION INFORMATION:
<302> TITLE: FGF10
<310> PATENT DOCUMENT NUMBER: NM004465

<400> SEQUENCE: 55
atgtggaaat ggatactgac acattgtgcc tcagcctttc cccacctgcc cggctgctgc      60
tgctgctgct ttttgttgct gttcttggtg tcttccgtcc ctgtcacctg ccaagccctt     120
ggtcaggaca tggtgtcacc agaggccacc aactcttctt cctcctcctt ctcctctcct     180
tccagcgcgg gaaggcatgt gcggagctac aatcaccttc aaggagatgt ccgctggaga     240
aagctattct ctttcaccaa gtactttctc aagattgaga gaacgggaa ggtcagcggg     300 accaagaagg agaactgccc gtacagcatc ctggagataa catcagtaga aatcggagtt     360
```

```
gttgccgtca aagccattaa cagcaactat tacttagcca tgaacaagaa ggggaaactc      420
tatggctcaa aagaatttaa caatgactgt aagctgaagg agaggataga ggaaaatgga      480 tacaataccct atgcatcatt taactggcag cataatggga ggcaaatgta tgtggcattg     540
aatggaaaag gagctccaag gagaggacag aaaacacgaa ggaaaaacac ctctgctcac     600
tttcttccaa tggtggtaca ctcatag                                          627

<210> SEQ ID NO 56
<211> LENGTH: 679
<212> TYPE: DNA
<213> ORGANISM: Homo sapiens
<300> PUBLICATION INFORMATION:
<302> TITLE: FGF11
<310> PATENT DOCUMENT NUMBER: XM008660

<400> SEQUENCE: 56
aatggcggcg ctggccagta gcctgatccg gcagaagcgg gaggtccgcg agcccggggg      60
cagccggccg tgtcggcgc agcggcgcgt gtgtccccgc ggcaccaagt cccttttgcca     120 gaagcagctc ctcatcctgc tgtccaaggt gcgactgtgc gggggcggc ccgcgcggcc     180 ggaccgcggc ccggagcctc agctcaaagg catcgtcacc aaactgttct gccgccaggg     240
tttctacctc caggcgaatc ccgacggaag catccagggc accccagagg ataccagctc     300
cttcacccac ttcaacctga tccctgtggg cctccgtgtg gtcaccatcc agagcgccaa     360
gctgggtcac tacatggcca tgaatgctga gggactgctc tacagttcgc cgcatttcac     420
agctgagtgt cgctttaagg agtgtgtctt tgagaattac tacgtcctgt acgcctctgc     480
tctctaccgc cagcgtcgtt ctggccgggc ctggtacctc ggcctggaca aggagggcca     540
ggtcatgaag ggaaaccgag ttaagaagac caaggcagct gcccactttc tgcccaagct     600
cctggaggtg gccatgtacc aggagccttc tctccacagt gtccccgagg cctccccttc     660
cagtccccct gcccccctga                                                 679

<210> SEQ ID NO 57
<211> LENGTH: 732
<212> TYPE: DNA
<213> ORGANISM: Homo sapiens
<300> PUBLICATION INFORMATION:
<302> TITLE: FGF12
<310> PATENT DOCUMENT NUMBER: NM021032

<400> SEQUENCE: 57
atggctgcgg cgatagccag ctccttgatc cggcagaagc ggcaggcgag ggagtccaac      60
agcgaccgag tgtcggcctc caagcgccgc tccagcccca gcaaagacgg cgctccctg     120 tgcgagaggc acgtcctcgg ggtgttcagc aaagtgcgct ctgcagcgg ccgcaagagg     180 ccggtgaggc ggagaccaga accccagctc aaagggattg tgacaaggtt attcagccag     240
cagggatact cctgcagat gcacccagat ggtaccattg atgggaccaa ggacgaaaac     300
agcgactaca ctctcttcaa tctaattccc gtgggcctgc gtgtagtggc catccaagga    360
gtgaaggcta gcctctatgt ggccatgaat ggtgaaggct atctctacag ttcagatgtt     420
ttcactccag aatgcaaatt caaggaatct gtgtttgaaa actactatgt gatctattct     480
tccacactgt accgccagca agaatcaggc cgagcttggt ttctgggact caataaagaa     540
ggtcaaatta tgaaggggaa cagagtgaag aaaaccaagc cctcatcaca tttttgtaccg    600 aaacctattg agtgtgtat gtacagagaa ccatcgctac atgaaattgg agaaaaacaa     660
gggcgttcaa ggaaaagttc tggaacacca accatgaatg gaggcaaagt tgtgaatcaa     720
```

```
gattcaacat ag                                                      732

<210> SEQ ID NO 58
<211> LENGTH: 738
<212> TYPE: DNA
<213> ORGANISM: Homo sapiens
<300> PUBLICATION INFORMATION:
<302> TITLE: FGF13
<310> PATENT DOCUMENT NUMBER: XM010269

<400> SEQUENCE: 58
atggcggcgg ctatcgccag ctcgctcatc cgtcagaaga ggcaagcccg cgagcgcgag     60
aaatccaacg cctgcaagtg tgtcagcagc cccagcaaag gcaagaccag ctgcgacaaa    120
aacaagttaa atgtcttttc ccgggtcaaa ctcttcggct ccaagaagag cgcagaaga    180 agaccagagc ctcagcttaa gggtatagtt accaagctat acagccgaca aggctaccac    240
ttgcagctgc aggcggatgg aaccattgat ggcaccaaag atgaggacag cacttacact    300
ctgtttaacc tcatccctgt gggtctgcga gtggtggcta tccaaggagt tcaaaccaag    360
ctgtacttgg caatgaacag tgagggatac ttgtacacct cggaactttt cacacctgag    420
tgcaaattca agaatcagt gtttgaaaat tattatgtga catattcatc aatgatatac    480
cgtcagcagc agtcaggccg agggtggtat ctgggtctga caaagaagg agagatcatg    540 aaaggcaacc atgtgaagaa gaacaagcct gcagctcatt ttctgcctaa ccactgaaa    600 gtggccatgt acaaggagcc atcactgcac gatctcacgg agttctcccg atctggaagc    660
gggaccccaa ccaagagcag aagtgtctct ggcgtgctga acggaggcaa atccatgagc    720
cacaatgaat caacgtag                                                 738

<210> SEQ ID NO 59
<211> LENGTH: 624
<212> TYPE: DNA
<213> ORGANISM: Homo sapiens
<300> PUBLICATION INFORMATION:
<302> TITLE: FGF16
<310> PATENT DOCUMENT NUMBER: NM003868

<400> SEQUENCE: 59
atggcagagg tggggggcgt cttcgcctcc ttggactggg atctacacgg cttctcctcg     60
tctctgggga acgtgccctt agctgactcc ccaggtttcc tgaacgagcg cctgggccaa    120
atcgagggga agctgcagcg tggctcaccc acagacttcg cccacctgaa ggggatcctg    180
cggcgccgcc agctctactg ccgcaccggc ttccacctgg atcttccc caacggcacg    240 gtgcacggga cccgccacga ccacagccgc ttcggaatcc tggagtttat cagcctggct    300
gtggggctga tcagcatccg gggagtggac tctggcctgt acctaggaat gaatgagcga    360
ggagaactct atgggtcgaa gaaactcaca cgtgaatgtg ttttccggga acagtttgaa    420
gaaaactggt acaacaccta tgcctcaacc ttgtacaaac attcggactc agagagacag    480
tattacgtgg ccctgaacaa agatggctca ccccgggagg atacaggac taaacgacac    540 cagaaattca ctcactttt acccaggcct gtagatcctt ctaagttgcc ctccatgtcc    600
agagacctct ttcactatag gtaa                                          624

<210> SEQ ID NO 60
<211> LENGTH: 651
<212> TYPE: DNA
<213> ORGANISM: Homo sapiens
<300> PUBLICATION INFORMATION:
```

<302> TITLE: FGF17
<310> PATENT DOCUMENT NUMBER: XM005316

<400> SEQUENCE: 60

| | | | | | |
|---|---|---|---|---|---|
| atgggagccg | cccgcctgct | gcccaacctc | actctgtgct | tacagctgct | gattctctgc | 60 |
| tgtcaaactc | aggggagaa | tcacccgtct | cctaatttta | accagtacgt | gagggaccag | 120 |
| ggcgccatga | ccgaccagct | gagcaggcgg | cagatccgcg | agtaccaact | ctacagcagg | 180 |
| accagtggca | agcacgtgca | ggtcaccggg | cgtcgcatct | ccgccaccgc | cgaggacggc | 240 |
| aacaagtttg | ccaagctcat | agtggagacg | gacacgtttg | gcagccgggt | tcgcatcaaa | 300 |
| ggggctgaga | gtgagaagta | catctgtatg | aacaagaggg | gcaagctcat | cgggaagccc | 360 |
| agcgggaaga | gcaaagactg | cgtgttcacg | gagatcgtgc | tggagaacaa | ctatacggcc | 420 |
| ttccagaacg | cccggcacga | gggctggttc | atggccttca | cgcggcaggg | gcggccccgc | 480 |
| caggcttccc | gcagccgcca | gaaccagcgc | gaggcccact | tcatcaagcg | cctctaccaa | 540 |
| ggccagctgc | ccttccccaa | ccacgccgag | aagcagaagc | agttcgagtt | tgtgggctcc | 600 |
| gcccccaccc | gccggaccaa | gcgcacacgg | cggccccagc | ccctcacgta | g | 651 |

<210> SEQ ID NO 61
<211> LENGTH: 624
<212> TYPE: DNA
<213> ORGANISM: Homo sapiens
<300> PUBLICATION INFORMATION:
<302> TITLE: FGF18
<310> PATENT DOCUMENT NUMBER: AF075292

<400> SEQUENCE: 61

| | | | | | |
|---|---|---|---|---|---|
| atgtattcag | cgccctccgc | ctgcacttgc | ctgtgtttac | acttcctgct | gctgtgcttc | 60 |
| caggtacagg | tgctggttgc | cgaggagaac | gtggacttcc | gcatccacgt | ggagaaccag | 120 |
| acgcgggctc | gggacgatgt | gagccgtaag | cagctgcggc | tgtaccagct | ctacagccgg | 180 |
| accagtggga | aacacatcca | ggtcctgggc | cgcaggatca | gtgcccgcgg | cgaggatggg | 240 |
| gacaagtatg | cccagctcct | agtggagaca | gacaccttcg | gtagtcaagt | ccggatcaag | 300 |
| ggcaaggaga | cggaattcta | cctgtgcatg | aaccgcaaag | gcaagctcgt | ggggaagccc | 360 |
| gatggcacca | gcaaggagtg | tgtgttcatc | gagaaggttc | tggagaacaa | ctacacggcc | 420 |
| ctgatgtcgg | ctaagtactc | cggctggtac | gtgggcttca | ccaagaaggg | gcggccgcgg | 480 |
| aagggcccca | agacccggga | gaaccagcag | gacgtgcatt | tcatgaagcg | ctaccccaag | 540 |
| gggcagccgg | agcttcagaa | gcccttcaag | tacacgacgg | tgaccaagag | gtcccgtcgg | 600 |
| atccggccca | cacaccctgc | ctag | | | | 624 |

<210> SEQ ID NO 62
<211> LENGTH: 651
<212> TYPE: DNA
<213> ORGANISM: Homo sapiens
<300> PUBLICATION INFORMATION:
<302> TITLE: FGF19
<310> PATENT DOCUMENT NUMBER: AF110400

<400> SEQUENCE: 62

| | | | | | |
|---|---|---|---|---|---|
| atgcggagcg | ggtgtgtggt | ggtccacgta | tggatcctgg | ccggcctctg | gctggccgtg | 60 |
| gccgggcgcc | ccctcgcctt | ctcggacgcg | gggccccacg | tgcactacgg | ctgggcgac | 120 |
| cccatccgcc | tgcggcacct | gtacacctcc | ggcccccacg | gctctccag | ctgcttcctg | 180 |
| cgcatccgtg | ccgacggcgt | cgtggactgc | gcgcggggcc | agagcgcgca | cagtttgctg | 240 |

```
gagatcaagg cagtcgctct gcggaccgtg gccatcaagg gcgtgcacag cgtgcggtac    300
ctctgcatgg gcgccgacgg caagatgcag gggctgcttc agtactcgga ggaagactgt    360
gctttcgagg aggagatccg cccagatggc tacaatgtgt accgatccga aagcaccgc     420 ctcccggtct ccctgagcag tgccaaacag cggcagctgt acaagaacag aggcttcctt    480
ccactctctc atttcctgcc catgctgccc atggtcccag aggagcctga ggacctcagg    540
ggccacttgg aatctgacat gttctcttcg cccctggaga ccgacagcat ggacccattt    600
gggcttgtca ccggactgga ggccgtgagg agtcccagct ttgagaagta a             651

<210> SEQ ID NO 63
<211> LENGTH: 468
<212> TYPE: DNA
<213> ORGANISM: Homo sapiens

<400> SEQUENCE: 63
atggctgaag gggaaatcac caccttcaca gccctgaccg agaagtttaa tctgcctcca    60
gggaattaca agaagcccaa actcctctac tgtagcaacg ggggccactt cctgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatatat ccaagaagca tgcagagaag    360
aattggtttg ttggcctcaa gaagaatggg agctgcaaac gcggtcctcg gactcactat    420
ggccagaaag caatcttgtt tctcccccctg ccagtctctt ctgattaa                468

<210> SEQ ID NO 64
<211> LENGTH: 636
<212> TYPE: DNA
<213> ORGANISM: Homo sapiens
<300> PUBLICATION INFORMATION:
<302> TITLE: FGF20
<310> PATENT DOCUMENT NUMBER: NM019851

<400> SEQUENCE: 64
atggctccct tagccgaagt cgggggcttt ctgggcggcc tggagggctt gggccagcag    60
gtgggttcgc atttcctgtt gcctcctgcc ggggagcggc cgccgctgct gggcgagcgc    120
aggagcgcgc cggagcggag cgcccgcggc gggccggggg ctgcgcagct ggcgcacctg    180
cacggcatcc tgcgccgccg gcagctctat tgccgcaccg gcttccacct gcagatcctg    240
cccgacggca gctgcagggc acccggcag gaccacagcc tcttcggtat cttggaattc    300
atcagtgtgg cagtgggact ggtcagtatt agaggtgtgg acagtggtct ctatcttgga    360
atgaatgaca aggagaact ctatggatca gagaaactta cttccgaatg catctttagg    420
gagcagtttg aagagaactg gtataacacc tattcatcta acatatataa acatggagac    480
actggccgca gtattttgt ggcacttaac aaagacggaa ctccaagaga tggcgccagg    540 tccaagagg catcagaaatt tacacatttc ttacctagac cagtggatcc agaaagagtt    600
ccagaattgt acaaggacct actgatgtac acttga                              636

<210> SEQ ID NO 65
<211> LENGTH: 630
<212> TYPE: DNA
<213> ORGANISM: Homo sapiens
<300> PUBLICATION INFORMATION:
<302> TITLE: FGF21
<310> PATENT DOCUMENT NUMBER: XM009100
```

<400> SEQUENCE: 65

```
atggactcgg acgagaccgg gttcgagcac tcaggactgt gggtttctgt gctggctggt    60
cttctgctgg gagcctgcca ggcacacccc atccctgact ccagtcctct cctgcaattc   120
gggggccaag tccggcagcg gtacctctac acagatgatg cccagcagac agaagcccac   180
ctggagatca gggaggatgg gacggtgggg ggcgctgctg accagagccc cgaaagtctc   240
ctgcagctga aagccttgaa gccgggagtt attcaaatct tgggagtcaa gacatccagg   300
ttcctgtgcc agcggccaga tggggccctg tatggatcgc tccactttga ccctgaggcc   360
tgcagcttcc gggagctgct tcttgaggac ggatacaatg tttaccagtc cgaagcccac   420
ggcctcccgc tgcacctgcc agggaacaag tccccacacc gggaccctgc accccgagga   480
ccagctcgct tcctgccact accaggcctg ccccccgcac tcccggagcc acccggaatc   540
ctggcccccc agcccccccga tgtgggctcc tcggaccctc tgagcatggt gggaccttcc   600
cagggccgaa gccccagcta cgcttcctga                                    630
```

<210> SEQ ID NO 66
<211> LENGTH: 513
<212> TYPE: DNA
<213> ORGANISM: Homo sapiens
<300> PUBLICATION INFORMATION:
<302> TITLE: FGF22
<310> PATENT DOCUMENT NUMBER: XM009271

<400> SEQUENCE: 66

```
atgcgccgcc gcctgtggct gggcctggcc tggctgctgc tggcgcgggc gccggacgcc    60
gcgggaaccc cgagcgcgtc gcggggaccg cgcagctacc cgcacctgga gggcgacgtg   120
cgctggcggc gcctcttctc ctccactcac ttcttcctgc gcgtggatcc cggcggccgc   180
gtgcagggca cccgctggcg ccacggccag gacagcatcc tggagatccg ctctgtacac   240
gtgggcgtcg tggtcatcaa agcagtgtcc tcaggcttct acgtggccat gaaccgccgg   300
ggccgcctct acgggtcgcg actctacacc gtggactgca ggttccggga gcgcatcgaa   360
gagaacggcc acaacaccta cgcctcacag cgctggcgcc ccgcggcca gcccatgttc   420
ctggcgctgg acaggagggg ggggcccgg ccaggcggcc ggacgcggcg gtaccacctg   480
tccgcccact cctgcccgt cctggtctcc tga                                 513
```

<210> SEQ ID NO 67
<211> LENGTH: 621
<212> TYPE: DNA
<213> ORGANISM: Homo sapiens
<300> PUBLICATION INFORMATION:
<302> TITLE: FGF4
<310> PATENT DOCUMENT NUMBER: NM002007

<400> SEQUENCE: 67

```
atgtcggggc ccgggacggc cgcggtagcg ctgctcccgg cggtcctgct ggccttgctg    60
gcgccctggg cgggccgagg gggcgccgcc gcacccactg cacccaacgg cacgctggag   120
gccgagctgg agcgccgctg ggagagcctg gtggcgctct cgttggcgcg cctgccggtg   180
gcagcgcagc ccaaggaggc ggccgtccag agcggcgccg cgactacct gctgggcatc   240
aagcggctgc ggcggctcta ctgcaacgtg ggcatcggct tccacctcca ggcgctcccc   300
gacgccgcca tcgcggcgc gcacgcggac cccgcgaca gctgctgga gctctcgccc   360
gtggagcggg gcgtggtgag catcttcggc gtggccagcc ggttcttcgt ggccatgagc   420
```

```
agcaagggca agctctatgg ctcgcccttc ttcaccgatg agtgcacgtt caaggagatt    480
ctccttccca acaactacaa cgcctacgag tcctacaagt accccggcat gttcatcgcc    540
ctgagcaaga atgggaagac caagaagggg aaccgagtgt cgcccaccat gaaggtcacc    600
cacttcctcc ccaggctgtg a                                              621

<210> SEQ ID NO 68
<211> LENGTH: 597
<212> TYPE: DNA
<213> ORGANISM: Homo sapiens
<300> PUBLICATION INFORMATION:
<302> TITLE: FGF6
<310> PATENT DOCUMENT NUMBER: NM020996

<400> SEQUENCE: 68
atgtcccggg gagcaggacg tctgcagggc acgctgtggg ctctcgtctt cctaggcatc     60
ctagtgggca tggtggtgcc ctcgcctgca ggcacccgtg ccaacaacac gctgctggac    120
tcgaggggct ggggcaccct gctgtccagg tctcgcgcgg ggctagctgg agagattgcc    180
ggggtgaact gggaaagtgg ctatttggtg gggatcaagc ggcagcggag gctctactgc    240
aacgtgggca tcggctttca cctccaggtg ctccccgacg gccggatcag cgggacccac    300
gaggagaacc cctacagcct gctggaaatt tccactgtgg agcgaggcgt ggtgagtctc    360
tttggagtga gaagtgccct cttcgttgcc atgaacagta aaggaagatt gtacgcaacg    420
cccagcttcc aagaagaatg caagttcaga gaaaccctcc tgcccaacaa ttacaatgcc    480
tacgagtcag acttgtacca agggacctac attgccctga gcaaatacgg acgggtaaag    540
cggggcagca aggtgtcccc gatcatgact gtcactcatt tccttcccag gatctaa      597

<210> SEQ ID NO 69
<211> LENGTH: 150
<212> TYPE: DNA
<213> ORGANISM: Homo sapiens
<300> PUBLICATION INFORMATION:
<302> TITLE: FGF7
<310> PATENT DOCUMENT NUMBER: XM007559

<400> SEQUENCE: 69
atgtcttggc aatgcacttc atacacaatg actaatctat actgtgatga tttgactcaa     60
aaggagaaaa gaaattatgt agtttttcaat tctgattcct attcaccttt tgtttatgaa    120
tggaaagctt tgtgcaaaat atacatataa                                     150

<210> SEQ ID NO 70
<211> LENGTH: 628
<212> TYPE: DNA
<213> ORGANISM: Homo sapiens
<300> PUBLICATION INFORMATION:
<302> TITLE: FGF9
<310> PATENT DOCUMENT NUMBER: XM007105

<400> SEQUENCE: 70
gatggctccc ttaggtgaag ttgggaacta tttcggtgtg caggatgcgg taccgtttgg     60
gaatgtgccc gtgttgccgg tggacagccc ggttttgtta agtgaccacc tgggtcagtc    120
cgaagcaggg gggctcccca ggggacccgc agtcacggac ttggatcatt taaaggggat    180
tctcaggcgg aggcagctat actgcaggac tggatttcac ttagaaatct tccccaatgg    240
tactatccag ggaaccagga aagaccacag ccgatttggc attctggaat ttatcagtat    300
agcagtgggc ctggtcagca ttcgaggcgt ggacagtgga ctctacctcg ggatgaatga    360
```

-continued

| | |
|---|---|
| gaaggggggag ctgtatggat cagaaaaact aacccaagag tgtgtattca gagaacagtt | 420 |
| cgaagaaaac tggtataata cgtactcatc aaacctatat aagcacgtgg acactggaag | 480 |
| gcgatactat gttgcattaa ataaagatgg accccgaga aagggacta ggactaaacg | 540 |
| gcaccagaaa ttcacacatt ttttacctag accagtggac cccgacaaag tacctgaact | 600 |
| gtataaggat attctaagcc aaagttga | 628 |

<210> SEQ ID NO 71
<211> LENGTH: 2469
<212> TYPE: DNA
<213> ORGANISM: Homo sapiens
<300> PUBLICATION INFORMATION:
<302> TITLE: FGFR1
<310> PATENT DOCUMENT NUMBER: NM000604

<400> SEQUENCE: 71

| | |
|---|---|
| atgtggagct ggaagtgcct cctcttctgg gctgtgctgg tcacagccac actctgcacc | 60 |
| gctaggccgt ccccgacctt gcctgaacaa gcccagccct ggggagcccc tgtggaagtg | 120 |
| gagtccttcc tggtccaccc cggtgacctg ctgcagcttc gctgtcggct gcgggacgat | 180 |
| gtgcagagca tcaactggct gcgggacggg gtgcagctgg cggaaagcaa ccgcacccgc | 240 |
| atcacagggg aggaggtgga ggtgcaggac tccgtgcccg cagactccgg cctctatgct | 300 |
| tgcgtaacca gcagcccctc gggcagtgac accaccctact tctccgtcaa tgtttcagat | 360 |
| gctctcccct cctcggagga tgatgatgat gatgatgact cctcttcaga ggagaaagaa | 420 |
| acagataaca ccaaaccaaa ccgtatgccc gtagctccat attggacatc cccagaaaag | 480 |
| atggaaaaga aattgcatgc agtgccggct gccaagacag tgaagttcaa atgcccttcc | 540 |
| agtgggaccc caaaccccac actgcgctgg ttgaaaaatg gcaaagaatt caaacctgac | 600 |
| cacagaattg gaggctacaa ggtccgttat gccacctgga gcatcataat ggactctgtg | 660 |
| gtgccctctg acaagggcaa ctacacctgc attgtgagaa atgagtacgg cagcatcaac | 720 |
| cacacatacc agctggatgt cgtggagcgg tcccctcacc ggcccatcct gcaagcaggg | 780 |
| ttgcccgcca acaaaacagt ggccctgggt agcaacgtgg agttcatgtg taaggtgtac | 840 |
| agtgacccgc agccgcacat ccagtggcta agcacatcg aggtgaatgg gagcaagatt | 900 |
| ggcccagaca acctgcctta tgtccagatc ttgaagactg ctggagttaa taccaccgac | 960 |
| aaagagatgg aggtgcttca cttaagaaat gtctcctttg aggacgcagg ggagtatacg | 1020 |
| tgcttggcgg gtaactctat cggactctcc catcactctg catggttgac cgttctggaa | 1080 |
| gccctggaag agaggccggc agtgatgacc tcgcccctgt acctggagat catcatctat | 1140 |
| tgcacagggg ccttcctcat ctcctgcatg gtggggtcgg tcatcgtcta caagatgaag | 1200 |
| agtggtacca agaagagtga cttccacagc cagatggctg tgcacaagct ggccaagagc | 1260 |
| atccctctgc gcagacaggt aacagtgtct gctgactcca gtgcatccat gaactctggg | 1320 |
| gttcttctgg ttcggccatc acggctctcc tccagtggga ctcccatgct agcagggggtc | 1380 |
| tctgagtatg agcttcccga agaccctcgc tgggagctgc ctcgggacag actggtctta | 1440 |
| ggcaaacccc tgggagaggg ctgctttggg caggtggtgt ggcagaggc tatcgggctg | 1500 |
| gacaaggaca aacccaaccg tgtgaccaaa gtggctgtga agatgttgaa gtcggacgca | 1560 |
| acagagaaag acttgtcaga cctgatctca gaaatggaga tgatgaagat gatcgggaag | 1620 |
| cataagaata tcatcaacct gctggggccc tgcacgcagg atggtccctt gtatgtcatc | 1680 |
| gtggagtatg cctccaaggg caacctgcgg gagtacctgc aggcccggag gccccaggg | 1740 |

| | |
|---|---|
| ctggaatact gctacaaccc cagccacaac ccagaggagc agctctcctc caaggacctg | 1800 |
| gtgtcctgcg cctaccaggt ggcccgaggc atggagtatc tggcctccaa gaagtgcata | 1860 |
| caccgagacc tggcagccag gaatgtcctg gtgacagagg acaatgtgat gaagatagca | 1920 |
| gactttggcc tcgcacggga cattcaccac atcgactact ataaaaagac aaccaacggc | 1980 |
| cgactgcctg tgaagtggat ggcacccgag gcattatttg accggatcta cacccaccag | 2040 |
| agtgatgtgt ggtctttcgg ggtgctcctg tgggagatct tcactctggg cggctcccca | 2100 |
| taccccggtg tgcctgtgga ggaacttttc aagctgctga aggagggtca ccgcatggac | 2160 |
| aagcccagta actgcaccaa cgagctgtac atgatgatgc gggactgctg gcatgcagtg | 2220 |
| ccctcacaga gacccacctt caagcagctg gtggaagacc tggaccgcat cgtggccttg | 2280 |
| acctccaacc aggagtacct ggacctgtcc atgcccctgg accagtactc ccccagcttt | 2340 |
| cccgacaccc ggagctctac gtgctcctca ggggaggatt ccgtcttctc tcatgagccg | 2400 |
| ctgcccgagg agccctgcct gccccgacac ccagcccagc ttgccaatgg cggactcaaa | 2460 |
| cgccgctga | 2469 |

<210> SEQ ID NO 72
<211> LENGTH: 2409
<212> TYPE: DNA
<213> ORGANISM: Homo sapiens
<300> PUBLICATION INFORMATION:
<302> TITLE: FGFR4
<310> PATENT DOCUMENT NUMBER: XM003910

<400> SEQUENCE: 72

| | |
|---|---|
| atgcggctgc tgctggccct gttgggggtc ctgctgagtg tgcctgggcc tccagtcttg | 60 |
| tccctggagg cctctgagga agtggagctt gagccctgcc tggctcccag cctggagcag | 120 |
| caagagcagg agctgacagt agcccttggg cagcctgtgc ggctgtgctg tgggcgggct | 180 |
| gagcgtggtg gccactggta caaggagggc agtcgcctgg cacctgctgg ccgtgtacgg | 240 |
| ggctggaggg gccgcctaga gattgccagc ttcctacctg aggatgctgg ccgctacctc | 300 |
| tgcctggcac gaggctccat gatcgtcctg cagaatctca ccttgattac aggtgactcc | 360 |
| ttgacctcca gcaacgatga tgaggacccc aagtcccata gggacctctc gaataggcac | 420 |
| agttaccccc agcaagcacc ctactggaca caccccagc gcatggagaa gaaactgcat | 480 |
| gcagtacctg cggggaacac cgtcaagttc cgctgtccag ctgcaggcaa ccccacgccc | 540 |
| accatccgct ggcttaagga tggacaggcc tttcatgggg agaaccgcat tggaggcatt | 600 |
| cggctgcgca tcagcactg gagtctcgtg atggagagcg tggtgccctc ggaccgcggc | 660 |
| acatacacct gcctggtaga aaacgctgtg ggcagcatcc gttataacta cctgctagat | 720 |
| gtgctggagc ggtccccgca ccggcccatc ctgcaggccg gctcccggc caacaccaca | 780 |
| gccgtggtgg gcagcgacgt ggagctgctg tgcaaggtgt acagcgatgc ccagccccac | 840 |
| atccagtggc tgaagcacat cgtcatcaac ggcagcagct tcggagccga cggtttcccc | 900 |
| tatgtgcaag tcctaaagac tgcagacatc aatagctcag aggtggaggt cctgtacctg | 960 |
| cggaacgtgt cagccgagga cgcaggcgag tacacctgcc tcgcaggcaa ttccatcggc | 1020 |
| ctctcctacc agtctgcctg gctcacggtg ctgccagagg aggacccac atggaccgca | 1080 |
| gcagcgcccg aggccaggta tacggacatc atcctgtacg cgtcgggctc cctggccttg | 1140 |
| gctgtgctcc tgctgctggc caggctgtat cgagggcagg cgctccacgg ccggcacccc | 1200 |
| cgcccgccg ccactgtgca gaagctctcc cgcttccctc tggcccgaca gttctccctg | 1260 |

| | |
|---|---|
| gagtcaggct cttccggcaa gtcaagctca tccctggtac gaggcgtgcg tctctcctcc | 1320 |
| agcggcccccg ccttgctcgc cggcctcgtg agtctagatc tacctctcga cccactatgg | 1380 |
| gagttccccc gggacaggct ggtgcttggg aagccctag gcgagggctg ctttggccag | 1440 |
| gtagtacgtg cagaggcctt tggcatggac cctgcccggc ctgaccaagc cagcactgtg | 1500 |
| gccgtcaaga tgctcaaaga caacgcctct gacaaggacc tggccgacct ggtctcggag | 1560 |
| atggaggtga tgaagctgat cggccgacac aagaacatca tcaacctgct tggtgtctgc | 1620 |
| acccaggaag ggcccctgta cgtgatcgtg gagtgcgccg ccaagggaaa cctgcgggag | 1680 |
| ttcctgcggg cccggcgccc cccaggcccc gacctcagcc ccgacggtcc tcggagcagt | 1740 |
| gaggggccgc tctccttccc agtcctggtc tcctgcgcct accaggtggc ccgaggcatg | 1800 |
| cagtatctgg agtcccggaa gtgtatccac cgggacctgg ctgcccgcaa tgtgctggtg | 1860 |
| actgaggaca atgtgatgaa gattgctgac tttgggctgg cccgcggcgt ccaccacatt | 1920 |
| gactactata agaaaaccag caacggccgc ctgcctgtga agtggatggc gcccgaggcc | 1980 |
| ttgtttgacc gggtgtacac acaccagagt gacgtgtggg cttttgggat cctgctatgg | 2040 |
| gagatcttca ccctcggggg ctccccgtat cctggcatcc cggtggagga gctgttctcg | 2100 |
| ctgctgcggg agggacatcg gatggaccga cccccacact gcccccagag ctgtacgggg | 2160 |
| ctgatgcgtg agtgctggca cgcagcgccc tcccagaggc ctaccttcaa gcagctggtg | 2220 |
| gaggcgctga caaggtcct gctggccgtc tctgaggagt acctcgacct ccgcctgacc | 2280 |
| ttcggaccct attcccccctc tggtggggac gccagcagca cctgctcctc cagcgattct | 2340 |
| gtcttcagcc acgaccccct gccattggga tccagctcct tccccttcgg gtctggggtg | 2400 |
| cagacatga | 2409 |

<210> SEQ ID NO 73
<211> LENGTH: 1695
<212> TYPE: DNA
<213> ORGANISM: Homo sapiens
<300> PUBLICATION INFORMATION:
<302> TITLE: MT2MMP
<310> PATENT DOCUMENT NUMBER: D86331

<400> SEQUENCE: 73

| | |
|---|---|
| atgaagcggc cccgctgtgg ggtgccagac cagttcgggg tacgagtgaa agccaacctg | 60 |
| cggcggcgtc ggaagcgcta cgccctcacc gggaggaagt ggaacaacca ccatctgacc | 120 |
| tttagcatcc agaactacac ggagaagttg gctggtacc actcgatgga ggcggtgcgc | 180 |
| agggccttcc gcgtgtggga gcaggccacg ccccctggtct tccaggaggt gcccatgag | 240 |
| gacatccggc tgcggcgaca gaaggaggcc gacatcatgg tactctttgc ctctggcttc | 300 |
| cacggcgaca gctcgccgtt tgatggcacc ggtggctttc tggcccacgc ctatttccct | 360 |
| ggccccggcc taggcgggga cacccatttt gacgcagatg agccctggac cttctccagc | 420 |
| actgacctgc atggaaacaa cctcttcctg gtgcagtgc atgagctggg ccacgcgctg | 480 |
| gggctggagc actccagcaa ccccaatgcc atcatggcgc cgttctacca gtggaaggac | 540 |
| gttgacaact tcaagctgcc cgaggacgat ctccgtggca tccagcagct ctacggtacc | 600 |
| ccagacggtc agccacagcc tacccagcct ctccccactg tgacgccacg gcggccaggc | 660 |
| cggcctgacc accggccgcc ccggcctccc cagccaccac cccaggtgg aagccagag | 720 |
| cggccccccaa agccgggccc cccagtccag ccccgagcca cagagcggcc cgaccagtat | 780 |
| ggccccaaca tctgcgacgg ggactttgac acagtggcca tgcttcgcgg ggagatgttc | 840 |

```
gtgttcaagg gccgctggtt ctggcgagtc cggcacaacc gcgtcctgga caactatccc      900
atgcccatcg ggcacttctg gcgtggtctg cccggtgaca tcagtgctgc ctacgagcgc      960
caagacggtc gttttgtctt tttcaaaggt gaccgctact ggctctttcg agaagcgaac     1020
ctggagcccg gctacccaca gccgctgacc agctatggcc tgggcatccc ctatgaccgc     1080
attgacacgg ccatctggtg ggagcccaca ggccacacct tcttcttcca agaggacagg     1140
tactggcgct tcaacgagga gacacagcgt ggagaccctg ggtacccccaa gcccatcagt    1200 gtctggcagg ggatccctgc ctccccctaaa ggggccttcc tgagcaatga cgcagcctac    1260
acctacttct acaagggcac caaatactgg aaattcgaca atgagcgcct gcggatggag    1320
cccggctacc ccaagtccat cctgcgggac ttcatgggct gccaggagca cgtggagcca    1380
ggcccccgat ggcccgacgt ggcccggccg cccttcaacc cccacggggg tgcagagccc    1440
ggggcggaca gcgcagaggg cgacgtgggg gatggggatg gggactttgg ggccggggtc    1500
aacaaggaca ggggcagccg cgtggtggtg cagatggagg aggtggcacg gacggtgaac    1560
gtggtgatgg tgctggtgcc actgctgctg ctgctctgcg tcctgggcct cacctacgcg    1620
ctggtgcaga tgcagcgcaa gggtgcgcca cgtgtcctgc tttactgcaa gcgctcgctg    1680
caggagtggg tctga                                                     1695
```

<210> SEQ ID NO 74
<211> LENGTH: 1824
<212> TYPE: DNA
<213> ORGANISM: Homo sapiens
<300> PUBLICATION INFORMATION:
<302> TITLE: MT3MMP
<310> PATENT DOCUMENT NUMBER: D85511

<400> SEQUENCE: 74

```
atgatcttac tcacattcag cactggaaga cggttggatt tcgtgcatca ttcgggggtg       60
tttttcttgc aaaccttgct ttggatttta tgtgctacag tctgcggaac ggagcagtat      120
ttcaatgtgg aggtttggtt acaaaagtac ggctaccttc caccgactga ccccagaatg      180
tcagtgctgc gctctgcaga gaccatgcag tctgccctag ctgccatgca gcagttctat      240
ggcattaaca tgacaggaaa agtggacaga aacacaattg actggatgaa gaagcccga      300 tgcggtgtac ctgaccagac aagaggtagc tccaaatttc atattcgtcg aaagcgatat      360
gcattgacag gacagaaatg gcagcacaag cacatcactt acagtataaa gaacgtaact      420
ccaaaagtag agaccctga ctcgtaaa gctattcgcc gtgcctttga tgtgtggcag         480
aatgtaactc ctctgacatt tgaagaagtt ccctacagta attagaaaa tggcaaacgt       540 gatgtggata taaccattat ttttgcatct ggtttccatg gggacagctc tccctttgat      600
ggagagggag gattttggc acatgcctac ttccctggac caggaattgg aggagatacc       660
cattttgact cagatgagcc atggacacta ggaaatccta atcatgatgg aaatgactta      720
tttcttgtag cagtccatga actgggacat gctctgggat tggagcattc caatgacccc      780
actgccatca tggctccatt ttaccagtac atggaaacag acaacttcaa actacctaat     840
gatgatttac agggcatcca gaagatatat ggtccacctg acaagattcc tccacctaca    900
agacctctac cgacagtgcc cccacaccgc tctattcctc cggctgaccc aaggaaaaat     960
gacaggccaa aacctcctcg gcctccaacc ggcagaccct cctatcccgg agccaaaccc    1020
aacatctgtg atgggaactt taacactcta gctattcttc gtcgtgagat gtttgttttc    1080
aaggaccagt ggttttggcg agtgagaaac aacagggtga tggatggata cccaatgcaa    1140
```

| | |
|---|---|
| attacttact tctggcgggg cttgcctcct agtatcgatg cagtttatga aaatagcgac | 1200 |
| gggaattttg tgttctttaa aggtaacaaa tattgggtgt tcaaggatac aactcttcaa | 1260 |
| cctggttacc ctcatgactt gataaccctt ggaagtggaa ttcccccctca tggtattgat | 1320 |
| tcagccattt ggtgggagga cgtcgggaaa acctatttct tcaagggaga cagatattgg | 1380 |
| agatatagtg aagaaatgaa aacaatggac cctggctatc caagccaat cacagtctgg | 1440 |
| aaagggatcc ctgaatctcc tcagggagca tttgtacaca agaaaaatgg ctttacgtat | 1500 |
| ttctacaaag gaaggagta ttggaaattc aacaaccaga tactcaaggt agaacctgga | 1560 |
| tatccaagat ccatcctcaa ggattttatg ggctgtgatg gaccaacaga cagagttaaa | 1620 |
| gaaggacaca gcccaccaga tgatgtagac attgtcatca aactggacaa cacagccagc | 1680 |
| actgtgaaag ccatagctat tgtcattccc tgcatcttgg ccttatgcct ccttgtattg | 1740 |
| gtttacactg tgttccagtt caagaggaaa ggaacacccc gccacatact gtactgtaaa | 1800 |
| cgctctatgc aagagtgggt gtga | 1824 |

<210> SEQ ID NO 75
<211> LENGTH: 1818
<212> TYPE: DNA
<213> ORGANISM: Homo sapiens
<300> PUBLICATION INFORMATION:
<302> TITLE: MT4MMP
<310> PATENT DOCUMENT NUMBER: AB021225

<400> SEQUENCE: 75

| | |
|---|---|
| atgcggcgcc gcgcagcccg gggacccggc ccgccgcccc cagggcccgg actctcgcgg | 60 |
| ctgccgctgc tgccgctgcc gctgctgctg ctgctggcgc tggggacccg cggggctgc | 120 |
| gccgcgccgg aacccgcgcg gcgcgccgag gacctcagcc tgggagtgga gtggctaagc | 180 |
| aggttcggtt acctgccccc ggctgacccc acaacagggc agctgcagac gcaagaggag | 240 |
| ctgtctaagg ccatcacagc catgcagcag tttggtggcc tggaggccac cggcatcctg | 300 |
| gacgaggcca ccctggccct gatgaaaacc ccacgctgct ccctgccaga cctccctgtc | 360 |
| ctgacccagg ctcgcaggag acgccaggct ccagcccca ccaagtggaa caagaggaac | 420 |
| ctgtcgtgga gggtccggac gttcccacgg gactcaccac tggggcacga cacggtgcgt | 480 |
| gcactcatgt actacgccct caaggtctgg agcgacattg cgccctgaa cttccacgag | 540 |
| gtggcgggca gcaccgccga catccagatc gacttctcca aggccgacca taacgacggc | 600 |
| taccccttcg acgccggcg gcaccgtgcc cacgccttct tccccggcca ccaccacacc | 660 |
| gccgggtaca cccactttaa cgatgacgag gcctggacct tccgctcctc ggatgcccac | 720 |
| gggatggacc tgtttgcagt ggctgtccac gagtttggcc acgccattgg gttaagccat | 780 |
| gtggccgctg cacactccat catgcggccg tactaccagg gccggtggg tgacccgctg | 840 |
| cgctacggc tcccctacga ggacaaggtg cgcgtctggc agctgtacgg tgtgcgggag | 900 |
| tctgtgtctc ccacgcgca gcccgaggag cctcccctgc tgccggagcc cccagacaac | 960 |
| cggtccagcg ccccgcccag gaaggacgtg ccccacagat gcagcactca ctttgacgcg | 1020 |
| gtggcccaga tccggggtga agctttcttc ttcaaaggca agtacttctg gcggctgacg | 1080 |
| cgggaccggc acctggtgtc cctgcagccg gcacagatgc accgcttctg gcggggcctg | 1140 |
| ccgctgcacc tggacagcgt ggacgccgtg tacgagcgca ccagcgacca caagatcgtc | 1200 |
| ttctttaaag agacaggta ctgggtgttc aaggacaata acgtagagga aggatacccg | 1260 |
| cgccccgtct ccgacttcag cctcccgcct ggcggcatcg acgctgcctt ctcctgggcc | 1320 |

| | |
|---|---|
| cacaatgaca ggacttattt ctttaaggac cagctgtact ggcgctacga tgaccacacg | 1380 |
| aggcacatgg accccggcta ccccgcccag agcccctgt ggaggggtgt ccccagcacg | 1440 |
| ctggacgacg ccatgcgctg gtccgacggt gcctcctact tcttccgtgg ccaggagtac | 1500 |
| tggaaagtgc tggatggcga gctggaggtg cacccgggt acccacagtc cacggcccgg | 1560 |
| gactggctgg tgtgtggaga ctcacaggcc gatggatctg tggctgcggg cgtggacgcg | 1620 |
| gcagaggggc cccgcgcccc tccaggacaa catgaccaga gccgctcgga ggacggttac | 1680 |
| gaggtctgct catgcacctc tggggcatcc tctcccccgg ggccccagg cccactggtg | 1740 |
| gctgccacca tgctgctgct gctgccgcca ctgtcaccag gcgccctgtg gacagcggcc | 1800 |
| caggccctga cgctatga | 1818 |

<210> SEQ ID NO 76
<211> LENGTH: 1938
<212> TYPE: DNA
<213> ORGANISM: Homo sapiens
<300> PUBLICATION INFORMATION:
<302> TITLE: MT5MMP
<310> PATENT DOCUMENT NUMBER: AB021227

<400> SEQUENCE: 76

| | |
|---|---|
| atgccgagga gccggggcgg ccgcgccgcg ccggggccgc cgccgccgcc gccgccgccg | 60 |
| ggccaggccc cgcgctggag ccgctggcgg gtccctgggc ggctgctgct gctgctgctg | 120 |
| cccgcgctct gctgcctccc gggcgccgcg cgggcggcg cggcggcggc ggggcaggg | 180 |
| aaccgggcag cggtggcggt ggcggtggcg cgggcggacg aggcggaggc gcccttcgcc | 240 |
| gggcagaact ggttaaagtc ctatggctat ctgcttccct atgactcacg ggcatctgcg | 300 |
| ctgcactcag cgaaggcctt gcagtcggca gtctccacta tgcagcagtt ttacgggatc | 360 |
| ccggtcaccg gtgtgttgga tcagacaacg atcgagtgga tgaagaaacc ccgatgtggt | 420 |
| gtccctgatc accccacttt aagccgtagg cggagaaaca agcgctatgc cctgactgga | 480 |
| cagaagtgga ggcaaaaaca catcacctac agcattcaca actatacccc aaaagtgggt | 540 |
| gagctagaca cgcggaaagc tattcgccag gctttcgatg tgtggcagaa ggtgaccca | 600 |
| ctgacctttg aagaggtgcc ataccatgag atcaaaagtg accggaagga ggcagacatc | 660 |
| atgatctttt ttgcttctgg tttccatggc gacagctccc catttgatgg agaaggggga | 720 |
| ttcctggccc atgcctactt ccctggccca gggattggag agacaccca ctttgactcc | 780 |
| gatgagccat ggacgctagg aaacgccaac catgacggga cgacctcttc cctggtggct | 840 |
| gtgcatgagc tgggccacgc gctgggactg agcactcca cgaccccag cgccatcatg | 900 |
| gcgcccttct accagtacat ggagacgcac aacttcaagc tgccccagga cgatctccag | 960 |
| ggcatccaga gatctatgg accccagcc gagcctctgg agcccacaag gccactcct | 1020 |
| acactccccg tccgcaggat ccactcacca tcggagagga acacgagcg ccagcccagg | 1080 |
| cccctcggc cgccctcgg ggaccggcca tccacaccag caccaaacc caacatctgt | 1140 |
| gacggcaact tcaacacagt ggccctcttc cggggcgaga tgtttgtctt taaggatcgc | 1200 |
| tggttctggc gtctgcgcaa taaccgagtg caggagggct acccccatgca gatcgagcag | 1260 |
| ttctggaagg gcctgcctgc ccgcatcgac gcagcctatg aaaggggcga tgggagattt | 1320 |
| gtcttcttca aggtgacaa gtattgggtg tttaaggagg tgacggtgga gcctgggtac | 1380 |
| ccccacagcc tggggagct gggcagctgt tgccccgtg aaggcattga cacagctctg | 1440 |
| cgctgggaac ctgtgggcaa gacctacttt ttcaaaggcg agcggtactg gcgctacagc | 1500 |

```
gaggagcggc gggccacgga ccctggctac cctaagccca tcaccgtgtg aagggcatc   1560 ccacaggctc cccaaggagc cttcatcagc aaggaaggat attacaccta tttctacaag  1620
ggccgggact actggaagtt tgacaaccag aaactgagcg tggagccagg ctaccgcgc   1680 aacatcctgc gtgactggat gggctgcaac cagaaggagg tggagcggcg aaggagcgg   1740 cggctgcccc aggacgacgt ggacatcatg gtgaccatca cgatgtgcc gggctccgtg   1800 aacgccgtgg ccgtggtcat cccctgcatc ctgtccctct gcatcctggt gctggtctac  1860
accatcttcc agttcaagaa caagacaggc cctcagcctg tcacctacta taagcggcca  1920
gtccaggaat gggtgtga                                                1938
```

<210> SEQ ID NO 77
<211> LENGTH: 1689
<212> TYPE: DNA
<213> ORGANISM: Homo sapiens
<300> PUBLICATION INFORMATION:
<302> TITLE: MT6MMP
<310> PATENT DOCUMENT NUMBER: AJ27137

<400> SEQUENCE: 77

```
atgcggctgc ggctccggct tctggcgctg ctgcttctgc tgctggcacc gcccgcgcgc   60
gccccgaagc cctcggcgca ggacgtgagc ctgggcgtgg actggctgac tcgctatggt  120
tacctgccgc caccccaccc tgcccaggcc cagctgcaga gcctgagaa gttgcgcgat  180 gccatcaaag tcatgcagag gttcgcgggg ctgccggaga ccggccgcat ggacccaggg  240
acagtggcca ccatgcgtaa gccccgctgc tccctgcctg acgtgctggg ggtggcgggg  300
ctggtcaggc ggcgtcgccg gtacgctctg agcggcagcg tgtggaagaa gcgaaccctg  360
acatggaggg tacgttcctt cccccagagc tcccagctga ccaggagac cgtgcgggtc  420 ctcatgagct atgccctgat ggcctggggc atggagtcag gcctcacatt tcatgaggtg  480 gattccccc agggccagga gcccgacatc ctcatcgact tgccccgcgc cttccaccag  540
gacagctacc ccttcgacgg gttgggggc acccctagccc atgccttctt ccctggggag  600 cacccccatct ccggggacac tcactttgac gatgaggaga cctggacttt tgggtcaaaa  660
gacggcgagg ggaccgacct gtttgccgtg gctgtccatg agtttggcca cgcccctggg  720
ctgggccact cctcagcccc caactccatt atgaggccct tctaccaggg tccggtgggc  780
gaccctgaca gtaccgcct gtctcaggat gaccgcgatg gcctgcagca actctatggg  840
aaggcgcccc aaaccccata tgacaagccc acaaggaaac ccctggctcc tccgccccag  900
cccccggcct cgcccacaca cagcccatcc ttccccatcc ctgatcgatg tgagggcaat  960
tttgacgcca tcgccaacat ccgagggga actttcttct tcaaaggccc tggttctgg   1020 cgcctccagc cctccggaca gctggtgtcc ccgcgaccg cacggctgca ccgcttctgg  1080 gagggctgc ccgcccaggt gagggtggtg caggccgcct atgctcggca ccgagacggc  1140
cgaatcctcc tctttagcgg gccccagttc tgggtgttcc aggaccggca gctggagggc  1200
ggggcgcggc cgctcacgga gctggggctg ccccgggag aggaggtgga cgccgtgttc  1260
tcgtggccac agaacgggaa gacctacctg gtccgcgcc ggcagtactg gcgctacgac  1320
gaggcggcgc gcgcccgga cccggctac cctcgcgacc tgagcctctg gaaggcgcg   1380 cccccctccc ctgacgatgt caccgtcagc aacgcaggtg acacctactt cttcaagggc  1440
gcccactact ggcgcttccc caagaacagc atcaagaccg agccggacgc ccccagccc   1500 atgggcccca actggctgga ctgccccgcc ccgagctctg gtccccgcgc cccaggcccc  1560
```

| cccaaagcga | ccccgtgtc | cgaaacctgc | gattgtcagt | gcgagctcaa | ccaggccgca | 1620 |
| ggacgttggc | ctgctcccat | cccgctgctc | ctcttgcccc | tgctggtggg | gggtgtagcc | 1680 |
| tcccgctga | | | | | | 1689 |

<210> SEQ ID NO 78
<211> LENGTH: 1749
<212> TYPE: DNA
<213> ORGANISM: Homo sapiens
<300> PUBLICATION INFORMATION:
<302> TITLE: MTMMP
<310> PATENT DOCUMENT NUMBER: X90925

<400> SEQUENCE: 78

| atgtctcccg | ccccaagacc | ctcccgttgt | ctcctgctcc | cctgctcac | gctcggcacc | 60 |
| gcgctcgcct | ccctcggctc | ggcccaaagc | agcagcttca | gccccgaagc | ctggctacag | 120 |
| caatatggct | acctgcctcc | cggggaccta | cgtacccaca | cacagcgctc | accccagtca | 180 |
| ctctcagcgg | ccatcgctgc | catgcagaag | ttttacggct | tgcaagtaac | aggcaaagct | 240 |
| gatgcagaca | ccatgaaggc | catgaggcgc | cccgatgtg | gtgttccaga | caagtttggg | 300 |
| gctgagatca | aggccaatgt | tcgaaggaag | cgctacgcca | tccagggtct | caaatggcaa | 360 |
| cataatgaaa | tcactttctg | catccagaat | tacacccca | aggtgggcga | gtatgccaca | 420 |
| tacgaggcca | ttcgcaaggc | gttccgcgtg | tgggagagtg | ccacaccact | gcgcttccgc | 480 |
| gaggtgccct | atgcctacat | ccgtgagggc | catgagaagc | aggccgacat | catgatcttc | 540 |
| tttgccgagg | gcttccatgg | cgacagcacg | cccttcgatg | gtgagggcgg | cttcctggcc | 600 |
| catgcctact | cccaggcccc | aacattgga | ggagacaccc | actttgactc | tgccgagcct | 660 |
| tggactgtca | ggaatgagga | tctgaatgga | aatgacatct | tcctggtggc | tgtgcacgag | 720 |
| ctgggccatg | ccctgggggct | cgagcattcc | agtgacccct | cggccatcat | ggcacccttt | 780 |
| taccagtgga | tggacacgga | gaattttgtg | ctgcccgatg | atgaccgccg | gggcatccag | 840 |
| caactttatg | ggggtgagtc | agggttcccc | accaagatgc | cccctcaacc | caggactacc | 900 |
| tcccggcctt | ctgttcctga | taaacccaaa | aaccccacct | atgggcccaa | catctgtgac | 960 |
| gggaactttg | acaccgtggc | catgctccga | ggggagatgt | ttgtcttcaa | ggagcgctgg | 1020 |
| ttctggcggg | tgaggaataa | ccaagtgatg | gatggatacc | caatgccat | tggccagttc | 1080 |
| tggcggggcc | tgcctgcgtc | catcaacact | gcctacgaga | ggaaggatgg | caaattcgtc | 1140 |
| ttcttcaaag | gagacaagca | ttgggtgttt | gatgaggcgt | ccctggaacc | tggctacccc | 1200 |
| aagcacatta | ggagctgggg | ccgagggctg | cctaccgaca | agattgatgc | tgctctcttc | 1260 |
| tggatgccca | atggaaagac | ctacttcttc | cgtggaaaca | agtactaccg | tttcaacgaa | 1320 |
| gagctcaggg | cagtggatag | cgagtacccc | aagaacatca | agtctggga | agggatccct | 1380 |
| gagtctccca | gagggtcatt | catgggcagc | gatgaagtct | tcacttactt | ctacaagggg | 1440 |
| aacaaatact | ggaaattcaa | caaccagaag | ctgaaggtag | aaccgggcta | ccccaagcca | 1500 |
| gccctgaggg | actggatggg | ctgcccatcg | ggaggccggc | cggatgaggg | gactgaggag | 1560 |
| gagacggagg | tgatcatcat | tgaggtggac | gaggagggcg | gcggggcggt | gagcgcggct | 1620 |
| gccgtggtgc | tgcccgtgct | gctgctgctc | ctggtgctgg | cggtgggcct | tgcagtcttc | 1680 |
| ttcttcagac | gccatgggac | ccccaggcga | ctgctctact | gccagcgttc | cctgctggac | 1740 |
| aaggtctga | | | | | | 1749 |

<210> SEQ ID NO 79

```
<211> LENGTH: 744
<212> TYPE: DNA
<213> ORGANISM: Homo sapiens
<300> PUBLICATION INFORMATION:
<302> TITLE: FGF1
<310> PATENT DOCUMENT NUMBER: XM003647

<400> SEQUENCE: 79
atggccgcgg ccatcgctag cggcttgatc cgccagaagc ggcaggcgcg ggagcagcac      60
tgggaccggc cgtctgccag caggaggcgg agcagcccca gcaagaaccg cgggctctgc     120
aacggcaacc tggtggatat cttctccaaa gtgcgcatct tcggcctcaa gaagcgcagg     180
ttgcggcgcc aagatcccca gctcaagggt atagtgacca ggttatattg caggcaaggc     240
tactacttgc aaatgcaccc cgatggagct ctcgatggaa ccaaggatga cagcactaat     300
tctacactct tcaacctcat accagtggga ctacgtgttg ttgccatcca gggagtgaaa     360
acagggttgt atatagccat gaatggagaa ggttacctct acccatcaga acttttttacc    420
cctgaatgca gtttaaaga atctgttttt gaaaattatt atgtaatcta ctcatccatg      480
ttgtacagac aacaggaatc tggtagagcc tggtttttgg gattaaataa ggaagggcaa     540
gctatgaaag ggaacagagt aaagaaaacc aaaccagcag ctcatttttct acccaagcca    600
ttggaagttg ccatgtaccg agaaccatct ttgcatgatg ttggggaaac ggtcccgaag     660
cctggggtga cgccaagtaa agcacaagt gcgtctgcaa taatgaatgg aggcaaacca      720
gtcaacaaga gtaagacaac atag                                            744

<210> SEQ ID NO 80
<211> LENGTH: 468
<212> TYPE: DNA
<213> ORGANISM: Homo sapiens
<300> PUBLICATION INFORMATION:
<302> TITLE: FGF2
<310> PATENT DOCUMENT NUMBER: NM002006

<400> SEQUENCE: 80
atggcagccg ggagcatcac cacgctgccc gccttgcccg aggatggcgg cagcggcgcc      60
ttcccgcccg ccacttcaa ggaccccaag cggctgtact gcaaaaacgg ggcttcttc       120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cgttacctgg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata acttggatc caaaacagga     420
cctgggcaga aagctatact tttcttcca atgtctgcta agagctga                   468

<210> SEQ ID NO 81
<211> LENGTH: 756
<212> TYPE: DNA
<213> ORGANISM: Homo sapiens
<300> PUBLICATION INFORMATION:
<302> TITLE: FGF23
<310> PATENT DOCUMENT NUMBER: NM020638

<400> SEQUENCE: 81
atgttggggg cccgcctcag gctctgggtc tgtgccttgt gcagcgtctg cagcatgagc      60
gtcctcagag cctatcccaa tgcctcccca ctgctcggct ccagctgggg tggcctgatc     120
cacctgtaca cagccacagc caggaacagc taccacctgc agatccacaa gaatggccat     180
```

```
gtggatggcg cacccccatca gaccatctac agtgccctga tgatcagatc agaggatgct    240
ggctttgtgg tgattacagg tgtgatgagc agaagatacc tctgcatgga tttcagaggc    300 aacattttg  gatcacacta tttcgacccg gagaactgca ggttccaaca ccagacgctg    360
gaaaacgggt acgacgtcta ccactctcct cagtatcact tcctggtcag tctgggccgg    420
gcgaagagag ccttcctgcc aggcatgaac ccaccccgt  actcccagtt cctgtcccgg    480
aggaacgaga tccccctaat tcacttcaac ccccatac  acggcggca cacccggagc     540 gccgaggacg actcggagcg ggacccctg  aacgtgctga gccccgggc  ccggatgacc    600 ccggccccgg cctcctgttc acaggagctc ccgagcgccg aggacaacag cccgatggcc    660
agtgacccat taggggtggt cagggcggt  cgagtgaaca cgcacgctgg gggaacgggc    720
ccggaaggct gccgccccctt cgccaagttc atctag                             756

<210> SEQ ID NO 82
<211> LENGTH: 720
<212> TYPE: DNA
<213> ORGANISM: Homo sapiens
<300> PUBLICATION INFORMATION:
<302> TITLE: FGF3
<310> PATENT DOCUMENT NUMBER: NM005247

<400> SEQUENCE: 82
atgggcctaa tctggctgct actgctcagc ctgctggagc ccggctggcc cgcagcgggc     60
cctggggcgc ggttgcggcg cgatgcgggc ggccgtggcg gcgtctacga gcaccttggc    120
ggggcgcccc ggcgccgcaa gctctactgc gccacgaagt accacctcca gctgcacccg    180
agcggccgcg tcaacggcag cctggagaac agcgcctaca gtattttgga gataacggca    240
gtggaggtgg gcattgtggc catcagggg  ctcttctccg gcggtaccct ggccatgaac    300 aagagggac  gactctatgc ttcggagcac tacagcgccg agtgcgagtt tgtggagcgg    360
atccacgagc tgggctataa tacgtatgcc tcccggctgt accggacggt gtctagtacg    420
cctggggccc gccggcagcc cagcgccgag agactgtggt acgtgtctgt gaacggcaag    480
ggccggcccc gcaggggctt caagacccgc gcacacagga gtcctcccct gttcctgccc    540
cgcgtgctgg accacaggga ccacgagatg gtgcggcagc tacagagtgg gctgcccaga    600 cccccctggta gggggtccag ccccgacgg  cggcggcaga agcagagccc ggataacctg    660
gagccctctc acgttcaggc ttcgagactg ggctcccagc tggaggccag tgcgcactag    720

<210> SEQ ID NO 83
<211> LENGTH: 807
<212> TYPE: DNA
<213> ORGANISM: Homo sapiens
<300> PUBLICATION INFORMATION:
<302> TITLE: FGF5
<310> PATENT DOCUMENT NUMBER: NM004464

<400> SEQUENCE: 83
atgagcttgt ccttcctcct cctcctcttc ttcagccacc tgatcctcag cgcctgggct     60
cacgggagag agcgtctcgc ccccaaaggg caacccggac ccgctgccac tgataggaac    120
cctataggct ccagcagcag acagagcagc agtagcgcta tgtcttcctc ttctgcctcc    180 tcctccccg  cagcttctct gggcagccaa ggaagtggct tggagcagag cagtttccag    240 tggagccct  cggggcgccg gaccggcagc ctctactgca gagtgggcat cggtttccat    300
ctgcagatct acccgatgg  caaagtcaat ggatcccacg aagccaatat gttaagtgtt    360
ttggaaatat ttgctgtgtc tcagggggat tgtaggaatac gaggagtttt cagcaacaaa    420
```

```
tttttagcga tgtcaaaaaa aggaaaactc catgcaagtg ccaagttcac agatgactgc      480
aagttcaggg agcgttttca agaaaatagc tataatacct atgcctcagc aatacataga      540
actgaaaaaa cagggcggga gtggtatgtt gccctgaata aaagaggaaa agccaaacga      600
gggtgcagcc cccgggttaa accccagcat atctctaccc attttcttcc aagattcaag      660
cagtcggagc agccagaact ttctttcacg gttactgttc ctgaaaagaa aaatccacct      720
agccctatca agtcaaagat tccccttcct gcacctcgga aaaataccaa ctcagtgaaa      780
tacagactca agtttcgctt tggataa                                          807

<210> SEQ ID NO 84
<211> LENGTH: 649
<212> TYPE: DNA
<213> ORGANISM: Homo sapiens
<300> PUBLICATION INFORMATION:
<302> TITLE: FGF8
<310> PATENT DOCUMENT NUMBER: NM006119

<400> SEQUENCE: 84
atgggcagcc cccgctccgc gctgagctgc ctgctgttgc acttgctggt cctctgcctc       60
caagcccagg taactgttca gtcctcacct aattttacac agcatgtgag ggagcagagc      120
ctggtgacgg atcagctcag ccgccgcctc atcggacct accaactcta cagccgcacc      180
agcgggaagc acgtgcaggt cctggccaac aagcgcatca cgccatggc agaggacggc      240 gacccccttcg caaagctcat cgtggagacg gacacctttg aagcagagt tcgagtccga      300 ggagccgaga cgggcctcta catctgcatg aacaagaagg ggaagctgat cgccaagagc      360
aacggcaaag gcaaggactg cgtcttcacg gagattgtgc tggagaacaa ctacacagcg      420
ctgcagaatg ccaagtacga gggctggtac atggccttca cccgcaaggg ccggccccgc      480
aagggctcca agacgcggca gcaccagcgt gaggtccact tcatgaagcg gctgcccgg       540 ggccaccaca ccaccgagca gagcctgcgc ttcgagttcc tcaactaccc gcccttcacg      600
cgcagcctgc gcggcagcca gaggacttgg gcccccggaac ccgatagg                 649

<210> SEQ ID NO 85
<211> LENGTH: 2466
<212> TYPE: DNA
<213> ORGANISM: Homo sapiens
<300> PUBLICATION INFORMATION:
<302> TITLE: FGFR2
<310> PATENT DOCUMENT NUMBER: NM000141

<400> SEQUENCE: 85
atggtcagct ggggtcgttt catctgcctg gtcgtggtca ccatggcaac cttgtccctg       60
gcccggccct ccttcagttt agttgaggat accacattag agccagaaga gccaccaacc      120
aaataccaaa tctctcaacc agaagtgtac gtggctgcgc aggggagtc gctagaggtg      180 cgctgcctgt tgaaagatgc cgccgtgatc agttggacta aggatgggt gcacttgggg      240 cccaacaata ggacagtgct tattggggag tacttgcaga taaagggcgc cacgcctaga      300
gactccggcc tctatgcttg tactgccagt aggactgtag acagtgaaac ttggtacttc      360
atggtgaatg tcacagatgc catctcatcc ggagatgatg aggatgacac cgatggtgcg      420
gaagattttg tcagtgagaa cagtaacaac aagagagcac catactggac caacacagaa      480
aagatggaaa agcggctcca tgctgtgcct gcggccaaca ctgtcaagtt cgctgccca       540 gccgggggga acccaatgcc aaccatgcgg tggctgaaaa acgggaagga gtttaagcag      600
```

| | |
|---|---|
| gagcatcgca ttggaggcta caaggtacga aaccagcact ggagcctcat tatgaaaagt | 660 |
| gtggtcccat ctgacaaggg aaattatacc tgtgtggtgg agaatgaata cgggtccatc | 720 |
| aatcacacgt accacctgga tgttgtggag cgatcgcctc accggcccat cctccaagcc | 780 |
| ggactgccgg caaatgcctc cacagtggtc ggaggagacg tagagtttgt ctgcaaggtt | 840 |
| tacagtgatg cccagcccca catccagtgg atcaagcacg tggaaaagaa cggcagtaaa | 900 |
| tacgggcccg acgggctgcc ctacctcaag gttctcaagg ccgccggtgt taacaccacg | 960 |
| gacaaagaga ttgaggttct ctatattcgg aatgtaactt ttgaggacgc tggggaatat | 1020 |
| acgtgcttgg cgggtaattc tattgggata tcctttcact ctgcatggtt gacagttctg | 1080 |
| ccagcgcctg gaagagaaaa ggagattaca gcttccccag actacctgga gatagccatt | 1140 |
| tactgcatag gggtcttctt aatcgcctgt atggtggtaa cagtcatcct gtgccgaatg | 1200 |
| aagaacacga ccaagaagcc agacttcagc agccagccgg ctgtgcacaa gctgaccaaa | 1260 |
| cgtatccccc tgcggagaca ggtaacagtt tcggctgagt ccagctcctc catgaactcc | 1320 |
| aacaccccgc tggtgaggat aacaacacgc ctctcttcaa cggcagacac ccccatgctg | 1380 |
| gcagggtct ccgagtatga acttccagag gacccaaaat gggagtttcc aagagataag | 1440 |
| ctgacactgg gcaagcccct gggagaaggt tgctttgggc aagtggtcat ggcggaagca | 1500 |
| gtgggaattg acaaagacaa gcccaaggag gcggtcaccg tggccgtgaa gatgttgaaa | 1560 |
| gatgatgcca cagagaaaga cctttctgat ctggtgtcag agatggagat gatgaagatg | 1620 |
| attgggaaac acaagaatat cataaatctt cttggagcct gcacacagga tgggcctctc | 1680 |
| tatgtcatag ttgagtatgc ctctaaaggc aacctccgag aatacctccg agcccggagg | 1740 |
| ccacccggga tggagtactc ctatgacatt aaccgtgttc ctgaggagca gatgaccttc | 1800 |
| aaggacttgg tgtcatgcac ctaccagctg gccagaggca tggagtactt ggcttcccaa | 1860 |
| aaatgtattc atcgagattt agcagccaga aatgttttgg taacagaaaa caatgtgatg | 1920 |
| aaaatagcag actttggact cgccagagat atcaacaata tagactatta caaaaagacc | 1980 |
| accaatgggc ggcttccagt caagtggatg gctccagaag ccctgtttga tagagtatac | 2040 |
| actcatcaga gtgatgtctg gtccttcggg gtgttaatgt gggagatctt cactttaggg | 2100 |
| ggctcgccct acccagggat tcccgtggag gaacttttta agctgctgaa ggaaggacac | 2160 |
| agaatggata gccagccaa ctgcaccaac gaactgtaca tgatgatgag ggactgttgg | 2220 |
| catgcagtgc cctcccagag accaacgttc aagcagttgg tagaagactt ggatcgaatt | 2280 |
| ctcactctca caaccaatga ggaatacttg gacctcagcc aacctctcga acagtattca | 2340 |
| cctagttacc ctgacacaag aagttcttgt tcttcaggag atgattctgt tttttctcca | 2400 |
| gaccccatgc cttacgaacc atgccttcct cagtatccac acataaacgg cagtgttaaa | 2460 |
| acatga | 2466 |

<210> SEQ ID NO 86
<211> LENGTH: 2421
<212> TYPE: DNA
<213> ORGANISM: Homo sapiens
<300> PUBLICATION INFORMATION:
<302> TITLE: FGFR3
<310> PATENT DOCUMENT NUMBER: NM000142

<400> SEQUENCE: 86

| | |
|---|---|
| atgggcgccc ctgcctgcgc cctcgcgctc tgcgtggccg tggccatcgt ggccggcgcc | 60 |
| tcctcggagt ccttggggac ggagcagcgc gtcgtggggc gagcggcaga agtcccgggc | 120 |

```
ccagagcccg gccagcagga gcagttggtc ttcggcagcg gggatgctgt ggagctgagc    180
tgtcccccgc ccgggggtgg tcccatgggg cccactgtct gggtcaagga tggcacaggg    240
ctggtgccct cggagcgtgt cctggtgggg ccccagcggc tgcaggtgct gaatgcctcc    300
cacgaggact ccggggccta cagctgccgg cagcggctca cgcagcgcgt actgtgccac    360
ttcagtgtgc gggtgacaga cgctccatcc tcgggagatg acgaagacgg ggaggacgag    420
gctgaggaca caggtgtgga cacaggggcc ccttactgga cacggcccga gcggatggac    480
aagaagctgc tggccgtgcc ggccgccaac accgtccgct tccgctgccc agccgctggc    540
aaccccactc cctccatctc ctggctgaag aacggcaggg agttccgcgg cgagcaccgc    600
attggaggca tcaagctgcg gcatcagcag tggagcctgg tcatggaaag cgtggtgccc    660
tcggaccgcg gcaactacac ctgcgtcgtg gagaacaagt ttggcagcat ccggcagacg    720
tacacgctgg acgtgctgga gcgctccccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga cggcagcaa ggtggggcccg    900 gacggcacac cctacgttac cgtgctcaag acggcgggcg ctaacaccac cgacaaggag    960
ctagaggttc tctccttgca caacgtcacc tttgaggacg ccggggagta cacctgcctg   1020
gcgggcaatt ctattgggtt ttctcatcac tctgcgtggc tggtggtgct gccagccgag   1080
gaggagctgt ggaggctga cgaggcgggc agtgtgtatg caggcatcct cagctacggg   1140
gtgggcttct tcctgttcat cctggtggtg gcggctgtga cgctctgccg cctgcgcagc   1200 cccccccaaga aaggcctggg ctcccccacc gtgcacaaga tctcccgctt cccgctcaag   1260
cgacaggtgt ccctggagtc caacgcgtcc atgagctcca acacaccact ggtgcgcatc   1320
gcaaggctgt cctcagggga gggccccacg ctggccaatg tctccgagct cgagctgcct   1380
gccgacccca atgggagct gtctcgggcc cggctgaccc tgggcaagcc ccttggggag   1440
ggctgcttcg gccaggtggt catggcgag gccatcggca ttgacaagga ccgggccgcc   1500
aagcctgtca ccgtagccgt gaagatgctg aaagacgatg ccactgacaa ggacctgtcg   1560
gacctggtgt ctgagatgga gatgatgaag atgatcggga acacaaaaaa catcatcaac   1620
ctgctgggcg cctgcacgca gggcgggccc ctgtacgtgc tggtggagta cgcggccaag   1680
ggtaacctgc gggagtttct gcgggcgcgg cggccccggg gcctggacta ctccttcgac   1740
acctgcaagc cgcccgagga gcagctcacc ttcaaggacc tggtgtcctg tgcctaccag   1800
gtggcccggg gcatggagta cttggcctcc cagaagtgca tccacaggga cctggctgcc   1860
cgcaatgtgc tggtgaccga ggacaacgtg atgaagatcg cagacttcgg gctggcccgg   1920
gacgtgcaca acctcgacta ctacaagaag acaaccaacg gccggctgcc cgtgaagtgg   1980
atggcgcctg aggccttgtt tgaccgagtc tacactcacc agagtgacgt ctggtccttt   2040
ggggtcctgc tctgggagat cttcacgctg ggggctccc cgtacccggg catccctgtg   2100
gaggagctct tcaagctgct gaaggagggc caccgcatgg acaagcccgc caactgcaca   2160
cacgacctgt acatgatcat gcgggagtgc tggcatgccg cgccctccca gaggcccacc   2220
ttcaagcagc tggtggagga cctggaccgt gtccttaccg tgacgtccac cgacgagtac   2280
ctggacctgt cggcgccttt cgagcagtac tccccgggtg ccaggacac ccccagctcc   2340 agctcctcag gggacgactc cgtgtttgcc cacgacctgc tgccccggc cccacccagc   2400 agtgggggct cgcggacgtg a                                             2421
```

<210> SEQ ID NO 87
<211> LENGTH: 2102
<212> TYPE: DNA
<213> ORGANISM: Homo sapiens
<300> PUBLICATION INFORMATION:
<302> TITLE: HGF
<310> PATENT DOCUMENT NUMBER: E08541

<400> SEQUENCE: 87

```
atgcagaggg acaaaggaaa agaagaaata caattcatga attcaaaaaa tcagcaaaga      60
ctaccctaat caaaatagat ccagcactga agataaaaac caaaaaagtg aatactgcag     120
accaatgtgc taatagatgt actaggaata aaggacttcc attcacttgc aaggcttttg     180
tttttgataa agcaagaaaa caatgcctct ggttccccct caatagcatg tcaagtggag     240
tgaaaaaga atttggccat gaatttgacc tctatgaaaa caagactac attagaaact      300
gcatcattgg taaaggacgc agctacaagg gaacagtatc tatcactaag agtggcatca     360
aatgtcagcc ctggagttcc atgataccac acgaacacag cttttttgcct tcgagctatc    420
ggggtaaaga cctacaggaa aactactgtc gaaatcctcg aggggaagaa ggggacccct     480
ggtgtttcac aagcaatcca gaggtacgct acgaagtctg tgacattcct cagtgttcag     540
aagttgaatg catgaccctgc aatggggaga gttatcgagg tctcatggat atacagaat     600
caggcaagat ttgtcagcgc tgggatcatc agacaccaca ccggcacaaa ttcttgcctg     660
aaagatatcc cgacaagggc tttgatgata attattgccg caatcccgat ggccagccga     720
ggccatggtg ctatactctt gaccctcaca cccgctggga gtactgtgca attaaaacat     780
gcgctgacaa tactatgaat gacactgatg ttccttttgga acaactgaa tgcatccaag     840
gtcaaggaga aggctacagg ggcactgtca ataccatttg aatggaatt ccatgtcagc     900
gttgggattc tcagtatcct cacgagcatg acatgactcc tgaaaatttc aagtgcaagg     960
acctacgaga aaattactgc cgaaatccag atgggtctga atcaccctgg tgttttacca    1020
ctgatccaaa catccgagtt ggctactgct cccaaattcc aaactgtgat atgtcacatg    1080
gacaagattg ttatcgtggg aatggcaaaa attatatggg caacttatcc caaacaagat    1140
ctggactaac atgttcaatg tgggacaaga acatggaaga cttacatcgt catatcttct    1200
gggaaccaga tgcaagtaag ctgaatgaga attactgccg aaatccagat gatgatgctc    1260
atggaccctg tgctacacgg ggaaatccac tcattccttg ggattattgc cctatttctc    1320
gttgtgaagg tgataccaca cctacaatag tcaatttaga ccatcccgta atatcttgtg    1380
ccaaaaggaa acaattgcga gttgtaaatg ggattccaac acgaacaaac ataggatgga    1440
tggttagttt gagatacaga aataaacata tctgcggagg atcattgata aaggagagtt    1500
gggttcttac tgcacgacag tgtttcccctt ctcgagactt gaaagattat gaagcttggc    1560
ttggaattca tgatgtccac ggaagaggag atgagaaatg caaacaggtt ctcaatgttt    1620
cccagctggt atatgcccct gaaggatcag atctggtttt aatgaagctt gccaggcctg    1680
ctgtcctgga tgattttgtt agtacgattg atttacctaa ttatgatgc acaattcctg    1740
aaaagaccag ttgcagtgtt tatggctggg gctacactgg attgatcaac tatgatggcc    1800
tattacgagt ggcacatctc tatataatgg gaaatgagaa atgcagccag catcatcgag    1860
ggaaggtgac tctgaatgag tctgaaatat gtgctggggc tgaaagatt ggatcaggac     1920
catgtgaggg ggattatggt ggcccacttg tttgtgagca ataaaaatg agaatggttc     1980
ttggtgtcat tgttcctggt cgtggatgtg ccattccaaa tcgtcctggt attttttgtcc   2040
gagtagcata ttatgcaaaa tggatacaca aaattatttt aacatataag gtaccacagt    2100
```

| ca | 2102 |

<210> SEQ ID NO 88
<211> LENGTH: 360
<212> TYPE: DNA
<213> ORGANISM: Homo sapiens
<300> PUBLICATION INFORMATION:
<302> TITLE: ID3
<310> PATENT DOCUMENT NUMBER: XM001539

<400> SEQUENCE: 88

| atgaaggcgc tgagcccggt gcgcggctgc tacgaggcgg tgtgctgcct gtcggaacgc | 60 |
| agtctggcca tcgcccgggg ccgagggaag ggcccggcag ctgaggagcc gctgagcttg | 120 |
| ctggacgaca tgaaccactg ctactcccgc ctgcgggaac tggtaccegg agtcccgaga | 180 |
| ggcactcagc ttagccaggt ggaaatccta cagcgcgtca tcgactacat tctcgacctg | 240 |
| caggtagtcc tggccgagcc agcccctgga ccccctgatg gccccaccct tcccatccag | 300 |
| acagccgagc tcactccgga acttgtcatc tccaacgaca aaaggagctt tgccactga | 360 |

<210> SEQ ID NO 89
<211> LENGTH: 743
<212> TYPE: DNA
<213> ORGANISM: Homo sapiens
<300> PUBLICATION INFORMATION:
<302> TITLE: IGF2
<310> PATENT DOCUMENT NUMBER: NM000612

<400> SEQUENCE: 89

| atgggaatcc caatggggaa gtcgatgctg gtgcttctca ccttcttggc cttcgcctcg | 60 |
| tgctgcattg ctgcttaccg ccccagtgag accctgtgcg gcggggagct ggtggacacc | 120 |
| ctccagttcg tctgtgggga ccgcggcttc tacttcagca ggcccgcaag ccgtgtgagc | 180 |
| cgtcgcagcc gtggcatcgt tgaggagtgc tgtttccgca gctgtgacct ggccctcctg | 240 |
| gagacgtact gtgctacccc cgccaagtcc gagagggacg tgtcgacccc tccgaccgtg | 300 |
| cttccggaca acttccccag ataccccgtg ggcaagttct ccaatatga cacctggaag | 360 |
| cagtccaccc agcgcctgcg caggggcctg cctgccctcc tgcgtgcccg ccggggtcac | 420 |
| gtgctcgcca aggagctcga ggcgttcagg gaggccaaac gtcaccgtcc cctgattgct | 480 |
| ctacccaccc aagaccccgc ccacgggggc gccccccag agatggccag caatcggaag | 540 |
| tgagcaaaac tgccgcaagt ctgcagcccg cgccaccat cctgcagcct cctcctgacc | 600 |
| acggacgttt ccatcaggtt ccatcccgaa aatctctcgg ttccacgtcc ccctgggggct | 660 |
| tctcctgacc cagtccccgt gccccgcctc cccgaaacag gctactctcc tcggcccccct | 720 |
| ccatcgggct gaggaagcac agc | 743 |

<210> SEQ ID NO 90
<211> LENGTH: 7476
<212> TYPE: DNA
<213> ORGANISM: Homo sapiens
<300> PUBLICATION INFORMATION:
<302> TITLE: IGF2R
<310> PATENT DOCUMENT NUMBER: NM000876

<400> SEQUENCE: 90

| atgggggccg ccgccggccg gagccccac ctggggcccg cgccgcccg ccgcccgcag | 60 |
| cgctctctgc tcctgctgca gctgctgctg ctcgtcgctg ccccggggtc cacgcaggcc | 120 |
| caggccgccc cgttccccga gctgtgcagt tatacatggg aagctgttga taccaaaaat | 180 |

-continued

```
aatgtacttt ataaaatcaa catctgtgga agtgtggata ttgtccagtg cgggccatca    240
agtgctgttt gtatgcacga cttgaagaca cgcacttatc attcagtggg tgactctgtt    300
ttgagaagtg caaccagatc tctcctggaa ttcaacacaa cagtgagctg tgaccagcaa    360
ggcacaaatc acagagtcca gagcagcatt gccttcctgt gtgggaaaac cctgggaact    420
cctgaatttg taactgcaac agaatgtgtg cactactttg agtggaggac cactgcagcc    480
tgcaagaaag acatatttaa agcaaataag gaggtgccat gctatgtgtt tgatgaagag    540
ttgaggaagc atgatctcaa tcctctgatc aagcttagtg gtgcctactt ggtggatgac    600
tccgatccgg acacttctct attcatcaat gtttgtagag acatagacac actacgagac    660
ccaggttcac agctgcgggc ctgtcccccc ggcactgccg cctgcctggt aagaggacac    720
caggcgtttg atgttggcca gcccgggac ggactgaagc tggtgcgcaa ggacaggctt    780
gtcctgagtt acgtgaggga agaggcagga aagctagact tttgtgatgg tcacagccct    840
gcggtgacta ttacatttgt ttgcccgtcg gagcggagag agggcaccat tcccaaactc    900
acagctaaat ccaactgccg ctatgaaatt gagtggatta ctgagtatgc ctgccacaga    960
gattacctgg aaagtaaaac ttgttctctg agcggcgagc agcaggatgt ctccatagac   1020
ctcacaccac ttgcccagag cggaggttca tcctatattt cagatggaaa agaatatttg   1080
ttttatttga atgtctgtgg agaaactgaa atacagttct gtaataaaaa acaagctgca   1140
gtttgccaag tgaaaaagag cgatacctct caagtcaaag cagcaggaag ataccacaat   1200
cagaccctcc gatattcgga tggagacctc accttgatat attttggagg tgatgaatgc   1260
agctcagggt ttcagcggat gagcgtcata aactttgagt gcaataaaac cgcaggtaac   1320
gatgggaaag gaactcctgt attcacaggg gaggttgact gcacctactt cttcacatgg   1380
gacacggaat acgcctgtgt taaggagaag gaagacctcc tctgcggtgc caccgacggg   1440
aagaagcgct atgacctgtc cgcgctggtc cgccatgcag aaccagagca gaattgggaa   1500
gctgtggatg gcagtcagac ggaaacagag aagaagcatt ttttcattaa tatttgtcac   1560
agagtgctgc aggaaggcaa ggcacgaggg tgtcccgagg acgcggcagt gtgtgcagtg   1620
gataaaaatg gaagtaaaaa tctgggaaaa tttatttcct ctcccatgaa agagaaagga   1680
aacattcaac tctcttattc agatggtgat gattgtggtc atggcaagaa aattaaaact   1740
aatatcacac ttgtatgcaa gccaggtgat ctggaaagtg caccagtgtt gagaacttct   1800
ggggaaggcg gttgctttta tgagtttgag tggcgcacag ctgcggcctg tgtgctgtct   1860
aagacagaag gggagaactg cacggtcttt gactcccagg cagggttttc ttttgactta   1920
tcacctctca caaagaaaaa tggtgcctat aaagttgaga caaagaagta tgacttttat   1980
ataaatgtgt gtggcccggt gtctgtgagc ccctgtcagc cagactcagg agcctgccag   2040
gtggcaaaaa gtgatgagaa acttggaac ttgggtctga gtaatgcgaa gctttcatat   2100
tatgatggga tgatccaact gaactacaga ggcggcacac cctataacaa tgaaagacac   2160
acaccgagag ctacgctcat caccctttctc tgtgatcgag acgcgggagt gggcttccct   2220
gaatatcagg aagaggataa ctccacctac aacttccggt ggtacaccag ctatgcctgc   2280
ccggaggagc ccctggaatg cgtagtgacc gaccctccca cgctggagca gtacgacctc   2340
tccagtctgg caaaatctga aggtggcctt ggaggaaact ggtatgccat ggacaactca   2400
ggggaacatg tcacgtggag gaaatactac attaacgtgt gtcggcctct gaatccagtg   2460
ccgggctgca accgatatgc atcggcttgc cagatgaagt atgaaaaaga tcagggctcc   2520
```

```
ttcactgaag tggtttccat cagtaacttg ggaatggcaa agaccggccc ggtggttgag    2580
gacagcggca gcctccttct ggaatacgtg aatgggtcgg cctgcaccac cagcgatggc    2640
agacagacca catataccac gaggatccat ctcgtctgct ccaggggcag gctgaacagc    2700 cacccccatct tttctctcaa ctgggagtgt gtggtcagtt tcctgtggaa cacagaggct    2760
gcctgtccca ttcagacaac gacggataca gaccaggctt gctctataag ggatcccaac    2820
agtggatttg tgtttaatct taatccgcta aacagttcgc aaggatataa cgtctctggc    2880
attgggaaga tttttatgtt taatgtctgc ggcacaatgc ctgtctgtgg gaccatcctg    2940
ggaaaacctg cttctggctg tgaggcagaa acccaaactg aagagctcaa gaattggaag    3000
ccagcaaggc cagtcggaat tgagaaaagc ctccagctgt ccacagaggg cttcatcact    3060
ctgacctaca aagggcctct ctctgccaaa ggtaccgctg atgctttat cgtccgcttt    3120 gtttgcaatg atgatgttta ctcagggccc ctcaaattcc tgcatcaaga tatcgactct    3180
gggcaaggga tccgaaacac ttactttgag tttgaaaccg cgttggcctg tgttccttct    3240
ccagtggact gccaagtcac cgacctggct ggaaatgagt acgacctgac tggcctaagc    3300
acagtcagga aaccttggac ggctgttgac acctctgtcg atgggagaaa gaggactttc    3360
tatttgagcg tttgcaatcc tctcccttac attcctggat gccagggcag cgcagtgggg    3420
tcttgcttag tgtcagaagg caatagctgg aatctgggtg tggtgcagat gagtccccaa    3480
gccgcggcga atggatcttt gagcatcatg tatgtcaacg tgacaagtg tgggaaccag    3540 cgcttctcca ccaggatcac gtttgagtgt gctcagatat cgggctcacc agcatttcag    3600
cttcaggatg gttgtgagta cgtgtttatc tggagaactg tggaagcctg tcccgttgtc    3660
agagtggaag gggacaactg tgaggtgaaa gacccaaggc atggcaactt gtatgacctg    3720
aagcccctgg gcctcaacga caccatcgtg agcgctggcg aatacactta ttacttccgg    3780
gtctgtggga agctttcctc agacgtctgc cccacaagtg acaagtccaa ggtggtctcc    3840
tcatgtcagg aaaagcggga accgcaggga tttcacaaag tggcaggtct cctgactcag    3900
aagctaactt atgaaaatgg cttgttaaaa atgaacttca cgggggggga cacttgccat    3960
aaggtttatc agcgctccac agccatcttc ttctactgtg accgcggcac ccagcggcca    4020
gtatttctaa aggagacttc agattgttcc tacttgtttg agtggcgaac gcagtatgcc    4080
tgcccacctt tcgatctgac tgaatgttca ttcaaagatg gggctggcaa ctccttcgac    4140
ctctcgtccc tgtcaaggta cagtgacaac tgggaagcca tcactgggac ggggaccccg    4200
gagcactacc tcatcaatgt ctgcaagtct ctggccccgc aggctggcac tgagccgtgc    4260
cctccagaag cagccgcgtg tctgctgggt ggctccaagc ccgtgaacct cggcagggta    4320
agggacggac ctcagtggag agatggcata attgtcctga atacgttga tggcgactta    4380 tgtccagatg ggattcggaa aaagtcaacc accatccgat tcacctgcag cgagagccaa    4440
gtgaactcca ggcccatgtt catcagcgcc gtggaggact gtgagtacac ctttgcctgg    4500
cccacagcca cagcctgtcc catgaagagc aacgagcatg atgactgcca ggtcaccaac    4560
ccaagcacag gacacctgtt tgatctgagc tccttaagtg cagggcggg attcacagct    4620 gcttacagcg agaaggggtt ggtttacatg agcatctgtg gggagaatga aaactgccct    4680
cctggcgtgg gggcctgctt tggacagacc aggattagcg tgggcaaggc caacaagagg    4740
ctgagatacg tggaccaggt cctgcagctg gtgtacaagg atgggtcccc ttgtccctcc    4800
aaatccggcc tgagctataa gagtgtgatc agtttcgtgt gcaggcctga ggccgggcca    4860
accaataggc ccatgctcat ctccctggac aagcagacat gcactctctt cttctcctgg    4920
```

```
cacacgccgc tggcctgcga gcaagcgacc gaatgttccg tgaggaatgg aagctctatt    4980
gttgacttgt ctccccttat tcatcgcact ggtggttatg aggcttatga tgagagtgag    5040
gatgatgcct ccgataccaa ccctgatttc tacatcaata tttgtcagcc actaaatccc    5100
atgcacgcag tgcccgtcc tgccggagcc gctgtgtgca agttcctat tgatggtccc    5160 cccatagata tcggccgggt agcaggacca ccaatactca atccaatagc aaatgagatt    5220
tacttgaatt ttgaaagcag tactccttgc ttagcggaca agcatttcaa ctacacctcg    5280
ctcatcgcgt ttcactgtaa gagaggtgtg agcatgggaa cgcctaagct gttaaggacc    5340
agcgagtgcg actttgtgtt cgaatgggag actcctgtcg tctgtcctga tgaagtgagg    5400
atggatggct gtaccctgac agatgagcag ctcctctaca gcttcaactt gtccagcctt    5460
tccacgagca cctttaaggt gactcgcgac tcgcgcacct acagcgttgg ggtgtgcacc    5520
tttgcagtcg ggccagaaca aggaggctgt aaggacggag gagtctgtct gctctcaggc    5580
accaaggggg catcctttgg acggctgcaa tcaatgaaac tggattacag gcaccaggat    5640
gaagcggtcg ttttaagtta cgtgaatggt gatcgttgcc ctccagaaac cgatgacggc    5700
gtcccctgtg tcttccccctt catattcaat gggaagagct acgaggagtg catcatagag    5760
agcagggcga agctgtggtg tagcacaact gcggactacg acagagacca cgagtggggc    5820
ttctgcagac actcaaacag ctaccggaca tccagcatca tatttaagtg tgatgaagat    5880
gaggacattg ggaggccaca agtcttcagt gaagtgcgtg ggtgtgatgt gacatttgag    5940
tggaaaacaa aagttgtctg ccctccaaag aagttggagt gcaaattcgt ccagaaacac    6000
aaaacctacg acctgcggct gctctcctct ctcaccgggt cctggtccct ggtccacaac    6060
ggagtctcgt actatataaa tctgtgccag aaaatatata aagggcccct gggctgctct    6120
gaaagggcca gcatttgcag aaggaccaca actggtgacg tccaggtcct gggactcgtt    6180
cacacgcaga agctgggtgt cataggtgac aaagttgttg tcacgtactc caaaggttat    6240
ccgtgtggtg gaaataagac cgcatcctcc gtgatagaat tgacctgtac aaagacggtg    6300
ggcagacctg cattcaagag gtttgatatc gacagctgca cttactactt cagctgggac    6360
tcccgggctg cctgcgccgt gaagcctcag gaggtgcaga tggtgaatgg gaccatcacc    6420
aaccctataa atggcaagag cttcagcctc ggagatattt attttaagct gttcagagcc    6480
tctggggaca tgaggaccaa tggggacaac tacctgtatg agatccaact ttcctccatc    6540
acaagctcca gaaacccggc gtgctctgga gccaacatat gccaggtgaa gcccaacgat    6600
cagcacttca gtcggaaagt tggaacctct gacaagacca agtactacct tcaagacggc    6660
gatctcgatg tcgtgtttgc ctcttcctct aagtgcggaa aggataagac caagtctgtt    6720
tcttccacca tcttcttcca ctgtgaccct ctggtggagg acgggatccc cgagttcagt    6780
cacgagactg ccgactgcca gtacctcttc tcttggtaca cctcagccgt gtgtcctctg    6840
ggggtgggct ttgacagcga gaatcccggg acgacgggc agatgcacaa ggggctgtca    6900
gaacggagcc aggcagtcgg cgcggtgctc agcctgctgc tggtggcgct cacctgctgc    6960
ctgctggccc tgttgctcta caagaaggag aggaggggaa cagtgataag taagctgacc    7020
acttgctgta ggagaagttc caacgtgtcc tacaaatact caaaggtgaa taaggaagaa    7080
gagacagatg agaatgaaac agagtggctg atggaagaga tccagctgcc tcctccacgg    7140
cagggaaagg aagggcagga gaacggccat attaccacca gtcagtgaa agccctcagc    7200 tcccctgcatg gggatgacca ggacagtgag gatgaggttc tgaccatccc agaggtgaaa    7260
```

| | |
|---|---|
| gttcactcgg gcagggagc tggggcagag agctcccacc cagtgagaaa cgcacagagc | 7320 |
| aatgcccttc aggagcgtga ggacgatagg gtggggctgg tcaggggtga aaggcgagg | 7380 |
| aaagggaagt ccagctctgc acagcagaag acagtgagct ccaccaagct ggtgtccttc | 7440 |
| catgacgaca gcgacgagga cctcttacac atctga | 7476 |

<210> SEQ ID NO 91
<211> LENGTH: 4104
<212> TYPE: DNA
<213> ORGANISM: Homo sapiens
<300> PUBLICATION INFORMATION:
<302> TITLE: IGF1R
<310> PATENT DOCUMENT NUMBER: NM000875

<400> SEQUENCE: 91

| | |
|---|---|
| atgaagtctg gctccggagg agggtcccg acctcgctgt gggggctcct gtttctctcc | 60 |
| gccgcgctct cgctctggcc gacgagtgga gaaatctgcg ggccaggcat cgacatccgc | 120 |
| aacgactatc agcagctgaa gcgcctggag aactgcacgg tgatcgaggg ctacctccac | 180 |
| atcctgctca tctccaaggc cgaggactac cgcagctacc gcttccccaa gctcacggtc | 240 |
| attaccgagt acttgctgct gttccgagtg gctggcctcg agagcctcgg agacctcttc | 300 |
| cccaacctca cggtcatccg cggctggaaa ctcttctaca ctacgccct ggtcatcttc | 360 |
| gagatgacca atctcaagga tattgggctt tacaacctga ggaacattac tcgggggggcc | 420 |
| atcaggattg agaaaaatgc tgacctctgt taccctctcca ctgtggactg gtccctgatc | 480 |
| ctggatgcgg tgtccaataa ctacattgtg gggaataagc ccccaaagga atgtggggac | 540 |
| ctgtgtccag ggaccatgga ggagaagccg atgtgtgaga agaccaccat caacaatgag | 600 |
| tacaactacc gctgctggac cacaaaccgc tgccagaaaa tgtgcccaag cacgtgtggg | 660 |
| aagcgggcgt gcaccgagaa caatgagtgc tgccaccccg agtgcctggg cagctgcagc | 720 |
| gcgcctgaca acgacacggc ctgtgtagct tgccgccact actactatgc cggtgtctgt | 780 |
| gtgcctgcct gcccgcccaa cacctacagg tttgagggct ggcgctgtgt ggaccgtgac | 840 |
| ttctgcgcca acatcctcag cgccgagagc agcgactccg aggggttttgt gatccacgac | 900 |
| ggcgagtgca tgcaggagtg ccctcggggc ttcatccgca acggcagcca gagcatgtac | 960 |
| tgcatccctt gtgaaggtcc ttgcccgaag gtctgtgagg aagaaaagaa aacaaagacc | 1020 |
| attgattctg ttacttctgc tcagatgctc caaggatgca ccatcttcaa gggcaatttg | 1080 |
| ctcattaaca tccgacgggg gaataacatt gcttcagagc tggagaactt catggggctc | 1140 |
| atcgaggtgg tgacgggcta cgtgaagatc cgccattctc atgccttggt ctccttgtcc | 1200 |
| ttcctaaaaa accttcgcct catcctagga gaggagcagc tagaagggaa ttactccttc | 1260 |
| tacgtcctcg acaaccagaa cttgcagcaa ctgtgggact gggaccaccg caacctgacc | 1320 |
| atcaaagcag ggaaaatgta ctttgctttc aatcccaaat tatgtgtttc cgaaattac | 1380 |
| cgcatggagg aagtgacggg gactaaaggg cgccaaagca aggggacat aaacaccagg | 1440 |
| aacaacgggg agagagcctc ctgtgaaagt gacgtcctgc atttcacctc caccaccacg | 1500 |
| tcgaagaatc gcatcatcat aacctggcac cggtaccggc cccctgacta cagggatctc | 1560 |
| atcagcttca ccgtttacta caaggaagca ccctttaaga atgtcacaga gtatgatggg | 1620 |
| caggatgcct gcggctccaa cagctggaac atggtggacg tggacctccc gcccaacaag | 1680 |
| gacgtggagc ccggcatctt actacatggg ctgaagcct ggactcagta cgccgtttac | 1740 |
| gtcaaggctg tgaccctcac catggtggag aacgaccata tccgtgggc caagagtgag | 1800 |

```
atcttgtaca ttcgcaccaa tgcttcagtt ccttccattc ccttggacgt tctttcagca   1860
tcgaactcct cttctcagtt aatcgtgaag tggaaccctc cctctctgcc caacggcaac   1920
ctgagttact acattgtgcg ctggcagcgg cagcctcagg acggctacct ttaccggcac   1980
aattactgct ccaaagacaa aatccccatc aggaagtatg ccgacggcac catcgacatt   2040
gaggaggtca cagagaaccc caagactgag gtgtgtggtg gggagaaagg gccttgctgc   2100
gcctgcccca aaactgaagc cgagaagcag gccgagaagg aggaggctga ataccgcaaa   2160
gtctttgaga atttcctgca caactccatc ttcgtgccca gacctgaaag gaagcggaga   2220
gatgtcatgc aagtggccaa caccaccatg tccagccgaa gcaggaacac cacggccgca   2280
gacacctaca acatcaccga cccggaagag ctggagacag agtacccttt ctttgagagc   2340
agagtggata caaggagag aactgtcatt tctaaccttc ggcctttcac attgtaccgc   2400
atcgatatcc acagctgcaa ccacgaggct gagaagctgg gctgcagcgc ctccaacttc   2460
gtctttgcaa ggactatgcc cgcagaagga gcagatgaca ttcctgggcc agtgacctgg   2520
gagccaaggc ctgaaaactc catcttttta aagtggccgg aacctgagaa tcccaatgga   2580
ttgattctaa tgtatgaaat aaaatacgga tcacaagttg aggatcagcg agaatgtgtg   2640
tccagacagg aatacaggaa gtatggaggg gccaagctaa accggctaaa cccggggaac   2700
tacacagccc ggattcaggc cacatctctc tctgggaatg ggtcgtggac agatcctgtg   2760
ttcttctatg tccaggccaa aacaggatat gaaaacttca tccatctgat catcgctctg   2820
cccgtcgctg tcctgttgat cgtgggaggg ttggtgatta tgctgtacgt cttccataga   2880
aagagaaata acagcaggct ggggaatgga gtgctgtatg cctctgtgaa cccggagtac   2940
ttcagcgctg ctgatgtgta cgttcctgat gagtgggagg tggctcggga agatcacc    3000 atgagccgga aacttgggca ggggtcgttt gggatggtct atgaaggagt tgccaagggt   3060
gtggtgaaag atgaacctga aaccagagtg gccattaaaa cagtgaacga ggccgcaagc   3120
atgcgtgaga ggattgagtt tctcaacgaa gcttctgtga tgaaggagtt caattgtcac   3180
catgtggtgc gattgctggg tgtggtgtcc caaggccagc caacactggt catcatggaa   3240
ctgatgacac ggggcgatct caaaagttat ctccggtctc tgaggccaga aatggagaat   3300
aatccagtcc tagcacctcc aagcctgagc aagatgattc agatggccgg agagattgca   3360
gacggcatgg catacctcaa cgccaataag ttcgtccaca gagaccttgc tgcccggaat   3420
tgcatggtag ccgaagattt cacagtcaaa atcggagatt ttggtatgac gcgagatatc   3480
tatgagacag actattaccg gaaaggaggc aaagggctgc tgcccgtgcg ctggatgtct   3540
cctgagtccc tcaaggatgg agtcttcacc acttactcgg acgtctggtc cttcggggtc   3600
gtcctctggg agatcgccac actggccgag cagccctacc agggcttgtc caacgagcaa   3660
gtccttcgct tcgtcatgga gggcggcctt ctggacaagc cagacaactg tcctgacatg   3720
ctgtttgaac tgatgcgcat gtgctggcag tataaccccca agatgaggcc ttccttcctg   3780
gagatcatca gcagcatcaa agaggagatg gagcctggct ccgggaggt ctccttctac   3840 tacagcgagg agaacaagct gcccgagccg gaggagctgg acctggagcc agagaacatg   3900
gagagcgtcc ccctggaccc ctcggcctcc tcgtcctccc tgccactgcc cgacagacac   3960
tcaggacaca aggccgagaa cggccccggc cctggggtgc tggtcctccg cgccagcttc   4020
gacgagagac agcccttacgc ccacatgaac gggggccgca agaacgagcg ggccttgccg   4080
ctgccccagt cttcgacctg ctga                                          4104
```

-continued

```
<210> SEQ ID NO 92
<211> LENGTH: 726
<212> TYPE: DNA
<213> ORGANISM: Homo sapiens
<300> PUBLICATION INFORMATION:
<302> TITLE: PDGFB
<310> PATENT DOCUMENT NUMBER: NM002608

<400> SEQUENCE: 92
atgaatcgct gctgggcgct cttcctgtct ctctgctgct acctgcgtct ggtcagcgcc    60 gaggggggacc ccattcccga ggagctttat gagatgctga gtgaccactc gatccgctcc   120
tttgatgatc tccaacgcct gctgcacgga acccccggag aggaagatgg ggccgagttg   180
gacctgaaca tgacccgctc ccactctgga ggcgagctgg agagcttggc tcgtggaaga   240
aggagcctgg gttccctgac cattgctgag ccggccatga tcgccgagtg caagacgcgc   300
accgaggtgt tcgagatctc ccggcgcctc atagaccgca ccaacgccaa cttcctggtg   360
tggccgccct gtgtggaggt gcagcgctgc tccggctgct gcaacaaccg caacgtgcag   420
tgccgcccca cccaggtgca gctgcgacct gtccaggtga aaagatcga gattgtgcgc   480 aagaagccaa tctttaagaa ggccacggtg acgctggaag accacctggc atgcaagtgt   540
gagacagtgg cagctgcacg gcctgtgacc cgaagcccgg ggggttccca ggagcagcga   600
gccaaaacgc cccaaactcg ggtgaccatt cggacggtgc agtccgccg gcccccaag   660 ggcaagcacc ggaaattcaa gcacacgcat gacaagacgg cactgaagga gacccttgga   720
gcctag                                                              726

<210> SEQ ID NO 93
<211> LENGTH: 1512
<212> TYPE: DNA
<213> ORGANISM: Homo sapiens
<300> PUBLICATION INFORMATION:
<302> TITLE: TGFbetaR1
<310> PATENT DOCUMENT NUMBER: NM004612

<400> SEQUENCE: 93
atggaggcgg cggtcgctgc tccgcgtccc cggctgctcc tcctcgtgct ggcggcggcg    60
gcggcggcgg cggcggcgct gctcccgggg gcgacggcgt tacagtgttt ctgccacctc   120
tgtacaaaag acaattttac ttgtgtgaca gatgggctct gctttgtctc tgtcacagag   180
accacagaca aagttataca caacagcatg tgtatagctg aaattgactt aattcctcga   240
gataggccgt ttgtatgtgc accctcttca aaaactgggt ctgtgactac aacatattgc   300
tgcaatcagg accattgcaa taaaatagaa cttccaacta ctgtaaagtc atcacctggc   360
cttggtcctg tggaactggc agctgtcatt gctggaccag tgtgcttcgt ctgcatctca   420
ctcatgttga tggtctatat ctgccacaac cgcactgtca ttcaccatcg agtgccaaat   480
gaagaggacc cttcattaga tcgcccttttt atttcagagg gtactacgtt gaaagactta   540
atttatgata tgcaacgtc aggttctggc tcaggtttac cattgcttgt tcagagaaca   600
attgcgagaa ctattgtgtt acaagaaagc attggcaaag tcgatttgg agaagtttgg   660 agaggaaagt ggcgggggaga agaagttgct gttaagatat ctcctctag agaagaacgt   720 tcgtggttcc gtgaggcaga gatttatcaa actgtaatgt acgtcatga aaacatcctg   780 ggatttatag cagcagacaa taaagacaat ggtacttgga ctcagctctg gttggtgtca   840
gattatcatg agcatggatc ccttttttgat tacttaaaca gatacacagt tactgtggaa   900
ggaatgataa aacttgctct gtccacggcg agcggtcttg cccatcttca catggagatt   960
```

```
gttggtaccc aaggaaagcc agccattgct catagagatt tgaaatcaaa gaatatcttg    1020
gtaaagaaga atggaacttg ctgtattgca gacttaggac tggcagtaag acatgattca    1080
gccacagata ccattgatat tgctccaaac cacagagtgg gaacaaaaag gtacatggcc    1140
cctgaagttc tcgatgattc cataaatatg aaacattttg aatccttcaa acgtgctgac    1200
atctatgcaa tgggcttagt attctgggaa attgctcgac gatgttccat tggtggaatt    1260
catgaagatt accaactgcc ttattatgat cttgtacctt ctgacccatc agttgaagaa    1320
atgagaaaag ttgtttgtga acagaagtta aggccaaata tcccaaacag atggcagagc    1380
tgtgaagcct tgagagtaat ggctaaaatt atgagagaat gttggtatgc caatggagca    1440
gctaggctta cagcattgcg gattaagaaa acattatcgc aactcagtca acaggaaggc    1500
atcaaaatgt aa                                                        1512
```

<210> SEQ ID NO 94
<211> LENGTH: 4044
<212> TYPE: DNA
<213> ORGANISM: Homo sapiens
<300> PUBLICATION INFORMATION:
<302> TITLE: Flk1
<310> PATENT DOCUMENT NUMBER: AF035121

<400> SEQUENCE: 94

```
atgcagagca aggtgctgct ggccgtcgcc ctgtggctct gcgtggagac ccggccgcc      60 tctgtgggtt tgcctagtgt ttctcttgat ctgcccaggc tcagcataca aaagacata    120 cttacaatta aggctaatac aactcttcaa attacttgca ggggacagag ggacttggac    180
tggctttggc ccaataatca gagtggcagt gagcaaaggg tggaggtgac tgagtgcagc    240
gatggcctct tctgtaagac actcacaatt ccaaaagtga tcggaaatga cactggagcc    300
tacaagtgct tctaccggga aactgacttg gcctcggtca tttatgtcta tgttcaagat    360
tacagatctc catttattgc ttctgttagt gaccaacatg gagtcgtgta cattactgag    420
aacaaaaaca aaactgtggt gattccatgt ctcgggtcca tttcaaatct caacgtgtca    480
ctttgtgcaa gatacccaga aaagagattt gttcctgatg gtaacagaat ttcctgggac    540
agcaagaagg gctttactat tcccagctac atgatcagct atgctggcat ggtcttctgt    600
gaagcaaaaa ttaatgatga agttaccag tctattatgt acatagttgt cgttgtaggg    660
tataggattt atgatgtggt tctgagtccg tctcatggaa ttgaactatc tgttggagaa    720
aagcttgtct taaattgtac agcaagaact gaactaaatg tggggattga cttcaactgg    780
gaataccctt cttcgaagca tcagcataag aaacttgtaa accgagacct aaaaacccag    840
tctgggagtg agatgaagaa attttttgagc accttaacta tagatggtgt aacccggagt    900
gaccaaggat tgtacacctg tgcagcatcc agtgggctga tgaccaagaa gaacagcaca    960
tttgtcaggg tccatgaaaa acctttttgtt gcttttggaa gtggcatgga atctctggtg    1020
gaagccacgg tggggagcg tgtcagaatc cctgcgaagt accttggtta cccaccccca    1080
gaaataaaat ggtataaaaa tggaataccc cttgagtcca atcacacaat taaagcgggg    1140
catgtactga cgattatgga agtgagtgaa agagacacag gaaattacac tgtcatcctt    1200
accaatccca tttcaaagga agcagagc catgtggtct ctctggttgt gtatgtccca    1260
ccccagattg gtgagaaatc tctaatctct cctgtggatt cctaccagta cggcaccact    1320
caaacgctga catgtacggt ctatgccatt cctccccgc atcacatcca ctggtattgg    1380
cagttggagg aagagtgcgc caacgagccc agccaagctg tctcagtgac aaacccatac    1440
```

-continued

```
ccttgtgaag aatggagaag tgtggaggac ttccagggag gaaataaaat tgaagttaat    1500
aaaaatcaat ttgctctaat tgaaggaaaa aacaaaactg taagtaccct tgttatccaa    1560
gcggcaaatg tgtcagcttt gtacaaatgt gaagcggtca acaaagtcgg gagaggagag    1620
agggtgatct ccttccacgt gaccaggggt cctgaaatta cttttgcaacc tgacatgcag   1680
cccactgagc aggagagcgt gtctttgtgg tgcactgcag acagatctac gtttgagaac    1740
ctcacatggt acaagcttgg cccacagcct ctgccaatcc atgtgggaga gttgcccaca    1800
cctgtttgca agaacttgga tactctttgg aaattgaatg ccaccatgtt ctctaatagc    1860
acaaatgaca ttttgatcat ggagcttaag aatgcatcct tgcaggacca aggagactat    1920
gtctgccttg ctcaagacag gaagaccaag aaaagacatt gcgtggtcag gcagctcaca    1980
gtcctagagc gtgtggcacc cacgatcaca ggaaacctgg agaatcagac gacaagtatt    2040
ggggaaagca tcgaagtctc atgcacggca tctgggaatc cccctccaca gatcatgtgg   2100
tttaaagata tgagaccct tgtagaagac tcaggcattg tattgaagga tgggaaccgg    2160
aacctcacta tccgcagagt gaggaaggag gacgaaggcc tctacacctg ccaggcatgc   2220
agtgttcttg gctgtgcaaa agtggaggca ttttttcataa tagaaggtgc ccaggaaaag   2280
acgaacttgg aaatcattat tctagtaggc acggcggtga ttgccatgtt cttctggcta    2340
cttcttgtca tcatcctacg gaccgttaag cgggccaatg gaggggaact gaagacaggc    2400
tacttgtcca tcgtcatgga tccagatgaa ctcccattgg atgaacattg tgaacgactg   2460
ccttatgatg ccagcaaatg ggaattcccc agagaccggc tgaagctagg taagcctctt   2520
ggccgtggtg cctttggcca agtgattgaa gcagatgcct ttggaattga caagacagca   2580
acttgcagga cagtagcagt caaaatgttg aaagaaggag caacacacag tgagcatcga   2640
gctctcatgt ctgaactcaa gatcctcatt catattggtc accatctcaa tgtggtcaac   2700
cttctaggtg cctgtaccaa gccaggaggg ccactcatgg tgattgtgga attctgcaaa   2760
tttggaaacc tgtccactta cctgaggagc aagagaaatg aatttgtccc ctacaagacc   2820
aaaggggcac gattccgtca agggaaagac tacgttggag caatccctgt ggatctgaaa   2880
cggcgcttgg acagcatcac cagtagccag agctcagcca gctctggatt tgtggaggag   2940
aagtccctca gtgatgtaga agaagaggaa gctcctgaag atctgtataa ggacttcctg   3000
accttggagc atctcatctg ttacagcttc caagtggcta agggcatgga gttcttggca   3060
tcgcgaaagt gtatccacag ggacctggcg gcacgaaata tcctcttatc ggagaagaac   3120
gtggttaaaa tctgtgactt tggccttgcc cgggatattt ataaagatcc agattatgtc   3180
agaaaaggag atgctcgcct cccctttgaaa tggatggccc cagaaacaat ttttgacaga   3240
gtgtacacaa tccagagtga cgtctggtct tttggtgttt tgctgtggga aatattttcc   3300
ttaggtgctt ctccatatcc tggggtaaag attgatgaag aattttgtag gcgattgaaa   3360
gaaggaacta gaatgagggc ccctgattat actacaccag aaatgtacca gaccatgctg   3420
gactgctggc acgggagcc cagtcagaga cccacgtttt cagagttggt ggaacatttg   3480
ggaaatctct tgcaagctaa tgctcagcag gatggcaaag actacattgt tcttccgata   3540
tcagagactt tgagcatgga agaggattct ggactctctc tgcctacctc acctgttttcc   3600
tgtatggagg aggaggaagt atgtgacccc aaattccatt atgacaacac agcaggaatc   3660
agtcagtatc tgcagaacag taagcgaaag agccggcctg tgagtgtaaa aacatttgaa   3720
gatatcccgt tagaagaacc agaagtaaaa gtaatcccag atgacaacca gacggacagt   3780
ggtatggttc ttgcctcaga agagctgaaa actttggaag acagaaccaa attatctcca   3840
```

| | |
|---|---:|
| tcttttggtg gaatggtgcc cagcaaaagc agggagtctg tggcatctga aggctcaaac | 3900 |
| cagacaagcg gctaccagtc cggatatcac tccgatgaca cagacaccac cgtgtactcc | 3960 |
| agtgaggaag cagaactttt aaagctgata gagattggag tgcaaaccgg tagcacagcc | 4020 |
| cagattctcc agcctgactc gggg | 4044 |

<210> SEQ ID NO 95
<211> LENGTH: 4017
<212> TYPE: DNA
<213> ORGANISM: Homo sapiens
<300> PUBLICATION INFORMATION:
<302> TITLE: Flt1
<310> PATENT DOCUMENT NUMBER: AF063657

<400> SEQUENCE: 95

| | |
|---|---:|
| atggtcagct actgggacac cggggtcctg ctgtgcgcgc tgctcagctg tctgcttctc | 60 |
| acaggatcta gttcaggttc aaaattaaaa gatcctgaac tgagtttaaa aggcacccag | 120 |
| cacatcatgc aagcaggcca gacactgcat ctccaatgca ggggggaagc agcccataaa | 180 |
| tggtctttgc ctgaaatggt gagtaaggaa agcgaaaggc tgagcataac taaatctgcc | 240 |
| tgtggaagaa atggcaaaca attctgcagt actttaacct tgaacacagc tcaagcaaac | 300 |
| cacactggct tctacagctg caaatatcta gctgtaccta cttcaaagaa gaaggaaaca | 360 |
| gaatctgcaa tctatatatt tattagtgat acaggtagac tttcgtaga gatgtacagt | 420 |
| gaaatccccg aaattataca catgactgaa ggaagggagc tcgtcattcc ctgccgggtt | 480 |
| acgtcaccta acatcactgt tactttaaaa aagtttccac ttgacacttt gatccctgat | 540 |
| ggaaaacgca taatctggga cagtagaaag ggcttcatca tatcaaatgc aacgtacaaa | 600 |
| gaaatagggc ttctgacctg tgaagcaaca gtcaatgggc atttgtataa gacaaactat | 660 |
| ctcacacatc gacaaaccaa tacaatcata gatgtccaaa taagcacacc acgcccagtc | 720 |
| aaattactta aggccatac tcttgtcctc aattgtactg ctaccactcc cttgaacacg | 780 |
| agagttcaaa tgacctggag ttaccctgat gaaaaaaata gagagcttc cgtaaggcga | 840 |
| cgaattgacc aaagcaattc ccatgccaac atattctaca gtgttcttac tattgacaaa | 900 |
| atgcagaaca agacaaagg acttatact tgtcgtgtaa ggagtggacc atcattcaaa | 960 |
| tctgttaaca cctcagtgca tatatatgat aaagcattca tcactgtgaa acatcgaaaa | 1020 |
| cagcaggtgc ttgaaaccgt agctggcaag cggtcttacc ggctctctat gaaagtgaag | 1080 |
| gcatttccct cgccggaagt tgtatggtta aagatgggt acctgcgac tgagaaatct | 1140 |
| gctcgctatt tgactcgtgg ctactcgtta attatcaagg acgtaactga agaggatgca | 1200 |
| gggaattata caatcttgct gagcataaaa cagtcaaatg tgtttaaaaa cctcactgcc | 1260 |
| actctaattg tcaatgtgaa accccagatt tacgaaaagg ccgtgtcatc gtttccagac | 1320 |
| ccggctctct acccactggg cagcagacaa atcctgactt gtaccgcata tggtatccct | 1380 |
| caacctacaa tcaagtggtt ctggcacccc tgtaaccata tcattccga agcaaggtgt | 1440 |
| gactttgtt ccaataatga agagtccttt atcctggatg ctgacagcaa catgggaaac | 1500 |
| agaattgaga gcatcactca gcgcatggca ataatagaag gaagaataa gatggctagc | 1560 |
| accttggttg tggctgactc tagaattcct ggaatctaca tttgcatagc ttccaataaa | 1620 |
| gttgggactg tgggaagaaa cataagcttt tatatcacag atgtgccaaa tgggtttcat | 1680 |
| gttaacttgg aaaaaatgcc gacgaagga gaggacctga actgtcttg cacagttaac | 1740 |
| aagttcttat acagagacgt tacttggatt ttactgcgga cagttaataa cagaacaatg | 1800 |

```
cactacagta ttagcaagca aaaaatggcc atcactaagg agcactccat cactcttaat    1860
cttaccatca tgaatgtttc cctgcaagat tcaggcacct atgcctgcag agccaggaat    1920
gtatacacag gggaagaaat cctccagaag aaagaaatta caatcagaga tcaggaagca    1980
ccatacctcc tgcgaaacct cagtgatcac acagtggcca tcagcagttc caccacttta    2040
gactgtcatg ctaatggtgt ccccgagcct cagatcactt ggtttaaaaa caaccacaaa    2100
atacaacaag agcctggaat tattttagga ccaggaagca gcacgctgtt tattgaaaga    2160
gtcacagaag aggatgaagg tgtctatcac tgcaaagcca ccaaccagaa gggctctgtg    2220
gaaagttcag catacctcac tgttcaagga acctcggaca agtctaatct ggagctgatc    2280
actctaacat gcacctgtgt ggctgcgact ctcttctggc tcctattaac cctctttatc    2340
cgaaaaatga aaaggtcttc ttctgaaata aagactgact acctatcaat tataatggac    2400
ccagatgaag ttcctttgga tgagcagtgt gagcggctcc cttatgatgc agcaagtgg    2460
gagtttgccc gggagagact taaactgggc aaatcacttg gaagagggggc ttttggaaaa    2520
gtggttcaag catcagcatt tggcattaag aaatcaccta cgtgccggac tgtggctgtg    2580
aaaatgctga aagaggggc cacggccagc gagtacaaag ctctgatgac tgagctaaaa    2640
atcttgaccc acattggcca ccatctgaac gtggttaacc tgctgggagc ctgcaccaag    2700
caaggagggc ctctgatggt gattgttgaa tactgcaaat atggaaatct ctccaactac    2760
ctcaagagca acgtgacttt atttttctc aacaaggatg cagcactaca catggagcct    2820
aagaaagaaa aaatggagcc aggcctggaa caaggcaaga accaagact agatagcgtc    2880
accagcagcg aaagctttgc gagctccggc tttcaggaag ataaaagtct gagtgatgtt    2940
gaggaagagg aggattctga cggtttctac aaggagccca tcactatgga agatctgatt    3000
tcttacagtt ttcaagtggc cagaggcatg gagttcctgt cttccagaaa gtgcattcat    3060
cgggacctgg cagcgagaaa cattcttttta tctgagaaca cgtggtgaa gatttgtgat    3120
tttggccttg cccgggatat ttataagaac cccgattatg tgagaaaagg agatactcga    3180
cttcctctga aatggatggc tcctgaatct atctttgaca aaatctacag caccaagagc    3240
gacgtgtggt cttacggagt attgctgtgg gaaatcttct ccttaggtgg gtctccatac    3300
ccaggagtac aaatggatga ggactttttgc agtcgcctga gggaaggcat gaggatgaga    3360
gctcctgagt actctactcc tgaaatctat cagatcatgc tggactgctg gcacagagac    3420
ccaaaagaaa ggccaagatt tgcagaactt gtggaaaaac taggtgattt gcttcaagca    3480
aatgtacaac aggatggtaa agactacatc ccaatcaatg ccatactgac aggaaatagt    3540
gggtttacat actcaactcc tgccttctct gaggacttct tcaaggaaag tatttcagct    3600
ccgaagttta attcaggaag ctctgatgat gtcagatatg taaatgcttt caagttcatg    3660
agcctggaaa gaatcaaaac ctttgaagaa cttttaccga atgccacctc catgtttgat    3720
gactaccagg gcgacagcag cactctgttg gcctctccca tgctgaagcg cttcacctgg    3780
actgacagca aacccaaggc ctcgctcaag attgacttga gagtaaccag taaaagtaag    3840
gagtcggggc tgtctgatgt cagcaggccc agtttctgcc attccagctg tgggcacgtc    3900
agcgaaggca agcgcaggtt cacctacgac cacgctgagc tggaaggaa aatcgcgtgc    3960
tgctccccgc ccccagacta caactcggtg gtcctgtact ccaccccacc catctag    4017
```

<210> SEQ ID NO 96
<211> LENGTH: 3897
<212> TYPE: DNA

<213> ORGANISM: Homo sapiens
<300> PUBLICATION INFORMATION:
<302> TITLE: Flt4
<310> PATENT DOCUMENT NUMBER: XM003852

<400> SEQUENCE: 96

| | | | | | |
|---|---|---|---|---|---|
| atgcagcggg | gcgccgcgct | gtgcctgcga | ctgtggctct | gcctgggact | cctggacggc | 60 |
| ctggtgagtg | gctactccat | gacccccccg | accttgaaca | tcacggagga | gtcacacgtc | 120 |
| atcgacaccg | tgacagcct | gtccatctcc | tgcaggggac | agcaccccct | cgagtgggct | 180 |
| tggccaggag | ctcaggaggc | gccagccacc | ggagacaagg | acagcgagga | cacggggtg | 240 |
| gtgcgagact | gcgagggcac | agacgccagg | ccctactgca | aggtgttgct | gctgcacgag | 300 |
| gtacatgcca | acgacacagg | cagctacgtc | tgctactaca | agtacatcaa | ggcacgcatc | 360 |
| gagggcacca | cggccgccag | ctcctacgtg | ttcgtgagag | actttgagca | gccattcatc | 420 |
| aacaagcctg | acacgctctt | ggtcaacagg | aaggacgcca | tgtgggtgcc | ctgtctggtg | 480 |
| tccatccccg | gcctcaatgt | cacgctgcgc | tcgcaaagct | cggtgctgtg | ccagacgggg | 540 |
| caggaggtgg | tgtgggatga | ccggcggggc | atgctcgtgt | ccacgccact | gctgcacgat | 600 |
| gccctgtacc | tgcagtgcga | gaccacctgg | ggagaccagg | acttcctttc | caaccccttc | 660 |
| ctggtgcaca | tcacaggcaa | cgagctctat | gacatccagc | tgttgcccag | gaagtcgctg | 720 |
| gagctgctgg | tagggagaa | gctggtcctg | aactgcaccg | tgtgggctga | gtttaactca | 780 |
| ggtgtcacct | ttgactggga | ctacccaggg | aagcaggcag | agcggggtaa | gtgggtgccc | 840 |
| gagcgacgct | cccagcagac | ccacacagaa | ctctccagca | tcctgaccat | ccacaacgtc | 900 |
| agccagcacg | acctgggctc | gtatgtgtgc | aaggccaaca | acggcatcca | gcgatttcgg | 960 |
| gagagcaccg | aggtcattgt | gcatgaaaat | cccttcatca | gcgtcgagtg | gctcaaagga | 1020 |
| cccatcctgg | aggccacggc | aggagacgag | ctggtgaagc | tgcccgtgaa | gctggcagcg | 1080 |
| tacccccgc | ccgagttcca | gtggtacaag | gatggaaagg | cactgtccgg | gcgccacagt | 1140 |
| ccacatgccc | tggtgctcaa | ggaggtgaca | gaggccagca | caggcaccta | caccctcgcc | 1200 |
| ctgtggaact | ccgctgctgg | cctgaggcgc | aacatcagcc | tggagctggt | ggtgaatgtg | 1260 |
| cccccccaga | tacatgagaa | ggaggcctcc | tcccccagca | tctactcgcg | tcacagccgc | 1320 |
| caggccctca | cctgcacggc | ctacgggtg | cccctgcctc | tcagcatcca | gtggcactgg | 1380 |
| cggccctgga | caccctgcaa | gatgtttgcc | cagcgtagtc | tccggcggcg | gcagcagcaa | 1440 |
| gacctcatgc | cacagtgccg | tgactggagg | gcggtgaccg | cgcaggatgc | cgtgaacccc | 1500 |
| atcgagagcc | tggacacctg | gaccgagttt | gtggagggaa | agaataagac | tgtgagcaag | 1560 |
| ctggtgatcc | agaatgccaa | cgtgtctgcc | atgtacaagt | gtgtggtctc | caacaaggtg | 1620 |
| ggccaggatg | agcggctcat | ctacttctat | gtgaccacca | tccccgacgg | cttcaccatc | 1680 |
| gaatccaagc | catccgagga | gctactagag | ggccagccgg | tgctcctgag | ctgccaagcc | 1740 |
| gacagctaca | agtacgagca | tctgcgctgg | taccgcctca | acctgtccac | gctgcacgat | 1800 |
| gcgcacggga | acccgcttct | gctcgactgc | aagaacgtgc | atctgttcgc | cacccctctg | 1860 |
| gccgccagcc | tggaggaggt | ggcacctggg | gcgcgccacg | ccacgctcag | cctgagtatc | 1920 |
| ccccgcgtcg | cgcccgagca | cgagggccac | tatgtgtgcg | aagtgcaaga | ccggcgcagc | 1980 |
| catgacaagc | actgccacaa | gaagtacctg | tcggtgcagg | ccctggaagc | ccctcggctc | 2040 |
| acgcagaact | tgaccgacct | cctggtgaac | gtgagcgact | cgctggagat | gcagtgcttg | 2100 |
| gtggccggag | cgcacgcgcc | cagcatcgtg | tggtacaaag | acgagaggct | gctggaggaa | 2160 |

```
aagtctggag tcgacttggc ggactccaac cagaagctga gcatccagcg cgtgcgcgag    2220
gaggatgcgg gacgctatct gtgcagcgtg tgcaacgcca agggctgcgt caactcctcc    2280
gccagcgtgg ccgtggaagg ctccgaggat aagggcagca tggagatcgt gatccttgtc    2340
ggtaccggcg tcatcgctgt cttcttctgg gtcctcctcc tcctcatctt ctgtaacatg    2400
aggaggccgg cccacgcaga catcaagacg ggctacctgt ccatcatcat ggaccccggg    2460
gaggtgcctc tggaggagca atgcgaatac ctgtcctacg atgccagcca gtgggaattc    2520
ccccgagagc ggctgcacct ggggagagtg ctcggctacg gcgccttcgg aaggtggtg    2580 gaagcctccg ctttcggcat ccacaagggc agcagctgtg acaccgtggc cgtgaaaatg    2640
ctgaaagagg gcgccacggc cagcgagcag cgcgcgctga tgtcggagct caagatcctc    2700
attcacatcg gcaaccacct caacgtggtc aacctcctcg ggcgtgcac caagccgcag    2760 ggccccctca tggtgatcgt ggagttctgc aagtacggca acctctccaa cttcctgcgc    2820
gccaagcggg acgccttcag cccctgcgcg gagaagtctc ccgagcagcg cggacgcttc    2880
cgcgccatgg tggagctcgc caggctggat cggaggcggc cggggagcag cgacagggtc    2940
ctcttcgcgc ggttctcgaa gaccgagggc ggagcgaggc gggcttctcc agaccaagaa    3000
gctgaggacc tgtggctgag cccgctgacc atggaagatc ttgtctgcta cagcttccag    3060
gtggccagag ggatggagtt cctggcttcc cgaaagtgca tccacagaga cctggctgct    3120
cggaacattc tgctgtcgga aagcgacgtg gtgaagatct gtgactttgg ccttgcccgg    3180
gacatctaca agaccccga ctacgtccgc aagggcagtg cccggctgcc cctgaagtgg    3240
atggcccctg aaagcatctt cgacaaggtg tacaccacgc agagtgacgt gtggtccttt    3300
ggggtgcttc tctgggagat cttctctctg ggggcctccc cgtaccctgg ggtgcagatc    3360
aatgaggagt tctgccagcg gctgagagac ggcacaagga tgagggcccc ggagctggcc    3420
actcccgcca tacgccgcat catgctgaac tgctggtccg agaccccaa ggcgagacct    3480 gcattctcgg agctggtgga gatcctgggg gacctgctcc agggcagggg cctgcaagag    3540
gaagaggagg tctgcatggc cccgcgcagc tctcagagct cagaagaggg cagcttctcg    3600
caggtgtcca ccatggccct acacatcgcc caggctgacg ctgaggacag cccgccaagc    3660
ctgcagcgcc acagcctggc cgccaggtat tacaactggg tgtcctttcc cgggtgcctg    3720
gccagagggg ctgagacccg tggttcctcc aggatgaaga catttgagga attccccatg    3780
accccaacga cctacaaagg ctctgtggac aaccagacag acagtgggat ggtgctggcc    3840
tcggaggagt ttgagcagat agagagcagg catagacaag aaagcggctt caggtag     3897
```

<210> SEQ ID NO 97
<211> LENGTH: 4071
<212> TYPE: DNA
<213> ORGANISM: Homo sapiens
<300> PUBLICATION INFORMATION:
<302> TITLE: KDR
<310> PATENT DOCUMENT NUMBER: AF063658

<400> SEQUENCE: 97

```
atggagagca aggtgctgct ggccgtcgcc ctgtggctct gcgtggagac ccgggccgcc     60
tctgtgggtt tgcctagtgt ttctcttgat ctgcccaggc tcagcataca aaaagacata    120
cttacaatta aggctaatac aactcttcaa attacttgca ggggacagag ggacttggac    180 tggcttttggc ccaataatca gagtggcagt gagcaaaggg tggaggtgac tgagtgcagc    240
gatgccctct tctgtaagac actcacaatt ccaaaagtga tcggaaatga cactgggagcc    300
```

```
tacaagtgct tctaccggga aactgacttg gcctcggtca tttatgtcta tgttcaagat    360
tacagatctc catttattgc ttctgttagt gaccaacatg gagtcgtgta cattactgag    420
aacaaaaaca aaactgtggt gattccatgt ctcgggtcca tttcaaatct caacgtgtca    480
ctttgtgcaa gatacccaga aaagagattt gttcctgatg gtaacagaat ttcctgggac    540
agcaagaagg gctttactat tcccagctac atgatcagct atgctggcat ggtcttctgt    600
gaagcaaaaa ttaatgatga aagttaccag tctattatgt acatagttgt cgttgtaggg    660
tataggattt atgatgtggt tctgagtccg tctcatggaa ttgaactatc tgttggagaa    720
aagcttgtct taaattgtac agcaagaact gaactaaatg tggggattga cttcaactgg    780
gaatacccctt cttcgaagca tcagcataag aaacttgtaa accgagacct aaaaacccag    840
tctgggagtg agatgaagaa attttttgagc accttaacta tagatggtgt aacccggagt    900
gaccaaggat tgtacacctg tgcagcatcc agtgggctga tgaccaagaa gaacagcaca    960
tttgtcaggg tccatgaaaa accttttgtt gcttttggaa gtggcatgga atctctggtg   1020
gaagccacgg tgggggagcg tgtcagaatc cctgcgaagt accttggtta cccaccccca   1080
gaaataaaat ggtataaaaa tggaataccc cttgagtcca atcacacaat taaagcgggg   1140
catgtactga cgattatgga agtgagtgaa agagacacag gaaattacac tgtcatcctt   1200
accaatccca tttcaaagga gaagcagagc catgtggtct ctctggttgt gtatgtccca   1260
ccccagattg gtgagaaatc tctaatctct cctgtggatt cctaccagta cggcaccact   1320
caaacgctga catgtacggt ctatgccatt cctcccccgc atcacatcca ctggtattgg   1380
cagttggagg aagagtgcgc caacgagccc agcaagctg tctcagtgac aaacccatac   1440
ccttgtgaag aatggagaag tgtggaggac ttccagggag gaaataaaat tgaagttaat   1500
aaaaatcaat ttgctctaat tgaaggaaaa aacaaaactg taagtaccct tgttatccaa   1560
gcggcaaatg tgtcagcttt gtacaaatgt gaagcggtca acaaagtcgg gagaggagag   1620
agggtgatct cctccacgt gaccagggt cctgaaatta cttttgcaacc tgacatgcag   1680
cccactgagc aggagagcgt gtctttgtgg tgcactgcag acagatctac gtttgagaac   1740
ctcacatggt acaagcttgg cccacagcct ctgccaatcc atgtgggaga gttgcccaca   1800
cctgtttgca agaacttgga tactcttttgg aaattgaatg ccaccatgtt ctctaatagc   1860
acaaatgaca ttttgatcat ggagcttaag aatgcatcct gcaggacca aggagactat   1920
gtctgccttg ctcaagacag gaagaccaag aaaagacatt gcgtggtcag gcagctcaca   1980
gtcctagagc gtgtggcacc cacgatcaca ggaaacctgg agaatcagac gacaagtatt   2040
ggggaaagca tcgaagtctc atgcacggca tctgggaatc cccctccaca gatcatgtgg   2100
tttaaagata tgagaccct tgtagaagac tcaggcattg tattgaagga tgggaaccgg   2160
aacctcacta tccgcagagt gaggaaggag gacgaaggcc tctacacctg ccaggcatgc   2220
agtgttcttg gctgtgcaaa agtggaggca ttttttcataa tagaaggtgc ccaggaaaag   2280
acgaacttgg aaatcattat tctagtaggc acggcgtga ttgccatgtt cttctggcta   2340
cttcttgtca tcatcctacg gaccgttaag cgggccaatg gagggaact gaagacaggc   2400
tacttgtcca tcgtcatgga tccagatgaa ctcccattgg atgaacattg tgaacgactg   2460
ccttatgatg ccagcaaatg ggaattcccc agagaccggc tgaagctagg taagcctctt   2520
ggccgtggtg ccttttggcca agtgattgaa gcagatgcct ttggaattga caagacagca   2580
acttgcagga cagtagcagt caaaatgttg aaagaaggag caacacacag tgagcatcga   2640
gctctcatgt ctgaactcaa gatcctcatt catattggtc accatctcaa tgtggtcaac   2700
```

```
cttctaggtg cctgtaccaa gccaggaggg ccactcatgg tgattgtgga attctgcaaa    2760
tttggaaacc tgtccactta cctgaggagc aagagaaatg aatttgtccc ctacaagacc    2820
aaaggggcac gattccgtca agggaaagac tacgttggag caatccctgt ggatctgaaa    2880
cggcgcttgg acagcatcac cagtagccag agctcagcca gctctggatt tgtggaggag    2940
aagtccctca gtgatgtaga agaagaggaa gctcctgaag atctgtataa ggacttcctg    3000
accttggagc atctcatctg ttacagcttc caagtggcta agggcatgga gttcttggca    3060
tcgcgaaagt gtatccacag ggacctggcg gcacgaaata tcctcttatc ggagaagaac    3120
gtggttaaaa tctgtgactt tggcttggcc cgggatattt ataaagatcc agattatgtc    3180
agaaaaggag atgctcgcct ccctttgaaa tggatggccc cagaaacaat ttttgacaga    3240
gtgtacacaa tccagagtga cgtctggtct tttggtgttt tgctgtggga aatattttcc    3300
ttaggtgctt ctccatatcc tggggtaaag attgatgaag aattttgtag gcgattgaaa    3360
gaaggaacta gaatgagggc ccctgattat actacaccag aaatgtacca gaccatgctg    3420
gactgctggc acggggagcc cagtcagaga cccacgtttt cagagttggt ggaacatttg    3480
ggaaatctct gcaagctaa tgctcagcag gatggcaaag actacattgt tcttccgata    3540
tcagagactt tgagcatgga agaggattct ggactctctc tgcctacctc acctgtttcc    3600
tgtatggagg aggaggaagt atgtgacccc aaattccatt atgacaacac agcaggaatc    3660
agtcagtatc tgcagaacag taagcgaaag agccggcctg tgagtgtaaa acatttgaa    3720 gatatcccgt tagaagaacc agaagtaaaa gtaatcccag atgacaacca gacggacagt    3780
ggtatggttc ttgcctcaga agagctgaaa actttggaag acagaaccaa attatctcca    3840
tcttttggtg gaatggtgcc cagcaaaagc agggagtctg tggcatctga aggctcaaac    3900
cagacaagcg gctaccagtc cggatatcac tccgatgaca cagacaccac cgtgtactcc    3960
agtgaggaag cagaactttt aaagctgata gagattggag tgcaaaccgg tagcacagcc    4020
cagattctcc agcctgactc ggggaccaca ctgagctctc ctcctgttta a             4071
```

<210> SEQ ID NO 98
<211> LENGTH: 1410
<212> TYPE: DNA
<213> ORGANISM: Homo sapiens
<300> PUBLICATION INFORMATION:
<302> TITLE: MMP1
<310> PATENT DOCUMENT NUMBER: M13509

<400> SEQUENCE: 98

```
atgcacagct ttcctccact gctgctgctg ctgttctggg gtgtggtgtc tcacagcttc     60
ccagcgactc tagaaacaca agagcaagat gtggacttag tccagaaata cctggaaaaa    120
tactacaacc tgaagaatga tgggaggcaa gttgaaaagc ggagaaatag tggcccagtg    180
gttgaaaaat tgaagcaaat gcaggaattc tttgggctga agtgactgg gaaaccagat     240 gctgaaaccc tgaaggtgat gaagcagccc agatgtggag tgcctgatgt ggctcagttt    300
gtcctcactg agggaaaccc tcgctgggag caaacacatc tgaggtacag gattgaaaat    360
tacacgccag atttgccaag agcagatgtg accatgccat tgagaaagc cttccaactc    420 tggagtaatg tcacacctct gacattcacc aaggtctctg agggtcaagc agacatcatg    480
atatcttttg tcaggggaga tcatcgggac aactctcctt ttgatggacc tggagaaat    540 cttgctcatg cttttcaacc aggcccaggt attgaggggg atgctcattt tgatgaagat    600
gaaaggtgga ccaacaattt cagagagtac aacttacatc gtgttgcggc tcatgaactc    660
```

```
ggccattctc ttggactctc ccattctact gatatcgggg ctttgatgta ccctagctac    720
accttcagtg gtgatgttca gctagctcag gatgacatta tggcatcca agccatatat     780 ggacgttccc aaaatcctgt ccagcccatc ggcccacaaa ccccaaaagc gtgtgacagt    840
aagctaacct ttgatgctat aactacgatt cggggagaaa tgatgttctt aaagacaga    900 ttctacatgc gcacaaatcc cttctacccg gaagttgagc tcaatttcat ttctgttttc    960
tggccacaac tgccaaatgg gcttgaagct gcttacgaat tgccgacag agatgaagtc    1020 cggttttca agggaataa gtactgggct gttcagggac agaatgtgct acacggatac    1080
cccaaggaca tctacagctc ctttggcttc cctagaactg tgaagcatat cgatgctgct    1140
ctttctgagg aaaacactgg aaaaacctac ttctttgttg ctaacaaata ctggaggtat    1200
gatgaatata aacgatctat ggatccaagt tatcccaaaa tgatagcaca tgactttcct    1260
ggaattggcc acaaagttga tgcagttttc atgaaagatg gattttcta tttctttcat    1320 ggaacaagac aatacaaatt tgatcctaaa acgaagagaa ttttgactct ccagaaagct    1380
aatagctggt tcaactgcag gaaaaattga                                      1410
```

```
<210> SEQ ID NO 99
<211> LENGTH: 1743
<212> TYPE: DNA
<213> ORGANISM: Homo sapiens
<300> PUBLICATION INFORMATION:
<302> TITLE: MMP10
<310> PATENT DOCUMENT NUMBER: XM006269

<400> SEQUENCE: 99
```

```
aaagaaggta agggcagtga gaatgatgca tcttgcattc cttgtgctgt tgtgtctgcc     60
agtctgctct gcctatcctc tgagtggggc agcaaaagag gaggactcca acaaggatct    120
tgcccagcaa tactagaaa agtactacaa cctcgaaaag gatgtgaaac agtttagaag    180
aaaggacagt aatctcattg ttaaaaaaat ccaaggaatg cagaagttcc ttgggttgga    240
ggtgacaggg aagctagaca ctgacactct ggaggtgatg cgcaagccca ggtgtggagt    300
tcctgacgtt ggtcacttca gctccttttcc tggcatgccg aagtggagga aaacccacct    360
tacatacagg attgtgaatt atacaccaga tttgccaaga gatgctgttg attctgccat    420
tgagaaagct ctgaaagtct gggaagaggt gactccactc acattctcca ggctgtatga    480
aggagaggct gatataatga tctcttttgc agttaaagaa catggagact tttactcttt    540
tgatggccca ggacacagtt tggctcatgc ctacccacct ggacctgggc tttatggaga    600
tattcacttt gatgatgatg aaaaatggac agaagatgca tcaggcacca atttattcct    660
cgttgctgct catgaacttg gccactccct ggggctcttt cactcagcca acactgaagc    720
tttgatgtac ccactctaca actcattcac agagctcgcc cagttccgcc tttcgcaaga    780
tgatgtgaat ggcattcagt ctctctacgg acctcccct gcctctactg aggaaccct    840 ggtgcccaca aaatctgttc cttcgggatc tgagatgcca gccaagtgtg atcctgcttt    900
gtccttcgat gccatcagca ctctgagggg agaatatctg ttctttaaag acagatattt    960
ttggcgaaga tccccactgga accctgaacc tgaatttcat ttgatttctg cattttggcc    1020
ctctcttcca tcatatttgg atgctgcata tgaagttaac agcagggaca ccgttttat    1080 ttttaaagga aatgagttct gggccatcag aggaaatgag gtacaagcag gttatccaag    1140
aggcatccat accctgggtt ttcctccaac cataaggaaa attgatgcag ctgtttctga    1200
caaggaaaag aagaaaacat acttctttgc agcggacaaa tactggagat tgatgaaaa    1260
```

```
tagccagtcc atggagcaag gcttccctag actaatagct gatgactttc caggagttga    1320
gcctaaggtt gatgctgtat tacaggcatt tggattttc tacttcttca gtggatcatc    1380
acagtttgag tttgacccca atgccaggat ggtgacacac atattaaaga gtaacagctg    1440
gttacattgc taggcgagat aggggggaaga cagatatggg tgtttttaat aaatctaata    1500
attattcatc taatgtatta tgagccaaaa tggttaattt ttcctgcatg ttctgtgact    1560
gaagaagatg agccttgcag atatctgcat gtgtcatgaa gaatgtttct ggaattcttc    1620
acttgctttt gaattgcact gaacagaatt aagaaatact catgtgcaat aggtgagaga    1680
atgtattttc atagatgtgt tattacttcc tcaataaaaa gttttatttt gggcctgttc    1740
ctt                                                                  1743

<210> SEQ ID NO 100
<211> LENGTH: 1467
<212> TYPE: DNA
<213> ORGANISM: Homo sapiens
<300> PUBLICATION INFORMATION:
<302> TITLE: MMP11
<310> PATENT DOCUMENT NUMBER: XM009873

<400> SEQUENCE: 100
atggctccgg ccgcctggct ccgcagcgcg gccgcgcgcg ccctcctgcc cccgatgctg      60
ctgctgctgc tccagccgcc gccgctgctg gcccgggctc tgccgccgga cgcccaccac     120
ctccatgccg agaggagggg gccacagccc tggcatgcag ccctgcccag tagcccggca     180
cctgcccctg ccacgcagga agcccccegg cctgccagca gctcaggcc tccccgctgt     240 ggcgtgcccg acccatctga tgggctgagt gcccgcaacc gacagaagag gttcgtgctt     300
tctggcgggc gctgggagaa gacgacctc acctacagga tccttcggtt cccatggcag     360
ttggtgcagg agcaggtgcg gcagacgatg gcagaggccc taaaggtatg gagcgatgtg     420
acgccactca cctttactga ggtgcacgag ggccgtgctg acatcatgat cgacttcgcc     480
aggtactggc atggggacga cctgccgttt gatgggcctg ggggcatcct ggcccatgcc     540
ttcttcccca agactcaccg agaagggat gtccacttcg actatgatga acctggact     600 atcggggatg accagggcac agacctgctg caggtggcag cccatgaatt tggccacgtg     660
ctggggctgc agcacacaac agcagccaag gccctgatgt ccgccttcta cacctttcgc     720
tacccactga gtctcagccc agatgactgc agggggcgttc aacacctata tggccagccc     780
tggcccactg tcacctccag gaccccagcc ctgggccccc aggctgggat agacaccaat     840
gagattgcac cgctggagcc agacgccccg ccagatgcct gtgaggcctc ctttgacgcg     900
gtctccacca tccgaggcga gctcttttc ttcaaagcgg gctttgtgtg gcgcctccgt     960 ggggggccagc tgcagcccgg ctacccagca ttggcctctc gccactggca gggactgccc    1020
agccctgtgg acgctgcctt cgaggatgcc caggccaca tttggttctt ccaaggtgct    1080
cagtactggg tgtacgacgg tgaaaagcca gtcctgggcc ccgcaccct caccgagctg    1140 ggcctggtga ggttcccggt ccatgctgcc ttggtctggg gtcccgagaa gaacaagatc    1200
tacttcttcc gaggcaggga ctactggcgt ttccacccca gcaccggcg tgtagacagt    1260 cccgtgcccc gcagggccac tgactggaga ggggtgccct ctgagatcga cgctgccttc    1320
caggatgctg atggctatgc ctacttcctg cgcggccgcc tctactggaa gtttgaccct    1380
gtgaaggtga aggctctgga aggcttccc cgtctcgtgg gtcctgactt ctttggctgt    1440
gccgagcctg ccaacacttt cctctga                                       1467
```

<210> SEQ ID NO 101
<211> LENGTH: 1653
<212> TYPE: DNA
<213> ORGANISM: Homo sapiens
<220> FEATURE:
<221> NAME/KEY: misc_feature
<222> LOCATION: (626)..(925)
<223> OTHER INFORMATION: n=A, T, G, C or gap
<300> PUBLICATION INFORMATION:
<302> TITLE: MMP12
<310> PATENT DOCUMENT NUMBER: XM006272

<400> SEQUENCE: 101

```
atgaagtttc ttctaatact gctcctgcag gccactgctt ctggagctct tccctgaac        60
agctctacaa gcctggaaaa aaataatgtg ctatttggtg agagatactt agaaaaattt      120
tatggccttg agataaacaa acttccagtg acaaaaatga atatagtgg aaacttaatg       180
aaggaaaaaa tccaagaaat gcagcacttc ttgggtctga agtgaccgg gcaactggac       240
acatctaccc tggagatgat gcacgcacct cgatgtggag tccccgatgt ccatcatttc      300
agggaaatgc caggggggcc cgtatggagg aaacattata tcacctacag aatcaataat      360
tacacacctg acatgaaccg tgaggatgtt gactacgcaa tccggaaagc tttccaagta     420
tggagtaatg ttacccccct gaaattcagc aagattaaca caggcatggc tgacattttg     480
gtggttttg cccgtggagc tcatggagac ttccatgctt tgatggcaa aggtggaatc       540
ctagcccatg cttttggacc tggatctggc attggagggg atgcacattt cgatgaggac      600
gaattctgga ctacacattc aggagnnnnn nnnnnnnnnn nnnnnnnnnn nnnnnnnnnn      660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnngagag gatccaaagg ccgtaatgtt ccccacctac     960
aaatatgttg acatcaacac atttcgcctc tctgctgatg acatacgtgg cattcagtcc    1020
ctgtatggag acccaaaaga gaaccaacgc ttgccaaatc ctgacaattc agraccagct    1080
ctctgtgacc ccaatttgag ttttgatgct gtcactaccg tgggaaataa gatctttttc    1140
ttcaaagaca ggttcttctg gctgaaggtt tctgagagac caaagaccag tgttaattta    1200
atttcttcct tatggccaac cttgccatct ggcattgaag ctgcttatga aattgaagcc    1260
agaaatcaag tttttctttt taaagatgac aaatactggt taattagcaa tttaagacca    1320
gagccaaatt atcccaagag catacattct tttggttttc ctaactttgt gaaaaaaatt    1380
gatgcagctg ttttttaaccc acgtttttat aggacctact ctttgtaga taaccagtat    1440
tggaggtatg atgaaaggag acagatgatg gaccctggtt atcccaaact gattaccaag    1500
aacttccaag gaatcgggcc taaaattgat gcagtcttct actctaaaaa caaatactac    1560
tatttcttcc aaggatctaa ccaatttgaa tatgacttcc tactccaacg tatcaccaaa    1620
acactgaaaa gcaatagctg gtttggttgt tag                                  1653
```

<210> SEQ ID NO 102
<211> LENGTH: 1416
<212> TYPE: DNA
<213> ORGANISM: Homo sapiens

<400> SEQUENCE: 102

```
atgcatccag gggtcctggc tgccttcctc ttcttgagct ggactcattg tcgggccctg      60
cccttccca gtggtggtga tgaagatgat ttgtctgagg aagacctcca gtttgcagag     120
cgctacctga gatcatacta ccatcctaca aatctcgcgg gaatcctgaa ggagaatgca     180
gcaagctcca tgactgagag gctccgagaa atgcagtctt tcttcggctt agaggtgact     240
ggcaaacttg acgataacac cttagatgtc atgaaaaagc aagatgcgg ggttcctgat      300
gtgggtgaat acaatgtttt ccctcgaact cttaaatggt ccaaaatgaa tttaacctac     360
agaattgtga attacacccc tgatatgact cattctgaag tcgaaaaggc attcaaaaaa     420
gccttcaaag tttggtccga tgtaactcct ctgaattta ccagcttca cgatggcatt       480
gctgacatca tgatctcttt tggaattaag gagcatggcg acttctaccc atttgatggg     540
ccctctggcc tgctggctca tgcttttcct cctgggccaa attatggagg agatgcccat     600
tttgatgatg atgaaacctg acaagtagt tccaaaggct acaacttgtt tcttgttgct      660
gcgcatgagt tcggccactc cttaggtctt gaccactcca aggaccctgg agcactcatg     720
tttcctatct acacctacac cggcaaaagc cactttatgc ttcctgatga cgatgtacaa     780
gggatccagt ctctctatgg tccaggagat gaagacccca accctaaaca tccaaaaacg     840
ccagacaaat gtgacccttc cttatccctt gatgccatta ccagtctccg aggagaaaca     900
atgatcttta aagacagatt cttctggcgc ctgcatcctc agcaggttga tgcggagctg     960
ttttaacga aatcattttg ccagaacttc cccaaccgta ttgatgctgc atatgagcac    1020
ccttctcatg acctcatctt catcttcaga ggtagaaaat tttgggctct taatggttat    1080
gacattctgg aaggttatcc caaaaaaata tctgaactgg gtcttccaaa agaagttaag    1140
aagataagtg cagctgttca ctttgaggat acaggcaaga ctctcctgtt ctcaggaaac    1200
caggtctgga gatatgatga tactaaccat attatggata aagactatcc gagactaata    1260
gaagaagact cccaggaat tggtgataaa gtagatgctg tctatgagaa aaatggttat    1320
atctattttt caacggacc catacagttt gaatacagca tctggagtaa ccgtattgtt    1380
cgcgtcatgc cagcaaattc catttgtgg tgttaa                              1416
```

<210> SEQ ID NO 103
<211> LENGTH: 1749
<212> TYPE: DNA
<213> ORGANISM: Homo sapiens
<300> PUBLICATION INFORMATION:
<302> TITLE: MMP14
<310> PATENT DOCUMENT NUMBER: NM004995

<400> SEQUENCE: 103

```
atgtctcccg ccccaagacc cccccgttgt ctcctgctcc cctgctcac gctcggcacc       60
gcgctcgcct cccctcggctc ggcccaaagc agcagcttca gccccgaagc ctggctacag     120
caatatggct acctgcctcc cggggaccta cgtacccaca cacagcgctc acccagtca      180
ctctcagcgg ccatcgctgc catgcagaag ttttacggct gcaagtaac aggcaaagct     240
gatgcagaca ccatgaaggc catgaggcgc cccgatgtg tgttccaga caagtttggg       300
gctgagatca aggccaatgt tcgaaggaag cgctacgcca tccagggtct caaatggcaa    360
cataatgaaa tcactttctg catccagaat tacacccca aggtgggcga gtatgccaca     420
tacgaggcca ttcgcaaggc gttccgcgtg tgggagagtg ccacaccact gcgcttccgc    480
gaggtgccct atgcctacat ccgtgagggc catgagaagc aggccgacat catgatcttc    540
tttgccgagg gcttccatgg cgacagcacg cccttcgatg gtgagggcgg cttcctggcc    600
```

```
catgcctact tcccaggccc caacattgga ggagacaccc actttgactc tgccgagcct      660
tggactgtca ggaatgagga tctgaatgga aatgacatct tcctggtggc tgtgcacgag      720
ctgggccatg ccctggggct cgagcattcc agtgacccct cggccatcat ggcaccctt       780 taccagtgga tggacacgga gaattttgtg ctgcccgatg atgaccgccg gggcatccag      840
caactttatg ggggtgagtc agggttcccc accaagatgc cccctcaacc caggactacc      900
tcccggcctt ctgttcctga taaacccaaa aaccccacct atgggcccaa catctgtgac      960
gggaactttg acaccgtggc catgctccga ggggagatgt tgtcttcaa ggagcgctgg      1020 ttctggcggg tgaggaataa ccaagtgatg gatggatacc caatgcccat ggccagttc      1080 tggcggggcc tgcctgcgtc catcaacact gcctacgaga ggaaggatgg caaattcgtc      1140
ttcttcaaag gagacaagca ttgggtgttt gatgaggcgt ccctggaacc tggctacccc      1200
aagcacatta aggagctggg ccgagggctg cctaccgaca agattgatgc tgctctcttc      1260
tggatgccca atgaaagac ctacttcttc cgtggaaaca agtactaccg tttcaacgaa      1320
gagctcaggg cagtggatag cgagtacccc aagaacatca aagtctggga agggatccct      1380
gagtctccca gagggtcatt catgggcagc gatgaagtct tcacttactt ctacaagggg      1440
aacaaatact ggaaattcaa caaccagaag ctgaaggtag aaccgggcta ccccaagtca      1500
gccctgaggg actggatggg ctgcccatcg ggaggccggc cggatgaggg gactgaggag      1560
gagacggagg tgatcatcat tgaggtggac gaggagggcg gcgggcggt gagcgcggct      1620 gccgtggtgc tgcccgtgct gctgctgctc ctggtgctgg cggtgggcct tgcagtcttc      1680
ttcttcagac gccatgggac ccccaggcga ctgctctact gccagcgttc cctgctggac      1740
aaggtctga                                                            1749

<210> SEQ ID NO 104
<211> LENGTH: 2010
<212> TYPE: DNA
<213> ORGANISM: Homo sapiens
<300> PUBLICATION INFORMATION:
<302> TITLE: MMP15
<310> PATENT DOCUMENT NUMBER: NM002428

<400> SEQUENCE: 104
atgggcagcg acccgagcgc gcccggacgg ccgggctgga cgggcagcct cctcggcgac       60
cgggaggagg cggcgcggcc gcgactgctg ccgctgctcc tggtgcttct gggctgcctg      120
ggccttggcg tagcggccga agacgcggag gtccatgccg agaactggct gcggctttat      180
ggctacctgc ctcagcccag ccgccatatg tccaccatgc gttccgccca gatcttggcc      240
tcggcccttg cagagatgca gcgcttctac gggatcccag tcaccggtgt gctcgacgaa      300
gagaccaagg agtggatgaa gcggccccgc tgtgggtgc cagaccagtt cggggtacga      360
gtgaaagcca acctgcggcg cgtcggaag cgctacgccc tcaccgggag gaagtggaac      420
aaccaccatc tgacctttag catccagaac tacacggaga agttgggctg gtaccactcg      480
atggaggcgg tgcgcagggc cttccgcgtg tgggagcagg ccacgccct ggtcttccag      540 gaggtgccct atgaggacat ccggctgcgc gacagaagg aggccgacat catggtactc      600
tttgcctctg gcttccacgg cgacagctcg ccgtttgatg gcaccggtgg ctttctggcc      660
cacgcctatt ccctggcccc cggcctaggc ggggacaccc attttgacgc agatgagccc      720
tggaccttct ccagcactga cctgcatgga acaacctct tcctggtggc agtgcatgag      780
ctgggccacg cgctggggct ggagcactcc agcaacccca tgccatcat ggcgccgttc      840
```

-continued

```
taccagtgga aggacgttga caacttcaag ctgcccgagg acgatctccg tggcatccag    900
cagctctacg gtaccccaga cggtcagcca cagcctaccc agcctctccc cactgtgacg    960
ccacggcggc caggccggcc tgaccaccgg ccgccccggc ctccccagcc accaccccca   1020
ggtgggaagc cagagcggcc cccaaagccg ggccccccag tccagccccg agccacagag   1080
cggcccgacc agtatggccc caacatctgc gacggggact tgacacagt ggccatgctt    1140 cgcgggagga tgttcgtgtt caagggccgc tggttctggc gagtccggca caaccgcgtc   1200
ctggacaact atcccatgcc catcgggcac ttctggcgtg gtctgcccgg tgacatcagt   1260
gctgcctacg agcgccaaga cggtcgtttt gtcttttca aaggtgaccg ctactggctc    1320
tttcgagaag cgaacctgga gcccggctac ccacagccgc tgaccagcta tggcctgggc   1380
atccccctat gaccgcattga cacggccatc tggtgggagc ccacaggcca caccttcttc   1440
ttccaagagg acaggtactg gcgcttcaac gaggagacac agcgtggaga ccctgggtac   1500
cccaagccca tcagtgtctg gcaggggatc cctgcctccc ctaaagggc cttcctgagc    1560 aatgacgcag cctacaccta cttctacaag ggcaccaaat actggaaatt cgacaatgag   1620
cgcctgcgga tggagcccgg ctaccccaag tccatcctgc gggacttcat gggctgccag   1680
gagcacgtgg agccaggccc ccgatggccc gacgtggccc ggccgccctt caaccccac    1740 gggggtgcag agcccgggc ggacagcgca gagggcgacg tggggatgg ggatggggac    1800 tttggggccg gggtcaacaa ggacggggc agccgcgtgg tggtgcagat ggaggaggtg   1860
gcacggacgg tgaacgtggt gatggtgctg gtgccactgc tgctgctgct ctgcgtcctg   1920
ggcctcacct acgcgctggt gcagatgcag cgcaagggtg cgccacgtgt cctgctttac   1980
tgcaagcgct cgctgcagga gtgggtctga                                    2010
```

<210> SEQ ID NO 105
<211> LENGTH: 1824
<212> TYPE: DNA
<213> ORGANISM: Homo sapiens
<300> PUBLICATION INFORMATION:
<302> TITLE: MMP16
<310> PATENT DOCUMENT NUMBER: NM005941

<400> SEQUENCE: 105

```
atgatcttac tcacattcag cactggaaga cggttggatt tcgtgcatca ttcgggggtg     60 ttttcttgc aaaccttgct ttggatttta tgtgctacag tctgcggaac ggagcagtat    120
ttcaatgtgg aggtttggtt acaaaagtac ggctaccttc caccgactga ccccagaatg    180
tcagtgctgc gctctgcaga gaccatgcag tctgccctag ctgccatgca gcagttctat    240
ggcattaaca tgacaggaaa agtggacaga aacacaattg actggatgaa gaagcccga    300 tgcggtgtac ctgaccagac aagaggtagc tccaaatttc atattcgtcg aaagcgatat    360
gcattgacag gacagaaatg gcagcacaag cacatcactt acagtataaa gaacgtaact    420
ccaaaagtag agaccctga actcgtaaa gctattcgcc gtgcctttga tgtgtggcag     480
aatgtaactc ctctgacatt tgaagaagtt ccctacagtg aattagaaaa tggcaaacgt    540
gatgtggata taaccattat ttttgcatct ggtttccatg gggacagctc tccctttgat    600
ggagagggag gatttttggc acatgcctac ttccctggac aggaattggg aggagatacc    660
cattttgact cagatgagcc atggacacta ggaaatccta atcatgatgg aaatgactta    720
tttcttgtag cagtccatga actgggacat gctctgggat tggagcattc caatgacccc    780
actgccatca tggctccatt ttaccagtac atggaaacag acaacttcaa actacctaat    840
```

```
gatgatttac agggcatcca gaaaatatat ggtccacctg acaagattcc tccacctaca    900
agacctctac cgacagtgcc cccacaccgc tctattcctc cggctgaccc aaggaaaaat    960
gacaggccaa aacctcctcg gcctccaacc ggcagaccct cctatcccgg agccaaaccc   1020
aacatctgtg atgggaactt taacactcta gctattcttc gtcgtgagat gtttgttttc   1080
aaggaccagt ggttttggcg agtgagaaac aacagggtga tggatggata cccaatgcaa   1140
attacttact tctggcgggg cttgcctcct agtatcgatg cagtttatga aaatagcgac   1200
gggaattttg tgttctttaa aggtaacaaa tattgggtgt tcaaggatac aactcttcaa   1260
cctggttacc ctcatgactt gataacccct ggaagtggaa ttccccctca tggtattgat   1320
tcagccattt ggtgggagga cgtcgggaaa acctatttct tcaagggaga cagatattgg   1380
agatatagtg aagaaatgaa acaatggac cctggctatc ccaagccaat cacagtctgg    1440
aaagggatcc ctgaatctcc tcaggagca tttgtacaca agaaaatgg ctttacgtat     1500
ttctacaaag gaaaggagta ttggaaattc aacaaccaga tactcaaggt agaacctgga   1560
catccaagat ccatcctcaa ggattttatg ggctgtgatg gaccaacaga cagagttaaa   1620
gaaggacaca gcccaccaga tgatgtagac attgtcatca aactggacaa cacagccagc   1680
actgtgaaag ccatagctat tgtcattccc tgcatcttgg ccttatgcct ccttgtattg   1740
gtttacactg tgttccagtt caagaggaaa ggaacacccc gccacatact gtactgtaaa   1800
cgctctatgc aagagtgggt gtga                                          1824

<210> SEQ ID NO 106
<211> LENGTH: 1560
<212> TYPE: DNA
<213> ORGANISM: Homo sapiens
<300> PUBLICATION INFORMATION:
<302> TITLE: MMP17
<310> PATENT DOCUMENT NUMBER: NM004141

<400> SEQUENCE: 106
atgcagcagt ttggtggcct ggaggccacc ggcatcctgg acgaggccac cctggccctg     60
atgaaaaccc cacgctgctc cctgccagac ctccctgtcc tgacccaggc tcgcaggaga    120
cgccaggctc cagcccccac caagtggaac aagaggaacc tgtcgtggag ggtccggacg    180
ttcccacggg actcaccact ggggcacgac acggtgcgtg cactcatgta ctacgccctc    240
aaggtctgga gcgacattgc gccctgaac ttccacgagg tggcgggcag caccgccgac    300
atccagatcg acttctccaa ggccgaccat aacgacggct accccttcga cggccccggc    360
ggcaccgtgg cccacgcctt cttccccggc caccaccaca ccgccgggga cacccactt     420
gacgatgacg aggcctggac cttccgctcc tcggatgccc acgggatgga cctgtttgca    480
gtggctgtcc acgagtttgg ccacgccatt gggttaagcc atgtggccgc tgcacactcc    540
atcatgcggc cgtactacca gggcccggtg ggtgacccgc tgcgctacgg gctcccctac    600
gaggacaagg tgcgcgtctg gcagctgtac ggtgtgcggg agtctgtgtc tcccacggcg    660
cagcccgagg agcctcccct gctgccggag cccccagaca accggtccag cgccccgccc    720
aggaaggacg tgcccacag atgcagcact cactttgacg cggtgcccca gatcggggt     780
gaagctttct tcttcaaagg caagtacttc tggcggctga cgcgggaccg gcacctggtg    840
tcctgcagc cggcacagat gcaccgcttc tggcggggcc tgccgctgca cctggacagc    900
gtggacgccg tgtacgagcg caccagcgac acaagatcg tcttcttaa aggagacagg    960
tactgggtgt tcaaggacaa taacgtagag gaaggatacc cgcgcccgt ctccgacttc   1020
```

| | |
|---|---|
| agcctcccgc ctggcggcat cgacgctgcc ttctcctggg cccacaatga caggacttat | 1080 |
| ttctttaagg accagctgta ctggcgctac gatgaccaca cgaggcacat ggaccccggc | 1140 |
| taccccgccc agagccccct gtggaggggt gtcccagca cgctggacga cgccatgcgc | 1200 |
| tggtccgacg gtgcctccta cttcttccgt ggccaggagt actggaaagt gctggatggc | 1260 |
| gagctggagg tggcacccgg gtacccacag tccacggccc gggactggct ggtgtgtgga | 1320 |
| gactcacagg ccgatggatc tgtggctgcg ggcgtgacg cggcagaggg gccccgcgcc | 1380 |
| cctccaggac aacatgacca gagccgctcg gaggacggtt acgaggtctg ctcatgcacc | 1440 |
| tctgggcat cctctccccc gggggcccca ggcccactgg tggctgccac catgctgctg | 1500 |
| ctgctgccgc cactgtcacc aggcgccctg tggacagcgg cccaggccct gacgctatga | 1560 |

<210> SEQ ID NO 107
<211> LENGTH: 1983
<212> TYPE: DNA
<213> ORGANISM: Homo sapiens
<300> PUBLICATION INFORMATION:
<302> TITLE: MMP2
<310> PATENT DOCUMENT NUMBER: NM004530

<400> SEQUENCE: 107

| | |
|---|---|
| atggaggcgc taatggcccg gggcgcgctc acgggtcccc tgagggcgct ctgtctcctg | 60 |
| ggctgcctgc tgagccacgc cgccgccgcg ccgtcgccca tcatcaagtt ccccggcgat | 120 |
| gtcgccccca aaacggacaa agagttggca gtgcaatacc tgaacacctt ctatggctgc | 180 |
| cccaaggaga gctgcaacct gtttgtgctg aaggacacac taaagaagat gcagaagttc | 240 |
| tttggactgc cccagacagg tgatcttgac cagaatacca tcgagaccat gcggaagcca | 300 |
| cgctgcggca acccagatgt ggccaactac aacttcttcc ctcgcaagcc caagtgggac | 360 |
| aagaaccaga tcacatacag gatcattggc tacacacctg atctggaccc agagacagtg | 420 |
| gatgatgcct ttgctcgtgc cttccaagtc tggagcgatg tgaccccact gcggttttct | 480 |
| cgaatccatg atggagaggc agacatcatg atcaactttg ccgctgggga gcatggcgat | 540 |
| ggatacccct ttgacggtaa ggacggactc ctggctcatg ccttcgcccc aggcactggt | 600 |
| gttgggggag actcccattt tgatgacgat gagctatgga ccttgggaga aggccaagtg | 660 |
| gtccgtgtga agtatggcaa cgccgatggg gagtactgca gttccccctt cttgttcaat | 720 |
| ggcaaggagt acaacagctg cactgatact ggccgcagcg atggcttcct ctggtgctcc | 780 |
| accacctaca actttgagaa ggatggcaag tacggcttct gtccccatga agccctgttc | 840 |
| accatgggcg gcaacgctga aggacagccc tgcaagtttc cattccgctt ccagggcaca | 900 |
| tcctatgaca gctgcaccac tgagggccgc acggatggct accgctggtg cggcaccact | 960 |
| gaggactacg accgcgacaa gaagtatggc ttctgccctg agaccgccat gtccactgtt | 1020 |
| ggtgggaact cagaaggtgc ccctgtgtc ttcccttca ctttcctggg caacaaatat | 1080 |
| gagagctgca ccagcgccgg ccgcagtgac ggaaagatgt ggtgtgcgac cacagccaac | 1140 |
| tacgatgacg accgcaagtg gggcttctgc cctgaccaag ggtacagcct gttcctcgtg | 1200 |
| gcagcccacg agtttggcca cgccatgggg ctggagcact ccaagacccc tgggccctg | 1260 |
| atggcaccca tttacaccta caccaagaac ttccgtctgt cccaggatga catcaagggc | 1320 |
| attcaggagc tctatggggc ctctcctgac attgaccttg caccggccc cacccccaca | 1380 |
| ctgggccctg tcactcctga gatctgcaaa caggacattg tatttgatgg catcgctcag | 1440 |
| atccgtggtg agatcttctt cttcaaggac cggttcattt ggcggactgt gacgccacgt | 1500 |

```
gacaagccca tggggcccct gctggtggcc acattctggc ctgagctccc ggaaaagatt    1560
gatgcggtat acgaggcccc acaggaggag aaggctgtgt tctttgcagg gaatgaatac    1620
tggatctact cagccagcac cctggagcga gggtacccca agccactgac cagcctggga    1680 ctgcccctg atgtccagcg agtggatgcc gcctttaact ggagcaaaaa caagaagaca    1740
tacatctttg ctggagacaa attctggaga tacaatgagg tgaagaagaa aatggatcct    1800
ggctttccca agctcatcgc agatgcctgg aatgccatcc ccgataacct ggatgccgtc    1860
gtggacctgc agggcggcgg tcacagctac ttcttcaagg gtgcctatta cctgaagctg    1920
gagaaccaaa gtctgaagag cgtgaagttt ggaagcatca atccgactg gctaggctgc    1980 tga                                                                  1983
```

<210> SEQ ID NO 108
<211> LENGTH: 1434
<212> TYPE: DNA
<213> ORGANISM: Homo sapiens
<300> PUBLICATION INFORMATION:
<302> TITLE: MMP2
<310> PATENT DOCUMENT NUMBER: XM006271
<300> PUBLICATION INFORMATION:
<302> TITLE: MMP3
<310> PATENT DOCUMENT NUMBER: XM006271

<400> SEQUENCE: 108

```
atgaagagtc ttccaatcct actgttgctg tgcgtggcag tttgctcagc ctatccattg      60
gatggagctg caaggggtga ggacaccagc atgaaccttg ttcagaaata tctagaaaac     120
tactacgacc tcgaaaaaga tgtgaaacag tttgttagga aaggacag tggtcctgtt      180 gttaaaaaaa tccgagaaat gcagaagttc cttggattgg aggtgacggg gaagctggac     240
tccgacactc tggaggtgat gcgcaagccc aggtgtggag ttcctgacgt tggtcacttc     300
agaacctttc ctggcatccc gaagtggagg aaaaccccacc ttacatacag gattgtgaat     360
tatacaccag atttgccaaa agatgctgtt gattctgctg ttgagaaagc tctgaaagtc     420
tgggaagagg tgactccact cacattctcc aggctgtatg aaggagggc tgatataatg     480 atctcttttg cagttagaga acatggagac ttttacccct tgatggacc tggaaatgtt     540 ttggcccatg cctatgcccc tgggccaggg attaatggag atgcccactt tgatgatgat     600
gaacaatgga caaaggatac aacagggacc aatttatttc tcgttgctgc tcatgaaatt     660
ggccactccc tgggtctctt tcactcagcc aacactgaag ctttgatgta cccactctat     720
cactcactca cagacctgac tcggttccgc ctgtctcaag atgatataaa tggcattcag     780
tccctctatg gacctcccc tgactcccct gagaccccc tggtaccac ggaacctgtc     840 cctccagaac ctgggacgcc agccaactgt gatcctgctt tgtcctttga tgctgtcagc     900
actctgaggg gagaaatcct gatctttaaa gacaggcact tttggcgcaa atccctcagg     960
aagcttgaac ctgaattgca tttgatctct tcatttttggc catctcttcc ttcaggcgtg    1020
gatgccgcat atgaagttac tagcaaggac ctcgttttca tttttaaagg aaatcaattc    1080
tgggccatca gaggaaatga ggtacgagct ggatacccaa gaggcatcca caccctaggt    1140
ttccctccaa ccgtgaggaa aatcgatgca gccatttctg ataaggaaaa gaacaaaaca    1200
tatttctttg tagaggacaa atactggaga tttgatgaga agagaaattc catggagcca    1260
ggctttccca agcaaatagc tgaagacttt ccagggattg actcaaagat tgatgctgtt    1320
tttgaagaat ttgggttctt ttatttcttt actggatctc cacagttgga gtttgaccca    1380
```

```
aatgcaaaga aagtgacaca cactttgaag agtaacagct ggcttaattg ttga          1434
```

<210> SEQ ID NO 109
<211> LENGTH: 1404
<212> TYPE: DNA
<213> ORGANISM: Homo sapiens
<300> PUBLICATION INFORMATION:
<302> TITLE: MMP8
<310> PATENT DOCUMENT NUMBER: NM002424

<400> SEQUENCE: 109

```
atgttctccc tgaagacgct tccatttctg ctcttactcc atgtgcagat ttccaaggcc     60
tttcctgtat cttctaaaga gaaaaataca aaaactgttc aggactacct ggaaaagttc    120
taccaattac caagcaacca gtatcagtct acaaggaaga atggcactaa tgtgatcgtt    180
gaaaagctta agaaaatgca gcgattttt gggttaatg tgacggggaa gccaaatgag      240
gaaactctgg acatgatgaa aaagcctcgc tgtggagtgc ctgacagtgg tggttttatg    300
ttaaccccag gaaaccccaa gtgggaacgc actaacttga cctacaggat cgaaaactat    360
accccacagc tgtcagaggc tgaggtagaa agagctatca aggatgcctt tgaactctgg    420
agtgttgcat cacctctcat cttcaccagg atctcacagg gagaggcaga tatcaacatt    480
gcttttttacc aaagagatca cggtgacaat tctccatttg atggacccaa tggaatcctt    540
gctcatgcct tcagccagg ccaaggtatt ggaggagatg ctcatttga tgccgaagaa       600
acatggacca cacctccgc aaattacaac ttgtttcttg ttgctgctca tgaatttggc      660
cattctttgg ggctcgctca ctcctctgac cctggtgcct tgatgtatcc caactatgct    720
ttcagggaaa ccagcaacta ctcactccct caagatgaca tcgatggcat tcaggccatc    780
tatggacttt caagcaaccc tatccaacct actggaccaa gcacacccaa accctgtgac    840
cccagtttga catttgatgc tatcaccaca ctccgtggag aaatactttt ctttaaagac    900
aggtacttct ggagaaggca tcctcagcta caaagagtcg aaatgaattt tatttctcta    960
ttctggccat cccttccaac tggtatacag gctgcttatg aagattttga cagagacctc    1020
attttcctat ttaaaggcaa ccaatactgg gctctgagtg ctatgatat tctgcaaggt    1080
tatcccaagg atatatcaaa ctatggcttc cccagcagcg tccaagcaat tgacgcagct    1140
gttttctaca gaagtaaaac atacttcttt gtaaatgacc aattctggag atatgataac    1200
caaagacaat tcatggagcc aggttatccc aaaagcatat caggtgcctt tccaggaata    1260
gagagtaaag ttgatgcagt tttccagcaa gaacatttct ccatgtcttt cagtggacca    1320
agatattacg catttgatct tattgctcag agagttacca gagttgcaag aggcaataaa    1380
tggcttaact gtagatatgg ctga                                            1404
```

<210> SEQ ID NO 110
<211> LENGTH: 2124
<212> TYPE: DNA
<213> ORGANISM: Homo sapiens
<300> PUBLICATION INFORMATION:
<302> TITLE: MMP9
<310> PATENT DOCUMENT NUMBER: XM009491

<400> SEQUENCE: 110

```
atgagcctct ggcagcccct ggtcctggtg ctcctggtgc tgggctgctg ctttgctgcc     60
cccagacagc gccagtccac ccttgtgctc ttccctggag acctgagaac caatctcacc    120
gacaggcagc tggcagagga atacctgtac cgctatggtt acactcgggt ggcagagatg    180
cgtggagagt cgaaatctct ggggcctgcg ctgctgcttc tccagaagca actgtccctg    240
```

```
cccgagaccg gtgagctgga tagcgccacg ctgaaggcca tgcgaacccc acggtgcggg     300
gtcccagacc tgggcagatt ccaaacctt gagggcgacc tcaagtggca ccaccacaac     360
atcacctatt ggatccaaaa ctactcggaa gacttgccgc gggcggtgat tgacgacgcc     420
tttgcccgcg ccttcgcact gtggagcgcg gtgacgccgc tcaccttcac tcgcgtgtac     480
agccgggacg cagacatcgt catccagttt ggtgtcgcgg agcacggaga cgggtatccc     540
ttcgacggga aggacgggct cctggcacac gcctttcctc ctggcccegg cattcaggga     600 gacgcccatt cgacgatga cgagttgtgg tccctgggca agggcgtcgt ggttccaact     660
cggtttggaa acgcagatgg cgcggcctgc cacttcccct tcatcttcga gggccgctcc     720
tactctgcct gcaccaccga cggtcgctcc gacggcttgc cctggtgcag taccacggcc     780
aactacgaca ccgacgaccg gtttggcttc tgccccagcg agagactcta cacccaggac     840
ggcaatgctg atgggaaacc ctgccagttt ccattcatct tccaaggcca atcctactcc     900
gcctgcacca cggacggtcg ctccgacggc tacgcctggt gcgccaccac cgccaactac     960
gaccgggaca agctcttcgg cttctgcccg acccgagctg actcgacggt gatggggggc     1020
aactcggcgg gggagctgtg cgtcttcccc ttcactttcc tgggtaagga gtactcgacc     1080
tgtaccagcg agggccgcgg agatgggcgc ctctggtgcg ctaccacctc gaactttgac     1140
agcgacaaga gtggggctt ctgcccggac caaggataca gtttgttcct cgtggcggcg     1200
catgagttcg ccacgcgct gggcttagat cattcctcag tgccggaggc gctcatgtac     1260
cctatgtacc gcttcactga ggggcccccc ttgcataagg acgacgtgaa tggcatccgg     1320
cacctctatg gtcctcgccc tgaacctgag ccacggcctc caaccaccac cacaccgcag     1380
cccacgcctc cccgacggt ctgccccacc ggaccccca ctgtccaccc ctcagagcgc     1440
cccacagctg gccccacagg tccccctca gctggcccca caggtcccccc cactgctggc     1500 ccttctacgg ccactactgt gcctttgagt ccggtggacg atgcctgcaa cgtgaacatc     1560
ttcgacgcca tcgcggagat tgggaaccag ctgtatttgt tcaaggatgg gaagtactgg     1620
cgattctctg agggcagggg gagccggccg cagggccct tccttatcgc cgacaagtgg     1680
cccgcgctgc cccgcaagct ggactcggtc tttgaggagc ggctctccaa gaagcttttc     1740
ttcttctctg ggcgccaggt gtgggtgtac acaggcgcgt cggtgctggg cccgaggcgt     1800
ctggacaagc tgggcctggg agccgacgtg gcccaggtga ccggggccct ccggagtggc     1860
agggggaaga tgctgctgtt cagcgggcgg cgcctctgga ggttcgacgt gaaggcgcag     1920
atggtggatc cccggagcgc cagcgaggtg accggatgt tccccggggt gcctttggac     1980
acgcacgacg tcttccagta ccgagagaaa gcctatttct gccaggaccg cttctactgg     2040
cgcgtgagtt cccggagtga gttgaaccag gtggaccaag tgggctacgt gacctatgac     2100
atcctgcagt gccctgagga ctag                                            2124
```

<210> SEQ ID NO 111
<211> LENGTH: 2019
<212> TYPE: DNA
<213> ORGANISM: Homo sapiens
<300> PUBLICATION INFORMATION:
<302> TITLE: PKC alpha
<310> PATENT DOCUMENT NUMBER: NM002737

<400> SEQUENCE: 111

```
atggctgacg ttttcccggg caacgactcc acggcgtctc aggacgtggc caaccgcttc     60
gcccgcaaag gggcgctgag gcagaagaac gtgcacgagg tgaaggacca caattcatc    120
```

```
gcgcgcttct tcaagcagcc caccttctgc agccactgca ccgacttcat ctgggggttt      180
gggaaacaag gcttccagtg ccaagtttgc tgttttgtgg tccacaagag gtgccatgaa      240
tttgttactt tttcttgtcc gggtgcggat aagggacccg acactgatga ccccaggagc      300
aagcacaagt tcaaaatcca cacttacgga agccccacct tctgcgatca ctgtgggtca      360
ctgctctatg gacttatcca tcaagggatg aaatgtgaca cctgcgatat gaacgttcac      420
aagcaatgcg tcatcaatgt ccccagcctc tgcggaatgg atcacactga agaggggg       480 cggatttacc taaaggctga ggttgctgat gaaaagctcc atgtcacagt acgagatgca      540
aaaaatctaa tccctatgga tccaaacggg ctttcagatc cttatgtgaa gctgaaactt      600
attcctgatc caagaatga agcaagcaa aaaccaaaa ccatccgctc cacactaaat        660
ccgcagtgga atgagtcctt tacattcaaa ttgaaacctt cagacaaaga ccgacgactg      720
tctgtagaaa tctgggactg ggatcgaaca acaaggaatg acttcatggg atcccttcc      780 tttggagttt cggagctgat gaagatgccg gccagtggat ggtacaagtt gcttaaccaa      840
gaagaaggtg agtactacaa cgtacccatt ccggaagggg acgaggaagg aaacatggaa      900
ctcaggcaga aattcgagaa agccaaactt ggccctgctg caacaaagt catcagtccc       960 tctgaagaca ggaaacaacc ttccaacaac cttgaccgag tgaaactcac ggacttcaat     1020
ttcctcatgg tgttgggaaa ggggagtttt ggaaaggtga tgcttgccga caggaagggc     1080
acagaagaac tgtatgcaat caaaatcctg aagaaggatg tggtgattca ggatgatgac     1140
gtggagtgca ccatggtaga aaagcgagtc ttggccctgc ttgacaaacc cccgttcttg     1200
acgcagctgc actcctgctt ccagacagtg gatcggctgt acttcgtcat ggaatatgtc     1260
aacggtgggg acctcatgta ccacattcag caagtaggaa aatttaagga accacaagca     1320
gtattctatg cggcagagat ttccatcgga ttgttctttc ttcataaaag aggaatcatt     1380
tatagggatc tgaagttaga taacgtcatg ttggattcag aaggacatat caaaattgct     1440
gactttggga tgtgcaagga acacatgatg gatgagtca cgaccaggac cttctgtggg     1500
actccagatt atatcgcccc agagataatc gcttatcagc cgtatggaaa atctgtggac     1560
tggtgggcct atggcgtcct gttgtatgaa atgcttgccg ggcagcctcc atttgatggt     1620
gaagatgaag acgagctatt tcagtctatc atggagcaca cgtttccta tccaaaatcc     1680 ttgtccaagg aggctgtttc tatctgcaaa ggactgatga ccaaacaccc agccaagcgg     1740
ctgggctgtg ggcctgaggg ggagagggac gtgagagagc atgccttctt ccggaggatc     1800
gactgggaaa aactggagaa cagggagatc cagccaccat tcaagcccaa agtgtgtggc     1860
aaaggagcag agaactttga caagttcttc acacgaggac agcccgtctt aacaccacct     1920
gatcagctgg ttattgctaa catagaccag tctgattttg aagggttctc gtatgtcaac     1980
ccccagtttg tgcaccccat cttacagagt gcagtatga                            2019
```

<210> SEQ ID NO 112
<211> LENGTH: 2022
<212> TYPE: DNA
<213> ORGANISM: Homo sapiens
<300> PUBLICATION INFORMATION:
<302> TITLE: PKC beta
<310> PATENT DOCUMENT NUMBER: X07109

<400> SEQUENCE: 112

```
atggctgacc cggctgcggg gccgccgccg agcgagggcg aggagagcac cgtgcgcttc      60
gcccgcaaag gcgccctccg gcagaagaac gtgcatgagg tcaagaacca caaattcacc     120
```

```
gcccgcttct tcaagcagcc caccttctgc agccactgca ccgacttcat ctggggcttc    180
gggaagcagg gattccagtg ccaagtttgc tgctttgtgg tgcacaagcg gtgccatgaa    240
tttgtcacat tctcctgccc tggcgctgac aagggtccag cctccgatga ccccgcagc    300 aaacacaagt ttaagatcca cacgtactcc agccccacgt tttgtgacca ctgtgggtca    360
ctgctgtatg gactcatcca ccaggggatg aaatgtgaca cctgcatgat gaatgtgcac    420
aagcgctgcg tgatgaatgt tcccagcctg tgtggcacgg accacacgga cgccgcggc     480 cgcatctaca tccaggccca catcgacagg gacgtcctca ttgtcctcgt aagagatgct    540
aaaaaccttg tacctatgga ccccaatggc ctgtcagatc cctacgtaaa actgaaactg    600
attcccgatc ccaaaagtga gagcaaacag aagaccaaaa ccatcaaatg ctccctcaac    660
cctgagtgga atgagacatt tagatttcag ctgaaagaat cggacaaaga cagaagactg    720
tcagtagaga tttgggattg ggatttgacc agcaggaatg acttcatggg atctttgtcc    780
tttgggattt ctgaacttca gaaggccagt gttgatggct ggtttaagtt actgagccag    840
gaggaaggcg agtacttcaa tgtgcctgtg ccaccagaag gaagtgaggc caatgaagaa    900
ctgcggcaga aatttgagag ggccaagatc agtcagggaa ccaaggtccc ggaagaaaag    960
acgaccaaca ctgtctccaa atttgacaac aatggcaaca gagaccggat gaaactgacc   1020 gatttttaact tcctaatggt gctggggaaa ggcagctttg gcaaggtcat gctttcagaa   1080
cgaaaaggca cagatgagct ctatgctgtg aagatcctga agaaggacgt tgtgatccaa   1140
gatgatgacg tggagtgcac tatggtggag aagcgggtgt tggccctgcc tgggaagccg   1200
cccttcctga cccagctcca ctcctgcttc cagaccatgg accgcctgta ctttgtgatg   1260
gagtacgtga atggggcga cctcatgtat cacatccagc aagtcggccg gttcaaggag   1320
ccccatgctg tattttacgc tgcagaaatt gccatcggtc tgttcttctt acagagtaag   1380
ggcatcattt accgtgacct aaaacttgac aacgtgatgc tcgattctga gggacacatc   1440
aagattgccg attttggcat gtgtaaggaa acatctgggg atggggtgac aaccaagaca   1500
ttctgtggca ctccagacta catcgccccc gagataattg cttatcagcc ctatgggaag   1560
tccgtggatt ggtgggcatt tggagtcctg ctgtatgaaa tgttggctgg gcaggcaccc   1620
tttgaagggg aggatgaaga tgaactcttc caatccatca tggaacacaa cgtagcctat   1680
cccaagtcta tgtccaagga agctgtgcc atctgcaaag gctgatgac caaacaccca   1740 ggcaaacgtc tgggttgtgg acctgaaggc gaacgtgata tcaaagagca tgcattttc    1800 cggtatattg attgggagaa acttgaacgc aaagagatcc agccccctta taagccaaaa    1860
gcttgtgggc gaaatgctga aaacttcgac cgattttttca cccgccatcc accagtccta    1920
acacctcccg accaggaagt catcaggaat attgaccaat cagaattcga aggattttcc    1980
tttgttaact ctgaattttt aaaacccgaa gtcaagagct aa                       2022
```

<210> SEQ ID NO 113
<211> LENGTH: 2031
<212> TYPE: DNA
<213> ORGANISM: Homo sapiens
<300> PUBLICATION INFORMATION:
<302> TITLE: PKC delta
<310> PATENT DOCUMENT NUMBER: NM006254

<400> SEQUENCE: 113

```
atggcgccgt tcctgcgcat cgccttcaac tcctatgagc tgggctccct gcaggccgag     60
gacgaggcga accagccctt ctgtgccgtg aagatgaagg aggcgctcag cacagagcgt    120
```

```
gggaaaacac tggtgcagaa gaagccgacc atgtatcctg agtggaagtc gacgttcgat      180
gcccacatct atgagggggcg cgtcatccag attgtgctaa tgcgggcagc agaggagcca     240
gtgtctgagg tgaccgtggg tgtgtcggtg ctggccgagc gctgcaagaa gaacaatggc     300
aaggctgagt tctggctgga cctgcagcct caggccaagg tgttgatgtc tgttcagtat     360
ttcctggagg acgtggattg caaacaatct atgcgcagtg aggacgaggc caagttccca     420
acgatgaacc gccgcggagc catcaaacag gccaaaatcc actacatcaa gaaccatgag     480
tttatcgcca ccttctttgg gcaacccacc ttctgttctg tgtgcaaaga ctttgtctgg     540
ggcctcaaca agcaaggcta caaatgcagg caatgtaacg ctgccatcca caagaaatgc     600
atcgacaaga tcatcggcag atgcactggc accgcggcca acagccggga cactatattc     660
cagaaagaac gcttcaacat cgacatgccg caccgcttca aggttcacaa ctacatgagc     720
cccaccttct gtgaccactg cggcagcctg ctctggggac tggtgaagca gggattaaag     780
tgtgaagact gcggcatgaa tgtgcaccat aaatgccggg agaaggtggc caacctctgc     840
ggcatcaacc agaagctttt ggctgaggcc ttgaaccaag tcacccagag agcctcccgg     900
agatcagact cagcctcctc agagcctgtt gggatatatc agggtttcga agaagaccc     960 ggagttgctg gggaggacat gcaagacaac agtgggacct acggcaagat ctgggagggc    1020
agcagcaagt gcaacatcaa caacttcatc ttccacaagg tcctgggcaa aggcagcttc    1080
gggaaggtgc tgcttggaga gctgaagggc agaggagagt actctgccat caaggccctc    1140
aagaaggatg tggtcctgat cgacgacgac gtggagtgca ccatggttga aagcggtgtg    1200
ctgacacttg ccgcagagaa tccctttctc acccacctca tctgcacctt ccagaccaag    1260
gaccacctgt tctttgtgat ggagttcctc aacggggggg acctgatgta ccacatccag    1320
gacaaaggcc gctttgaact ctaccgtgcc acgttttatg ccgctgagat aatgtgtgga    1380
ctgcagtttc tacacagcaa gggcatcatt tacagggacc tcaaactgga caatgtgctg    1440
ttggaccggg atgccacat caagattgcc gactttggga tgtgcaaaga gaacatattc    1500
ggggagagcc gggccagcac cttctgcggc acccctgact atatcgcccc tgagatccta    1560
cagggcctga agtacacatt ctctgtggac tggtggtctt tcggggtcct tctgtacgag    1620
atgctcattg gccagtcccc cttccatggt gatgatgagg atgaactctt cgagtccatc    1680
cgtgtggaca cgccacatta tccccgctgg atcaccaagg agtccaagga catcctggag    1740
aagctctttg aaagggaacc aaccaagagg ctgggaatga cgggaaacat caaaatccac    1800
cccttcttca agaccataaa ctggactctg ctggaaaagc ggaggttgga gccaccccttc    1860 aggcccaaag tgaagtcacc cagagactac agtaactttg accaggagtt cctgaacgag    1920
aaggcgcgcc tctcctacag cgacaagaac ctcatcgact ccatggacca gtctgcattc    1980
gctggcttct cctttgtgaa ccccaaattc gagcacctcc tggaagattg a              2031
```

<210> SEQ ID NO 114
<211> LENGTH: 2049
<212> TYPE: DNA
<213> ORGANISM: Homo sapiens
<300> PUBLICATION INFORMATION:
<302> TITLE: PKC eta
<310> PATENT DOCUMENT NUMBER: NM006255

<400> SEQUENCE: 114

```
atgtcgtctg gcaccatgaa gttcaatggc tatttgaggg tccgcatcgg tgaggcagtg      60
gggctgcagc ccacccgctg gtccctgcgc cactcgctct tcaagaaggg ccaccagctg     120
```

```
ctggacccct atctgacggt gagcgtggac caggtgcgcg tgggccagac cagcaccaag      180
cagaagacca acaaacccac gtacaacgag gagttttgcg ctaacgtcac cgacggcggc      240
cacctcgagt tggccgtctt ccacgagacc cccctgggct acgacttcgt ggccaactgc      300
accctgcagt tccaggagct cgtcggcacg accggcgcct cggacacctt cgagggttgg      360
gtggatctcg agccagaggg gaaagtattt gtggtaataa cccttaccgg gagtttcact      420
gaagctactc tccagagaga ccggatcttc aaacatttta ccaggaagcg ccaaagggct      480
atgcgaaggc gagtccacca gatcaatgga cacaagttca tggccacgta tctgaggcag      540
cccacctact gctctcactg cagggagttt atctggggag tgtttgggaa acagggttat      600
cagtgccaag tgtgcacctg tgtcgtccat aaacgctgcc atcatctaat tgttacagcc      660
tgtacttgcc aaaacaatat taacaaagtg gattcaaaga ttgcagaaca gaggttcggg      720
atcaacatcc cacacaagtt cagcatccac aactacaaag tgccaacatt ctgcgatcac      780
tgtggctcac tgctctgggg aataatgcga caaggacttc agtgtaaaat atgtaaaatg      840
aatgtgcata ttcgatgtca agcgaacgtg gcccctaact gtggggtaaa tgcggtggaa      900
cttgccaaga ccctgcagg gatgggtctc caacccggaa atatttctcc aacctcgaaa      960
ctcgtttcca gatcgaccct aagacgacag ggaaaggaga gcagcaaaga aggaaatggg     1020
attggggtta attcttccaa ccgacttggt atcgacaact ttgagttcat ccgagtgttg     1080
gggaagggga gttttgggaa ggtgatgctt gcaagagtaa aagaaacagg agacctctat     1140
gctgtgaagg tgctgaagaa ggacgtgatt ctgctggatg atgatgtgga atgcaccatg     1200
accgagaaaa ggatcctgtc tctggcccgc aatcacccct tcctcactca gttgttctgc     1260
tgctttcaga cccccgatcg tctgtttttt gtgatggagt ttgtgaatgg gggtgacttg     1320
atgttccaca ttcagaagtc tcgtcgtttt gatgaagcac gagctcgctt ctatgctgca     1380
gaaatcattt cggctctcat gttcctccat gataaaggaa tcatctatag agatctgaaa     1440
ctggacaatg tcctgttgga ccacgagggt cactgtaaac tggcagactt cggaatgtgc     1500
aaggagggga tttgcaatgg tgtcaccacg gccacattct gtggcacgcc agactatatc     1560
gctccagaga tcctccagga aatgctgtac gggcctgcag tagactggtg ggcaatgggc     1620
gtgttgctct atgagatgct ctgtggtcac gcgccttttg aggcagagaa tgaagatgac     1680
ctctttgagg ccatactgaa tgatgaggtg gtctacccta cctggctcca tgaagatgcc     1740
acagggatcc taaaatcttt catgaccaag aaccccacca tgcgcttggg cagcctgact     1800
cagggaggcg agcacgccat cttgagacat ccttttttta aggaaatcga ctgggcccag     1860
ctgaaccatc gccaaataga accgccttc agacccagaa tcaaatcccg agaagatgtc     1920
agtaattttg accctgactt cataaaggaa gagccagttt taactccaat tgatgaggga     1980
catcttccaa tgattaacca ggatgagttt agaaactttt cctatgtgtc tccagaattg     2040
caaccatag                                                             2049
```

<210> SEQ ID NO 115
<211> LENGTH: 948
<212> TYPE: DNA
<213> ORGANISM: Homo sapiens
<300> PUBLICATION INFORMATION:
<302> TITLE: PKC epsilon
<310> PATENT DOCUMENT NUMBER: XM002370

<400> SEQUENCE: 115

```
atgttggcag aactcaaggg caaagatgaa gtatatgctg tgaaggtctt aaagaaggac       60
```

| | |
|---|---|
| gtcatccttc aggatgatga cgtggactgc acaatgacag agaagaggat tttggctctg | 120 |
| gcacggaaac acccgtacct tacccaactc tactgctgct tccagaccaa ggaccgcctc | 180 |
| ttttcgtca tggaatatgt aaatggtgga gacctcatgt ttcagattca gcgctcccga | 240 |
| aaattcgacg agcctcgttc acggttctat gctgcagagg tcacatcggc cctcatgttc | 300 |
| ctccaccagc atggagtcat ctacagggat ttgaaactgg acaacatcct tctggatgca | 360 |
| gaaggtcact gcaagctggc tgacttcggg atgtgcaagg aagggattct gaatggtgtg | 420 |
| acgaccacca cgttctgtgg gactcctgac tacatagctc ctgagatcct gcaggagttg | 480 |
| gagtatggcc cctccgtgga ctggtgggcc ctggggtgc tgatgtacga gatgatggct | 540 |
| ggacagcctc cctttgaggc cgacaatgag gacgacctat ttgagtccat cctccatgac | 600 |
| gacgtgctgt acccagtctg gctcagcaag gaggctgtca gcatcttgaa agctttcatg | 660 |
| acgaagaatc cccacaagcg cctgggctgt gtggcatcgc agaatggcga ggacgccatc | 720 |
| aagcagcacc cattcttcaa agagattgac tgggtgctcc tggagcagaa aagatcaag | 780 |
| ccacccttca aaccacgcat taaaaccaaa agagacgtca ataattttga ccaagacttt | 840 |
| acccgggaag agccggtact caccccttgtg gacgaagcaa ttgtaaagca gatcaaccag | 900 |
| gaggaattca aaggtttctc ctactttggt gaagacctga tgccctga | 948 |

<210> SEQ ID NO 116
<211> LENGTH: 1764
<212> TYPE: DNA
<213> ORGANISM: Homo sapiens
<300> PUBLICATION INFORMATION:
<302> TITLE: PKC iota
<310> PATENT DOCUMENT NUMBER: NM002740

<400> SEQUENCE: 116

| | |
|---|---|
| atgtcccaca cggtcgcagg cggcggcagc ggggaccatt cccaccaggt ccgggtgaaa | 60 |
| gcctactacc gcggggatat catgataaca cattttgaac cttccatctc ctttgagggc | 120 |
| ctttgcaatg aggttcgaga catgtgttct tttgacaacg aacagctctt caccatgaaa | 180 |
| tggatagatg aggaaggaga cccgtgtaca gtatcatctc agttggagtt agaagaagcc | 240 |
| tttagacttt atgagctaaa caaggattct gaactcttga ttcatgtgtt cccttgtgta | 300 |
| ccagaacgtc ctgggatgcc ttgtccagga gaagataaat ccatctaccg tagaggtgca | 360 |
| cgccgctgga gaaagcttta ttgtgccaat ggccacactt tccaagccaa gcgtttcaac | 420 |
| aggcgtgctc actgtgccat ctgcacagac cgaatatggg gacttggacg ccaaggatat | 480 |
| aagtgcatca actgcaaact cttggttcat aagaagtgcc ataaactcgt cacaattgaa | 540 |
| tgtgggcggc attctttgcc acaggaacca gtgatgccca tggatcagtc atccatgcat | 600 |
| tctgaccatg cacagacagt aattccatat aatccttcaa gtcatgagag tttggatcaa | 660 |
| gttggtgaag aaaagaggc aatgaacacc agggaaagtg gcaaagcttc atccagtcta | 720 |
| ggtcttcagg atttttgattt gctccgggta ataggaagag gaagttatgc caaagtactg | 780 |
| ttggttcgat taaaaaaaac agatcgtatt tatgcaatga agttgtgaa aaagagctt | 840 |
| gttaatgatg atgaggatat tgattgggta cagacagaga agcatgtgtt tgagcaggca | 900 |
| tccaatcatc ctttccttgt tgggctgcat tcttgctttc agacagaaag cagattgttc | 960 |
| tttgttatag agtatgtaaa tggaggagac ctaatgtttc atatgcagcg acaaagaaaa | 1020 |
| cttcctgaag aacatgccag attttactct gcagaaatca gtctagcatt aaattatctt | 1080 |
| catgagcgag ggataattta tagagatttg aaactggaca atgtattact ggactctgaa | 1140 |

```
ggccacatta aactcactga ctacggcatg tgtaaggaag gattacggcc aggagataca    1200
accagcactt tctgtggtac tcctaattac attgctcctg aaattttaag aggagaagat    1260
tatggtttca gtgttgactg gtgggctctt ggagtgctca tgtttgagat gatggcagga    1320
aggtctccat ttgatattgt tgggagctcc gataaccctg accagaacac agaggattat    1380
ctcttccaag ttattttgga aaaacaaatt cgcataccac gttctctgtc tgtaaaagct    1440
gcaagtgttc tgaagagttt tcttaataag gaccctaagg aacgattggg ttgtcatcct    1500
caaacaggat ttgctgatat tcagggacac ccgttcttcc gaaatgttga ttgggatatg    1560
atggagcaaa acaggtggt  acctcccttt aaaccaaata tttctgggga atttggtttg    1620
gacaactttg attctcagtt tactaatgaa cctgtccagc tcactccaga tgacgatgac    1680
attgtgagga agattgatca gtctgaattt gaaggttttg agtatatcaa tcctcttttg    1740
atgtctgcag aagaatgtgt ctga                                           1764

<210> SEQ ID NO 117
<211> LENGTH: 2451
<212> TYPE: DNA
<213> ORGANISM: Homo sapiens
<300> PUBLICATION INFORMATION:
<302> TITLE: PKC mu
<310> PATENT DOCUMENT NUMBER: XM007234

<400> SEQUENCE: 117
atgtatgata agatcctgct ttttcgccat gaccctacct ctgaaaacat ccttcagctg      60
gtgaaagcgg ccagtgatat ccaggaaggc gatcttattg aagtggtctt gtcagcttcc     120
gccacctttg aagactttca gattcgtccc cacgctctct tgttcattc  atacagagct     180 ccagctttct gtgatcactg tggagaaatg ctgtgggggc tggtacgtca aggtcttaaa     240
tgtgaagggt gtggtctgaa ttaccataag agatgtgcat ttaaaatacc caacaattgc     300
agcggtgtga ggcggagaag gctctcaaac gtttccctca ctgggggtcag caccatccgc     360 acatcatctg ctgaactctc tacaagtgcc cctgatgagc cccttctgca aaaatcacca     420
tcagagtcgt ttattggtcg agagaagagg tcaaattctc aatcatacat tggacgacca     480
attcaccttg acaagatttt tgatgtctaa agttaaagtgc cgcacacatt tgtcatccac     540
tcctacaccc ggcccacagt gtgccagtac tgcaagaagc ttctgaaggg cttttcagg     600 cagggcttgc agtgcaaaga ttgcagattc aactgccata acgttgtgc  accgaaagta     660 ccaaacaact gccttggcga agtgaccatt aatggagatt tgcttagccc tggggcagag     720
tctgatgtgg tcatggaaga agggagtgat gacaatgata gtgaaaggaa cagtgggctc     780
atggatgata tggaagaagc aatggtccaa gatgcagaga tggcaatggc agagtgccag     840
aacgacagtg gcgagatgca agatccagac ccagaccacg aggacgccaa cagaaccatc     900
agtccatcaa caagcaacaa tatcccactc atgagggtag tgcagtctgt caaacacacg     960
aagaggaaaa gcagcacagt catgaaagaa ggatggatgg tccactacac cagcaaggac    1020
acgctgcgga acggcacta  ttggagattg atagcaaat  gtattaccct ctttcagaat    1080
gacacaggaa gcaggtacta caaggaaatt cctttatctg aaattttgtc tctggaacca    1140
gtaaaaactt cagctttaat tcctaatggg gccaatcctc attgtttcga aatcactacg    1200
gcaaatgtag tgtattatgt gggagaaaat gtggtcaatc cttccagccc atcaccaaat    1260
aacagtgttc tcaccagtgg cgttggtgca gatgtggcca ggatgtggga gatagccatc    1320
cagcatgccc ttatgcccgt cattcccaag ggctcctccg tgggtacagg aaccaacttg    1380
```

```
cacagagata tctctgtgag tatttcagta tcaaattgcc agattcaaga aaatgtggac    1440
atcagcacag tatatcagat ttttcctgat gaagtactgg gttctggaca gtttggaatt    1500
gtttatggag gaaaacatcg taaaacagga agagatgtag ctattaaaat cattgacaaa    1560
ttacgatttc caacaaaaca agaaagccag cttcgtaatg aggttgcaat tctacagaac    1620
cttcatcacc ctggtgttgt aaatttggag tgtatgtttg agacgcctga aagagtgttt    1680
gttgttatgg aaaaactcca tggagacatg ctggaaatga tcttgtcaag tgaaaagggc    1740
aggttgccag agcacataac gaagttttta attactcaga tactcgtggc tttgcggcac    1800
cttcatttta aaaatatcgt tcactgtgac ctcaaaccag aaaatgtgtt gctagcctca    1860
gctgatcctt ttcctcaggt gaaactttgt gattttggtt ttgcccggat cattggagag    1920
aagtctttcc ggaggtcagt ggtgggtacc cccgcttacc tggctcctga ggtcctaagg    1980
aacaagggct acaatcgctc tctagacatg tggtctgttg gggtcatcat ctatgtaagc    2040
ctaagcggca cattcccatt taatgaagat gaagacatac acgaccaaat tcagaatgca    2100
gctttcatgt atccaccaaa tccctggaag gaaatatctc atgaagccat tgatcttatc    2160
aacaatttgc tgcaagtaaa aatgagaaag cgctacagtg tggataagac cttgagccac    2220
ccttggctac aggactatca gacctggtta gatttgcgag agctggaatg caaaatcggg    2280
gagcgctaca tcacccatga aagtgatgac ctgaggtggg agaagtatgc aggcgagcag    2340
gggctgcagt accccacaca cctgatcaat ccaagtgcta gccacagtga cactcctgag    2400
actgaagaaa cagaaatgaa agccctcggt gagcgtgtca gcatcctatg a            2451
```

<210> SEQ ID NO 118
<211> LENGTH: 2673
<212> TYPE: DNA
<213> ORGANISM: Homo sapiens
<300> PUBLICATION INFORMATION:
<302> TITLE: PKC nu
<310> PATENT DOCUMENT NUMBER: NM005813

<400> SEQUENCE: 118

```
atgtctgcaa ataattcccc tccatcagcc cagaagtctg tattacccac agctattcct      60
gctgtgcttc cagctgcttc tccgtgttca agtcctaaga cgggactctc tgcccgactc     120
tctaatggaa gcttcagtgc accatcactc accaactcca gaggctcagt gcatacagtt     180
tcatttctac tgcaaattgg cctcacacgg gagagtgtta ccattgaagc ccaggaactg     240 tcttatctg ctgtcaagga tcttgtgtgc tccatagttt atcaaaagtt tccagagtgt     300
ggattctttg gcatgtatga caaaattctt ctctttcgcc atgacatgaa ctcagaaaac     360
attttgcagc tgattacctc agcagatgaa atacatgaag gagacctagt ggaagtggtt     420
ctttcagctt tagccacagt agaagacttc cagattcgtc cacatactct ctatgtacat     480
tcttacaaag ctcctacttt ctgtgattac tgtggtgaga tgctgtgggg attggtacgt     540
caaggactga aatgtgaagg ctgtggatta aattaccata acgatgtgc cttcaagatt     600 ccaaataact gtagtggagt aagaaagaga cgtctgtcaa atgtatcttt accaggaccc     660
ggcctctcag ttccaagacc cctacagcct gaatatgtag cccttcccag tgaagagtca     720
catgtccacc aggaaccaag taagagaatt ccttcttgga gtggtcgccc aatctggatg     780
gaaaagatgg taatgtgcag agtgaaagtt ccacacacat tgctgttca ctcttacacc     840 cgtcccacga tatgtcagta ctgcaagcgg ttactgaaag gcctctttcg ccaaggaatg     900
cagtgtaaag attgcaaatt caactgccat aaacgctgtg catcaaaagt accaagagac     960
```

```
tgccttggag aggttacttt caatggagaa ccttccagtc tgggaacaga tacagatata    1020
ccaatggata ttgacaataa tgacataaat agtgatagta gtcggggttt ggatgacaca    1080
gaagagccat cacccccaga agataagatg ttcttcttgg atccatctga tctcgatgtg    1140
gaaagagatg aagaagccgt taaaacaatc agtccatcaa caagcaataa tattccgcta    1200
atgagggttg tacaatccat caagcacaca aagaggaaga gcagcacaat ggtgaaggaa    1260
gggtggatgg tccattacac cagcagggat aacctgagaa agaggcatta ttggagactt    1320
gacagcaaat gtctaacatt atttcagaat gaatctggat caaagtatta taggaaatt     1380 ccactttcag aaattctccg catatcttca ccacgagatt tcacaaacat ttcacaaggc    1440
agcaatccac actgttttga aatcattact gatactatgg tatacttcgt tggtgagaac    1500
aatggggaca gctctcataa tcctgttctt gctgccactg gagttggact tgatgtagca    1560
cagagctggg aaaaagcaat tcgccaagcc ctcatgcctg ttactcctca agcaagtgtt    1620
tgcacttctc cagggcaagg gaaagatcac aaagatttgt ctacaagtat ctctgtatct    1680
aattgtcaga ttcaggagaa tgtggatatc agtactgttt accagatctt gcagatgag     1740 gtgcttggtt caggccagtt tggcatcgtt tatggaggaa acatagaaa gactgggagg     1800 gatgtggcta ttaaagtaat tgataagatg agattcccca caaaacaaga aagtcaactc    1860
cgtaatgaag tggctatttt acagaatttg caccatcctg ggattgtaaa cctgaatgt     1920 atgtttgaaa ccccagaacg agtctttgta gtaatggaaa agctgcatgg agatatgttg    1980
gaaatgattc tatccagtga gaaaagtcgg cttccagaac gaattactaa attcatggtc    2040
acacagatac ttgttgcttt gaggaatctg catttttaaga atattgtgca ctgtgattta    2100
aagccagaaa atgtgctgct tgcatcagca gagccatttc ctcaggtgaa gctgtgtgac    2160
tttggatttg cacgcatcat tggtgaaaag tcattcagga gatctgtggt aggaactcca    2220
gcatacttag cccctgaagt tctccggagc aaaggttaca accgttccct agatatgtgg    2280
tcagtgggag ttatcatcta tgtgagcctc agtggcacat ttccttttaa tgaggatgaa    2340
gatataaatg accaaatcca aaatgctgca tttatgtacc caccaaatcc atggagagaa    2400
atttctggtg aagcaattga tctgataaac aatctgcttc aagtgaagat gagaaaacgt    2460
tacagtgttg acaaatctct tagtcatccc tggctacagg actatcagac ttggcttgac    2520
cttagagaat ttgaaactcg cattggagaa cgttacatta cacatgaaag tgatgatgct    2580
cgctgggaaa tacatgcata cacacataac cttgtatacc caaagcactt cattatggct    2640
cctaatccag atgatatgga agaagatcct taa                                 2673
```

<210> SEQ ID NO 119
<211> LENGTH: 2121
<212> TYPE: DNA
<213> ORGANISM: Homo sapiens
<300> PUBLICATION INFORMATION:
<302> TITLE: PKC tau
<310> PATENT DOCUMENT NUMBER: NM006257

<400> SEQUENCE: 119

```
atgtcgccat tcttcggat tggcttgtcc aactttgact gcgggtcctg ccagtcttgt       60
cagggcgagg ctgttaaccc ttactgtgct gtgctcgtca agagtatgt cgaatcagag      120 aacgggcaga tgtatatcca gaaaaagcct accatgtacc caccctggga cagcactttt     180
gatgcccata tcaacaaggg aagagtcatg cagatcattg tgaaaggcaa aaacgtggac     240
ctcatctctg aaaccaccgt ggagctctac tcgctggctg agaggtgcag gaagaacaac    300
```

```
gggaagacag aaatatggtt agagctgaaa cctcaaggcc gaatgctaat gaatgcaaga    360
tactttctgg aaatgagtga cacaaaggac atgaatgaat tgagacgga aggcttcttt    420 gctttgcatc agcgccgggg tgccatcaag caggcaaagg tccaccacgt caagtgccac    480
gagttcactg ccaccttctt cccacagccc acattttgct ctgtctgcca cgagtttgtc    540
tggggcctga acaaacaggg ctaccagtgc cgacaatgca atgcagcaat tcacaagaag    600
tgtattgata aagttatagc aaagtgcaca ggatcagcta tcaatagccg agaaccatg     660 ttccacaagg agagattcaa aattgacatg ccacacagat ttaaagtcta caattacaag    720
agcccgacct tctgtgaaca ctgtgggacc ctgctgtggg gactggcacg gcaaggactc    780
aagtgtgatg catgtggcat gaatgtgcat catagatgcc agacaaaggt ggccaacctt    840
tgtggcataa accagaagct aatggctgaa gcgctggcca tgattgagag cactcaacag    900
gctcgctgct taagagatac tgaacagatc ttcagagaag gtccggttga aattggtctc    960
ccatgctcca tcaaaaatga agcaaggccg ccatgtttac cgacaccggg aaaaagagag   1020
cctcagggca tttcctggga gtctccgttg gatgaggtgg ataaaatgtg ccatcttcca   1080
gaacctgaac tgaacaaaga aagaccatct ctgcagatta aactaaaaat tgaggatttt   1140
atcttgcaca aaatgttggg gaaaggaagt tttggcaagg tcttcctggc agaattcaag   1200
aaaaccaatc aatttttcgc aataaaggcc ttaaagaaag atgtggtctt gatggacgat   1260
gatgttgagt gcacgatggt agagaagaga gttctttcct tggcctggga gcatccgttt   1320
ctgacgcaca tgttttgtac attccagacc aaggaaaaacc tctttttttgt gatggagtac   1380 ctcaacggag gggacttaat gtaccacatc caaagctgcc acaagttcga cctttccaga   1440
gcgacgtttt atgctgctga aatcattctt ggtctgcagt tccttcattc caaaggaata   1500
gtctacaggg acctgaagct agataacatc ctgttagaca aagatggaca tatcaagatc   1560
gcggattttg gaatgtgcaa ggagaacatg ttaggagatg ccaagacgaa taccttctgt   1620
gggacacctg actacatcgc cccagagatc ttgctgggtc agaaatacaa ccactctgtg   1680
gactggtggt ccttcggggt tctcctttat gaaatgctga ttggtcagtc gccttttccac   1740 gggcaggatg aggaggagct cttccactcc atccgcatgg acaatccctt ttacccacgg   1800
tggctggaga aggaagcaaa ggaccttctg tgaagctctt cgtgcgagaa acctgagaag   1860
aggctgggcg tgagggagagg catccgccag caccctttgt ttcggagat caactgggag    1920 gaacttgaac ggaaggagat tgacccaccg ttccggccga aagtgaaatc accatttgac   1980
tgcagcaatt tcgacaaaga attcttaaac gagaagcccc ggctgtcatt tgccgacaga   2040
gcactgatca acagcatgga ccagaatatg ttcaggaact tttccttcat gaaccccggg   2100
atggagcggc tgatatcctg a                                             2121
```

<210> SEQ ID NO 120
<211> LENGTH: 1779
<212> TYPE: DNA
<213> ORGANISM: Homo sapiens
<300> PUBLICATION INFORMATION:
<302> TITLE: PKC zeta
<310> PATENT DOCUMENT NUMBER: NM2744

<400> SEQUENCE: 120

```
atgcccagca ggaccgaccc caagatggaa gggagcggcg gccgcgtccg cctcaaggcg     60
cattacgggg gggacatctt catcaccagc gtggacgccg ccacgacctt cgaggagctc    120
tgtgaggaag tgagagacat gtgtcgtctg caccagcagc acccgctcac cctcaagtgg    180
```

-continued

```
gtggacagcg aaggtgaccc ttgcacggtg tcctcccaga tggagctgga agaggctttc      240
cgcctggccc gtcagtgcag ggatgaaggc ctcatcattc atgttttccc gagcaccccct    300 gagcagcctg gcctgccatg tccgggagaa gacaaatcta tctaccgccg gggagccaga    360
agatggagga agctgtaccg tgccaacggc cacctcttcc aagccaagcg ctttaacagg    420
agagcgtact gcggtcagtg cagcgagagg atatggggcc tcgcgaggca aggctacagg    480
tgcatcaact gcaaactgct ggtccataag cgctgccacg gctcgtccc gctgacctgc      540 aggaagcata tggattctgt catgccttcc caagagcctc cagtagacga caagaacgag    600
gacgccgacc ttccttccga ggagacagat ggaattgctt acatttcctc atcccggaag    660
catgacagca ttaaagacga ctcggaggac cttaagccag ttatcgatgg gatggatgga    720
atcaaaatct ctcaggggct tgggctgcag gactttgacc taatcagagt catcgggcgc    780
gggagctacg ccaaggttct cctggtgcgg ttgaagaaga atgaccaaat ttacgccatg    840
aaagtggtga agaaagagct ggtgcatgat gacgaggata ttgactgggt acagacagag    900
aagcacgtgt ttgagcaggc atccagcaac cccttcctgg tcggattaca ctcctgcttc    960
cagacgacaa gtcggttgtt cctggtcatt gagtacgtca acggcgggga cctgatgttc    1020
cacatgcaga ggcagaggaa gctccctgag gagcacgcca ggttctacgc ggccgagatc    1080
tgcatcgccc tcaacttcct gcacgagagg gggatcatct acagggacct gaagctggac    1140
aacgtcctcc tggatgcgga cggcacatc aagctcacag actacggcat gtgcaaggaa    1200
ggcctgggcc ctggtgacac aacgagcact ttctgcggaa ccccgaatta catcgccccc    1260
gaaatcctgc ggggagagga gtacgggttc agcgtggact ggtgggcgct gggagtcctc    1320
atgtttgaga tgatggccgg gcgctccccg ttcgacatca tcaccgacaa cccgacatg      1380 aacacagagg actaccttt ccaagtgatc ctggagaagc ccatccggat ccccggttc       1440 ctgtccgtca agcctcccca tgttttaaaa ggatttttaa ataaggaccc caaagagagg    1500
ctcggctgcc ggccacagac tggattttct gacatcaagt cccacgcgtt cttccgcagc    1560
atagactggg acttgctgga gaagaagcag gcgctcccctc cattccagcc acagatcaca    1620
gacgactacg gtctggacaa cttttgacaca cagttcacca gcgagcccgt gcagctgacc    1680
ccagacgatg aggatgccat aaagaggatc gaccagtcag agttcgaagg ctttgagtat    1740 atcaaccat tattgctgtc caccgaggag tcggtgtga                            1779
```

<210> SEQ ID NO 121
<211> LENGTH: 576
<212> TYPE: DNA
<213> ORGANISM: Homo sapiens
<300> PUBLICATION INFORMATION:
<302> TITLE: VEGF
<310> PATENT DOCUMENT NUMBER: NM003376

<400> SEQUENCE: 121

```
atgaactttc tgctgtcttg ggtgcattgg agccttgcct tgctgctcta cctccaccat      60
gccaagtggt cccaggctgc acccatggca gaaggaggag gcagaatca tcacgaagtg    120 gtgaagttca tggatgtcta tcagcgcagc tactgccatc caatcgagac cctggtggac    180
atcttccagg agtaccctga tgagatcgag tacatcttca gccatcctg tgtgcccctg      240 atgcgatgcg ggggctgctg caatgacgag ggcctggagt gtgtgccccac tgaggagtcc    300 aacatcacca tgcagattat gcggatcaaa cctcaccaag gccagcacat aggagagatg    360
agcttcctac agcacaacaa atgtgaatgc agaccaaaga aagatagagc aagacaagaa    420
```

| | |
|---|---|
| aatccctgtg ggccttgctc agagcggaga aagcatttgt ttgtacaaga tccgcagacg | 480 |
| tgtaaatgtt cctgcaaaaa cacagactcg cgttgcaagg cgaggcagct tgagttaaac | 540 |
| gaacgtactt gcagatgtga caagccgagg cggtga | 576 |

<210> SEQ ID NO 122
<211> LENGTH: 624
<212> TYPE: DNA
<213> ORGANISM: Homo sapiens
<300> PUBLICATION INFORMATION:
<302> TITLE: VEGF B
<310> PATENT DOCUMENT NUMBER: NM003377

<400> SEQUENCE: 122

| | |
|---|---|
| atgagccctc tgctccgccg cctgctgctc gccgcactcc tgcagctggc ccccgcccag | 60 |
| gcccctgtct cccagcctga tgcccctggc caccagagga aagtggtgtc atggatagat | 120 |
| gtgtatactc gcgctacctg ccagcccccgg gaggtggtgg tgcccttgac tgtggagctc | 180 |
| atgggcaccg tggccaaaca gctggtgccc agctgcgtga ctgtgcagcg ctgtggtggc | 240 |
| tgctgccctg acgatggcct ggagtgtgtg cccactgggc agcaccaagt ccggatgcag | 300 |
| atcctcatga tccggtaccc gagcagtcag ctggggagac tgtccctgga agaacacagc | 360 |
| cagtgtgaat gcagacctaa aaaaaaggac agtgctgtga agccagacag ggctgccact | 420 |
| ccccaccacc gtccccagcc ccgttctgtt ccgggctggg actctgcccc cggagcaccc | 480 |
| tccccagctg acatcaccca tcccactcca gccccaggcc cctctgccca cgctgcaccc | 540 |
| agcaccacca gcgccctgac ccccggacct gccgccgccg ctgccgacgc cgcagcttcc | 600 |
| tccgttgcca agggcggggc ttag | 624 |

<210> SEQ ID NO 123
<211> LENGTH: 1260
<212> TYPE: DNA
<213> ORGANISM: Homo sapiens
<300> PUBLICATION INFORMATION:
<302> TITLE: VEGF C
<310> PATENT DOCUMENT NUMBER: NM005429

<400> SEQUENCE: 123

| | |
|---|---|
| atgcacttgc tgggcttctt ctctgtggcg tgttctctgc tcgccgctgc gctgctcccg | 60 |
| ggtcctcgcg aggcgcccgc cgccgccgcc gccttcgagt ccggactcga cctctcggac | 120 |
| gcggagcccg acgcgggcga ggccacggct tatgcaagca agatctggga ggagcagtta | 180 |
| cggtctgtgt ccagtgtaga tgaactcatg actgtactct acccagaata ttggaaaatg | 240 |
| tacaagtgtc agctaaggaa aggaggctgg caacataaca gagaacaggc caacctcaac | 300 |
| tcaaggacag aagagactat aaaatttgct gcagcacatt ataatacaga gatcttgaaa | 360 |
| agtattgata tgagtggag aaagactcaa tgcatgccac gggaggtgtg tatagatgtg | 420 |
| gggaaggagt ttggagtcgc gacaaacacc ttctttaaac tccatgtgt gtccgtctac | 480 |
| agatgtgggg gttgctgcaa tagtgagggg ctgcagtgca tgaacaccag cacgagctac | 540 |
| ctcagcaaga cgttatttga aattacagtg cctctctctc aaggccccaa accagtaaca | 600 |
| atcagttttg ccaatcacac ttcctgccga tgcatgtcta actgatgtc ttacagacaa | 660 |
| gttcattcca ttattagacg ttccctgcca gcaacactac cacagtgtca ggcagcgaac | 720 |
| aagacctgcc ccaccaatta catgtggaat aatcacatct gcagatgcct ggctcaggaa | 780 |
| gattttatgt tttcctcgga tgctggagat gactcaacag atggattcca tgacatctgt | 840 |

```
ggaccaaaca aggagctgga tgaagagacc tgtcagtgtg tctgcagagc ggggcttcgg      900
cctgccagct gtggacccca caaagaacta gacagaaact catgccagtg tgtctgtaaa      960
aacaaactct tccccagcca atgtggggcc aaccgagaat ttgatgaaaa cacatgccag     1020
tgtgtatgta aagaacctg ccccagaaat caacccctaa atcctggaaa atgtgcctgt      1080
gaatgtacag aaagtccaca gaaatgcttg ttaaaggaa agaagttcca ccaccaaaca     1140
tgcagctgtt acagacggcc atgtacgaac cgccagaagg cttgtgagcc aggattttca     1200
tatagtgaag aagtgtgtcg ttgtgtccct tcatattgga aaagaccaca aatgagctaa     1260
```

```
<210> SEQ ID NO 124
<211> LENGTH: 1074
<212> TYPE: DNA
<213> ORGANISM: Homo sapiens
<300> PUBLICATION INFORMATION:
<302> TITLE: VEGF D
<310> PATENT DOCUMENT NUMBER: AJ000185

<400> SEQUENCE: 124
```

```
atattcaaaa tgtacagaga gtgggtagtg gtgaatgttt tcatgatgtt gtacgtccag       60
ctggtgcagg gctccagtaa tgaacatgga ccagtgaagc gatcatctca gtccacattg      120
gaacgatctg aacagcagat cagggctgct tctagtttgg aggaactact tcgaattact      180
cactctgagg actggaagct gtggagatgc aggctgaggc tcaaaagttt taccagtatg      240
gactctcgct cagcatccca tcggtccact aggtttgcgg caactttcta tgacattgaa      300
acactaaaag ttatagatga agaatggcaa agaactcagt gcagccctag agaaacgtgc      360
gtggaggtgg ccagtgagct ggggaagagt accaacacat tcttcaagcc cccttgtgtg      420
aacgtgttcc gatgtggtgg ctgttgcaat gaagagagcc ttatctgtat gaacaccagc      480
acctcgtaca tttccaaaca gctctttgag atatcagtgc ctttgacatc agtacctgaa      540
ttagtgcctg ttaaagttgc aatcataca ggttgtaagt gcttgccaac agcccccgc       600 catccatact caattatcag aagatccatc cagatccctg aagaagatcg ctgttcccat      660
tccaagaaac tctgtcctat tgacatgcta tgggatagca caaatgtaa atgtgtttg       720 caggaggaaa atccacttgc tggaacagaa gaccactctc atctccagga accagctctc      780
tgtgggccac acatgatgtt tgacgaagat cgttgcgagt gtgtctgtaa aacaccatgt      840
cccaaagatc taatccagca cccaaaaac tgcagttgct ttgagtgcaa agaaagtctg      900
gagacctgct gccagaagca caagctattt cacccagaca cctgcagctg tgaggacaga      960 tgccccttc ataccagacc atgtgcaagt ggcaaaacag catgtgcaaa gcattgccgc     1020
tttccaaagg agaaaagggc tgcccagggg cccacagcc gaaagaatcc ttga           1074
```

```
<210> SEQ ID NO 125
<211> LENGTH: 1314
<212> TYPE: DNA
<213> ORGANISM: Homo sapiens
<300> PUBLICATION INFORMATION:
<302> TITLE: E2F
<310> PATENT DOCUMENT NUMBER: M96577

<400> SEQUENCE: 125
```

```
atggccttgg ccggggcccc tgcgggcggc ccatgcgcgc cggcgctgga ggccctgctc       60
ggggccggcg cgctgcggct gctcgactcc tcgcagatcg tcatcatctc cgccgcgcag      120
gacgccagcg ccccgccggc tcccaccggc ccgcgcgcgc cgccgccgg ccctgcgac       180 cctgacctgc tgctcttcgc cacaccgcag gcgcccccggc ccacacccag tgcgccgcgg      240
```

```
cccgcgctcg gccgcccgcc ggtgaagcgg aggctggacc tggaaactga ccatcagtac    300
ctggccgaga gcagtgggcc agctcggggc agaggccgcc atccaggaaa aggtgtgaaa    360
tccccggggg agaagtcacg ctatgagacc tcactgaatc tgaccaccaa gcgcttcctg    420
gagctgctga gccactcggc tgacggtgtc gtcgacctga actgggctgc cgaggtgctg    480
aaggtgcaga gcggcgcat ctatgacatc accaacgtcc ttgagggcat ccagctcatt    540
gccaagaagt ccaagaacca catccagtgg ctgggcagcc acaccacagt gggcgtcggc    600
ggacggcttg aggggttgac ccaggacctc cgacagctgc aggagagcga gcagcagctg    660
gaccacctga tgaatatctg tactacgcag ctgcgcctgc tctccgagga cactgacagc    720
cagcgcctgg cctacgtgac gtgtcaggac cttcgtagca ttgcagaccc tgcagagcag    780
atggttatgg tgatcaaagc ccctcctgag acccagctcc aagccgtgga ctcttcggag    840
aactttcaga tctcccttaa gagcaaacaa ggcccgatcg atgttttcct gtgccctgag    900
gagaccgtag gtgggatcag ccctgggaag accccatccc aggaggtcac ttctgaggag    960
gagaacaggg ccactgactc tgccaccata gtgtcaccac caccatcatc tccccctca    1020 tccctcacca cagatcccag ccagtctcta ctcagcctgg agcaagaacc gctgttgtcc    1080
cggatgggca gcctgcgggc tcccgtggac gaggaccgcc tgtccccgct ggtggcggcc    1140
gactcgctcc tggagcatgt gcgggaggac ttctccggcc tcctccctga ggagttcatc    1200
agcctttccc caccccacga ggccctcgac taccacttcg gcctcgagga gggcgagggc    1260
atcagagacc tcttcgactg tgactttggg gacctcaccc ccctggattt ctga         1314

<210> SEQ ID NO 126
<211> LENGTH: 166
<212> TYPE: DNA
<213> ORGANISM: Human papillomavirus
<300> PUBLICATION INFORMATION:
<302> TITLE: EBER-1
<310> PATENT DOCUMENT NUMBER: Jo2078

<400> SEQUENCE: 126
ggacctacgc tgccctagag gttttgctag ggaggagacg tgtgtggctg tagccacccg     60
tcccgggtac aagtcccggg tggtgaggac ggtgtctgtg gttgtcttcc cagactctgc    120
tttctgccgt cttcggtcaa gtaccagctg gtggtccgca tgtttt                   166

<210> SEQ ID NO 127
<211> LENGTH: 172
<212> TYPE: DNA
<213> ORGANISM: Hepatitis C virus
<300> PUBLICATION INFORMATION:
<302> TITLE: EBER-2
<310> PATENT DOCUMENT NUMBER: J02078

<400> SEQUENCE: 127
ggacagccgt tgccctagtg gtttcggaca caccgccaac gctcagtgcg gtgctaccga     60
cccgaggtca agtcccgggg gaggagaaga gaggcttccc gcctagagca tttgcaagtc    120
aggattctct aatccctctg ggagaagggt attcggcttg tccgctatt tt             172

<210> SEQ ID NO 128
<211> LENGTH: 651
<212> TYPE: DNA
<213> ORGANISM: Hepatitis C virus
<300> PUBLICATION INFORMATION:
<302> TITLE: NS2
<310> PATENT DOCUMENT NUMBER: AJ238799
```

<400> SEQUENCE: 128

```
atggaccggg agatggcagc atcgtgcgga ggcgcggttt tcgtaggtct gatactcttg    60
accttgtcac cgcactataa gctgttcctc gctaggctca tatggtggtt acaatatttt   120
atcaccaggg ccgaggcaca cttgcaagtg tggatccccc ccctcaacgt tcggggggc    180
cgcgatgccg tcatcctcct cacgtgcgcg atccacccag agctaatctt taccatcacc   240
aaaatcttgc tcgccatact cggtccactc atggtgctcc aggctggtat aaccaaagtg   300
ccgtacttcg tgcgcgcaca cgggctcatt cgtgcatgca tgctggtgcg aaggttgct    360
gggggtcatt atgtccaaat ggctctcatg aagttggccg cactgacagg tacgtacgtt   420
tatgaccatc tcaccccact gcgggactgg gccacgcgg gcctacgaga ccttgcggtg    480
gcagttgagc ccgtcgtctt ctctgatatg gagaccaagg ttatcacctg ggggcagac    540
accgcggcgt gtgggacat catcttgggc ctgcccgtct ccgcccgcag ggggagggag    600
atacatctgg gaccggcaga cagccttgaa gggcagggt ggcgactcct c             651
```

<210> SEQ ID NO 129
<211> LENGTH: 161
<212> TYPE: DNA
<213> ORGANISM: Hepatitis C virus
<300> PUBLICATION INFORMATION:
<302> TITLE: NS4A
<310> PATENT DOCUMENT NUMBER: AJ238799

<400> SEQUENCE: 129

```
gcacctgggt gctggtaggc ggagtcctag cagctctggc cgcgtattgc ctgacaacag    60
gcagcgtggt cattgtgggc aggatcatct tgtccggaaa gccggccatc attcccgaca   120
gggaagtcct ttaccgggag ttcgatgaga tggaagagtg c                       161
```

<210> SEQ ID NO 130
<211> LENGTH: 783
<212> TYPE: DNA
<213> ORGANISM: Hepatitis C virus
<300> PUBLICATION INFORMATION:
<302> TITLE: NS4B
<310> PATENT DOCUMENT NUMBER: AJ238799

<400> SEQUENCE: 130

```
gcctcacacc tcccttacat cgaacaggga atgcagctcg ccgaacaatt caaacagaag    60
gcaatcgggt tgctgcaaac agccaccaag caagcggagg ctgctgctcc cgtggtggaa   120
tccaagtggc ggaccctcga agccttctgg gcgaagcata tgtggaattt catcagcggg   180
atacaatatt tagcaggctt gtccactctg cctggcaacc ccgcgatagc atcactgatg   240
gcattcacag cctctatcac cagcccgctc accaccaac atacccctcct gtttaacatc   300
ctgggggat gggtggccgc ccaacttgct cctcccagcg ctgcttctgc tttcgtaggc   360
gccggcatcg ctggagcggc tgttggcagc ataggccttg ggaaggtgct tgtggatatt   420
ttggcaggtt atggagcagg ggtggcaggc gcgctcgtgg cctttaaggt catgagcggc   480
gagatgccct ccaccgagga cctggttaac ctactccctg ctatcctctc ccctggcgcc   540
ctagtcgtcg gggtcgtgtg cgcagcgata ctgcgtcggc acgtgggccc aggggagggg   600
gctgtgcagt ggatgaaccg gctgatagcg ttcgcttcgc ggggtaacca cgtctccccc   660
acgcactatg tgcctgagag cgacgctgca gcacgtgtca ctcagatcct ctctagtctt   720
accatcactc agctgctgaa gaggcttcac cagtggatca cgaggactg ctccacgcca   780
```

|  |  |
|---|---:|
| tgc | 783 |

<210> SEQ ID NO 131
<211> LENGTH: 1341
<212> TYPE: DNA
<213> ORGANISM: Hepatitis C virus
<300> PUBLICATION INFORMATION:
<302> TITLE: NS5A
<310> PATENT DOCUMENT NUMBER: AJ238799

<400> SEQUENCE: 131

|  |  |
|---|---:|
| tccggctcgt ggctaagaga tgtttgggat tggatatgca cggtgttgac tgatttcaag | 60 |
| acctggctcc agtccaagct cctgccgcga ttgccgggag tcccttctt ctcatgtcaa | 120 |
| cgtgggtaca agggagtctg gcggggcgac ggcatcatgc aaaccacctg cccatgtgga | 180 |
| gcacagatca ccggacatgt gaaaaacggt tccatgagga tcgtggggcc taggacctgt | 240 |
| agtaacacgt ggcatggaac attccccatt aacgcgtaca ccacgggccc ctgcacgccc | 300 |
| tccccggcgc caaattattc tagggcgctg tggcgggtgg ctgctgagga gtacgtggag | 360 |
| gttacgcggg tgggggattt ccactacgtg acgggcatga ccactgacaa cgtaaagtgc | 420 |
| ccgtgtcagg ttccggcccc cgaattcttc acagaagtgg atggggtgcg gttgcacagg | 480 |
| tacgctccag cgtgcaaacc cctcctacgg gaggaggtca cattcctggt cgggctcaat | 540 |
| caatacctgg ttgggtcaca gctcccatgc gagcccgaac cggacgtagc agtgctcact | 600 |
| tccatgctca ccgacccctc ccacattacg gcggagacgg ctaagcgtag gctggccagg | 660 |
| ggatctcccc cctccttggc cagctcatca gctagccagc tgtctgcgcc ttccttgaag | 720 |
| gcaacatgca ctacccgtca tgactcccg gacgctgacc tcatcgaggc caacctcctg | 780 |
| tggcggcagg agatgggcgg gaacatcacc cgcgtggagt cagaaaataa ggtagtaatt | 840 |
| ttggactctt tcgagccgct ccaagcggag gaggatgaga gggaagtatc cgttccggcg | 900 |
| gagatcctgc ggaggtccag gaaattccct cgagcgatgc ccatatgggc acgcccggat | 960 |
| tacaaccctc cactgttaga gtcctggaag gacccggact acgtccctcc agtggtacac | 1020 |
| gggtgtccat tgccgcctgc caaggcccct ccgataccac ctccacggag gaagaggacg | 1080 |
| gttgtcctgt cagaatctac cgtgtcttct gccttggcgg agctcgccac aaagaccttc | 1140 |
| ggcagctccg aatcgtcggc cgtcgacagc ggcacggcaa cggcctctcc tgaccagccc | 1200 |
| tccgacgacg cgacgcggg atccgacgtt gagtcgtact cctccatgcc ccccttgag | 1260 |
| ggggagccgg gggatcccga tctcagcgac gggtcttggt ctaccgtaag cgaggaggct | 1320 |
| agtgaggacg tcgtctgctg c | 1341 |

<210> SEQ ID NO 132
<211> LENGTH: 1772
<212> TYPE: DNA
<213> ORGANISM: Hepatitis C virus
<300> PUBLICATION INFORMATION:
<302> TITLE: NS5B
<310> PATENT DOCUMENT NUMBER: AJ238799

<400> SEQUENCE: 132

|  |  |
|---|---:|
| tcgatgtcct acacatggac aggcgccctg atcacgccat cgctgcgga ggaaaccaag | 60 |
| ctgcccatca atgcactgag caactctttg ctccgtcacc acaacttggt ctatgctaca | 120 |
| acatctcgca gcgcaagcct gcggcagaag aaggtcacct ttgacagact gcaggtcctg | 180 |
| gacgaccact accgggacgt gctcaaggag atgaaggcga aggcgtccac agttaaggct | 240 |
| aaacttctat ccgtggagga agcctgtaag ctgacgcccc cacattcggc cagatctaaa | 300 |

```
tttggctatg gggcaaagga cgtccggaac ctatccagca aggccgttaa ccacatccgc    360
tccgtgtgga aggacttgct ggaagacact gagacaccaa ttgacaccac catcatggca    420
aaaaatgagg ttttctgcgt ccaaccagag aaggggggcc gcaagccagc tcgccttatc    480
gtattcccag atttgggggt tcgtgtgtgc gagaaaatgg ccctttacga tgtggtctcc    540
accctccctc aggccgtgat gggctcttca tacggattcc aatactctcc tggacagcgg    600
gtcgagttcc tggtgaatgc ctggaaagcg aagaaatgcc ctatgggctt cgcatatgac    660
acccgctgtt ttgactcaac ggtcactgag aatgacatcc gtgttgagga gtcaatctac    720
caatgttgtg acttggcccc cgaagccaga caggccataa ggtcgctcac agagcggctt    780
tacatcgggg gcccctgac taattctaaa gggcagaact gcggctatcg ccggtgccgc    840
gcgagcggtg tactgacgac cagctgcggt aataccctca catgttactt gaaggccgct    900
gcggcctgtc gagctgcgaa gctccaggac tgcacgatgc tcgtatgcgg agacgacctt    960
gtcgttatct gtgaaagcgc ggggacccaa gaggacgagg cgagcctacg ggccttcacg   1020
gaggctatga ctagatactc tgcccccccct ggggacccgc ccaaaccaga atacgacttg   1080
gagttgataa catcatgctc ctccaatgtg tcagtcgcgc acgatgcatc tggcaaaagg   1140
gtgtactatc tcacccgtga ccccaccacc cccttgcgc gggctgcgtg ggagacagct   1200
agacacactc cagtcaattc ctggctaggc aacatcatca tgtatgcgcc caccttgtgg   1260
gcaaggatga tcctgatgac tcatttcttc tccatccttc tagctcagga acaacttgaa   1320
aaagccctag attgtcagat ctacggggcc tgttactcca ttgagccact tgacctacct   1380
cagatcattc aacgactcca tggccttagc gcattttcac tccatagtta ctctccaggt   1440
gagatcaata gggtggcttc atgcctcagg aaacttgggg taccgccctt gcgagtctgg   1500
agacatcggg ccagaagtgt ccgcgctagg ctactgtccc agggggggag ggctgccact   1560
tgtggcaagt acctcttcaa ctgggcagta aggaccaagc tcaaactcac tccaatcccg   1620
gctgcgtccc agttggattt atccagctgg ttcgttgctg gttacagcgg gggagacata   1680
tatcacagcc tgtctcgtgc ccgaccccgc tggttcatgt ggtgcctact cctactttct   1740
gtaggggtag gcatctatct actccccaac cg                                  1772
```

<210> SEQ ID NO 133
<211> LENGTH: 1892
<212> TYPE: DNA
<213> ORGANISM: Hepatitis C virus
<300> PUBLICATION INFORMATION:
<302> TITLE: NS3
<310> PATENT DOCUMENT NUMBER: AJ238799

<400> SEQUENCE: 133

```
cgcctattac ggcctactcc caacagacgc gaggcctact ggctgcatc atcactagcc      60 tcacaggccg ggacaggaac caggtcgagg gggaggtcca agtggtctcc accgcaacac    120
aatctttcct ggcgacctgc gtcaatggcg tgtgttggac tgtctatcat ggtgccggct    180
caaagaccct tgccggccca aagggcccaa tcacccaaat gtacaccaat gtgaccagg    240 acctcgtcgg ctggcaagcg ccccccgggg gcgttccttt gacaccatgc acctgcggca    300
gctcggacct ttacttggtc acgaggcatg ccgatgtcat tccggtgcgc ggcggggcg    360 acagcagggg gagcctactc tccccccaggc ccgtctccta cttgaagggc tcttcgggcg    420
gtccactgct ctgccccctcg gggcacgctg tgggcatctt tcgggctgcc gtgtgcaccc    480
gaggggttgc gaaggcggtg gactttgtac ccgtcgagtc tatggaaacc actatgcggt    540
```

-continued

```
cccoggtctt cacggacaac tcgtccoctc cggccgtacc gcagacattc caggtggccc    600
atctacacgc ccctactggt agcggcaaga gcactaaggt gccggctgcg tatgcagccc    660
aagggtataa ggtgcttgtc ctgaacccgt ccgtcgccgc caccctaggt ttcggggcgt    720
atatgtctaa ggcacatggt atcgacccta acatcagaac cggggtaagg accatcacca    780
cgggtgcccc catcacgtac tccacctatg gcaagtttct tgccgacggt ggttgctctg    840
ggggcgccta tgacatcata atatgtgatg agtgccactc aactgactcg accactatcc    900
tgggcatcgg cacagtcctg gaccaagcgg agacggctgg agcgcgactc gtcgtgctcg    960
ccaccgctac gcctccggga tcggtcaccg tgccacatcc aaacatcgag gaggtggctc   1020
tgtccagcac tggagaaatc ccttttatg gcaaagccat ccccatcgag accatcaagg    1080
gggggaggca cctcattttc tgccattcca gaagaaatg tgatgagctc gccgcgaagc    1140
tgtccggcct cggactcaat gctgtagcat attaccgggg ccttgatgta ccgtcatac    1200
caactagcgg agacgtcatt gtcgtagcaa cggacgctct aatgacgggc tttaccggcg   1260
atttcgactc agtgatcgac tgcaatacat gtgtcaccca gacagtcgac ttcagcctgg   1320
acccgacctt caccattgag acgacgaccg tgccacaaga cgcggtgtca cgctcgcagc   1380
ggcgaggcag gactggtagg ggcaggatgg gcatttacag gtttgtgact ccaggagaac   1440
ggccctcggg catgttcgat tcctcggttc tgtgcgagtg ctatgacgcg ggctgtgctt   1500
ggtacgagct cacgcccgcc gagacctcag ttaggttgcg ggcttaccta aacacaccag   1560
ggttgcccgt ctgccaggac catctggagt tctgggagag cgtctttaca ggcctcaccc   1620
acatagacgc ccatttcttg tcccagacta agcaggcagg agacaacttc ccctacctgg   1680
tagcatacca ggctacggtg tgcgccaggg ctcaggctcc acctccatcg tgggaccaaa   1740
tgtggaagtg tctcatacgg ctaaagccta cgctgcacgg gccaacgccc ctgctgtata   1800
ggctgggagc cgttcaaaac gaggttacta ccacacaccc cataaccaaa tacatcatgg   1860
catgcatgtc ggctgacctg gaggtcgtca cg                                  1892
```

<210> SEQ ID NO 134
<211> LENGTH: 822
<212> TYPE: DNA
<213> ORGANISM: Homo sapiens
<300> PUBLICATION INFORMATION:
<302> TITLE: stmn cell factor
<310> PATENT DOCUMENT NUMBER: M59964

<400> SEQUENCE: 134

```
atgaagaaga cacaaacttg gattctcact tgcatttatc ttcagctgct cctatttaat     60
cctctcgtca aaactgaagg gatctgcagg aatcgtgtga ctaataatgt aaaagacgtc    120
actaaattgg tggcaaatct tccaaaagac tacatgataa ccctcaaata tgtccccggg    180
atggatgttt tgccaagtca ttgttggata agcgagatgg tagtacaatt gtcagacagc    240
ttgactgatc ttctggacaa gttttcaaat atttctgaag gcttgagtaa ttattccatc    300
atagacaaac ttgtgaatat agtcgatgac cttgtggagt gcgtcaaaga aaactcatct    360
aaggatctaa aaaatcatt caagagccca gaacccaggc tctttactcc tgaagaattc    420
tttagaattt ttaatagatc cattgatgcc ttcaaggact tgtagtggc atctgaaact    480
agtgattgtg tggttcttc aacattaagt cctgagaaag attccagagt cagtgtcaca    540
aaaccattta tgttacccc tgttgcagcc agctccctta ggaatgacag cagtagcagt    600
aataggaagg ccaaaaatcc ccctggagac tccagcctac actgggcagc catggcattg    660
```

```
ccagcattgt tttctcttat aattggcttt gcttttggag ccttatactg gaagaagaga      720
cagccaagtc ttacaagggc agttgaaaat atacaaatta atgaagagga taatgagata      780
agtatgttgc aagagaaaga gagagagttt caagaagtgt aa                         822

<210> SEQ ID NO 135
<211> LENGTH: 483
<212> TYPE: DNA
<213> ORGANISM: Homo sapiens
<300> PUBLICATION INFORMATION:
<302> TITLE: TGFalpha
<310> PATENT DOCUMENT NUMBER: AF123238

<400> SEQUENCE: 135
atggtcccct cggctggaca gctcgccctg ttcgctctgg gtattgtgtt ggctgcgtgc       60
caggccttgg agaacagcac gtccccgctg agtgcagacc cgccgtggc tgcagcagtg      120 gtgtcccatt ttaatgactg cccagattcc cacactcagt tctgcttcca tggaacctgc     180
aggttttggg tgcaggagga caagccagca tgtgtctgcc attctgggta cgttggtgca     240
cgctgtgagc atcgggacct cctggccgtg gtggctgcca gcagaagaa gcaggccatc     300 accgccttgg tggtggtctc catcgtggcc ctggctgtcc ttatcatcac atgtgtgctg     360
atacactgct gccaggtccg aaaacactgt gagtggtgcc gggccctcat ctgccggcac     420
gagaagccca cgccctcct gaagggaaga accgcttgct gccactcaga aacagtggtc      480
tga                                                                   483

<210> SEQ ID NO 136
<211> LENGTH: 1071
<212> TYPE: DNA
<213> ORGANISM: Homo sapiens
<300> PUBLICATION INFORMATION:
<302> TITLE: GD3 synthase
<310> PATENT DOCUMENT NUMBER: NM003034

<400> SEQUENCE: 136
atgagcccct gcgggcgggc ccggcgacaa acgtccagag gggccatggc tgtactggcg       60
tggaagttcc cgcggacccg gctgccatg ggagccagtg ccctctgtgt cgtggtcctc      120
tgttggctct acatcttccc cgtctaccgg ctgcccaacg agaaagagat cgtgcagggg     180
gtgctgcaac agggcacggc gtggaggagg aaccagaccg cggccagagc gttcaggaaa     240
caaatggaag actgctgcga ccctgcccat ctctttgcta tgactaaaat gaattcccct     300
atggggaaga gcatgtggta tgacggggag ttttatact cattcaccat tgacaattca     360
acttactctc tcttcccaca ggcaacccca ttccagctgc cattgaagaa atgcgcggtg     420
gtgggaaatg gtgggattct gaagaagagt ggctgtggcc gtcaaataga tgaagcaaat     480
tttgtcatgc gatgcaatct ccctcctttg tcaagtgaat acactaagga tgttggatcc     540
aaaagtcagt tagtgacagc taatccagc ataattcggc aaaggtttca gaaccttctg     600
tggtccagaa agacatttgt ggacaacatg aaaatctata accacagtta catctacatg     660
cctgcctttt ctatgaagac aggaacagag ccatctttga gggtttatta tacactgtca     720
gatgttggtg ccaatcaaac agtgctgttt gccaacccca actttctgcg tagcattgga     780
aagttctgga aaagtagagg aatccatgcc aagcgcctgt ccacaggact ttttctggtg     840
agcgcagctc tgggtctctg tgaagaggtg ccatctatg gcttctggcc cttctctgtg     900
aatatgcatg agcagcccat cagccaccac tactatgaca acgtcttacc ctttttctggc     960
```

| | |
|---|---|
| ttccatgcca tgcccgagga atttctccaa ctctggtatc ttcataaaat cggtgcactg | 1020 |
| agaatgcagc tggacccatg tgaagatacc tcactccagc ccacttccta g | 1071 |

<210> SEQ ID NO 137
<211> LENGTH: 744
<212> TYPE: DNA
<213> ORGANISM: Homo sapiens
<300> PUBLICATION INFORMATION:
<302> TITLE: FGF14
<310> PATENT DOCUMENT NUMBER: NM004115

<400> SEQUENCE: 137

| | |
|---|---|
| atggccgcgg ccatcgctag cggcttgatc cgccagaagc ggcaggcgcg ggagcagcac | 60 |
| tgggaccggc cgtctgccag caggaggcgg agcagcccca gcaagaaccg cgggctctgc | 120 |
| aacggcaacc tggtggatat cttctccaaa gtgcgcatct tcggcctcaa gaagcgcagg | 180 |
| ttgcggcgcc aagatcccca gctcaagggt atagtgacca ggttatattg caggcaaggc | 240 |
| tactacttgc aaatgcaccc cgatggagct ctcgatggaa ccaaggatga cagcactaat | 300 |
| tctacactct tcaacctcat accagtggga ctacgtgttg ttgccatcca gggagtgaaa | 360 |
| acagggttgt atatagccat gaatggagaa ggttacctct acccatcaga acttttttacc | 420 |
| cctgaatgca gtttaaaga atctgttttt gaaaattatt atgtaatcta ctcatccatg | 480 |
| ttgtacagac aacaggaatc tggtagagcc tggttttttgg gattaaataa ggaagggcaa | 540 |
| gctatgaaag ggaacagagt aaagaaaacc aaaccagcag ctcatttttct acccaagcca | 600 |
| ttggaagttg ccatgtaccg agaaccatct ttgcatgatg ttggggaaac ggtcccgaag | 660 |
| cctggggtga cgccaagtaa agcacaagt gcgtctgcaa taatgaatgg aggcaaacca | 720 |
| gtcaacaaga gtaagacaac atag | 744 |

<210> SEQ ID NO 138
<211> LENGTH: 1503
<212> TYPE: DNA
<213> ORGANISM: Human immunodeficiency virus
<300> PUBLICATION INFORMATION:
<302> TITLE: gag (HIV)
<310> PATENT DOCUMENT NUMBER: NC001802

<400> SEQUENCE: 138

| | |
|---|---|
| atgggtgcga gagcgtcagt attaagcggg ggagaattag atcgatggga aaaaattcgg | 60 |
| ttaaggccag ggggaaagaa aaaatataaa ttaaaacata tagtatgggc aagcagggag | 120 |
| ctagaacgat tcgcagttaa tcctggcctg ttagaaacat cagaaggctg tagacaaata | 180 |
| ctgggacagc tacaaccatc ccttcagaca ggatcagaag aacttagatc attatataat | 240 |
| acagtagcaa ccctctattg tgtgcatcaa aggatagaga taaaagacac caaggaagct | 300 |
| ttagacaaga tagaggaaga gcaaaacaaa agtaagaaaa agcacagca agcagcagct | 360 |
| gacacaggac acagcaatca ggtcagccaa aattacccta tagtgcagaa catccagggg | 420 |
| caaatggtac atcaggccat atcacctaga actttaaatg catgggtaaa agtagtagaa | 480 |
| gagaaggctt tcagcccaga agtgataccc atgttttcag cattatcaga aggagccacc | 540 |
| ccacaagatt taaacaccat gctaaacaca gtggggggac atcaagcagc catgcaaatg | 600 |
| ttaaaagaga ccatcaatga ggaagctgca gaatgggata gagtgcatcc agtgcatgca | 660 |
| gggcctattg caccaggcca gatgagagaa ccaaggggaa gtgacatagc aggaactact | 720 |
| agtacccttc aggaacaaat aggatggatg acaaataatc cacctatccc agtaggagaa | 780 |
| atttataaaa gatggataat cctgggatta aataaaatag taagaatgta tagccctacc | 840 |

```
agcattctgg acataagaca aggaccaaag gaaccctttta gagactatgt agaccggttc    900
tataaaactc taagagccga gcaagcttca caggaggtaa aaaattggat gacagaaacc    960
ttgttggtcc aaaatgcgaa cccagattgt aagactattt taaaagcatt gggaccagcg   1020
gctacactag aagaaatgat gacagcatgt cagggagtag gaggacccgg ccataaggca   1080
agagttttgg ctgaagcaat gagccaagta acaaattcag ctaccataat gatgcagaga   1140
ggcaatttta ggaaccaaag aaagattgtt aagtgtttca attgtggcaa agaagggcac   1200
acagccagaa attgcagggc ccctaggaaa aagggctgtt ggaaatgtgg aaggaagga   1260
caccaaatga aagattgtac tgagagacag gctaattttt tagggaagat ctggccttcc   1320
tacaagggaa ggccagggaa ttttcttcag agcagaccag agccaacagc cccaccagaa   1380
gagagcttca ggtctggggt agagacaaca actccccctc agaagcagga gccgatagac   1440
aaggaactgt atcctttaac ttccctcagg tcactctttg gcaacgaccc ctcgtcacaa   1500
taa                                                                  1503

<210> SEQ ID NO 139
<211> LENGTH: 1101
<212> TYPE: DNA
<213> ORGANISM: Human immunodeficiency virus
<300> PUBLICATION INFORMATION:
<302> TITLE: TARBP2
<310> PATENT DOCUMENT NUMBER: NM004178

<400> SEQUENCE: 139
atgagtgaag aggagcaagg ctccggcact accacgggct gcgggctgcc tagtatagag     60
caaatgctgg ccgccaaccc aggcaagacc ccgatcagcc ttctgcagga gtatgggacc    120
agaatagggg agacgcctgt gtacgacctt ctcaaagccg agggccaagc ccaccagcct    180
aatttcacct tccgggtcac cgttggcgac accagctgca ctggtcaggg ccccagcaag    240
aaggcagcca agcacaaggc agctgaggtg gccctcaaac acctcaaagg ggggagcatg    300
ctggagccgg ccctggagga cagcagttct ttttctcccc tagactcttc actgcctgag    360
gacattccgg tttttactgc tgcagcagct gctaccccag ttccatctgt agtcctaacc    420
aggagccccc ccatggaact gcagcccct gtctcccctc agcagtctga gtgcaacccc    480
gttggtgctc tgcaggagct ggtggtgcag aaaggctggc ggttgccgga gtacacagtg    540
acccaggagt ctgggccagc ccaccgcaaa gaattcacca tgacctgtcg agtggagcgt    600
ttcattgaga ttgggagtgg cacttccaaa aaattggcaa gcggaatgc ggcggccaaa    660
atgctgcttc gagtgcacac ggtgcctctg gatgcccggg atggcaatga ggtggagcct    720
gatgatgacc acttctccat tggtgtgggc ttccgcctgg atggtcttcg aaaccggggc    780
ccaggttgca cctgggattc tctacgaaat tcagtaggag agaagatcct gtccctccgc    840
agttgctccc tgggctccct gggtgccctg ggcctgcct gctgccgtgt cctcagtgag    900
ctctctgagg agcaggcctt tcacgtcagc tacctggata ttgaggagct gagcctgagt    960
ggactctgcc agtgcctggt ggaactgtcc acccagccgg ccactgtgtg tcatggctct   1020
gcaaccacca gggaggcagc ccgtggtgag gctgcccgcc gtgccctgca gtacctcaag   1080
atcatggcag gcagcaagtg a                                             1101

<210> SEQ ID NO 140
<211> LENGTH: 219
<212> TYPE: DNA
<213> ORGANISM: Human immunodeficiency virus
```

```
<300> PUBLICATION INFORMATION:
<302> TITLE: TAT (HIV)
<310> PATENT DOCUMENT NUMBER: U44023

<400> SEQUENCE: 140
atggagccag tagatcctag cctagagccc tggaagcatc caggaagtca gcctaagact        60
gcttgtacca cttgctattg taaagagtgt tgctttcatt gccaagtttg tttcataaca       120
aaaggcttag gcatctccta tggcaggaag aagcggagac agcgacgaag aactcctcaa       180
ggtcatcaga ctaatcaagt ttctctatca aagcagtaa                              219

<210> SEQ ID NO 141
<211> LENGTH: 22
<212> TYPE: RNA
<213> ORGANISM: Synthetic sequence
<220> FEATURE:
<223> OTHER INFORMATION: Description of the synthetic sequence: sense
      strand (R1A) of a dsRNA that is homologous to an MDR1 sequence

<400> SEQUENCE: 141
ccaucucgaa aagaaguuaa ga                                                 22

<210> SEQ ID NO 142
<211> LENGTH: 24
<212> TYPE: RNA
<213> ORGANISM: Synthetic sequence
<220> FEATURE:
<223> OTHER INFORMATION: Description of the synthetic sequence:
      antisense strand (R1B) of a dsRNA, that it
      complementary to an MDR1 sequence

<400> SEQUENCE: 142
ucuuaacuuc uuuucgagau gggu                                               24

<210> SEQ ID NO 143
<211> LENGTH: 22
<212> TYPE: RNA
<213> ORGANISM: Synthetic sequence
<220> FEATURE:
<223> OTHER INFORMATION: Description of the synthetic sequence: sense
      strand (R2A) of a dsRNA that is homologous to an MDR1 sequence

<400> SEQUENCE: 143
uauagguucc aggcuugcug ua                                                 22

<210> SEQ ID NO 144
<211> LENGTH: 22
<212> TYPE: RNA
<213> ORGANISM: Synthetic sequence
<220> FEATURE:
<223> OTHER INFORMATION: Description of the synthetic sequence: sense
      strand (R3A) of a dsRNA that is homologous to an MDR1 sequence

<400> SEQUENCE: 144
ccagagaagg ccgcaccugc au                                                 22

<210> SEQ ID NO 145
<211> LENGTH: 24
<212> TYPE: RNA
<213> ORGANISM: Synthetic sequence
<220> FEATURE:
<223> OTHER INFORMATION: Description of the synthetic sequence:
      antisense strand (R3B) of a dsRNA, that it
      complementary to an MDR1 sequence

<400> SEQUENCE: 145
```

```
augcaggugc ggccuucucu ggcu                                      24

<210> SEQ ID NO 146
<211> LENGTH: 21
<212> TYPE: RNA
<213> ORGANISM: Synthetic sequence
<220> FEATURE:
<223> OTHER INFORMATION: Description of the synthetic sequence: sense
      strand (R4A) of a dsRNA that is homologous to an MDR1 sequence

<400> SEQUENCE: 146
ccaucucgaa aagaaguuaa g                                         21

<210> SEQ ID NO 147
<211> LENGTH: 21
<212> TYPE: RNA
<213> ORGANISM: Synthetic sequence
<220> FEATURE:
<223> OTHER INFORMATION: Description of the synthetic sequence:
      antisense strand (R4B) of a dsRNA, that it
      complementary to an MDR1 sequence

<400> SEQUENCE: 147
uaacuucuuu ucgagauggg u                                         21

<210> SEQ ID NO 148
<211> LENGTH: 22
<212> TYPE: RNA
<213> ORGANISM: Synthetic sequence
<220> FEATURE:
<223> OTHER INFORMATION: Description of the synthetic sequence: sense
      strand (S1A) of a dsRNA, that is homologous to the YFP- and
      GFP sequence, respectively

<400> SEQUENCE: 148
ccacaugaag cagcacgacu uc                                        22

<210> SEQ ID NO 149
<211> LENGTH: 22
<212> TYPE: RNA
<213> ORGANISM: Synthetic sequence
<220> FEATURE:
<223> OTHER INFORMATION: Description of the synthetic sequence:
      antisense strand(S1B) of a dsRNA that is
      complementary to the YFP- and GFP sequence, respectively

<400> SEQUENCE: 149
gaagucgugc ugcuucaugu gg                                        22

<210> SEQ ID NO 150
<211> LENGTH: 21
<212> TYPE: RNA
<213> ORGANISM: Synthetic sequence
<220> FEATURE:
<223> OTHER INFORMATION: Description of the synthetic sequence:
      antisense strand(S7A) of a dsRNA that is homologous
      to the YFP- and GFP sequence, respectively

<400> SEQUENCE: 150
ccacaugaag cagcacgacu u                                         21

<210> SEQ ID NO 151
<211> LENGTH: 21
<212> TYPE: RNA
<213> ORGANISM: Synthetic sequence
<220> FEATURE:
<223> OTHER INFORMATION: Description of the synthetic sequence:
      antisense strand(S7B) of a dsRNA, that is
```

-continued complementary to the YFP- and GFP sequence, respectively

<400> SEQUENCE: 151
gucgugcugc uucauguggu c                                      21

<210> SEQ ID NO 152
<211> LENGTH: 24
<212> TYPE: RNA
<213> ORGANISM: Synthetic sequence
<220> FEATURE:
<223> OTHER INFORMATION: Description of the synthetic sequence:
      antisense strand(R2B) of a dsRNA that is
      complementary to the MDR-1 sequence

<400> SEQUENCE: 152
uacagcaagc cuggaaccua uagc                                   24

<210> SEQ ID NO 153
<211> LENGTH: 22
<212> TYPE: RNA
<213> ORGANISM: Synthetic sequence
<220> FEATURE:
<223> OTHER INFORMATION: Description of the synthetic sequence: sense
      strand (K1A) of a dsRNA that is homologous to the 5'-UTR of
      the neomycin sequence

<400> SEQUENCE: 153
acaggaugag gaucguuucg ca                                     22

<210> SEQ ID NO 154
<211> LENGTH: 22
<212> TYPE: RNA
<213> ORGANISM: Synthetic sequence
<220> FEATURE:
<223> OTHER INFORMATION: Description of the synthetic sequence:
      antisense strand(K1B) of a dsRNA that is
      complementary to the 5'-UTR of the neomycin sequence

<400> SEQUENCE: 154
ugcgaaacga uccucauccu gu                                     22

<210> SEQ ID NO 155
<211> LENGTH: 21
<212> TYPE: RNA
<213> ORGANISM: Synthetic sequence
<220> FEATURE:
<223> OTHER INFORMATION: Description of the synthetic sequence: sense
      strand (K3A) of a dsRNA that is homologous to the 5'-UTR of the
      neomycin sequence

<400> SEQUENCE: 155
gaugaggauc guuucgcaug a                                      21

<210> SEQ ID NO 156
<211> LENGTH: 21
<212> TYPE: RNA
<213> ORGANISM: Synthetic sequence
<220> FEATURE:
<223> OTHER INFORMATION: Description of the synthetic sequence:
      antisense strand(K3B) of a dsRNA that
      complementary to the 5'-UTR of the neomycin sequence

<400> SEQUENCE: 156
augcgaaacg auccucaucc u                                      21

<210> SEQ ID NO 157
<211> LENGTH: 24

```
<212> TYPE: RNA
<213> ORGANISM: Synthetic sequence
<220> FEATURE:
<223> OTHER INFORMATION: Description of the synthetic sequence: sense
      strand (K2A) of a dsRNA that is homologous to the 5'-UTR of the
      neomycin sequence

<400> SEQUENCE: 157
acaggaugag gaucguuucg caug                                            24

<210> SEQ ID NO 158
<211> LENGTH: 24
<212> TYPE: RNA
<213> ORGANISM: Synthetic sequence
<220> FEATURE:
<223> OTHER INFORMATION: Description of the synthetic sequence:
      antisense strand(K2B) of a dsRNA that is
      complementary to the 5'-UTR of the neomycin sequence

<400> SEQUENCE: 158
ugcgaaacga uccucauccu gucu                                            24

<210> SEQ ID NO 159
<211> LENGTH: 24
<212> TYPE: RNA
<213> ORGANISM: Synthetic sequence
<220> FEATURE:
<223> OTHER INFORMATION: Description of the synthetic sequence:
      antisense strand(S4B) of a dsRNA that is
      complementary to the YFP- and GFP sequence, respectively

<400> SEQUENCE: 159
gaagucgugc ugcuucaugu gguc                                            24

<210> SEQ ID NO 160
<211> LENGTH: 24
<212> TYPE: RNA
<213> ORGANISM: Synthetic sequence
<220> FEATURE:
<223> OTHER INFORMATION: Description of the synthetic sequence: sense
      strand (PKC1 A) of a dsRNA that is homologous to the
      proteinkinase C sequence

<400> SEQUENCE: 160
cuucuccgcc ucacaccgcu gcaa                                            24

<210> SEQ ID NO 161
<211> LENGTH: 22
<212> TYPE: RNA
<213> ORGANISM: Synthetic sequence
<220> FEATURE:
<223> OTHER INFORMATION: Description of the synthetic sequence:
      antisense strand(PKC2 B) of a dsRNA that is
      complementary to the proteinkinase C sequence

<400> SEQUENCE: 161
gcagcggugu gaggcggaga ag                                              22

<210> SEQ ID NO 162
<211> LENGTH: 21
<212> TYPE: RNA
<213> ORGANISM: Synthetic sequence
<220> FEATURE:
<223> OTHER INFORMATION: Description of the synthetic sequence:
      antisense strand(S12B) of a dsRNA that is
      complementary to the YFP- and GFP sequence, respectively

<400> SEQUENCE: 162
```
aagucgugcu gcuucaugug g                                         21

<210> SEQ ID NO 163
<211> LENGTH: 23
<212> TYPE: RNA
<213> ORGANISM: Synthetic sequence
<220> FEATURE:
<223> OTHER INFORMATION: Description of the synthetic sequence:
      antisense strand(S11B) of a dsRNA that is
      complementary to the YFP- and GFP sequence, respectively

<400> SEQUENCE: 163
aagucgugcu gcuucaugug guc                                       23

<210> SEQ ID NO 164
<211> LENGTH: 20
<212> TYPE: RNA
<213> ORGANISM: Synthetic sequence
<220> FEATURE:
<223> OTHER INFORMATION: Description of the synthetic sequence: sense
      strand (S13A) of a dsRNA that is homologous to the YFP- and
      GFP sequence, respectively

<400> SEQUENCE: 164
ccacaugaag cagcacgacu                                           20

<210> SEQ ID NO 165
<211> LENGTH: 22
<212> TYPE: RNA
<213> ORGANISM: Synthetic sequence
<220> FEATURE:
<223> OTHER INFORMATION: Description of the synthetic sequence:
      antisense strand(S13B) of a dsRNA that is
      complementary to the YFP- and GFP sequence, respectively

<400> SEQUENCE: 165
agucgugcug cuucaugugg uc                                        22

<210> SEQ ID NO 166
<211> LENGTH: 20
<212> TYPE: RNA
<213> ORGANISM: Synthetic sequence
<220> FEATURE:
<223> OTHER INFORMATION: Description of the synthetic sequence:
      antisense strand(S14B) of a dsRNA that is
      complementary to the YFP- and GFP sequence, respectively

<400> SEQUENCE: 166
agucgugcug cuucaugugg                                           20

<210> SEQ ID NO 167
<211> LENGTH: 24
<212> TYPE: RNA
<213> ORGANISM: Synthetic sequence
<220> FEATURE:
<223> OTHER INFORMATION: Description of the synthetic sequence: sense
      strand (S4A) of a dsRNA that is homologous to the YFP- and
      GFP sequence, respectively

<400> SEQUENCE: 167
ccacaugaag cagcacgacu ucuu                                      24

<210> SEQ ID NO 168
<211> LENGTH: 21
<212> TYPE: RNA
<213> ORGANISM: Synthetic sequence
<220> FEATURE:
<223> OTHER INFORMATION: Description of the synthetic sequence: sense

```
          strand (ES-7A) of a dsRNA that is homologous to the human
          EGFR sequence

<400> SEQUENCE: 168
aacaccgcag caugucaaga u                                              21

<210> SEQ ID NO 169
<211> LENGTH: 21
<212> TYPE: RNA
<213> ORGANISM: Synthetic sequence
<220> FEATURE:
<223> OTHER INFORMATION: Description of the synthetic sequence:
      antisense strand(ES-7B) of a dsRNA that is
      complementary to the human EGFR sequence

<400> SEQUENCE: 169
cuugacaugc ugcgguguuu u                                              21

<210> SEQ ID NO 170
<211> LENGTH: 22
<212> TYPE: RNA
<213> ORGANISM: Synthetic sequence
<220> FEATURE:
<223> OTHER INFORMATION: Description of the synthetic sequence: sense
      strand (ES-8A) of a dsRNA that is homologous to the human
      EGFR sequence

<400> SEQUENCE: 170
aaguuaaaau ucccgucgcu au                                             22

<210> SEQ ID NO 171
<211> LENGTH: 22
<212> TYPE: RNA
<213> ORGANISM: Synthetic sequence
<220> FEATURE:
<223> OTHER INFORMATION: Description of the synthetic sequence:
      antisense strand(ES-8B) of a dsRNA that is
      complementary to the human EGFR sequence

<400> SEQUENCE: 171
ugauagcgac gggaauuuua ac                                             22

<210> SEQ ID NO 172
<211> LENGTH: 22
<212> TYPE: RNA
<213> ORGANISM: Synthetic sequence
<220> FEATURE:
<223> OTHER INFORMATION: Description of the synthetic sequence: sense
      strand (ES-2A) of a dsRNA that is homologous to the human
      EGFR sequence

<400> SEQUENCE: 172
agugugaucc aagcuguccc aa                                             22

<210> SEQ ID NO 173
<211> LENGTH: 24
<212> TYPE: RNA
<213> ORGANISM: Synthetic sequence
<220> FEATURE:
<223> OTHER INFORMATION: Description of the synthetic sequence:
      antisense strand(ES-5B) of a dsRNA that is
      complementary to the human EGFR sequence

<400> SEQUENCE: 173
uugggacagc uuggaucaca cuuu                                           24
```

We claim:

1. A double-stranded ribonucleic acid (dsRNA) for inhibiting the expression of a target gene in a cell, comprising a complementary RNA strand and a sense RNA strand, wherein the sense RNA strand comprises a nucleotide sequence that is substantially identical to the corresponding part of the target gene, wherein the complementary RNA strand comprises a complementary nucleotide sequence that is complementary to an mRNA transcript formed during expression of the target gene, wherein the complementary strand specifically hybridizes with the mRNA transcript, wherein the complementary RNA strand and the sense strand each comprise a 3'-end and a 5'-end, wherein at least one end of one of the RNA strands is blunt, and wherein the dsRNA is 20 to 49 base pairs in length.

2. The dsRNA of claim 1, wherein at least one end of one of the RNA strands has a nucleotide overhang.

3. The dsRNA of claim 1, wherein the 3'-end of at least one RNA strand has a nucleotide overhang of 2 to 4 nucleotides.

4. The dsRNA of claim 3, wherein the nucleotide overhang is 2 nucleotides in length.

5. The dsRNA of claim 3, wherein the nucleotides of the nucleotide overhang are replaced with nucleoside thiophosphates.

6. The dsRNA of claim 1, wherein the 3'-end of the complementary RNA strand has a nucleotide overhang of 1 to 4 nucleotides.

7. The dsRNA of claim 1, wherein at least one of the complementary RNA strand and the sense RNA strand is 21 nucleotides in length.

8. The dsRNA of claim 1, wherein at least one of the complementary RNA strand and the sense RNA strand is 22 nucleotides in length.

9. The dsRNA of claim 1, wherein at least one of the complementary RNA strand and the sense RNA strand is 24 nucleotides in length.

10. The dsRNA of claim 1, wherein the ends of the dsRNA are unlinked.

11. A method of inhibiting the expression of the target gene in the cell, the method comprising:
   (a) introducing into the cell the double-stranded ribonucleic acid (dsRNA) of claim 1 for inhibiting the expression of the target gene in the cell; and
   (b) maintaining the cell produced in step (a) for a time sufficient to obtain degradation of the mRNA transcript of the target gene, thereby inhibiting expression of the target gene in the cell.

12. The method of claim 11, wherein at least one end of one of the RNA strands has a nucleotide overhang.

13. The method of claim 12, wherein the nucleotide overhang is 2 nucleotides in length.

14. The method of claim 12, wherein the nucleotides of the nucleotide overhang are replaced with nucleoside thiophosphates.

15. The method of claim 11, wherein at least one of the complementary RNA strand and the sense RNA strand is 21 nucleotides in length.

16. The method of claim 11, wherein at least one of the complementary RNA strand and the sense RNA strand is 22 nucleotides in length.

17. The method of claim 11, wherein at least one of the complementary RNA strand and the sense RNA strand is 24 nucleotides in length.

18. The method of claim 11, wherein the target gene comprises EGFR.

19. The method of claim 11, wherein the target gene comprises MDR1.

20. The method of claim 11, wherein the target gene comprises MDR1 or EGFR.

* * * * *